US010730955B2

(12) United States Patent
Yamazaki et al.

(10) Patent No.: US 10,730,955 B2
(45) Date of Patent: *Aug. 4, 2020

(54) POLYNUCLEOTIDES ENCODING ANTI-HUMAN RECEPTOR-TYPE PROTEIN TYROSINE PHOSPHATASE SIGMA ANTIBODIES

(71) Applicant: SBI Biotech Co., Ltd., Tokyo (JP)

(72) Inventors: Tomohide Yamazaki, Tokyo (JP); Jing Zhao, Tokyo (JP); Koji Ishida, Tokyo (JP); Yasue Shibata, Tokyo (JP); Minkwon Cho, Osaka (JP); Mayuki Endo, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 299 days.

This patent is subject to a terminal disclaimer.

(21) Appl. No.: 15/726,669

(22) Filed: Oct. 6, 2017

(65) Prior Publication Data
US 2018/0155446 A1 Jun. 7, 2018

Related U.S. Application Data

(63) Continuation of application No. 14/113,904, filed as application No. PCT/JP2012/061795 on Apr. 27, 2012, now Pat. No. 9,803,026.

(30) Foreign Application Priority Data

Apr. 28, 2011 (JP) ................. 2011-101752

(51) Int. Cl.
C07K 16/40 (2006.01)
C07K 16/28 (2006.01)
G01N 33/569 (2006.01)
G01N 33/50 (2006.01)

(52) U.S. Cl.
CPC .......... C07K 16/40 (2013.01); C07K 16/2803 (2013.01); G01N 33/5058 (2013.01); G01N 33/56972 (2013.01); C07K 2317/24 (2013.01); C07K 2317/33 (2013.01); C07K 2317/732 (2013.01); C07K 2317/734 (2013.01); C07K 2317/76 (2013.01)

(58) Field of Classification Search
None
See application file for complete search history.

(56) References Cited

U.S. PATENT DOCUMENTS 9,803,026 B2 * 10/2017 Yamazaki .......... C07K 16/2803
2006/0088521 A1 4/2006 Mahadevan
2008/0008719 A1 1/2008 Bowdish et al.
2013/0171164 A1 7/2013 Bottini et al.

FOREIGN PATENT DOCUMENTS

| WO | WO1995/09656 | 4/1995 |
| WO | WO2004/13325 | 2/2004 |
| WO | WO2007/041317 | 4/2007 |
| WO | WO2009/003274 | 1/2009 |
| WO | WO2010/056332 | 5/2010 |
| WO | 2011/022462 | 2/2011 |

OTHER PUBLICATIONS

Examination Report for European Application No. 17174348.7 dated May 22, 2018, 12 pages.
Lou et al., "Antibodies in haystacks: how selection strategy influences the outcome of selection from molecular diversity libraries", Journal of Immunological Meth, Elsevier Science Publishers B. V.., Amsterdam, Jul. 2001, 253(1-2):233-242.
Pulido R et al., "The Lar/Ptpdelta/Ptpsigma Subfamily of Transmembrane Protein-Tyrosine-Phosphatases: Multiple Human Lar, Ptpdelta, and Ptpsigma Isoforms are Expressed in a Tissue specific Manner and Associate With the Lar-Interacting Protein Lip. 1", Proceedings of the National Academy of Sciences, National Academy of Sciences, Dec. 1995, (92):11686-11690.
Strausberg et al.: "Homo sapiens protein tyrosine phosphatase, receptor type, S, mRNA (cDNA clone MGC:176807 Image:9051790), complete eds", GenBank, Jan. 2009, 3 pages.
Wu et al., "Identification of function-regulating antibodies targeting the receptor protein tyrosine phosphatase sigma ectodomain," PLOS One, May 2017, 12(5): e0178489 15 pages.
"PTPRS monoclonal antibody (M01), clone 1H6" online catalog (2012), Abnova.com.
Asselin-Pasturel, C., et al., "Mouse Strain Differences in Plasmacytoid Dendritic Cell Frequency and Function Revealed by a Novel Monoclonal Antibody," J. Immunol. (2003), 171:6466-6477.
Blanco, P. et al., "Induction of Dendritic Cell Differentiation by IFN-α in Systemic Lupus Erythematosus," Science (2001), 294:1540-1543.
Blaslus, A. et al., "A cell-surface molecule selectively expressed on murine natural interferon-producing cells that blocks secretion of interferon-alpha," Blood (2004), 103(11):4201-4206.
Carter, "Potent antibody therapeutics by design," Nat. Rev. Immunol. 6:343-57 (2006).
Chan et al., "Interferon-producing killer dendritic cells provide a link between innate and adaptive immunity", Nature Medicine, 12(2):207-213 (2006).
Communication from EP Patent Application No. 12 722 557.1 dated Dec. 8, 2015.
Data Base UniProtKB: Q13332; XP-002679489 (2012).
Data Base UniProtKB: Q64605; XP-002679490 (2012).
Dzionek, A. et al., "BDCA-2, a Novel Plasmacytoid Dendritic Cell-specific Type II C-Type Lectin, Mediates Antigen Capture and is a Potent Inhibitor of Interferon α/β Induction," J. Exp. Med. (2001), 194:1823-1834.
Dzionek, A. et al., "BDCA-2, BDCA-3, and BDCA-4: Three Markets for Distinct Subsets of Dendritic Cells in Human Peripheral Blood," J. Immunol. (2000), 165:6037-6046.

(Continued)

Primary Examiner — Sharon X Wen
(74) Attorney, Agent, or Firm — Fish & Richardson P.C.

(57) ABSTRACT

A monoclonal antibody that binds to an extracellular domain of human receptor-type protein tyrosine phosphatase σ (human PTPRS), or a fragment including an antigen-binding region thereof.

8 Claims, 61 Drawing Sheets
Specification includes a Sequence Listing.

(56) References Cited

OTHER PUBLICATIONS

English-Russian Glossary of Key Terms on Vaccinology and Immunization, World Health Organization, 2009, 9 pages. (with partial machine English translation).

Guler, H.P. et al., "A Phase 1, Single Dose Escalation Study of IL-1 Trap in Patients with Rheumatoid Arthritis," *Arthritis Rheum.* (2001), 44:S370.

Hopkins, S.J. et al., "Cytokines in synovial fluid: II. The presence of tumour necrosis factor and interferon," *Clin. Exp. Immunol.* (1988), 73:88-92.

Kamogawa-Schifter, Y. et al., "Ly49Q defines 2 pDC subsets in mice," *Blood* (2005), 105(7):2787-2792.

Kwon et al., Trans-synaptic Adhesions Between Netrin-G Ligand-3 . . . Synapse Formation, J. of Biol. Chem. 285(18):13966-13978 (2010).

Lande et al., "Plasmacytoid dendritic cells: key players in the initiation and regulation of immune responses", Ann. N.Y. Acad. Sci. 1183:89-103 (2010).

Ledig et al., "The Receptor Tyrosine Phosphatase CRYP α Promotes Intraretinal Axon Growth", J. Cell of Biology 147(2):375-388 (1999).

Nestle, F.O. et al., "Plasmacytoid predendritic cells initiate psoriasis through interferon-α production," *J. Exp. Med.* (2005), 202(1):135-143.

Office Action for Japanese Application No. 2013-549652 dated Feb. 17, 2016 with English translation.

Office Action issued in Russian Application No. 2013152816/10(082418), dated May 6, 2016, 20 pages (with English Translation).

Pérez, A. et al., "Myasthenia Gravis Induced by Alpha-Interferon Therapy," *Am. J. Hematol.* (1995), 49:365-366.

"Physiological Roles of Receptor-Like Tyrosine Phosphatases", with English translation, http://niwww3.nibb.ac.jp/RPTP.pdf.

Shiozawa, S. et al., "Interferon-Alpha in Lupus Psychosis," *Arthritis and Rheumatism* (1992) 35(4):417-422.

Stewart, T.A. et al., "Neutralizing interferon alpha as a therapeutic approach to autoimmune diseases," *Cytokine & Growth Factor Rev.* (2003), 14:139-154.

Tanuma, N. et al., "Functional Analysis of Tyrosine Phosphatase Induced Through Dendritic Cell Mature Process," http://www.noasec.jp/kinouindex/data2005/pdf01/01_20.pdf, with English translation (2005).

Tonks, N.K., "Protein tyrosine phosphatases from genes, to function, to disease," *Nat. Rev. Mol. Cell Biol.* (2006), 7:833-846.

Wada, M. et al., "Antithyroid Peroxidase Antibody and Development of Silent Thyroiditis during Interferon-α2a Treatment of Chronic Hepatitis C," *Am. J. Gastroenterol* (1995); 90(8):1366-1367.

Wilson, L.E. et al., "Autoimmune Disease Complicating Antiviral Therapy for Hepatitis C Virus Infections," *Semin. Arthritis. Rheum.* (2002), 32(3):163-173.

Yan, H. et al., "A Novel Receptor Tyrosine Phosphatase-α that is Highly Expressed in the Nervous System," *J. Biol. Chem.* (1993), 268(33):24880-24886.

International Search Report dated Jul. 25, 2012 issued in PCT Application No. PCT/JP2012/061795.

Office Action in Indian Patent Application No. 9262/DELNP/2013, dated Dec. 12, 2018, 7 pages (with English Translation).

\* cited by examiner

FIG. 1

MAPTWGPGMVSVVGPMGLLVVLVGGCAAEEPPRFIKEPKDQIGVSGGVASFVCQATGDPKPRVTWNKKGKKVNSQRFETIEFDE
Signal peptide                                                                    Ig-like domain SAGAVLRIQPLRTPRDENVYECVAQNSVGEITVHAKLTVLREDQLPSGFPNIDMGPQLKVVERTRTATMLCAASGNPDPEITWFKDF
                                                                                  Ig-like domain LPVDPSASNGRIKQLRSGALQIESSEETDQGKYECVAINSAGTRESEPANLYVRRVAPRESIPASHERIYECGNVNITCVAVGSP
                                                                                  Fibronectin type III-like domain MPYVWMKMQGAEDLTPEDDMPVGRNVLELTDVKDSANYTCVAMSSLGVIEAVAQITVKALPKAPPTIIEVLSASDSRITVSNIDPSSNPED
                                                                                  Fibronectin type III-like domain RIISYVIEYKSKSQDGPYQIKEDITTRYSIGGLSBNSEYEIKVSAINGKGKQWGSVRIIQEQAPASAEPRNVYARVSATTMMQ
                                                                                  Fibronectin type III-like domain WEEPKEPNGLIRGYRVYYTMEEDEHRKGNWKKNIVNGSLITTGSLLPEDTCYRIRTVATSVQGGAGSNDNIQDVRTQQSVIVGQEMIL
                                                                                  Fibronectin type III-like domain RAEARSETSITLSWEBPREEQESIIKYELLEBREQHCGREIVGRTEDPFTVVAGGDIKENTTEYAFRLAAEEDQLGAETNVARBQILQSICP
                                                                                  Fibronectin type III-like domain KMEKVVAWIKTSVLIQSWEFPRDMKASETEVKQVVNGLTLDVQGRTTKVLITHLKRLTEYVNQLINRGSSILGGLQQTYTAWTAFALLNQ KPSGVARKPDAQGFIMVYLPDCQSPVPVQSYFIVMVPLRKSRGGQFLTPLGSPEDLMQLEELIQDISRLQRRSLRHSRQLEVPRPYIAAR FSVLPPTFHPGDQKQYGGFQMRGLEPGHRYVLFVLAVLQKSEPTFAASPFSQPPQLDNPDQPQPIVDGEEGLIHVVIGPVILAVVFICIVI
                                                                                  Transmembrane region AILLYKNKPDSKRKQSEPRTKCLLNNADLAPHHPKDPVEMRRINFQTPGMLSHPPIPIADMAEHTERLKANDSLKLSQEYESIDPGQQ FTWEHSNLEVNRPKNRYANVIAYDHSRVILQPIEGIMGSDYINANYIDGYRCQNAYIATQGPLPRETFGDFWRMVWEQRSATIVMMT RLEEKSRIKCDQYWPNRGTETYGFIQVTLLDTIELATFCVRTFSLHKNGSSEKREVRQEFTAVNPQGHVPEYPTPELAFLRRVKTCN PPDAGPIVVHCSAGVGRTGCFIVIDAMLERIKPEKTVDVYGHVTLMRSQRNYMVQTEDQYSFIHEALLEAVQCGNTEVPARSLYAYIQ KLAQVEPGEHVTGMELEFKRLANSKAHTSRFISANLPCNKFKNRLVNIMPYESTRVLQPIRGVEGSDYINASFIDGYRQQKAYIATQ GPLAETTEDFWRMLWENNSTIVVMLTKLREMGREKCHQYWPAERSARSYQYFVVDPMAEYNMPQYILREFKVTDARDGQSRTVRQ EQFIDTWPEQGVPKSGEGFIDEICQVVHKTKEQFGQDGPIVVHCSAGVGRTGVFITLSIVLERMRYEGVVDIFQTVKMLRTQRPAMVQT

EDEYQFCYQAALEYLGSFDHYAT

CSN: Culture Supernatant

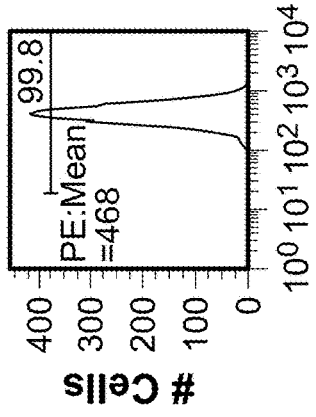
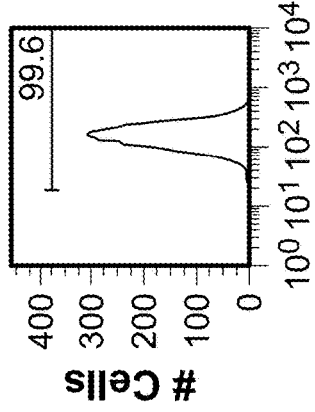
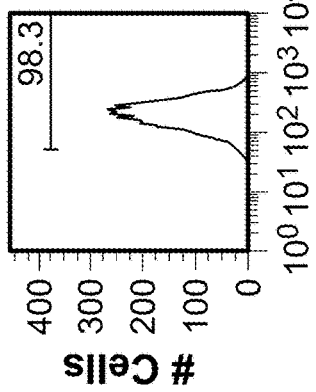
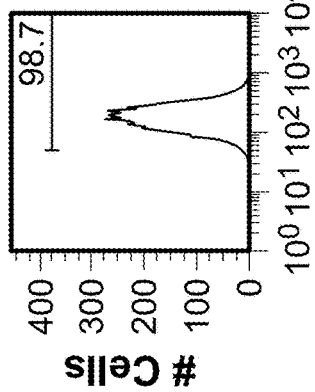
FIG. 13

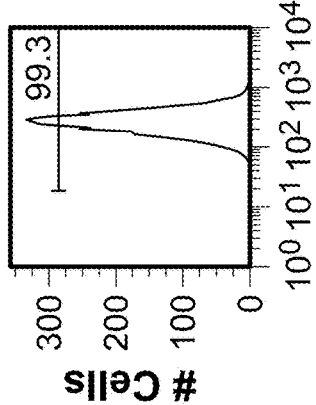
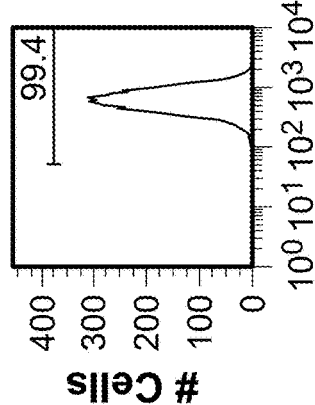
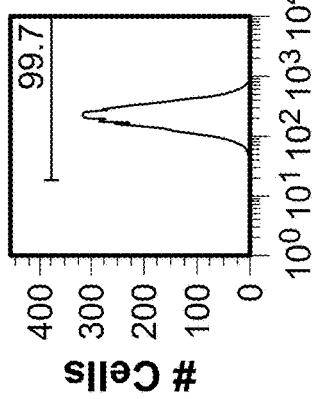
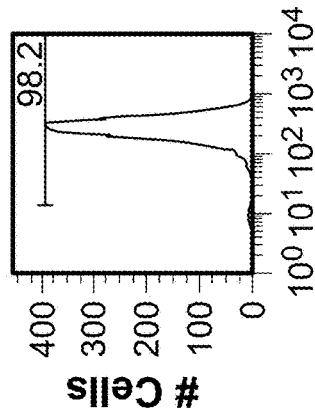
FIG. 13 (Cont.)

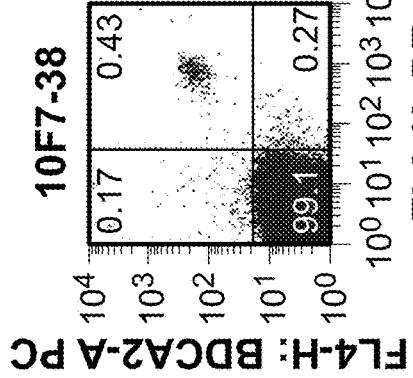
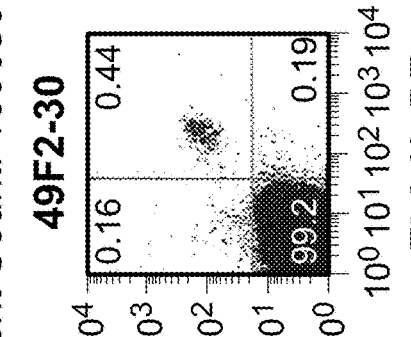
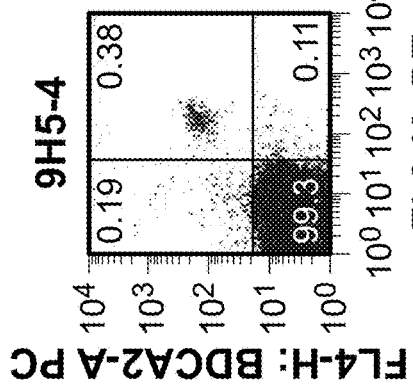
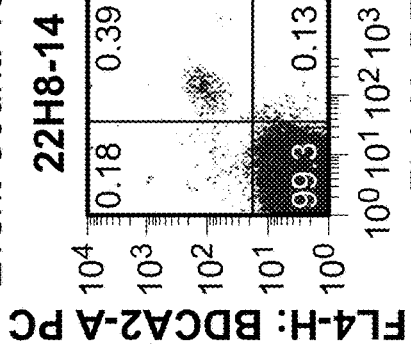
FIG. 14 (Cont.)

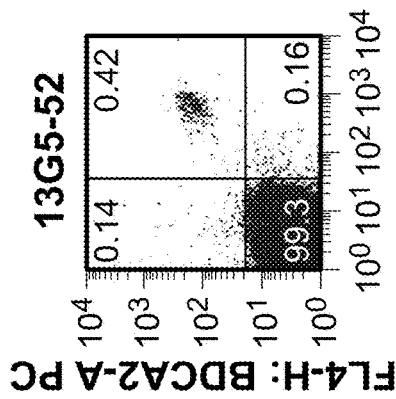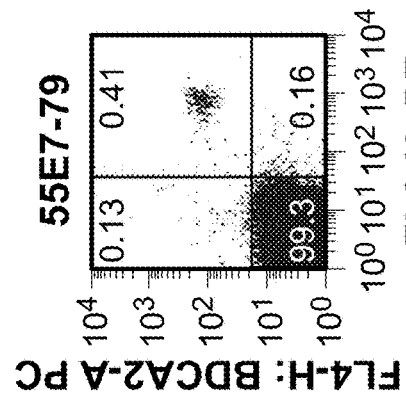
FIG. 14 (Cont.)

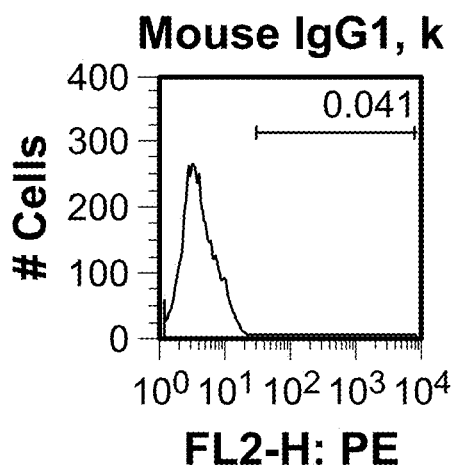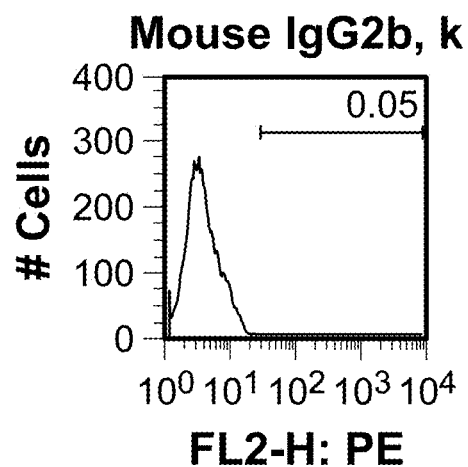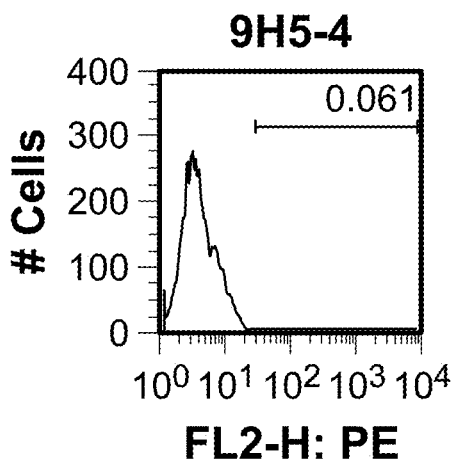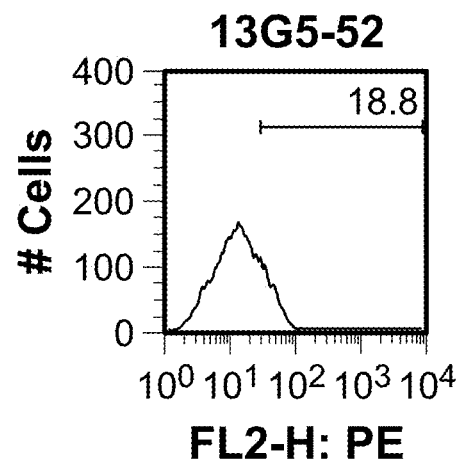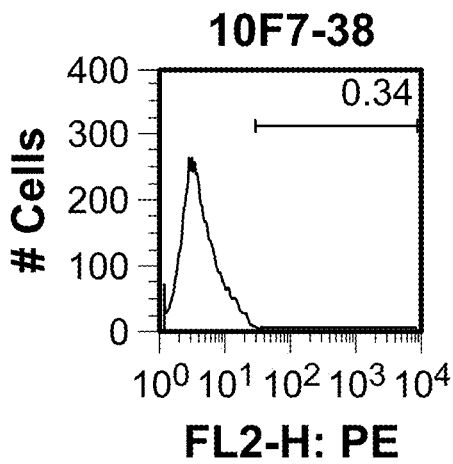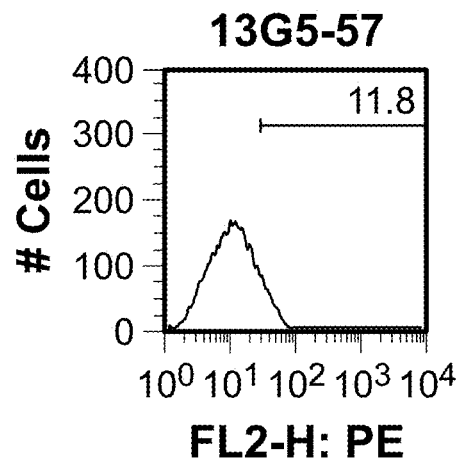
FIG. 15

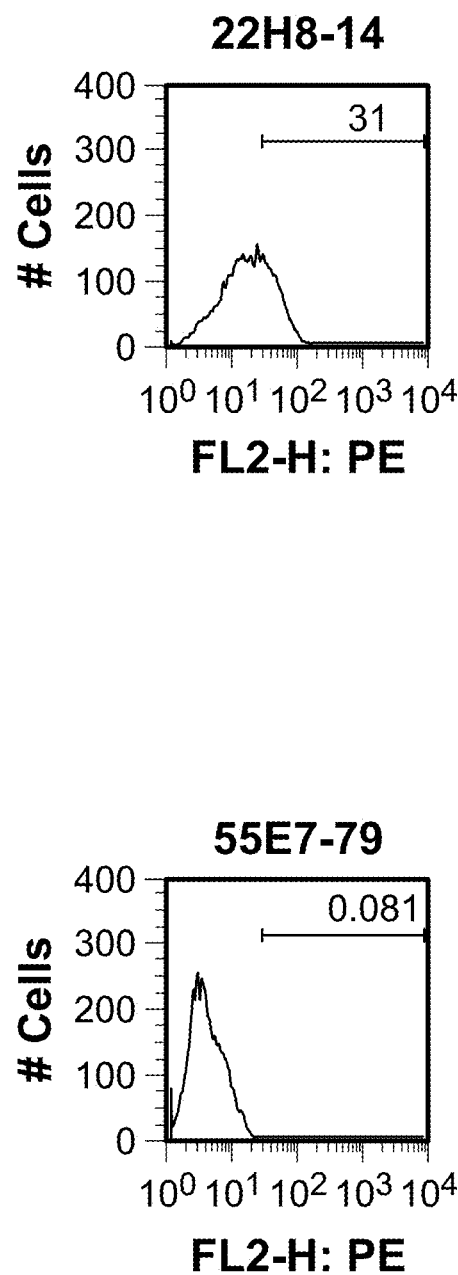
FIG. 15 (Cont.)

ated as PTP, "receptor-type protein tyrosine phosphatase" is abbreviated as RPTP or PTPR, "receptor-type protein tyrosine phosphatase σ" is sometimes abbreviates as RPTP-σ, PTP-σ or PTPRS, and "human" and "mouse" are sometimes represented by the prefixes h and m, respectively.

SEQUENCE LISTING

<160> NUMBER OF SEQ ID NOS: 102

<210> SEQ ID NO 1
<211> LENGTH: 1501
<212> TYPE: PRT
<213> ORGANISM: Homo sapiens
<220> FEATURE:
<221> NAME/KEY: PEPTIDE
<222> LOCATION: (1)..(1501)

<400> SEQUENCE: 1

Met Ala Pro Thr Trp Gly Pro Gly Met Val Ser Val Val Gly Pro Met
1               5                   10                  15

Gly Leu Leu Val Val Leu Leu Val Gly Gly Cys Ala Ala Glu Glu Pro
            20                  25                  30

Pro Arg Phe Ile Lys Glu Pro Lys Asp Gln Ile Gly Val Ser Gly Gly
        35                  40                  45

Val Ala Ser Phe Val Cys Gln Ala Thr Gly Asp Pro Lys Pro Arg Val
    50                  55                  60

Thr Trp Asn Lys Lys Gly Lys Lys Val Asn Ser Gln Arg Phe Glu Thr
65                  70                  75                  80

Ile Glu Phe Asp Glu Ser Ala Gly Ala Val Leu Arg Ile Gln Pro Leu
                85                  90                  95

Arg Thr Pro Arg Asp Glu Asn Val Tyr Glu Cys Val Ala Gln Asn Ser
            100                 105                 110

Val Gly Glu Ile Thr Val His Ala Lys Leu Thr Val Leu Arg Glu Asp
        115                 120                 125

Gln Leu Pro Ser Gly Phe Pro Asn Ile Asp Met Gly Pro Gln Leu Lys
    130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Gly Ala Leu
            180                 185                 190

Gln Ile Glu Ser Ser Glu Glu Thr Asp Gln Gly Lys Tyr Glu Cys Val
        195                 200                 205

Ala Thr Asn Ser Ala Gly Val Arg Tyr Ser Ser Pro Ala Asn Leu Tyr
    210                 215                 220

Val Arg Val Arg Arg Val Ala Pro Arg Phe Ser Ile Leu Pro Met Ser
225                 230                 235                 240

His Glu Ile Met Pro Gly Gly Asn Val Asn Ile Thr Cys Val Ala Val
                245                 250                 255

Gly Ser Pro Met Pro Tyr Val Lys Trp Met Gln Gly Ala Glu Asp Leu
            260                 265                 270

Thr Pro Glu Asp Asp Met Pro Val Gly Arg Asn Val Leu Glu Leu Thr
        275                 280                 285

Asp Val Lys Asp Ser Ala Asn Tyr Thr Cys Val Ala Met Ser Ser Leu
    290                 295                 300

Gly Val Ile Glu Ala Val Ala Gln Ile Thr Val Lys Ser Leu Pro Lys
305                 310                 315                 320

Ala Pro Gly Thr Pro Met Val Thr Glu Asn Thr Ala Thr Ser Ile Thr
                325                 330                 335

Ile Thr Trp Asp Ser Gly Asn Pro Asp Pro Val Ser Tyr Tyr Val Ile
            340                 345                 350

```
Glu Tyr Lys Ser Lys Ser Gln Asp Gly Pro Tyr Gln Ile Lys Glu Asp
            355                 360                 365
Ile Thr Thr Thr Arg Tyr Ser Ile Gly Gly Leu Ser Pro Asn Ser Glu
    370                 375                 380
Tyr Glu Ile Trp Val Ser Ala Val Asn Ser Ile Gly Gln Gly Pro Pro
385                 390                 395                 400
Ser Glu Ser Val Val Thr Arg Thr Gly Glu Gln Ala Pro Ala Ser Ala
                405                 410                 415
Pro Arg Asn Val Gln Ala Arg Met Leu Ser Ala Thr Thr Met Ile Val
            420                 425                 430
Gln Trp Glu Glu Pro Val Glu Pro Asn Gly Leu Ile Arg Gly Tyr Arg
        435                 440                 445
Val Tyr Tyr Thr Met Glu Pro Glu His Pro Val Gly Asn Trp Gln Lys
    450                 455                 460
His Asn Val Asp Asp Ser Leu Leu Thr Thr Val Gly Ser Leu Leu Glu
465                 470                 475                 480
Asp Glu Thr Tyr Thr Val Arg Val Leu Ala Phe Thr Ser Val Gly Asp
                485                 490                 495
Gly Pro Leu Ser Asp Pro Ile Gln Val Lys Thr Gln Gln Gly Val Pro
            500                 505                 510
Gly Gln Pro Met Asn Leu Arg Ala Glu Ala Arg Ser Glu Thr Ser Ile
        515                 520                 525
Thr Leu Ser Trp Ser Pro Pro Arg Gln Glu Ser Ile Ile Lys Tyr Glu
    530                 535                 540
Leu Leu Phe Arg Glu Gly Asp His Gly Arg Glu Val Gly Arg Thr Phe
545                 550                 555                 560
Asp Pro Thr Thr Ser Tyr Val Val Glu Asp Leu Lys Pro Asn Thr Glu
                565                 570                 575
Tyr Ala Phe Arg Leu Ala Ala Arg Ser Pro Gln Gly Leu Gly Ala Phe
            580                 585                 590
Thr Pro Val Val Arg Gln Arg Thr Leu Gln Ser Ile Ser Pro Lys Asn
        595                 600                 605
Phe Lys Val Lys Met Ile Met Lys Thr Ser Val Leu Leu Ser Trp Glu
    610                 615                 620
Phe Pro Asp Asn Tyr Asn Ser Pro Thr Pro Tyr Lys Ile Gln Tyr Asn
625                 630                 635                 640
Gly Leu Thr Leu Asp Val Asp Gly Arg Thr Thr Lys Lys Leu Ile Thr
                645                 650                 655
His Leu Lys Pro His Thr Phe Tyr Asn Phe Val Leu Thr Asn Arg Gly
            660                 665                 670
Ser Ser Leu Gly Gly Leu Gln Gln Thr Val Thr Ala Trp Thr Ala Phe
        675                 680                 685
Asn Leu Leu Asn Gly Lys Pro Ser Val Ala Pro Lys Pro Asp Ala Asp
    690                 695                 700
Gly Phe Ile Met Val Tyr Leu Pro Asp Gly Gln Ser Pro Val Pro Val
705                 710                 715                 720
Gln Ser Tyr Phe Ile Val Met Val Pro Leu Arg Lys Ser Arg Gly Gly
                725                 730                 735
Gln Phe Leu Thr Pro Leu Gly Ser Pro Glu Asp Met Asp Leu Glu Glu
            740                 745                 750
Leu Ile Gln Asp Ile Ser Arg Leu Gln Arg Arg Ser Leu Arg His Ser
        755                 760                 765
Arg Gln Leu Glu Val Pro Arg Pro Tyr Ile Ala Ala Arg Phe Ser Val
```

```
                770             775             780
Leu Pro Pro Thr Phe His Pro Gly Asp Gln Lys Gln Tyr Gly Gly Phe
785                 790             795                 800

Asp Asn Arg Gly Leu Glu Pro Gly His Arg Tyr Val Leu Phe Val Leu
                805             810              815

Ala Val Leu Gln Lys Ser Glu Pro Thr Phe Ala Ala Ser Pro Phe Ser
                820              825             830

Asp Pro Phe Gln Leu Asp Asn Pro Asp Pro Gln Pro Ile Val Asp Gly
                835             840             845

Glu Gly Leu Ile Trp Val Ile Gly Pro Val Leu Ala Val Val Phe
850             855             860

Ile Ile Cys Ile Val Ile Ala Ile Leu Leu Tyr Lys Asn Lys Pro Asp
865             870              875             880

Ser Lys Arg Lys Asp Ser Glu Pro Arg Thr Lys Cys Leu Leu Asn Asn
                885             890             895

Ala Asp Leu Ala Pro His His Pro Lys Asp Pro Val Glu Met Arg Arg
                900             905             910

Ile Asn Phe Gln Thr Pro Gly Met Leu Ser His Pro Pro Ile Pro Ile
915             920             925

Ala Asp Met Ala Glu His Thr Glu Arg Leu Lys Ala Asn Asp Ser Leu
930             935             940

Lys Leu Ser Gln Glu Tyr Glu Ser Ile Asp Pro Gly Gln Gln Phe Thr
945             950             955             960

Trp Glu His Ser Asn Leu Glu Val Asn Lys Pro Lys Asn Arg Tyr Ala
                965             970             975

Asn Val Ile Ala Tyr Asp His Ser Arg Val Ile Leu Gln Pro Ile Glu
                980             985             990

Gly Ile Met Gly Ser Asp Tyr Ile Asn Ala Asn Tyr Val Asp Gly Tyr
                995             1000            1005

Arg Arg Gln Asn Ala Tyr Ile Ala Thr Gln Gly Pro Leu Pro Glu
    1010            1015            1020

Thr Phe Gly Asp Phe Trp Arg Met Val Trp Glu Gln Arg Ser Ala
    1025            1030            1035

Thr Ile Val Met Met Thr Arg Leu Glu Glu Lys Ser Arg Ile Lys
    1040            1045            1050

Cys Asp Gln Tyr Trp Pro Asn Arg Gly Thr Glu Thr Tyr Gly Phe
    1055            1060            1065

Ile Gln Val Thr Leu Leu Asp Thr Ile Glu Leu Ala Thr Phe Cys
    1070            1075            1080

Val Arg Thr Phe Ser Leu His Lys Asn Gly Ser Ser Glu Lys Arg
    1085            1090            1095

Glu Val Arg Gln Phe Gln Phe Thr Ala Trp Pro Asp His Gly Val
    1100            1105            1110

Pro Glu Tyr Pro Thr Pro Phe Leu Ala Phe Leu Arg Arg Val Lys
    1115            1120            1125

Thr Cys Asn Pro Pro Asp Ala Gly Pro Ile Val Val His Cys Ser
    1130            1135            1140

Ala Gly Val Gly Arg Thr Gly Cys Phe Ile Val Ile Asp Ala Met
    1145            1150            1155

Leu Glu Arg Ile Lys Pro Glu Lys Thr Val Asp Val Tyr Gly His
    1160            1165            1170

Val Thr Leu Met Arg Ser Gln Arg Asn Tyr Met Val Gln Thr Glu
    1175            1180            1185
```

```
Asp Gln Tyr Ser Phe Ile His Glu Ala Leu Leu Glu Ala Val Gly
1190                1195                1200

Cys Gly Asn Thr Glu Val Pro Ala Arg Ser Leu Tyr Ala Tyr Ile
1205                1210                1215

Gln Lys Leu Ala Gln Val Glu Pro Gly Glu His Val Thr Gly Met
1220                1225                1230

Glu Leu Glu Phe Lys Arg Leu Ala Asn Ser Lys Ala His Thr Ser
1235                1240                1245

Arg Phe Ile Ser Ala Asn Leu Pro Cys Asn Lys Phe Lys Asn Arg
1250                1255                1260

Leu Val Asn Ile Met Pro Tyr Glu Ser Thr Arg Val Cys Leu Gln
1265                1270                1275

Pro Ile Arg Gly Val Glu Gly Ser Asp Tyr Ile Asn Ala Ser Phe
1280                1285                1290

Ile Asp Gly Tyr Arg Gln Gln Lys Ala Tyr Ile Ala Thr Gln Gly
1295                1300                1305

Pro Leu Ala Glu Thr Thr Glu Asp Phe Trp Arg Met Leu Trp Glu
1310                1315                1320

Asn Asn Ser Thr Ile Val Val Met Leu Thr Lys Leu Arg Glu Met
1325                1330                1335

Gly Arg Glu Lys Cys His Gln Tyr Trp Pro Ala Glu Arg Ser Ala
1340                1345                1350

Arg Tyr Gln Tyr Phe Val Val Asp Pro Met Ala Glu Tyr Asn Met
1355                1360                1365

Pro Gln Tyr Ile Leu Arg Glu Phe Lys Val Thr Asp Ala Arg Asp
1370                1375                1380

Gly Gln Ser Arg Thr Val Arg Gln Phe Gln Phe Thr Asp Trp Pro
1385                1390                1395

Glu Gln Gly Val Pro Lys Ser Gly Glu Gly Phe Ile Asp Phe Ile
1400                1405                1410

Gly Gln Val His Lys Thr Lys Glu Gln Phe Gly Gln Asp Gly Pro
1415                1420                1425

Ile Ser Val His Cys Ser Ala Gly Val Gly Arg Thr Gly Val Phe
1430                1435                1440

Ile Thr Leu Ser Ile Val Leu Glu Arg Met Arg Tyr Glu Gly Val
1445                1450                1455

Val Asp Ile Phe Gln Thr Val Lys Met Leu Arg Thr Gln Arg Pro
1460                1465                1470

Ala Met Val Gln Thr Glu Asp Glu Tyr Gln Phe Cys Tyr Gln Ala
1475                1480                1485

Ala Leu Glu Tyr Leu Gly Ser Phe Asp His Tyr Ala Thr
1490                1495                1500
```

<210> SEQ ID NO 2
<211> LENGTH: 4665
<212> TYPE: DNA
<213> ORGANISM: Homo sapiens
<220> FEATURE:
<221> NAME/KEY: gene
<222> LOCATION: (1)..(4665)
<300> PUBLICATION INFORMATION:
<301> AUTHORS: Strausberg t al.
<302> TITLE: Generation and initial analysis of more than 15,000 full-length human and mouse cDNA sequences
<303> JOURNAL: Proc. Natl. Acad. Sci. U.S.A.
<304> VOLUME: 99
<305> ISSUE: 26

<306> PAGES: 16899-16903
<307> DATE: 2002

<400> SEQUENCE: 2

```
gggctcgagg cctctctgtg agggaccggg gggccatccc cctccagggc ggagatcgga    60
ggtcgctgcc aagcatggcg cccacctggg gccctggcat ggtgtctgtg gttggtccca   120
tgggcctcct tgtggtcctg ctcgttggag gctgtgcagc agaagagccc cccaggttta   180
tcaaagaacc caaggaccag atcggcgtgt cgggggggtgt ggcctctttc gtgtgtcagg   240
ccacgggtga ccccaagcca cgagtgacct ggaacaagaa gggcaagaag gtcaactctc   300
agcgctttga cgattgag tttgatgaga gtgcagggc agtgctgagg atccagccgc   360
tgaggacacc gcgggatgaa aacgtgtacg agtgtgtggc ccagaactcg gttggggaga   420
tcacagtcca tgccaagctt actgtcctcc gagaggacca gctgccctct ggcttcccca   480
acatcgacat gggcccacag ttgaaggtgg tggagcggac acggacagcc accatgctct   540
gtgcagccag cggcaaccct gaccctgaga tcacctggtt caaggacttc ctgcctgtgg   600
atcctagtgc cagcaatgga cgcatcaaac agctgcgatc aggagccctg cagattgaaa   660
gcagtgagga aaccgaccag ggcaaatatg agtgtgtggc caccaacagc gccggcgtgc   720
gctactcctc acctgccaac ctctacgtgc gagtccgccg cgtggcccg cgcttctcca   780
tcctgcccat gagccacgag atcatgccag ggggcaacgt gaacatcacc tgcgtggccg   840
tgggctcgcc catgccatac gtgaagtgga tgcagggggc cgaggacctg accccgagg   900
atgacatgcc cgtgggtcgg aacgtgctgg aactcacaga tgtcaaggac tcggccaact   960
acacctgcgt ggccatgtcc agcctgggcg tcattgaggc ggttgctcag atcacggtga  1020
aatctctccc caaagctccc gggactccca tggtgactga aacacagcc accagcatca  1080
ccatcacgtg ggactcgggc aacccagatc ctgtgtccta ttacgtcatc gaatataaat  1140
ccaagagcca agacgggccg tatcagatta aagaggacat caccaccaca cgttacagca  1200
tcggcggcct gagcccaac tcggagtacg agatctgggt gtcggccgtc aactccatcg  1260
gccagggggcc ccccagcgag tccgtggtca cccgcacagg cgagcaggcc ccggccagcg  1320
cgccgcggaa cgtgcaagcc cggatgctca gcgcgaccac catgattgtg cagtgggagg  1380
agccggtgga gcccaacggc ctgatccgcg gctaccgcgt ctactacacc atggaaccgg  1440
agcacccgt gggcaactgg cagaagcaca acgtggacga cagcctgctg accaccgtgg  1500
gcagcctgct ggaggacgag acctacaccg tgcgggtgct cgccttcacc tccgtcggcg  1560
acgggccct ctcggacccc atccaggtca agacgcagca gggagtgccg ggccagccca  1620
tgaacctgcg ggccgaggcc aggtcggaga ccagcatcac gctgtcctgg agcccccgc  1680
ggcaggagag tatcatcaag tacgagctcc tcttccggga aggcgaccat ggccgggagg  1740
tgggaaggac cttcgacccg acgacttcct acgtggtgga ggacctgaag cccaacacgg  1800
agtacgcctt ccgcctggcg gcccgctcgc cgcagggcct gggcgccttc acccccgtgg  1860
tgcggcagcg cacgctgcag tccatctcgc ccaagaactt caaggtgaaa atgatcatga  1920
agacatcagt tctgctcagc tgggagttcc ctgacaacta caactcaccc acacctaca  1980
agatccagta caatgggctc acactggatg tggatgccg taccaccaag aagctcatca  2040
cgcacctcaa gccccacacc ttctacaact ttgtgctgac caatcgcggc agcagcctgg  2100
gcggcctcca gcagacggtc accgcctgga ctgccttcaa cctgctcaac ggcaagccca  2160
gcgtcgcccc caagcctgat gctgacggct tcatcatggt gtatcttcct gacggccaga  2220
```

```
gccccgtgcc tgtccagagc tatttcattg tgatggtgcc actgcgcaag tctcgtggag    2280
gccaattcct gacccgctg ggtagcccag aggacatgga tctggaagag ctcatccagg    2340
acatctcacg gctacagagg cgcagcctgc ggcactcgcg tcagctggag gtgccccggc    2400
cctatattgc agctcgcttc tctgtgctgc acccacgtt ccatcccggc gaccagaagc     2460
agtatggcgg cttcgataac cggggcctgg agcccggcca ccgctatgtc ctcttcgtgc    2520
ttgccgtgct tcagaagagc gagcctacct ttgcagccag tcccttctca gacccttcc    2580 agctggataa cccggacccc cagcccatcg tggatggcga ggaggggctt atctgggtga    2640
tcgggcctgt gctggccgtg gtcttcataa tctgcattgt cattgctatc ctgctctaca    2700
agaacaaacc cgacagtaaa cgcaaggact cagaaccccg caccaaatgc tcctgaaca     2760 atgccgacct cgcccctcac caccccaagg accctgtgga atgagacgc attaacttcc     2820 agactccagg catgcttagc cacccgccaa ttcccatcgc agacatggcg gagcacacgg    2880
agcggctcaa ggccaacgac agcctcaagc tctcccagga gtatgagtcc atcgaccctg   2940
gacagcagtt cacatgggaa cattccaacc tggaagtgaa caagccgaag aaccgctatg    3000
ccaacgtcat cgcctatgac cactcccgtg tcatcctcca gcccattgaa ggcatcatgg    3060
gcagtgatta catcaatgcc aactacgtgg acggctaccg cgtcagaac gcgtacattg     3120 ccacgcaggg gccgctgcct gagacctttg gggacttctg gcgtatggtg tgggagcagc   3180
ggtcggcgac catcgtcatg atgacgcgg tggaggagaa gtcacggatc aagtgtgatc    3240
agtattggcc caacagaggc acggagacct acggcttcat ccaggtcacg ttgctagata   3300
ccatcgagct ggccacattc tgcgtcagga cattctctct gcacaagaat ggctccagtg    3360
agaaacgcga ggtccgccag ttccagttta cggcgtggcc ggaccatggc gtgcccgaat   3420
acccaacgcc cttcctggct ttcctgcgga gagtcaagac ctgcaacccg ccagatgccg    3480
gccccatcgt ggttcactgc agtgccgtg tgggccgcac aggctgcttt atcgtcatcg    3540
acgccatgct tgagcggatc aagccagaga agacagtcga tgtctatggc cacgtgacgc    3600
tcatgaggtc ccagcgcaac tacatggtgc agacggagga ccagtacagc ttcatccacg    3660
aggccctgct ggaggccgtg ggctgtggca acacagaagt gccccgcacgc agcctctatg   3720 cctacatcca gaagctggcc caggtggagc ctggcgaaca cgtcactggc atggaactcg    3780
agttcaagcg gctggctaac tccaaggccc acacgtcacg cttcatcagt gccaatctgc    3840
cttgtaacaa gttcaagaac cgcctggtga acatcatgcc ctatgagagc acgggtct     3900 gtctgcaacc catccggggt gtggagggct ctgactacat caacgccagc ttcattgatg    3960
gctacaggca gcagaaggcc tacatcgcga cacagggcc gctggcggag accacggaag    4020
acttctggcg catgctgtgg gagaacaatt cgacgatcgt ggtgatgctg accaagctgc    4080
gggagatggg ccgggagaag tgtcaccagt actggccggc cgagcgctct gcccgctacc    4140
agtactttgt ggtagatccg atggcagaat acaacatgcc tcagtatatc ctgcgagagt    4200
tcaaggtcac agatgcccgg gatggccagt cccggactgt ccggcagttc cagttcacag    4260
actggccgga acagggtgtg ccaaagtcgg gggagggctt catcgacttc attggccaag    4320
tgcataagac taaggagcag tttgccagg acggccccat ctctgtccac tgcagtgccg     4380
gcgtgggcag gacgggcgtc ttcatcacgc ttagcatcgt gctggagcgg atgcggtatg    4440
aaggcgtggt ggacatcttt cagacggtga agatgctacg aacccagcgg ccggccatgg    4500
tgcagacaga ggatgagtac cagttctgtt accaggcggc actggagtac ctcggaagct    4560
ttgaccacta tgcaacctaa agccatggtt cccccaggc ccgacaccac tggccccgga    4620
```

-continued tgcctctgcc cctcccgggc ggacctcctg aggcctggac cccca        4665

<210> SEQ ID NO 3
<211> LENGTH: 18
<212> TYPE: DNA
<213> ORGANISM: Artificial Sequence
<220> FEATURE:
<223> OTHER INFORMATION: Forward primer

<400> SEQUENCE: 3
cacggcctat gacctcca        18

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
aagttcttgg gcgagacttg        20

<210> SEQ ID NO 5
<211> LENGTH: 18
<212> TYPE: DNA
<213> ORGANISM: Artificial Sequence
<220> FEATURE:
<223> OTHER INFORMATION: Forward primer

<400> SEQUENCE: 5
ccacccatgg caaattcc        18

<210> SEQ ID NO 6
<211> LENGTH: 22
<212> TYPE: DNA
<213> ORGANISM: Artificial Sequence
<220> FEATURE:
<223> OTHER INFORMATION: Reverse primer

<400> SEQUENCE: 6
tgggatttcc attgatgaca ag        22

<210> SEQ ID NO 7
<211> LENGTH: 21
<212> TYPE: DNA
<213> ORGANISM: Artificial Sequence
<220> FEATURE:
<223> OTHER INFORMATION: Forward primer

<400> SEQUENCE: 7
actcacccac accctacaag a        21

<210> SEQ ID NO 8
<211> LENGTH: 18
<212> TYPE: DNA
<213> ORGANISM: Artificial Sequence
<220> FEATURE:
<223> OTHER INFORMATION: Reverse primer

<400> SEQUENCE: 8
cttggtggta cggccatc        18

<210> SEQ ID NO 9
<211> LENGTH: 39
<212> TYPE: DNA

```
<213> ORGANISM: Artificial Sequence
<220> FEATURE:
<223> OTHER INFORMATION: Forward primer

<400> SEQUENCE: 9
aaagaattcg ccgccaccat ggcgcccacc tggggccct                              39

<210> SEQ ID NO 10
<211> LENGTH: 34
<212> TYPE: DNA
<213> ORGANISM: Artificial Sequence
<220> FEATURE:
<223> OTHER INFORMATION: Reverse primer

<400> SEQUENCE: 10
aaagcggccg cttaggttgc atagtggtca aagc                                   34

<210> SEQ ID NO 11
<211> LENGTH: 24
<212> TYPE: DNA
<213> ORGANISM: Artificial Sequence
<220> FEATURE:
<223> OTHER INFORMATION: Antisense primer

<400> SEQUENCE: 11
tccagagttc caggtcactg tcac                                              24

<210> SEQ ID NO 12
<211> LENGTH: 36
<212> TYPE: DNA
<213> ORGANISM: Artificial Sequence
<220> FEATURE:
<223> OTHER INFORMATION: Anchor primer
<220> FEATURE:
<221> NAME/KEY: modified_base
<222> LOCATION: (24)..(25)
<223> OTHER INFORMATION: n is deoxyinosine.
<220> FEATURE:
<221> NAME/KEY: modified_base
<222> LOCATION: (29)..(30)
<223> OTHER INFORMATION: n is deoxyinosine.
<220> FEATURE:
<221> NAME/KEY: modified_base
<222> LOCATION: (34)..(35)
<223> OTHER INFORMATION: n is deoxyinosine.

<400> SEQUENCE: 12
ggccacgcgt cgactagtac gggnngggnn gggnng                                 36

<210> SEQ ID NO 13
<211> LENGTH: 24
<212> TYPE: DNA
<213> ORGANISM: Artificial Sequence
<220> FEATURE:
<223> OTHER INFORMATION: Antisense primer

<400> SEQUENCE: 13
aggggccagt ggatagacag atgg                                              24

<210> SEQ ID NO 14
<211> LENGTH: 20
<212> TYPE: DNA
<213> ORGANISM: Artificial Sequence
<220> FEATURE:
<223> OTHER INFORMATION: AUAP primer

<400> SEQUENCE: 14
ggccacgcgt cgactagtac                                                   20
```

<210> SEQ ID NO 15
<211> LENGTH: 24
<212> TYPE: DNA
<213> ORGANISM: Artificial Sequence
<220> FEATURE:
<223> OTHER INFORMATION: Antisense primer

<400> SEQUENCE: 15
ttcactgcca tcaatcttcc actt                                          24

<210> SEQ ID NO 16
<211> LENGTH: 21
<212> TYPE: DNA
<213> ORGANISM: Artificial Sequence
<220> FEATURE:
<223> OTHER INFORMATION: Antisense primer

<400> SEQUENCE: 16
gatggataca gttggtgcag c                                             21

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
accaagcttg ccgccaccat gaacttcggg ctcaggttg                          39

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
cttggtgcta gctgaggaga cggtgaccgt ggt                                33

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
accgtctcct cagctagcac caagggccca tcg                                33

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
tttgaattct catttacccg gagacaggga                                    30

<210> SEQ ID NO 21
<211> LENGTH: 39
<212> TYPE: DNA
<213> ORGANISM: Artificial Sequence
<220> FEATURE:

<223> OTHER INFORMATION: Primer

<400> SEQUENCE: 21
accaagcttg ccgccaccat ggagtcacag attcaggtc          39

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
agccacagtt cgttttattt ccagcttggt ccc          33

<210> SEQ ID NO 23
<211> LENGTH: 33
<212> TYPE: DNA
<213> ORGANISM: Artificial Sequence
<220> FEATURE:
<223> OTHER INFORMATION: Primer

<400> SEQUENCE: 23
ctggaaataa aacgaactgt ggctgcacca tct          33

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
aaagaattcc tagcactctc ccctgttgaa          30

<210> SEQ ID NO 25
<211> LENGTH: 469
<212> TYPE: DNA
<213> ORGANISM: Mus musculus

<400> SEQUENCE: 25
atgaacttcg ggctcaggtt gattttcctt gccctcattt taaaaggtgt ccagtgtgag      60
gtgcagctgg tggagtctgg gggagactta gtgaagcctg agggtccct gaaactctcc     120
tgtgcagcct ctggattcat tttcagtagc tatggcatgt cttgggttcg ccagactcca     180
gacaagaggc tggagtgggt cgcaaccatt agtagtggtg gtagtgacac ctattatcca     240
gacagtgtga agggggcgatt caccatctcc agagacaatg ccaacaacac cctgtacctg     300
caaatgagca gtctgaagtc tgaggacaca gccatgtatt actgtgcaag acaggtctac     360
tatggtcttt actggtattt cgatgtctgg ggcgcaggga ccacggtcac cgtctcctca     420
gccaaaacga caccccatc tgtctatcca ctggccccta agggcgaat                  469

<210> SEQ ID NO 26
<211> LENGTH: 156
<212> TYPE: PRT
<213> ORGANISM: Mus musculus

<400> SEQUENCE: 26

Met Asn Phe Gly Leu Arg Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Ile Phe
         35                  40                  45

Ser Ser Tyr Gly Met Ser Trp Val Arg Gln Thr Pro Asp Lys Arg Leu
     50                  55                  60

Glu Trp Val Ala Thr Ile Ser Ser Gly Gly Ser Asp Thr Tyr Tyr Pro
65                  70                  75                  80

Asp Ser Val Lys Gly Arg Phe Thr Ile Ser Arg Asp Asn Ala Asn Asn
             85                  90                  95

Thr Leu Tyr Leu Gln Met Ser Ser Leu Lys Ser Glu Asp Thr Ala Met
             100                 105                 110

Tyr Tyr Cys Ala Arg Gln Val Tyr Tyr Gly Leu Tyr Trp Tyr Phe Asp
             115                 120                 125

Val Trp Gly Ala Gly Thr Thr Val Thr Val Ser Ser Ala Lys Thr Thr
130                 135                 140

Pro Pro Ser Val Tyr Pro Leu Ala Pro Lys Gly Glu
145                 150                 155

<210> SEQ ID NO 27
<211> LENGTH: 5
<212> TYPE: PRT
<213> ORGANISM: Mus musculus

<400> SEQUENCE: 27

Ser Tyr Gly Met Ser
1               5

<210> SEQ ID NO 28
<211> LENGTH: 17
<212> TYPE: PRT
<213> ORGANISM: Mus musculus

<400> SEQUENCE: 28

Thr Ile Ser Ser Gly Gly Ser Asp Thr Tyr Tyr Pro Asp Ser Val Lys
1               5                   10                  15
Gly

<210> SEQ ID NO 29
<211> LENGTH: 12
<212> TYPE: PRT
<213> ORGANISM: Mus musculus

<400> SEQUENCE: 29

Gln Val Tyr Tyr Gly Leu Tyr Trp Tyr Phe Asp Val
1               5                   10

<210> SEQ ID NO 30
<211> LENGTH: 413
<212> TYPE: DNA
<213> ORGANISM: Mus musculus

<400> SEQUENCE: 30
atggagtcac agattcaggt ctttgtattc gtgtttctct ggttgtctgg tgttgacgga      60
gacattgtga tgacccagtc tcacaaattc atgtccacat cagtaggaga cagggtcagc     120
atcatttgta aggccagtca ggatgtgaat actgctgtag cctggtatca acagaaacca     180
ggacaatctc ctaaattact gatttactcg gcatcctacc ggtacactgg agtccctgat     240
cgcttcactg gcagtggatc tgggacggat ttcactttca ccatcagcag tgtgcaggct     300
gaagacctgg caattttatt ctgtcagcaa cattatagta ctccgtacac gttcggaggg     360

```
gggaccaagc tggaaataaa acgggctgat gctgcaccaa ctgtatccat caa          413
```

<210> SEQ ID NO 31
<211> LENGTH: 137
<212> TYPE: PRT
<213> ORGANISM: Mus musculus

<400> SEQUENCE: 31

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Ile Cys Lys Ala Ser Gln Asp
        35                  40                  45

Val Asn Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Ile Tyr Tyr Cys Gln Gln His Tyr
            100                 105                 110

Ser Thr Pro Tyr Thr Phe Gly Gly Gly Thr Lys Leu Glu Ile Lys Arg
        115                 120                 125

Ala Asp Ala Ala Pro Thr Val Ser Ile
    130                 135

<210> SEQ ID NO 32
<211> LENGTH: 11
<212> TYPE: PRT
<213> ORGANISM: Mus musculus

<400> SEQUENCE: 32

Lys Ala Ser Gln Asp Val Asn Thr Ala Val Ala
1               5                   10

<210> SEQ ID NO 33
<211> LENGTH: 7
<212> TYPE: PRT
<213> ORGANISM: Mus musculus

<400> SEQUENCE: 33

Ser Ala Ser Tyr Arg Tyr Thr
1               5

<210> SEQ ID NO 34
<211> LENGTH: 7
<212> TYPE: PRT
<213> ORGANISM: Mus musculus

<400> SEQUENCE: 34

Gln Gln His Tyr Ser Thr Pro
1               5

<210> SEQ ID NO 35
<211> LENGTH: 1413
<212> TYPE: DNA
<213> ORGANISM: Artificial Sequence
<220> FEATURE:
<223> OTHER INFORMATION: Anti PTPRS chimera 49F2-30 antibody heavy chain
      nucleic acid sequence

<400> SEQUENCE: 35

```
atgaacttcg ggctcaggtt gattttcctt gccctcattt taaaaggtgt ccagtgtgag      60
gtgcagctgg tggagtctgg gggagactta gtgaagcctg agggtccct gaaactctcc     120
tgtgcagcct ctggattcat tttcagtagc tatggcatgt cttgggttcg ccagactcca     180
gacaagaggc tggagtgggt cgcaaccatt agtagtggtg gtagtgacac ctattatcca     240
gacagtgtga aggggcgatt caccatctcc agagacaatg ccaacaacac cctgtacctg     300
caaatgagca gtctgaagtc tgaggacaca gccatgtatt actgtgcaag acaggtctac     360
tatggtcttt actggtattt cgatgtctgg ggcgcaggga ccacggtcac cgtctcctca     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctggggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc catcgagaa aaccatctcc    1080
aaagccaaag ggcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tga                                  1413
```

<210> SEQ ID NO 36
<211> LENGTH: 470
<212> TYPE: PRT
<213> ORGANISM: Artificial Sequence
<220> FEATURE:
<223> OTHER INFORMATION: Anti PTPRS chimera 49F2-30 antibody heavy chain amino acid sequence

<400> SEQUENCE: 36

```
Met Asn Phe Gly Leu Arg Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Ile Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Asp Thr Tyr Tyr Pro
65                  70                  75                  80

Asp Ser Val Lys Gly Arg Phe Thr Ile Ser Arg Asp Asn Ala Asn Asn
                85                  90                  95
```

Thr Leu Tyr Leu Gln Met Ser Ser Leu Lys Ser Glu Asp Thr Ala Met
            100                 105                 110

Tyr Tyr Cys Ala Arg Gln Val Tyr Gly Leu Tyr Trp Tyr Phe Asp
        115                 120                 125

Val Trp Gly Ala Gly Thr Thr Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 37
<211> LENGTH: 705
<212> TYPE: DNA
<213> ORGANISM: Artificial Sequence
<220> FEATURE:

<223> OTHER INFORMATION: Anti PTPRS chimera 49F2-30 antibody light chain
       nucleic acid sequence

<400> SEQUENCE: 37

| | | | | | |
|---|---|---|---|---|---|
| atggagtcac | agattcaggt | ctttgtattc | gtgtttctct | ggttgtctgg | tgttgacgga     60 |
| gacattgtga | tgacccagtc | tcacaaattc | atgtccacat | cagtaggaga | cagggtcagc    120 |
| atcatttgta | aggccagtca | ggatgtgaat | actgctgtag | cctggtatca | acagaaacca    180 |
| ggacaatctc | ctaaattact | gatttactcg | gcatcctacc | ggtacactgg | agtccctgat    240 |
| cgcttcactg | gcagtggatc | tgggacggat | ttcactttca | ccatcagcag | tgtgcaggct    300 |
| gaagacctgg | caatttatta | ctgtcagcaa | cattatagta | ctccgtacac | gttcggaggg    360 |
| gggaccaagc | tggaaataaa | acgaactgtg | gctgcaccat | ctgtcttcat | cttcccgcca    420 |
| tctgatgagc | agttgaaatc | tggaactgcc | tctgttgtgt | gcctgctgaa | taacttctat    480 |
| cccagagagg | ccaaagtaca | gtggaaggtg | gataacgccc | tccaatcggg | taactcccag    540 |
| gagagtgtca | cagagcagga | cagcaaggac | agcacctaca | gcctcagcag | caccctgacg    600 |
| ctgagcaaag | cagactacga | gaaacacaaa | gtctacgcct | gcgaagtcac | ccatcagggc    660 |
| ctgagctcgc | ccgtcacaaa | gagcttcaac | aggggagagt | gctag                    705 |

<210> SEQ ID NO 38
<211> LENGTH: 234
<212> TYPE: PRT
<213> ORGANISM: Artificial Sequence
<220> FEATURE:
<223> OTHER INFORMATION: Anti PTPRS chimera 49F2-30 antibody light chain
       amino acid sequence

<400> SEQUENCE: 38

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Ile Cys Lys Ala Ser Gln Asp
        35                  40                  45

Val Asn Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Ile Tyr Tyr Cys Gln Gln His Tyr
            100                 105                 110

Ser Thr Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 39
<211> LENGTH: 36
<212> TYPE: DNA
<213> ORGANISM: Artificial
<220> FEATURE:
<223> OTHER INFORMATION: primer

<400> SEQUENCE: 39
ccaggagagt gggagaggct cttctcagta tggtgg                36

<210> SEQ ID NO 40
<211> LENGTH: 32
<212> TYPE: DNA
<213> ORGANISM: Artificial
<220> FEATURE:
<223> OTHER INFORMATION: primer

<400> SEQUENCE: 40
ggctcaggga aatagccctt gaccaggcat cc                    32

<210> SEQ ID NO 41
<211> LENGTH: 24
<212> TYPE: DNA
<213> ORGANISM: Artificial
<220> FEATURE:
<223> OTHER INFORMATION: primer

<400> SEQUENCE: 41
tccagagttc caagtcacag tcac                             24

<210> SEQ ID NO 42
<211> LENGTH: 24
<212> TYPE: DNA
<213> ORGANISM: Artificial
<220> FEATURE:
<223> OTHER INFORMATION: primer

<400> SEQUENCE: 42
aggggccagt ggatagactg atgg                             24

<210> SEQ ID NO 43
<211> LENGTH: 471
<212> TYPE: DNA
<213> ORGANISM: Mus musculus

<400> SEQUENCE: 43
atggagttgg gactgagctg ggtatttctt gtggctcttt tgaatggtgt ccagtgtcag    60
gtgcagcttg tagagaccgg gggaggcttg tgaggcctg gaaattctct gaaactctcc   120
tgtgttacct cgggattcac tttcagtaac taccggatgc actggcttcg ccagcctcca   180
gggaagaggc tggagtggat tgctgtaatt acagtcaaat ctgataatta tggagcaaat   240
tatgcagagt ctgtgaaagg cagattcact atttcaagag atgattcaaa aagcagtgtc   300
tacctgcaga tgaacagatt aagagaggaa gacactgcca cttattattg tagtagatcg   360
gtctactatg gttacgtcct agcctttgac tactggggcc aaggcaccac tctcacagtc   420
tcctcagcca aaacgacacc cccatctgtc tatccactgg ccccctaaggg c           471

```
<210> SEQ ID NO 44
<211> LENGTH: 157
<212> TYPE: PRT
<213> ORGANISM: Mus musculus

<400> SEQUENCE: 44

Met Glu Leu Gly Leu Ser Trp Val Phe Leu Val Ala Leu Leu Asn Gly
1               5                   10                  15

Val Gln Cys Gln Val Gln Leu Val Glu Thr Gly Gly Gly Leu Val Arg
            20                  25                  30

Pro Gly Asn Ser Leu Lys Leu Ser Cys Val Thr Ser Gly Phe Thr Phe
        35                  40                  45

Ser Asn Tyr Arg Met His Trp Leu Arg Gln Pro Pro Gly Lys Arg Leu
    50                  55                  60

Glu Trp Ile Ala Val Ile Thr Val Lys Ser Asp Asn Tyr Gly Ala Asn
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Arg Leu Arg Glu Glu Asp Thr
            100                 105                 110

Ala Thr Tyr Tyr Cys Ser Arg Ser Val Tyr Tyr Gly Tyr Val Leu Ala
        115                 120                 125

Phe Asp Tyr Trp Gly Gln Gly Thr Thr Leu Thr Val Ser Ser Ala Lys
    130                 135                 140

Thr Thr Pro Pro Ser Val Tyr Pro Leu Ala Pro Lys Gly
145                 150                 155

<210> SEQ ID NO 45
<211> LENGTH: 5
<212> TYPE: PRT
<213> ORGANISM: Mus musculus

<400> SEQUENCE: 45

Asn Tyr Arg Met His
1               5

<210> SEQ ID NO 46
<211> LENGTH: 19
<212> TYPE: PRT
<213> ORGANISM: Mus musculus

<400> SEQUENCE: 46

Val Ile Thr Val Lys Ser Asp Asn Tyr Gly Ala Asn Tyr Ala Glu Ser
1               5                   10                  15

Val Lys Gly

<210> SEQ ID NO 47
<211> LENGTH: 12
<212> TYPE: PRT
<213> ORGANISM: Mus musculus

<400> SEQUENCE: 47

Ser Val Tyr Tyr Gly Tyr Val Leu Ala Phe Asp Tyr
1               5                   10

<210> SEQ ID NO 48
<211> LENGTH: 402
<212> TYPE: DNA
<213> ORGANISM: Mus musculus

<400> SEQUENCE: 48
```

```
atgatgtcct ctgctcagtt cctttggtctc ctgttgctct gttttcaagg taccagatgt      60
gatatccaga tgacacagac tacatcctcc ctgtctgcct ctctgggaga cagagtcacc     120
atcagttgca gggcaagtca ggacattagc aattatttaa actggtatca gcagaaacca     180
gatggaactg ttaaactcct gatctactac acatcaagat tacactcagg agtcccatca     240
aggttcagtg gcagtgggtc tggaacagat tattctctca ccattagcaa cctggagcaa     300
gaagatattg ccacttactt ttgccaacag ggtaatacgc ttccgtggac gttcggtgga     360
ggcaccaagc tggaaatcaa acgggctgat gctgcaccaa ct                        402
```

<210> SEQ ID NO 49
<211> LENGTH: 134
<212> TYPE: PRT
<213> ORGANISM: Mus musculus

<400> SEQUENCE: 49

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys Arg
        115                 120                 125

Ala Asp Ala Ala Pro Thr
    130

<210> SEQ ID NO 50
<211> LENGTH: 11
<212> TYPE: PRT
<213> ORGANISM: Mus musculus

<400> SEQUENCE: 50

Arg Ala Ser Gln Asp Ile Ser Asn Tyr Leu Asn
1               5                   10

<210> SEQ ID NO 51
<211> LENGTH: 7
<212> TYPE: PRT
<213> ORGANISM: Mus musculus

<400> SEQUENCE: 51

Tyr Thr Ser Arg Leu His Ser
1               5

<210> SEQ ID NO 52
<211> LENGTH: 7
<212> TYPE: PRT
<213> ORGANISM: Mus musculus

<400> SEQUENCE: 52

Gln Gln Gly Asn Thr Leu Pro
1               5

<210> SEQ ID NO 53
<211> LENGTH: 465
<212> TYPE: DNA
<213> ORGANISM: Mus musculus

<400> SEQUENCE: 53
atgaacttgg ggctcagctt gattttcctt gtccttgttt taaaaggtgt ccagtgtgaa      60
gtgaagctgg tggagtctgg gggaggctta gtgcagcctg agggtccct gaaactctcc     120 tgtgcaacct ctggattcac tttcagtgac tattacatgt attgggttcg ccagactcca     180
gagaagaggc tggagtgggt cgcatacatt agtaatggtg gtggtagcac ctattatcca     240
gacactgtaa agggccgatt caccatctcc agagacaatg ccaagaacac cctgtacctg     300
caaatgagcc gtctgaagtc tgaggacaca gccatgtatt actgtgcaag acatgtttac     360
tacgggagga actatgctat ggactactgg ggtcaaggaa cctcagtcac cgtctcctca     420
gccaaaacaa cacccccatc agtctatcca ctggccccta agggc                     465

<210> SEQ ID NO 54
<211> LENGTH: 155
<212> TYPE: PRT
<213> ORGANISM: Mus musculus

<400> SEQUENCE: 54

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Tyr Ile Ser Asn Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg His Val Tyr Tyr Gly Arg Asn Tyr Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Lys Gly
145                 150                 155

<210> SEQ ID NO 55
<211> LENGTH: 5
<212> TYPE: PRT
<213> ORGANISM: Mus musculus

<400> SEQUENCE: 55

Asp Tyr Tyr Met Tyr
1               5

<210> SEQ ID NO 56

```
<211> LENGTH: 17
<212> TYPE: PRT
<213> ORGANISM: Mus musculus

<400> SEQUENCE: 56

Tyr Ile Ser Asn Gly Gly Gly Ser Thr Tyr Tyr Pro Asp Thr Val Lys
1               5                   10                  15
Gly

<210> SEQ ID NO 57
<211> LENGTH: 12
<212> TYPE: PRT
<213> ORGANISM: Mus musculus

<400> SEQUENCE: 57

His Val Tyr Tyr Gly Arg Asn Tyr Ala Met Asp Tyr
1               5                   10

<210> SEQ ID NO 58
<211> LENGTH: 465
<212> TYPE: DNA
<213> ORGANISM: Mus musculus

<400> SEQUENCE: 58
atgaacttgg ggctcagctt gattttcctt gtccttgttt taaaaggtgt ccagtgtgaa      60
gtgaagctgg tggagtctgg gggaggctta gtgcagcctg agggtccct gaaactctcc     120
tgtgcaacct ctggattcac tttcagtgac tattacatgt attgggttcg ccagactcca     180
gagaagaggc tggagtgggt cgcatacatt agtaatggtg gtggtagcac ctattatcca     240
gacactgtaa agggccgatt caccatctcc agagacaatg ccaagaacac cctgtacctg     300
caaatgagcc gtctgaagtc tgaggacaca gccatgtatt actgtgcaag acatgtttac     360
tacgggagga actatgctat ggactactgg ggtcaaggaa cctcagtcac cgtctcctca     420
gccaaaacaa cacccccatc agtctatcca ctggccccta agggc                    465

<210> SEQ ID NO 59
<211> LENGTH: 155
<212> TYPE: PRT
<213> ORGANISM: Mus musculus

<400> SEQUENCE: 59

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
                100                 105                 110

Thr Leu Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
```

```
                130                 135                 140
Leu Thr Ser Gly Gly Ala Ser Val Val Cys Phe
145                 150                 155

<210> SEQ ID NO 60
<211> LENGTH: 11
<212> TYPE: PRT
<213> ORGANISM: Mus musculus

<400> SEQUENCE: 60

Arg Ala Ser Gln Asp Ile Ser Asn Tyr Leu Asn
1               5                   10

<210> SEQ ID NO 61
<211> LENGTH: 7
<212> TYPE: PRT
<213> ORGANISM: Mus musculus

<400> SEQUENCE: 61

Tyr Thr Ser Arg Leu His Ser
1               5

<210> SEQ ID NO 62
<211> LENGTH: 8
<212> TYPE: PRT
<213> ORGANISM: Mus musculus

<400> SEQUENCE: 62

Gln Gln Gly Asn Thr Leu Pro Tyr
1               5

<210> SEQ ID NO 63
<211> LENGTH: 458
<212> TYPE: DNA
<213> ORGANISM: Mus musculus

<400> SEQUENCE: 63
atggaatgta actggatact tcctttattt ctgtcagtaa cttcaggtgt ctactcacag      60
gttcagctcc agcagtctgg ggctgagctg gcaagacctg gggcttcagt gaagttgtcc    120
tgcaaggctt ctggctacac ctttactagc tactggatgc agtgggtaaa acagaggcct    180
ggacagggtc tggaatggat tgggctatt tatcctggag atggtgatac taggtacact    240
cagaagttca gggcaaggc acattgact gcagataaat cctccagcac agcctacatg    300
caactcagca gcttggcatc tgaggactct gcggtctatt actgtgcaag aaggatttac    360
tacggctatt actatgctat ggactactgg ggtcaaggaa cctcagtcac cgtctcctca    420
gccaaaacga cacccccatc tgtctatcca ctggcccc                            458

<210> SEQ ID NO 64
<211> LENGTH: 152
<212> TYPE: PRT
<213> ORGANISM: Mus musculus

<400> SEQUENCE: 64

Met Glu Cys Asn Trp Ile Leu Pro Phe Ile Leu Ser Val Thr Ser Gly
1               5                   10                  15

Val Tyr Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45
```

```
Thr Ser Tyr Trp Met Gln Trp Val Lys Gln Arg Pro Gly Gln Gly Leu
    50                  55                  60
Glu Trp Ile Gly Ala Ile Tyr Pro Gly Asp Gly Asp Thr Arg Tyr Thr
 65                  70                  75                  80
Gln Lys Phe Lys Gly Lys Ala Thr Leu Thr Ala Asp Lys Ser Ser Ser
                 85                  90                  95
Thr Ala Tyr Met Gln Leu Ser Ser Leu Ala Ser Glu Asp Ser Ala Val
            100                 105                 110
Tyr Tyr Cys Ala Arg Arg Ile Tyr Tyr Gly Tyr Tyr Tyr Ala Met Asp
            115                 120                 125
Tyr Trp Gly Gln Gly Thr Ser Val Thr Val Ser Ser Ala Lys Thr Thr
       130                 135                 140
Pro Pro Ser Val Tyr Pro Leu Ala
145                 150
```

<210> SEQ ID NO 65
<211> LENGTH: 5
<212> TYPE: PRT
<213> ORGANISM: Mus musculus

<400> SEQUENCE: 65

```
Ser Tyr Trp Met Gln
1               5
```

<210> SEQ ID NO 66
<211> LENGTH: 17
<212> TYPE: PRT
<213> ORGANISM: Mus musculus

<400> SEQUENCE: 66

```
Ala Ile Tyr Pro Gly Asp Gly Asp Thr Arg Tyr Thr Gln Lys Phe Lys
1               5                   10                  15
Gly
```

<210> SEQ ID NO 67
<211> LENGTH: 12
<212> TYPE: PRT
<213> ORGANISM: Mus musculus

<400> SEQUENCE: 67

```
Arg Ile Tyr Tyr Gly Tyr Tyr Tyr Ala Met Asp Tyr
1               5                   10
```

<210> SEQ ID NO 68
<211> LENGTH: 430
<212> TYPE: DNA
<213> ORGANISM: Mus musculus

<400> SEQUENCE: 68

```
atggagacag acacaatcct gctatgggtg ctgctgctct gggttccagg ctccactggt      60
gacattgtgc tgacccaatc tccagcttct ttggctgtgt ctctagggca gagggccacc     120
atctcctgca aggccagcca agtgttgat tatgatggtg atagttatat gaactggtac     180
caacagaaac caggacagcc acccaaactc ctcatctatg ctgcatccaa tctagaatct     240
gggatcccag ccaggtttag tggcagtggg tctgggacag acttcaccct caacatccat     300
cctgtggagg aggaggatgc tgcaacctat tactgtcagc aaagtaatga ggatcctctc     360
acgttcggtg ctgggaccaa gctggagctg aaacgggctg atgctgcacc aactgtatcc     420
atcaagggcg                                                            430
```

<210> SEQ ID NO 69
<211> LENGTH: 143
<212> TYPE: PRT
<213> ORGANISM: Mus musculus

<400> SEQUENCE: 69

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Asn Glu Asp Pro Leu Thr Phe Gly Ala Gly Thr Lys Leu
        115                 120                 125

Glu Leu Lys Arg Ala Asp Ala Ala Pro Thr Val Ser Ile Lys Gly
    130                 135                 140

<210> SEQ ID NO 70
<211> LENGTH: 15
<212> TYPE: PRT
<213> ORGANISM: Mus musculus

<400> SEQUENCE: 70

Lys Ala Ser Gln Ser Val Asp Tyr Asp Gly Asp Ser Tyr Met Asn
1               5                   10                  15

<210> SEQ ID NO 71
<211> LENGTH: 7
<212> TYPE: PRT
<213> ORGANISM: Mus musculus

<400> SEQUENCE: 71

Ala Ala Ser Asn Leu Glu Ser
1               5

<210> SEQ ID NO 72
<211> LENGTH: 8
<212> TYPE: PRT
<213> ORGANISM: Mus musculus

<400> SEQUENCE: 72

Gln Gln Ser Asn Glu Asp Pro Leu
1               5

<210> SEQ ID NO 73
<211> LENGTH: 39
<212> TYPE: DNA
<213> ORGANISM: Artificial
<220> FEATURE:
<223> OTHER INFORMATION: forward primer

<400> SEQUENCE: 73
tttaagcttg ccgccaccat ggagttggga ctgagctgg                              39

<210> SEQ ID NO 74
<211> LENGTH: 42
<212> TYPE: DNA
<213> ORGANISM: Artificial
<220> FEATURE:
<223> OTHER INFORMATION: reverse primer

<400> SEQUENCE: 74
cgatgggccc ttggtgctag ctgaggagac tgtgagagtg gt                          42

<210> SEQ ID NO 75
<211> LENGTH: 39
<212> TYPE: DNA
<213> ORGANISM: Artificial
<220> FEATURE:
<223> OTHER INFORMATION: forward primer

<400> SEQUENCE: 75
accaagcttg ccgccaccat gatgtcctct gctcagttc                              39

<210> SEQ ID NO 76
<211> LENGTH: 33
<212> TYPE: DNA
<213> ORGANISM: Artificial
<220> FEATURE:
<223> OTHER INFORMATION: reverse primer

<400> SEQUENCE: 76
agccacagtt cgtttgattt ccagcttggt gcc                                    33

<210> SEQ ID NO 77
<211> LENGTH: 33
<212> TYPE: DNA
<213> ORGANISM: Artificial
<220> FEATURE:
<223> OTHER INFORMATION: forward primer

<400> SEQUENCE: 77
ctggaaatca acgaactgt ggctgcacca tct                                     33

<210> SEQ ID NO 78
<211> LENGTH: 30
<212> TYPE: DNA
<213> ORGANISM: Artificial
<220> FEATURE:
<223> OTHER INFORMATION: reverse primer

<400> SEQUENCE: 78
aaagaattcc tagcactctc ccctgttgaa                                        30

<210> SEQ ID NO 79
<211> LENGTH: 39
<212> TYPE: DNA
<213> ORGANISM: Artificial
<220> FEATURE:
<223> OTHER INFORMATION: forward primer

<400> SEQUENCE: 79
tttaagcttg ccgccaccat gaacttgggg ctcagcttg                              39

<210> SEQ ID NO 80
<211> LENGTH: 42
<212> TYPE: DNA
<213> ORGANISM: Artificial

<220> FEATURE:
<223> OTHER INFORMATION: reverse primer

<400> SEQUENCE: 80
cgatgggccc ttggtgctag ctgaggagac ggtgactgag gt                42

<210> SEQ ID NO 81
<211> LENGTH: 39
<212> TYPE: DNA
<213> ORGANISM: Artificial
<220> FEATURE:
<223> OTHER INFORMATION: forward primer

<400> SEQUENCE: 81
accaagcttg ccgccaccat gatgtcctct gctcagttc                    39

<210> SEQ ID NO 82
<211> LENGTH: 33
<212> TYPE: DNA
<213> ORGANISM: Artificial
<220> FEATURE:
<223> OTHER INFORMATION: reverse primer

<400> SEQUENCE: 82
agccacagtt cgtttgattt ccagcttggt gcc                          33

<210> SEQ ID NO 83
<211> LENGTH: 33
<212> TYPE: DNA
<213> ORGANISM: Artificial
<220> FEATURE:
<223> OTHER INFORMATION: forward primer

<400> SEQUENCE: 83
ctggaaatca acgaactgt ggctgcacca tct                           33

<210> SEQ ID NO 84
<211> LENGTH: 30
<212> TYPE: DNA
<213> ORGANISM: Artificial
<220> FEATURE:
<223> OTHER INFORMATION: reverse primer

<400> SEQUENCE: 84
aaagaattcc tagcactctc ccctgttgaa                              30

<210> SEQ ID NO 85
<211> LENGTH: 39
<212> TYPE: DNA
<213> ORGANISM: Artificial
<220> FEATURE:
<223> OTHER INFORMATION: forward primer

<400> SEQUENCE: 85
tttaagcttg ccgccaccat ggaatgtaac tggatactt                    39

<210> SEQ ID NO 86
<211> LENGTH: 42
<212> TYPE: DNA
<213> ORGANISM: Artificial
<220> FEATURE:
<223> OTHER INFORMATION: reverse primer

<400> SEQUENCE: 86
cgatgggccc ttggtgctag ctgaggagac ggtgactgag gt                42

<210> SEQ ID NO 87
<211> LENGTH: 39
<212> TYPE: DNA
<213> ORGANISM: Artificial
<220> FEATURE:
<223> OTHER INFORMATION: forward primer

<400> SEQUENCE: 87
accaagcttg ccgccaccat ggagacagac acaatcctg                                39

<210> SEQ ID NO 88
<211> LENGTH: 33
<212> TYPE: DNA
<213> ORGANISM: Artificial
<220> FEATURE:
<223> OTHER INFORMATION: reverse primer

<400> SEQUENCE: 88
agccacagtt cgtttcagct ccagcttggt ccc                                      33

<210> SEQ ID NO 89
<211> LENGTH: 33
<212> TYPE: DNA
<213> ORGANISM: Artificial
<220> FEATURE:
<223> OTHER INFORMATION: forward primer

<400> SEQUENCE: 89
ctggagctga aacgaactgt ggctgcacca tct                                      33

<210> SEQ ID NO 90
<211> LENGTH: 30
<212> TYPE: DNA
<213> ORGANISM: Artificial
<220> FEATURE:
<223> OTHER INFORMATION: reverse primer

<400> SEQUENCE: 90
aaagaattcc tagcactctc ccctgttgaa                                          30

<210> SEQ ID NO 91
<211> LENGTH: 1419
<212> TYPE: DNA
<213> ORGANISM: Artificial
<220> FEATURE:
<223> OTHER INFORMATION: anti-PTPRS chimera 9H5-4 antibody heavy chain
      nucleic acid sequence

<400> SEQUENCE: 91
atggagttgg gactgagctg ggtatttctt gtggctcttt tgaatggtgt ccagtgtcag        60
gtgcagcttg tagagaccgg gggaggcttg gtgaggcctg gaaattctct gaaactctcc       120
tgtgttacct cgggattcac tttcagtaac taccggatgc actggcttcg ccagcctcca       180
gggaagaggc tggagtggat tgctgtaatt acagtcaaat ctgataatta tggagcaaat       240
tatgcagagt ctgtgaaagg cagattcact atttcaagag atgattcaaa aagcagtgtc       300
tacctgcaga tgaacagatt aagagaggaa gacactgcca cttattattg tagtagatcg       360
gtctactatg gttacgtcct agcctttgac tactggggcc aaggcaccac tctcacagtc       420
tcctcagcta gcaccaaggg cccatcggtc ttccccctgg cacctcctc caagagcacc        480 tctgggggca gcggccct gggctgcctg tcaaggact acttccccga accggtgacg          540
gtgtcgtgga actcaggcgc cctgaccagc ggcgtgcaca ccttcccggc tgtcctacag       600

```
tcctcaggac tctactccct cagcagcgtg gtgaccgtgc cctccagcag cttgggcacc      660
cagacctaca tctgcaacgt gaatcacaag cccagcaaca ccaaggtgga caagaaagtt      720
gagcccaaat cttgtgacaa aactcacaca tgcccaccgt gcccagcacc tgaactcctg      780
gggggaccgt cagtcttcct cttccccccca aaacccaagg acaccctcat gatctcccgg     840
acccctgagg tcacatgcgt ggtggtggac gtgagccacg aagaccctga ggtcaagttc      900
aactggtacg tggacggcgt ggaggtgcat aatgccaaga caaagccgcg ggaggagcag      960
tacaacagca cgtaccgtgt ggtcagcgtc ctcaccgtcc tgcaccagga ctggctgaat     1020
ggcaaggagt acaagtgcaa ggtctccaac aaagccctcc cagcccccat cgagaaaacc     1080
atctccaaag ccaaagggca gccccgagaa ccacaggtgt acaccctgcc cccatcccgg     1140
gatgagctga ccaagaacca ggtcagcctg acctgcctgg tcaaaggctt ctatcccagc     1200
gacatcgccg tggagtggga gagcaatggg cagccggaga caactacaa gaccacgcct      1260 cccgtgctgg actccgacgg ctccttcttc ctctacagca agctcaccgt ggacaagagc     1320
aggtggcagc aggggaacgt cttctcatgc tccgtgatgc atgaggctct gcacaaccac     1380
tacacgcaga agagcctctc cctgtctccg ggtaaatga                            1419
```

<210> SEQ ID NO 92
<211> LENGTH: 472
<212> TYPE: PRT
<213> ORGANISM: Artificial
<220> FEATURE:
<223> OTHER INFORMATION: anti-PTPRS chimera 9H5-4 antibody heavy chain
      amino acid sequence

<400> SEQUENCE: 92

```
Met Glu Leu Gly Leu Ser Trp Val Phe Leu Val Ala Leu Leu Asn Gly
1               5                   10                  15

Val Gln Cys Gln Val Gln Leu Val Glu Thr Gly Gly Gly Leu Val Arg
            20                  25                  30

Pro Gly Asn Ser Leu Lys Leu Ser Cys Val Thr Ser Gly Phe Thr Phe
        35                  40                  45

Ser Asn Tyr Arg Met His Trp Leu Arg Gln Pro Gly Lys Arg Leu
    50                  55                  60

Glu Trp Ile Ala Val Ile Thr Val Lys Ser Asp Asn Tyr Gly Ala Asn
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Arg Leu Arg Glu Glu Asp Thr
            100                 105                 110

Ala Thr Tyr Tyr Cys Ser Arg Ser Val Tyr Tyr Gly Tyr Val Leu Ala
        115                 120                 125

Phe Asp Tyr Trp Gly Gln Gly Thr Thr Leu Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
```

```
                210                 215                 220
Cys Asn Val Asn His Lys Pro Ser Asn Thr Lys Val Asp Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
                290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys
465                 470

<210> SEQ ID NO 93
<211> LENGTH: 705
<212> TYPE: DNA
<213> ORGANISM: Artificial
<220> FEATURE:
<223> OTHER INFORMATION: anti-PTPRS chimera 9H5-4 antibody light chain
      nucleic acid sequence

<400> SEQUENCE: 93
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca ggcaagtca ggacattagc aattatttaa actggtatca gcagaaacca     180
gatggaactg ttaaactcct gatctactac acatcaagat tacactcagg agtcccatca     240
aggttcagtg gcagtgggtc tggaacagat tattctctca ccattagcaa cctggagcaa     300
gaagatattg ccacttactt tgccaacag ggtaatacgc ttccgtggac gttcggtgga     360
ggcaccaagc tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
```

```
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gctag                    705
```

<210> SEQ ID NO 94
<211> LENGTH: 234
<212> TYPE: PRT
<213> ORGANISM: Artificial
<220> FEATURE:
<223> OTHER INFORMATION: anti-PTPRS chimera 9H5-4 antibody light chain
      amino acid sequence

<400> SEQUENCE: 94

```
Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 95
<211> LENGTH: 1413
<212> TYPE: DNA
<213> ORGANISM: Artificial
<220> FEATURE:
<223> OTHER INFORMATION: anti-PTPRS chimera 13G5-57 antibody heavy chain
      nucleic acid sequence

<400> SEQUENCE: 95

```
atgaacttgg ggctcagctt gattttcctt gtccttgttt taaaaggtgt ccagtgtgaa    60
gtgaagctgg tggagtctgg gggaggctta gtgcagcctg agggtccct gaaactctcc    120 tgtgcaacct ctggattcac tttcagtgac tattacatgt attgggttcg ccagactcca    180
```

```
gagaagaggc tggagtgggt cgcatacatt agtaatggtg gtggtagcac ctattatcca    240
gacactgtaa agggccgatt caccatctcc agagacaatg ccaagaacac cctgtacctg    300
caaatgagcc gtctgaagtc tgaggacaca gccatgtatt actgtgcaag acatgtttac    360
tacgggagga actatgctat ggactactgg ggtcaaggaa cctcagtcac cgtctcctca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                 1413
```

<210> SEQ ID NO 96
<211> LENGTH: 470
<212> TYPE: PRT
<213> ORGANISM: Artificial
<220> FEATURE:
<223> OTHER INFORMATION: anti-PTPRS chimera 13G5-57 antibody heavy chain amino acid sequence

<400> SEQUENCE: 96

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Tyr Ile Ser Asn Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg His Val Tyr Tyr Gly Arg Asn Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 97
<211> LENGTH: 705
<212> TYPE: DNA
<213> ORGANISM: Artificial
<220> FEATURE:
<223> OTHER INFORMATION: anti-PTPRS chimera 13G5-57 antibody light chain
      nucleic acid sequence

<400> SEQUENCE: 97
atgatgtcct ctgctcagtt ccttggtctc ctgttgctct gttttcaagg taccagatgt      60
gatatccaga tgacacagac tacatcctcc ctgtctgcct ctctgggaga cagagtcacc     120

```
atcagttgca gggcaagtca ggacattagc aattatttaa actggtatca gcagaaacca    180
gatggaactg ttaaactcct gatctactac acatcaagat tacactcagg agtcccatca    240
aggttcagtg gcagtgggtc tggaacagat tattctctca ccattagcaa cctggagcaa    300
gaagatattg ccacttactt ttgccaacag ggtaatacgc ttccgtacac gttcggaggg    360
gggaccaagc tggaaataaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gctag                   705
```

<210> SEQ ID NO 98
<211> LENGTH: 234
<212> TYPE: PRT
<213> ORGANISM: Artificial
<220> FEATURE:
<223> OTHER INFORMATION: anti-PTPRS chimera 13G5-57 antibody light chain
      amino acid sequence

<400> SEQUENCE: 98

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 99
<211> LENGTH: 1413

<212> TYPE: DNA
<213> ORGANISM: Artificial
<220> FEATURE:
<223> OTHER INFORMATION: anti-PTPRS chimera 22H8-84 antibody heavy chain
      nucleic acid sequence

<400> SEQUENCE: 99

```
atggaatgta actggatact ccttttatt  ctgtcagtaa cttcaggtgt ctactcacag     60
gttcagctcc agcagtctgg ggctgagctg gcaagacctg gggcttcagt gaagttgtcc    120
tgcaaggctt ctggctacac ctttactagc tactggatgc agtgggtaaa acagaggcct    180
ggacagggtc tggaatggat tggggctatt tatcctggag atggtgatac taggtacact    240
cagaagttca agggcaaggc cacattgact gcagataaat cctccagcac agcctacatg    300
caactcagca gcttggcatc tgaggactct gcggtctatt actgtgcaag aaggatttac    360
tacggctatt actatgctat ggactactgg ggtcaaggaa cctcagtcac cgtctcctca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctggggga   780
ccgtcagtct tcctcttccc cccaaaaccc aaggacaccc tcatgatctc ccggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag gcagccccg agaaccacag gtgtacaccc tgcccccatc ccgggatgag  1140
ctgaccaaga accaggtcag cctgacctgc ctggtcaaag gcttctatcc cagcgacatc  1200
gccgtggagt gggagagcaa tgggcagccg gagaacaact acaagaccac gcctcccgtg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa tga                                1413
```

<210> SEQ ID NO 100
<211> LENGTH: 470
<212> TYPE: PRT
<213> ORGANISM: Artificial
<220> FEATURE:
<223> OTHER INFORMATION: anti-PTPRS chimera 22H8-84 antibody heavy chain
      amino acid sequence

<400> SEQUENCE: 100

```
Met Glu Cys Asn Trp Ile Leu Pro Phe Ile Leu Ser Val Thr Ser Gly
 1               5                   10                  15

Val Tyr Ser Gln Val Gln Leu Gln Gln Ser Gly Ala Glu Leu Ala Arg
             20                  25                  30

Pro Gly Ala Ser Val Lys Leu Ser Cys Lys Ala Ser Gly Tyr Thr Phe
         35                  40                  45

Thr Ser Tyr Trp Met Gln Trp Val Lys Gln Arg Pro Gly Gln Gly Leu
     50                  55                  60
```

```
Glu Trp Ile Gly Ala Ile Tyr Pro Gly Asp Gly Asp Thr Arg Tyr Thr
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Ala Ser Glu Asp Ser Ala Val
            100                 105                 110

Tyr Tyr Cys Ala Arg Arg Ile Tyr Tyr Gly Tyr Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470
```

-continued

```
<210> SEQ ID NO 101
<211> LENGTH: 717
<212> TYPE: DNA
<213> ORGANISM: Artificial
<220> FEATURE:
<223> OTHER INFORMATION: anti-PTPRS chimera 22H8-84 antibody light chain
      nucleic acid sequence

<400> SEQUENCE: 101
atggagacag acacaatcct gctatgggtg ctgctgctct gggttccagg ctccactggt     60
gacattgtgc tgacccaatc tccagcttct ttggctgtgt ctctagggca gagggccacc    120
atctcctgca aggccagcca agtgttgat tatgatggtg atagttatat gaactggtac     180
caacagaaac caggacagcc acccaaactc ctcatctatg ctgcatccaa tctagaatct    240
gggatcccag ccaggtttag tggcagtggg tctgggacag acttcaccct caacatccat    300
cctgtggagg aggaggatgc tgcaacctat tactgtcagc aaagtaatga ggatcctctc    360
acgttcggtg ctgggaccaa gctggagctg aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca caggggagag tgctag        717

<210> SEQ ID NO 102
<211> LENGTH: 238
<212> TYPE: PRT
<213> ORGANISM: Artificial
<220> FEATURE:
<223> OTHER INFORMATION: anti-PTPRS chimera 22H8-84 antibody light chain
      amino acid sequence

<400> SEQUENCE: 102

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Leu Thr Phe Gly Ala Gly Thr Lys Leu
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
```

-continued

```
            180                 185                 190
Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

POLYNUCLEOTIDES ENCODING ANTI-HUMAN RECEPTOR-TYPE PROTEIN TYROSINE PHOSPHATASE SIGMA ANTIBODIES

TECHNICAL FIELD

The present invention relates to an antibody that binds to human receptor-type protein tyrosine phosphatase σ. Hereinafter "protein tyrosine phosphatase" is abbreviated as PTP, "receptor-type protein tyrosine phosphatase" is abbreviated as RPTP or PTPR, "receptor-type protein tyrosine phosphatase σ" is sometimes abbreviates as RPTP-σ, PTP-σ or PTPRS, and "human" and "mouse" are sometimes represented by the prefixes h and m, respectively.

BACKGROUND ART

Interferons (hereinafter "interferon" is sometimes abbreviated as IFN) are the most important cytokines in antiviral immune response. An interferon-producing cell (IPC: IPC is an undifferentiated lymphocytic dendritic cell that is positioned as a precursor cell of a dendritic cell (DC). IPC is also sometimes called a plasmacytoid dendritic cell or a plasma cell-like dendritic cell (plasmacytoid dendritic cell: pDC). Hereinafter IPC and pDC are considered to have the same meaning herein, and are hereinafter standardized by the term pDC as a general rule.) in human blood expresses a major histocompatibility complex Class II protein together with CD4. However, since the number of such cells is small and the cells rapidly cause apoptosis and lack a lineage marker, those cells have not been isolated or characterized in detail until now. It was proved that pDC is a CD4+CD11c-2-type dendritic cell precursor cell, and that it produces IFN by 200 to 1,000 times greater than that produced by other blood cells after stimulation by a microorganism. Therefore, pDC2 is a decisive immune system effector cell in antiviral and antitumor immune responses.

IFNα and IFNβ are known as Type I IFNs having an antiviral activity or antitumor activity. On the other hand, it was clarified that IFNα relates to autoimmune diseases. For example, abnormal production of IFNα was reported in patients suffering from the following autoimmune diseases. Furthermore, possibility of alleviation of an autoimmune condition by neutralizing IFNα was suggested.

Systemic erythematosus (Shiozawa et al., Arthr. & Rheum. 35, 412, 1992) and chronic rheumatoid arthritis (Hopkins et al., Clin. Exp. Immunol 73, 88, 1988), and furthermore, examples in which a condition of an autoimmune disease was expressed or deteriorated by administering recombinant IFNα2 or IFNβ were reported (Wada et al., Am. J. Gastroenterol. 90, 136, 1995; Perez et al., Am. J. Hematol. 49, 365, 1995; Wilson L E et al., Semin Arthritis, Rheum. 32, 163-173, 2002).

Furthermore, it was also clarified that IFNα induces the differentiation of a dendritic cell (DC). Since a dendritic cell is also an antigen presenting cell, it is considered that the induction of differentiation of a dendritic cell constitutes an important mechanism in autoimmune diseases. In fact, it was suggested that the induction of differentiation of a dendritic cell of IFNα is intimately related to the onset of systemic erythematosus (Blanco et al., Science, 16: 294, 1540-1543, 2001). Therefore, the antitumor activity and intimate relation with autoimmune diseases of IFNα have been pointed out. Furthermore, IFNα also intimately relates to the onset of psoriasis (Nestle F O et al., J. Exp. Med. 202, 135-143, 2005).

Only a small amount of pDC is present in blood. It is considered that the ratio of pDC in peripheral blood lymphocyte is 1% or less. However, pDC has an extremely high ability of producing IFN. The ability of pDC to produce IFN reaches, for example, 3,000 pg/mL/$10^4$ cells. Namely, it can be considered that, although the number of cells is small, the major part of IFNα or IFNβ in blood is produced while viral infection is brought by pDC.

pDC differentiates into a dendritic cell by viral stimulation to induce the production of IFN-γ and IL-10 by a T cell. Furthermore, pDC also differentiates into a dendritic cell by the stimulation of IL-3. The dendritic cell differentiated by the stimulation of IL-3 induces the production of Th2 cytokines (IL-4, IL-5, IL-10) by a T cell. Thus, pDC has a characteristic that it differentiates into different dendritic cells depending on the difference of stimulation.

Therefore, pDC is a cell having two aspects: one is an aspect as an IFN-producing cell and other is an aspect as a precursor cell for a dendritic cell. Both cells play important roles in an immune system. Namely, pDC is one of important cells that support an immune system from various aspects.

For the control of the activity of a humoral factor such as IFN, administration of an antibody that recognizes the factor is effective. For example, an attempt to treat an autoimmune disease by an antibody against interleukin (IL)-1 or IL-4 was put to practical use (Guler et al., Arthritis Rheum, 44, S307, 2001). Furthermore, it is considered that a neutralized antibody may become a therapeutic drug for autoimmune diseases also in interferons (IFNs) (Stewart, T A. Cytokine Growth Factor Rev. 14; 139-154, 2003). It can be expected that a similar approach would be effective for IFNs produced by pDC. However, such approach is based on the inhibition of the action of the produced humoral factor. If the production of an objective humoral factor can be controlled directly, a more essential therapeutic effect can be achieved.

An antibody that recognizes human pDC was reported. For example, an anti-BDCA-2 monoclonal antibody is a monoclonal antibody that is specific to human pDC (Dzionek A. et al., J. Immunol 165: 6037-6046, 2000). It was clarified that the anti-BDCA-2 monoclonal antibody has an action of suppressing the IFN production of human pDC (J. Exp. Med. 194: 1823-1834, 2001). Furthermore, it was also reported that a monoclonal antibody that recognizes a mouse interferon-producing cell suppresses the production of interferons (Blood 2004 Jun. 1; 103/11: 4201-4206. Epub 2003 December). It was reported that a monoclonal antibody against mouse pDC decreased the number of dendritic cells (J. Immunol. 2003, 171: 6466-6477).

It is useful if an antibody that similarly recognizes human pDC and may control the activity thereof is provided. For example, the present inventors have already clarified that an antibody that recognizes Ly49Q specifically binds to mouse pDC. However, an antibody against Ly49Q did not interfere the activity of mouse pDC (Blood, 1 Apr. 2005, vol. 105, No. 7, pp. 2787-2792: WO2004/13325A1).

Protein phosphatases are dephosphorylated enzymes that were found in the studies of glycogen metabolism. Besides protein tyrosine phosphatase (PTP), protein serine/threonine phosphatase, phospholipid-specific phosphatase and the like have been found, and these form a superfamily of protein phosphatases. Of these, protein tyrosine phosphatase is an enzyme that is responsible for phosphorylation among reversible phosphorylation modifications that are observed in tyrosine residues of proteins. On the other hand, protein tyrosine kinase (PTK) is exemplified as an enzyme that is responsible for phosphorylation among reversible phosphorylation modifications that are observed in tyrosine residues of proteins.

Protein tyrosine phosphatase (PTP) converts the binding information of a ligand in an extracellular domain thereof to the phosphatase activity of an intracellular domain, and it is considered that protein tyrosine kinase (PTK) is activated by the binding of a ligand, whereas protein tyrosine phosphatase (PTP) is generally inactivated by the binding of a ligand. Therefore, in both of protein tyrosine phosphatase (PTP) and protein tyrosine kinase (PTK), stimulation of a ligand leads to increase in the phosphorylation level, whereas a great difference is expected in the signal properties. In the case of protein tyrosine kinase (PTK), positive feedback control in which receptors are phosphorylated with each other and activated is conducted, and the topical activation of the protein tyrosine kinase (PTK) molecules transmits to other protein tyrosine kinase (PTK) molecules on a cell membrane, thereby phosphorylation is increased over a wide range. On the other hand, only molecules to which ligands have bound are inactivated in protein tyrosine phosphatase (PTP), and the phosphorylation of the substrate is increased only topically. Protein tyrosine phosphatase (PTP) that is involved in many physiological functions and cellular functions gets a lot of attention in broad areas of brain neurobiochemistry, immunology, cancers, diabetes mellitus and the like (copy of the home page of the Division of Molecular Neurobiology, National Institute for Basic Biology, http://niwww3.nibb.acjp/RPTP.pdf).

The protein tyrosine phosphatase family can be classified into a receptor type having a cell membrane penetrating region and a non-receptor type. There are 21 molecules of receptor type protein tyrosine phosphatases (also abbreviated as RPTP or PTPR) in mammals, which are classified into eight subfamilies and each subfamily has an inherent extracellular structure in which a immunoglobulin-like domain, a fibronectin type III-like domain, a carbonate dehydratase-like domain, an MAM domain and the like are observed (Nat Rev Mol Cell Biol., Vol. 7, 833-846, 2006).

Human receptor-type protein tyrosine phosphatase σ (this is abbreviated as hRPTP-σ, hPTP-σ or hPTPRS, and the abbreviation hPTPRS that is mainly used herein) belongs to a R2A subfamily together with LAR (leukocyte antigen-related protein tyrosine phosphatase) and receptor-type protein tyrosine phosphatase δ (PTP-δ). Enzymes of the PTPR family are expressed in various tissues including nerve systems from initiation of generation to after maturation of animals, but few physiological functions thereof have been clarified since identification of ligand molecules and substrate molecules is not easy.

Dendritic cells (DCs) are major antigen presenting cells in a living body, which are present in blood, lymphoid tissues and the like and are roughly classified into myeloid dendritic cell (mDCs) and plasmacytoid dendritic cells (pDCs). pDC selectively expresses TLR7 and TLR9 as Toll-like receptors on the cell surfaces thereof, and produce Type I interferons α and β, specifically interferon α.

The recent studies have clarified various ligand molecules that act on dendritic cells to control their maturation and activation, and the intracellular signal transmission mechanisms from the receptors thereof have been becoming clear. However, there are many unclear points about the mechanisms of modification and control of the functions of dendritic cells. Similarly to the clarification in many other cells, it is considered that the phosphorylation of proteins plays an important role also in dendritic cells for the control of signal transmission from receptors, of motion/migration of cells, and the like.

Protein phosphatases that are negative controlling factors for protein phosphorylation are dominant candidates as factors for maintaining suitable intensities and lengths of signals to modulate the activation and functions of dendritic cells. (Nobuhiro Tanuma (Institute for Genetic Medicine, Hokkaido University), "Functional Analysis Of Tyrosine Phosphatase Induced in Maturing of Dendritic Cells" in the homepage of the Northern Advancement Center for Science & Technology (abbreviation: NOASTEC), http://www.noastec.jp/kinouindex/data2005/pdf/01/01_20.pdf)

International Publication No. WO95/9656A1 discloses RPTP-σ (PTPRS) and a nucleic acid coding therefor; however, the disclosed amino acid sequence is one derived from a rat, and the publication does not mention about an antibody specific to PTPRS. International Publication No. WO95/9656A1 also fails to disclose about an anti-human PTPRS antibody.

International Publication No. WO2007/41317A1 relates to an isolated antibody that specifically binds to at least RPTP-σ or RPTP-δ to suppress the immune response of an immune cell, or an antigen binding fragment thereof. The document describes that the binding of poxvirus polypeptide A41L and RPTP is competitively inhibited by using an antibody that specifically binds to RPTP, thereby suppression of the immune response of an immune cell is achieved. However, this document fails to disclose that the antibody that specifically binds to RPTP-σ (PTPRS) was actually obtained, and as far as the description of the Examples is called into account, the Examples merely confirmed that RPTP expressed in an immune cell that binds to A41L is a part of RPTP-σ, RPTP-δ and LAR that belong to the same subtype R2A and prepared a fusion protein of the immunoglobulin-like domain of LAR and Fc (LAR (Ig domain)-Fc fusion protein). It is hardly to say that International Publication No. WO2007/41317A1 discloses an antibody specific to only RPTP-σ and the preparation therefor.

An antibody that binds to only RPTP-σ, i.e., the specific site of PTPRS in the present application and an antibody that may specifically bind to RPTP-σ (PTPRS) but not to RPTP-δ and LAR that belong to the same subtype R2A have not been obtained yet. Human PTPRS is a molecule whose specific expression in pDC is observed, but any antibody against human PTPRS has not been obtained up until now.

CITATION LIST

Patent Literature

PTL 1: WO2004/13325A1
PTL 2: WO95/9656A1
PTL 3: WO2007/41317A1

Non Patent Literature

NPL 1: Shiozawa et al., Arthr. & Rheum. 35, 412, 1992
NPL 2: Hopkins et al., Clin. Exp. Immunol. 73, 88, 1988
NPL 3: Wada et al., Am. J. Gastroenterol. 90, 136, 1995
NPL 4: Perez et al., Am. J. Hematol. 49, 365, 1995
NPL 5: Wilson L E et al, Semin Arthritis. Rheum. 32, 163-173, 2002
NPL 6: Blanco et al., Science, 16:294, 1540-1543, 2001
NPL 7: Nestle F O et al., J. Exp. Med. 202, 135-143, 2005
NPL 8: Guler et al., Arthritis Rheum., 44. S307, 2001

NPL 9: Stewart, T A. Cytokine Growth Factor Rev. 14; 139-154, 2003
NPL 10: Dzionek, A. et al. J. Immunol. 165: 6037-6046, 2000
NPL 11: J. Exp. Med. 194:1823-1834, 2001
NPL 12: Blood 2004 Jun. 1; 103/11:4201-4206. Epub 2003 December
NPL 13: J. Immunol. 2003, 171:6466-6477
NPL 14: Blood, 1 Apr. 2005, Vol. 105, No. 7, pp. 2787-2792
NPL 15: http://niwww3.nibb.ac.jp/RPTP.pdf
NPL 16: Nat Rev Mol Cell Biol., Vol. 7, 833-846, 2006
NPL 17: http://www.noastec.jp/kinouindex/data2005/pdf/01/01_20.pdf

SUMMARY OF INVENTION

Technical Problem

The object of the present invention is to provide an antibody that binds to human receptor-type protein tyrosine phosphatase σ (human PTPRS, hRPTP-σ), and to detect, identify or isolate pDC. Furthermore, the object of the present invention is to modulate the activity of pDC.

The present inventors confirmed through the studies relating to human pDC that the expression of PTPRS in pDC is specifically enhanced. Therefore, the present inventors tried to prepare an antibody of PTPRS and clarify the action thereof.

In order to obtain an antibody that recognizes a trace amount of a protein derived from a living body, a protein prepared by a gene recombination technology is generally utilized as an immunogen. The present inventors have tried to express human PTPRS based on the base sequence of cDNA of human PTPRS, which has been already clarified, and the information on the amino acid sequence coded thereby (GenBank Accession No. NM_002856.3).

In order to obtain an antibody of a protein, utilization of a partial amino acid sequence of a natural protein as an immunogen is often tried. However, in order for an antibody to recognize a molecule on a cellular surface, a region that constitutes a part that is recognized by an antibody as an epitope on a cellular surface should be selected. Therefore, it was considered that obtainment of an antibody that is specific to human PTPRS by using a fragment amino acid sequence as an immunogen is distant.

Solution to Problem

Under such situation, the present inventors have clarified that an antibody that binds to pDC can be obtained by utilizing a special immunogen. Furthermore, they have also confirmed that the thus-obtained antibody specifically recognizes human pDC and has an action to modulate the activity thereof, and completed the present invention.

Therefore, the present invention relates to the following anti-human PTPRS antibody, the method for the production of the same, and the applications thereof.

The present invention is as follows.

(1) A monoclonal antibody that binds to an extracellular domain of human receptor-type protein tyrosine phosphatase σ (human PTPRS), or a fragment including an antigen-binding region thereof.

(2) The monoclonal antibody or a fragment including an antigen-binding region thereof according to the above-mentioned (1), which binds to a plasmacytoid dendritic cell.

(3) A monoclonal antibody produced by hybridoma 9H5-4 that was deposited as Accession No. FERM ABP-11356, hybridoma 10F7-38 that was deposited as Accession No. FERM ABP-11357, hybridoma 13G5-52 that was deposited as Accession No. FERM ABP-11358, hybridoma 13G5-57 that was deposited as Accession No. FERM ABP-11359, hybridoma 14A8-85 that was deposited as Accession No. FERM ABP-11360, hybridoma 22H8-84 that was deposited as Accession No. FERM ABP-11361, hybridoma 49F2-30 that was deposited as Accession No. FERM ABP-11362 or hybridoma 55E7-79 that was deposited as Accession No. FERM ABP-11363, or a fragment including an antigen-binding region thereof.

(4) A hybridoma that produces any of the monoclonal antibody according to the above-mentioned (1) or (2).

(5) A monoclonal antibody produced by hybridoma 9H5-4 that was deposited as Accession No. FERM ABP-11356, hybridoma 10F7-38 that was deposited as Accession No. FERM ABP-11357, hybridoma 13G5-52 that was deposited as Accession No. FERM ABP-11358, hybridoma 13G5-57 that was deposited as Accession No. FERM ABP-11359, hybridoma 14A8-85 that was deposited as Accession No. FERM ABP-11360, hybridoma 22H8-84 that was deposited as Accession No. FERM ABP-11361, hybridoma 49F2-30 that was deposited as Accession No. FERM ABP-11362 or hybridoma 55E7-79 that was deposited as Accession No. FERM ABP-11363, or a fragment including an antigen-binding region thereof.

(6) A method for the production of a monoclonal antibody, which includes culturing the hybridoma according to the above-mentioned (5), and collecting a monoclonal antibody from the culture.

(7) A method for the production of a cell that produces a monoclonal antibody that binds to human PTPRS, which includes:
1) administering a cell that expresses an exogenous protein including an extracellular domain of human PTPRS to an animal to be immunized, and
2) selecting an antibody-producing cell that produces an antibody that binds to human PTPRS from the antibody-producing cell of the immunized animal.

(8) The method according to the above-mentioned (7), wherein the cell that expresses human PTPRS is a cell that expressibly retains an exogenous polynucleotide that codes for an amino acid sequence including an extracellular domain of human PTPRS.

(9) The method according to the above-mentioned (8), wherein the cell is an animal cell.

(10) The method according to the above-mentioned (9), wherein the cell is a human-derived cell.

(11) The method according to the above-mentioned (10), wherein the human-derived cell is an HEK-293T cell.

(12) The method according to any one of the above-mentioned (7) to (11), which additionally includes cloning the obtained antibody-producing cell.

(13) A method for the production of a monoclonal antibody that binds to an extracellular domain of human PTPRS, which includes culturing an antibody-producing cell obtained by the method according to the above-mentioned (9), and collecting a monoclonal antibody from the culture.

(14) A monoclonal antibody that recognizes human PTPRS, which is obtainable by the following steps, or a fragment including an antigen-binding region thereof:
1) administering to an animal to be immunized a cell that exogenously expresses a protein including an extracellular domain of human PTPRS;
2) selecting an antibody-producing cell that produces an antibody that binds to human PTPRS from the antibody-producing cell of the immunized animal; and 3) culturing the antibody-producing cell selected in (2), and collecting an antibody that recognizes human PTPRS from the culture.

(15) (a) An immunogen for the production of an antibody that binds to human PTPRS, which includes an animal cell that retains exogenously and expressibly a polynucleotide that codes for an amino acid sequence including an extracellular domain of human PTPRS, or a cell membrane fraction thereof.

(16) The immunogen according to the above-mentioned (15), wherein the animal cell is a human-derived cell.

(17) A method for the detection of a plasmacytoid dendritic cell, which includes contacting a monoclonal antibody that binds to an extracellular domain of human PTPRS, or a fragment including an antigen-binding region thereof with a subject cell, and detecting the monoclonal antibody that has bound to the cell, or the fragment including an antigen-binding region thereof.

(18) An agent for the detection of a plasmacytoid dendritic cell, which includes a monoclonal antibody that binds to an extracellular domain of human PTPRS, or a fragment including an antigen-binding region thereof.

(19) A method for suppressing the activity of a plasmacytoid dendritic cell, which includes contacting any of the following components with the plasmacytoid dendritic cell:

(a) a monoclonal antibody that binds to human PTPRS to suppress the activity of the plasmacytoid dendritic cell, or a fragment including an antigen-binding region thereof, and (b) an immunoglobulin to which a complementarity determining region of the monoclonal antibody of (a) has been transplanted, or a fragment including an antigen-binding region thereof.

(20) A method for suppressing the activity of a plasmacytoid dendritic cell in a living body, which includes administering any of the following components to the living body:

(a) a monoclonal antibody that binds to human PTPRS to suppress the activity of a plasmacytoid dendritic cell, or a fragment including an antigen-binding region thereof, and (b) an immunoglobulin to which a complementarity determining region of the monoclonal antibody of (a) has been transplanted, or a fragment including an antigen-binding region thereof.

(21) The method according to the above-mentioned (19) or (20), wherein the activity of the plasmacytoid dendritic cell is one or both of an interferon-producing activity and the survival of an interferon-producing cell.

(22) An agent for suppressing the activity of a plasmacytoid dendritic cell, which includes any of the following components as an active ingredient:

(a) a monoclonal antibody that binds to human PTPRS to suppress the activity of a plasmacytoid dendritic cell, or a fragment including an antigen-binding region thereof, (b) an immunoglobulin to which a complementarity determining region of the monoclonal antibody of (a) has been transplanted, or a fragment including an antigen-binding region thereof.

(23) The agent for suppressing the activity of an interferon-producing cell according to the above-mentioned (22), wherein the activity of the plasmacytoid dendritic cell is one or both of an interferon-producing activity and the survival of the interferon-producing cell.

Advantageous Effects of the Invention

The present invention provides an antibody that specifically recognizes human PTPRS, an immunogen that is useful for the production of the antibody, and a method for the production of an anti-human PTPRS antibody utilizing the immunogen. Human PTPRS is a membrane protein that belongs to the RPTP family. The present inventors clarified that an antibody that specifically recognizes human PTPRS can be readily obtained. The anti-human PTPRS antibody that can be obtained by the present invention is an antibody having high specificity, which distinguishes human pDC from cells that express other RPTP families.

In a preferable embodiment, the anti-human PTPRS antibody provided by the present invention binds to human pDC. Furthermore, the antibody of the present invention specifically recognizes human pDC. Therefore, it is useful for detection and isolation of pDC. pDC is a cell that produces the major part of Type 1 IFN. Therefore, the detection and isolation thereof are important in the diagnoses and studies of diseases in which pDC is involved such as autoimmune diseases.

Furthermore, the anti-human PTPRS antibody provided by the present invention has an action to modulate the activity of human pDC in a preferable embodiment. Therefore, the anti-human PTPRS antibody of the present invention can be utilized for suppressing the activity of pDC. Therefore, if the suppression of the activity of pDC utilizing the antibody of the present invention is utilized, a therapeutic effect can be expected even in a patient with an autoimmune disease in which the expression of IFNα has enhanced.

pDC produces a large amount of IFN with little cells. For neutralization of IFN, an antibody corresponding to the molecular number of IFN is necessary. However, in the present invention, the activity of the produced cell is suppressed directly. As a result, a stronger effect of suppressing IFN can be expected with a smaller amount of antibody as compared to neutralization by an anti-IFN antibody. Furthermore, in the case when IFN is produced persistently, it is expected that neutralization of IFN by an antibody is suppressed only transiently, whereas the activity of pDC is suppressed and thus an effect of suppressing production of IFN for a long term can be expected in the present invention.

BRIEF DESCRIPTION OF DRAWINGS

FIG. 1 is the amino acid sequence of PTPRS (SEQ ID NO:1). PTPRS is a single transmembrane membrane protein having an immunoglobulin-like domain (Ig-like domain) and a fibronectin Type III-like domain in the extracellular region. Furthermore, it has two protein tyrosine phosphatase regions (PTP domains) in the intracellular region;

FIG. 15 is the result of testing whether or not the anti-human PTPRS antibodies also bind to mouse PTPRS. 49F2-30, 13G5-52, 13G5-57 and 22H8-84 bound to mPTPRS/CHO;

DESCRIPTION OF EMBODIMENTS

Figure 2:
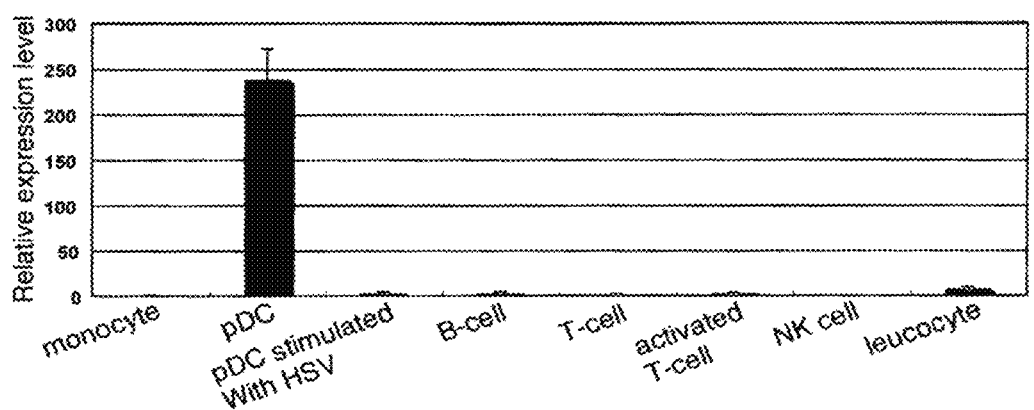
FIG. 2 is a graph showing the relative expression levels of PTPRS in various immune cells. It was shown that PTPRS expresses in a pDC-specific manner.

Human PTPRS is a molecule whose specific expression is observed in a plasma cell-like dendritic cell pDC. However, any method for the production of an antibody that recognizes human PTPRS has not been established yet.

Four isoforms of human PTPRS are known, which include isoform 1 that consists of 1,948 amino acid residues, isoform 2 that consists of 1,910 amino acid residues, isoform 3 that consists of 1,501 amino acid residues, and isoform 4 that consists of 1,505 amino acid residues. In the structures thereof, three immunoglobulin-like domains (first Ig domain, second Ig domain and third Ig domain), a fibronectin Type III-like domain, a transmembrane domain (transmembrane domain, TM region) as extracellular structures, and two phosphatase domains (D1 and D2 domains) as intracellular structures are observed. Only D1 domain that is close to the cell membrane has protein tyrosine phosphatase (PTP) activity. In FIG. 1, signal peptides and typical domains are marked in the amino acid sequence.

The isoform 3 of human PTPRS is a membrane penetrating protein including 831 to 851 of SEQ ID NO:1 (FIG. 1) as a transmembrane domain. Of the 1,501 amino acid residues including N terminus, 29 amino acid residues (1 to 29 in SEQ ID NO:1) constitute a signal sequence, and 30 to 830 constitute an extracellular domain. On the other hand, the C-terminus side is an intracellular domain. It is considered that the ligands in the extracellular environment control the activity in PTPRS.

Figure 8:
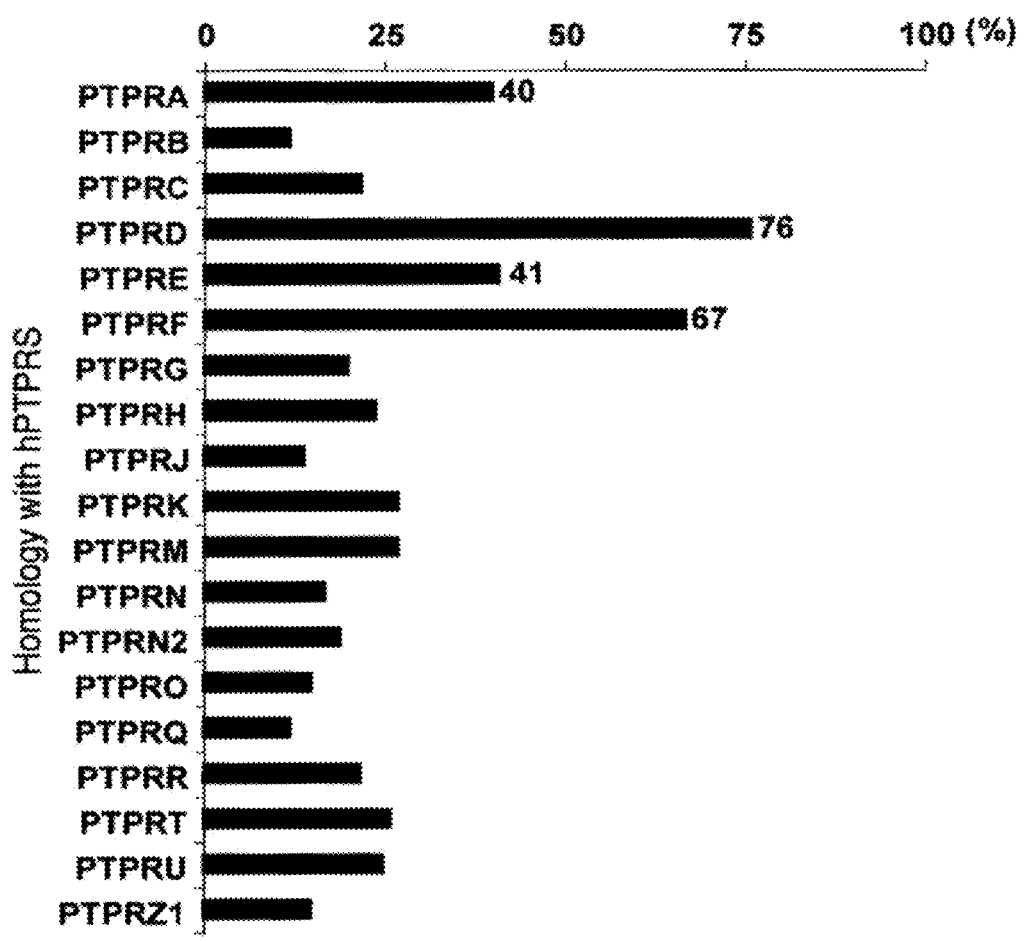
FIG. 8 is a graph showing the homology of hPTPRS with other PTPRs. PTPRS belongs to the PTPR family, of which the amino acid sequences of several family molecules have high homology against the amino acid sequence of PTPRS.

The present inventors have confirmed by a gene expression analysis that human PTPRS is specifically expressed in human pDC. They considered that, if an antibody that can distinguish human PTPRS from other molecules can be obtained, it would be useful for the studies of pDC. However, there are many molecules having similar structures in the PTP family including human PTPRS. Molecules such as PTPRS that is RPTP-σ and PTPRA (RPTP-α), PTPRD (RPTP-δ), PTPRE (RPTP-ε, PTPRF (RPTP-ζ) specifically include an amino acid sequence having high homology (FIG. 8). Therefore, they considered that it would be difficult to obtain an antibody that can differentiate these molecules from each other by using a domain peptide using the partial sequence of an amino acid sequence that constitutes an extracellular domain as an immunogen. Therefore, the present inventors tried to obtain an antibody against human PTPRS by using a cell that expresses human PTPRS as an immunogen.

The present inventors have done intensive studies so as to obtain an antibody that recognizes human PTPRS and clarified that the objective antibody can be obtained by using a specific transforming cell as an immunogen, and completed the present invention. Namely, the present invention relates to a monoclonal antibody that binds to an extracellular domain of human PTPRS, or a fragment including an antigen-binding region thereof.

In the present invention, human PTPRS can be defined as a natural molecule that expresses in human pDC, or a molecule that is immunologically equivalent to human PTPRS that expresses in human pDC. In the present invention, that the antibody binds to human PTPRS can be confirmed, for example, as follows.

Confirmation Based on Reactivity with Human Cell:

According to the finding obtained by the present inventors, it is considered that human PTPRS can be utilized as a marker for pDC since expression specific to human pDC is observed.

Based on such expression profile of human PTPRS, firstly, the activity of pDC to bind to at least a part of subset is one of important characteristics of the antibody that binds to human PTPRS in the present invention. That a certain cell is pDC can be confirmed by a cell surface marker that is inherent to each cell group. For example, binding to the objective cell is confirmed by double staining with an antibody that binds to a cell surface marker and an antibody whose binding activity is to be confirmed. Namely, pDC in the present invention includes, for example, a cell that expresses BDCA2.

Confirmation Based on Reactivity with Transforming Cell that Expresses Human PTPRS Gene:

The present inventors have confirmed that, when a human PTPRS gene is expressed under a specific condition, the immunological characteristics of human PTPRS expressed in human pDC is reconstituted. Therefore, the reactivity with human PTPRS can be confirmed based on the reactivity of an antibody against a cell to which a gene that codes for human PTPRS has been artificially introduced. Namely, the present invention relates to a monoclonal antibody that binds to a molecule including an amino acid sequence that constitutes an extracellular domain of human PTPRS as an extracellular domain, or a fragment including an antigen-binding region thereof. Meanwhile, the extracellular domain is constituted by the amino acid sequence corresponding to from 30 to 830 in SEQ ID NO:1 (FIG. 1) from the N-terminus of the amino acid sequence shown in SEQ ID NO:1.

For example, in a cell that has been transformed with an expression vector including a DNA that codes for human PTPRS, the immunological characteristics of PTPRS that expresses in human pDC are maintained. Therefore, a transforming cell that expresses human PTPRS is preferable as a cell for confirming the binding property of the antibody against an extracellular domain of human PTPRS in the present invention. When the reactivity of the antibody is confirmed by a transformation cell in the present invention, it is desirable to utilize a cell that has not been transformed as a control.

Next, the antibody that binds to human PTPRS in the present invention may be an antibody whose cross-reactivity with a cell group that is known to express PTP family other than human PTPRS is observed or not observed. The antibody whose cross-reactivity is not observed is preferable as the antibody that binds to human PTPRS in the present invention. Specifically, an antibody whose binding with a cell group that is known to express PTP family other than human PTPRS under the same condition as the condition under which binding to pDC has been confirmed is preferable as the antibody that binds to human PTPRS in the present invention.

Namely, a monoclonal antibody that binds to an extracellular domain of human PTPRS in the present invention preferably includes a monoclonal antibody having the following immunological characteristics.

a) it binds to human pDC, b) under the condition in which it binds to human pDC, its binding to one kind or plural kinds selected from the group consisting of a monocyte, a macrophage, a B cell and a CD34 positive cell, and dendritic cells derived from these cells, cannot be confirmed.

Specifically, an antibody whose binding to one kind or plural kinds selected from the group consisting of a monocyte, a macrophage, a B cell and a CD34 positive cell, and dendritic cells derived from these cells cannot be confirmed under the condition in which the antibody binds to human pDC is preferable as the monoclonal antibody of the present invention.

Alternatively, the monoclonal antibody that binds to the extracellular domain of human PTPRS in the present invention preferably includes a monoclonal antibody having the following immunological characteristics.

c) it binds to a transforming cell that has been transformed with an expression vector that expressibly retains a DNA that codes for human PTPRS, d) under the condition for binding to the transformed cell in c), binding to a host cell before the transformation in c) cannot be confirmed.

In the present invention, that the anti-human PTPRS monoclonal antibody does not cross-react with other molecules in the PTP family can be confirmed by using a cell in which each PTP family has been expressed forcibly. Namely, a cDNA that codes for an amino acid sequence of each PTP family is expressed forcibly by introducing into a suitable host cell. An anti-human PTPRS monoclonal antibody whose cross-reactivity is to be confirmed is contacted with the obtained transforming cell. Then, if the binding to a cell that expresses other PTP family molecule other than human PTPRS is not observed, it can be confirmed that the antibody can immunologically distinguish human PTPRS from other PTP family molecule. For example, in the Examples mentioned below, it was confirmed that most of the anti-human PTPRS monoclonal antibodies obtained by the present invention did not cross-react with PTPRA, PTPRD and PTPRF that specifically had high homology with PTPRS. Therefore, a monoclonal antibody that binds to human PTPRS and whose binding to PTPRA, PTPRD and PTPRF under the same condition is not detected is a preferable monoclonal antibody in the present invention. If an antibody that can immunologically distinguish these PTP family molecules from PTPRS is utilized, the change in the expression of PTPRS can be detected specifically. In addition, it was proved that, among the molecules having high homology with PTPRS, the expression of PTPRE can be confirmed in a cell but PTPRE does not express out of the cell. Therefore, it does not bind to PTPRE as an antibody.

The binding between a monoclonal antibody whose binding activity is to be confirmed and various cells can be confirmed by, for example, the principle of flow cytometry. In order to confirm the reactivity of the antibody by the principle of flow cytometry, it is advantageous to label the antibody in advance with a molecule or atomic group that generates a detectable signal. Generally, a fluorescence label or a light emission label is utilized. In order to analyze the binding between a fluorescence-labeled antibody and a cell by the principle of flow cytometry, a fluorescence-activated cell sorter (FACS) can be utilized. By utilizing the FACS, the binding between plural antibodies and cells can be confirmed effectively.

Specifically, for example, an antibody A that has been clarified in advance to be able to identify pDC, and an antibody B whose property to bind to pDC is to be analyzed are simultaneously reacted with a group of cells including pDC. The antibody A and antibody B are labeled with fluorescence signals that can be distinguished from each other in advance. If the two signals are detected in the same cell group, it can be confirmed that those antibodies bind to the same cell group. Namely, it can be found that the antibody A and antibody B have the same binding property. If they bind to different cell groups, it is apparent that their binding properties are different.

Examples of the preferable monoclonal antibody in the present invention may include a monoclonal antibody produced by hybridomas 9H5-4, 10F7-38, 13G5-52, 13G5-57, 14A8-85, 22H8-84, 49F2-30 or 55E7-79.

The hybridomas 9H5-4, 10F7-38, 13G5-52, 13G5-57, 14A8-85, 22H8-84, 49F2-30 and 55E7-79 were deposited as Accession Nos. FERM ABP-11356, FERM ABP-11357, FERM ABP-11358, FERM ABP-11359, FERM ABP-11360, FERM ABP-11361, FERM ABP-11362 and FERM ABP-11363 respectively, with International Patent Organism Depositary (IPOD), National Institute of Advanced Industrial Science and Technology (NAIST) on Apr. 1, 2011. Hereinafter the content for specifying the deposit will be described.

(a) Name of depositary organization: International Patent Organism Depositary (IPOD), National Institute of Advanced Industrial Science and Technology (NAIST)

Address: Tsukuba Central 6. 1-1-1 Higashi, Tsukuba, Ibaraki 305-8566, Japan (b) Date of deposition: Apr. 1, 2011

(c) Accession No. FERM ABP-11356 (hybridoma 9H5-4)

(c) Accession No. FERM: ABP-11357 (hybridoma 10F7-38)

(c) Accession No. FERM ABP-11358 (hybridoma 13G5-52)

(c) Accession No. FERM ABP-11359 (hybridoma 13G5-57)

(c) Accession No. FERM ABP-11360 (hybridoma 14A8-85)

(c) Accession No. FERM ABP-11361 (hybridoma 22H8-84)

(c) Accession No. FERM ABP-11362 (hybridoma 49F2-30)

(c) Accession No. FERM ABP-11363 (hybridoma 55E7-79)

The monoclonal antibody of the present invention may be a fragment including an antigen-binding region thereof. For example, an antibody fragment that includes an antigen binding site that is generated by enzymatic digestion of IgG can also be utilized as the antibody in the present invention. Specifically, an antibody fragment such as Fab or F(ab')2 can be obtained by digestion by papain or pepsin. It is well-known that these antibody fragments can be utilized as antibody molecules having binding affinity for an antigen. Alternatively, as long as necessary antigen binding activity is maintained, an antibody constructed by gene recombinant can also be used. Examples of the antibody constructed by gene recombination may include chimeric antibodies, CDR-transplanted antibodies, single chain Fv, diabodies, linear antibodies, multispecific antibodies that are formed from antibody fragments, and the like. Methods for obtaining these antibodies based on monoclonal antibodies or antibody-producing cells that produces the monoclonal antibodies are known.

The monoclonal antibody of the present invention can be obtained by using a specific transforming cell as an immunogen. Namely, the present invention relates to a method for the production of a cell that produces a monoclonal antibody that binds to an extracellular domain of human PTPRS, which includes:

(1) administering a cell that expresses an exogenous protein including an extracellular domain of human PTPRS to an animal to be immunized, and (2) selecting an antibody-producing cell that binds to human PTPRS from the antibody-producing cell of the immunized animal.

By culturing the thus-obtained antibody-producing cell or the antibody-producing cell that has been immortalized, the objective monoclonal antibody can be collected from the culture. Various methods are known for the method for immortalizing the antibody-producing cell.

The transforming cell that is used as an immunogen in the present invention can be obtained by, for example, preparing the following cell that expressibly retains an exogenous polynucleotide (a) that codes for an amino acid sequence including an extracellular domain of human PTPRS.

In the present invention, the exogenous polynucleotide refers to that the polynucleotide has been introduced artificially in a host cell. In the case when a human cell is used as the cell, a human gene is introduced into a human cell. Also in such combination, the artificially-introduced polynucleotide is called an exogenous polynucleotide. Therefore, the ectopic expression of human PTPRS is encompassed in the expression of the exogenous polynucleotide.

In the present invention, the extracellular domain of human PTPRS refers to the amino acid sequence from the 30 to 830 positions that correspond to the extracellular domain of the amino acid sequence described in SEQ ID NO:1. For example, an amino acid sequence that includes the respective regions in the order from the side of the N-terminus mentioned below is preferable as the amino acid sequence including an extracellular domain of human PTPRS in the present invention.

[Signal sequence+extracellular domain+transmembrane domain+intracellular region]

Alternatively, an amino acid sequence that partially lacks intracellular regions as follows is also encompassed in the amino acid sequence including an extracellular domain of human PTPRS in the present invention.

[Signal sequence+extracellular domain+transmembrane domain+part of intracellular region]

Furthermore, a structure that lacks an intracellular region as follows is also encompassed in the amino acid sequence including an extracellular domain of human PTPRS in the present invention.

[Signal sequence+extracellular domain+transmembrane domain]

In the above-mentioned structures, the regions other than the extracellular domain may have a sequence selected from the amino acid sequence shown in SEQ ID NO:1, or may include other homologous amino acid sequence in combination. For example, amino acid sequences that constitutes a signal sequence, a transmembrane domain and an intracellular region can be an amino acid sequence of PTP family molecules other than human PTPRS. Alternatively, an amino acid sequence of a PTP family of a species other than human can be combined. Furthermore, the amino acid sequences that constitute the regions other than the extracellular domain can include mutation to the extent that the functions of the respective regions can be maintained. Furthermore, other region can be interposed between the respective regions. For example, an epitope tag such as FLAG can be inserted between the signal sequence and extracellular domain. Specifically, the signal sequence is a region that is translated into a protein, processed in the stage of transferring to the surface of a cell membrane, and removed. Therefore, any amino acid sequence that induces passage of the cell membrane of the translated protein can be utilized as the signal sequence. More specifically, the amino acid sequence of human PTPRS (SEQ ID NO:1) is preferable as an amino acid sequence including an extracellular domain of human PTPRS.

Therefore, for the polynucleotide that constitutes the above-mentioned (a) in the present invention, any base sequence that codes for an amino acid sequence that constitutes the above-mentioned structure [signal sequence+extracellular domain+transmembrane domain+intracellular region] can be utilized. For example, the amino acid sequence of SEQ ID NO:1 is coded by the base sequence described in SEQ ID NO:2.

In the present invention, in order to obtain a transforming cell to be used as an immunogen, it is only necessary to introduce an expression vector in which the above-mentioned polynucleotide (a) is expressibly retained in a suitable host cell.

The host cell in the present invention is preferably a mammal cell. Specifically, a cell derived from a human, a monkey, a mouse or a rat can be utilized as a host cell. Specifically, a human-derived cell is preferably as the host cell. For example, an HEK-293T cell is a preferable human embryo-derived kidney cell line, which can be utilized as the host cell in the present invention. An HEK-293T cell is available as ATCC CRL-11268. Other cells derived from immunized animals can also be utilized as host cells. When a cell derived from an immunized animal is utilized as an immunogen, immune response against the host cell is small. Therefore, an antibody against an extracellular domain of human PTPRS that expresses exogenously can be obtained effectively. Therefore, for example, when a mouse is used as an immunized animal, a mouse-derived cell can also be used as a host cell.

The above-mentioned polynucleotide can be transformed into a cell by mounting the polynucleotide on a vector that can induce expression in a host cell. A commercially available vector that can induce expression in a mammal cell may be utilized. Expression vectors such as pCMV-Script (R) Vector, pSG5 vector (manufactured by Stratagene) and pcDNA3.1 (manufactured by Invitrogen) can be utilized in the present invention.

The thus-obtained transforming cell is administered to an animal to be immunized, together with additional components such as an adjuvant as necessary. As the adjuvant, Freund's complete adjuvant and the like can be utilized. In the case when a mouse is utilized as an immunized animal, the transforming cell can be administered by from $10^4$ to $10^9$ cells, more specifically by from $10^4$ to $10^6$ cells. In general, the immunogen is administered plural times at intervals until an antibody titer increases. For example, in the case of a short-period immunization process, the transforming cell can be administered at intervals of from 2 to 4 days, specifically 3 days, and the antibody-producing cell can be collected after 2 to 3 times of administration. Alternatively, the antibody-producing cell can be collected after 5 to 6 times of administration at intervals of about once a week.

In the present invention, the collected antibody-producing cell is cloned so as to obtain a monoclonal antibody. It is preferable for the cloning to immortalize the antibody-producing cell. For example, a cell fusion process such as a hybridoma process, or transformation by Epstein-Barr Virus (EBV) can be utilized as the process for the immortalization of the antibody-producing cell.

In the antibody-producing cell, one cell produces one kind of antibody. Therefore, if a cell group derived from one cell can be established (i.e., cloning), a monoclonal antibody can be obtained. The hybridoma process refers to a process in which an antibody-producing cell is fused with a suitable cell strain, immortalized and cloned. The immortalized antibody-producing cell can be cloned by a technique such as a limiting dilution method. Many cell strains that are useful for the hybridoma process are known. These cell strains have various genetic markers that are excellent in immortalization efficiency of a lymphocyte-based cell and necessary for the selection of a cell that has succeeded in cell fusion. Furthermore, in the case when the obtainment of an antibody-producing cell is intended, a cell strain that lacks antibody-producing ability can also be used.

For example, mouse myeloma P3×63Ag8.653 (ATCC CRL-1580) and P3×63Ag8U.1 (ATCC CRL-1597) are widely used as cell strains that are useful in cell fusion processes in mice and rats. In general, a hybridoma is prepared by fusing homologous cells, but a monoclonal antibody can be obtained from closely-related heterologous heterohybridomas.

A specific protocol of cell fusion is known. Namely, an antibody-producing cell of an immunized animal is mixed with a suitable fusion partner to effect cell fusion. For the antibody-producing cell, a spleen cell, a lymphocyte cell collected from a lymph node, a peripheral blood B cell and the like are used. As the fusion partner, various cell strains that have been mentioned above can be utilized. For the cell fusion, a polyethylene glycol process or an electric fusion process is used.

Next, the cell that has succeeded in cell fusion is selected based on a selection marker possessed by the fusion cell. For example, in the case when an HAT-sensitive cell strain is used for cell fusion, the cell that has succeeded in cell fusion is selected by selecting the cell that grows in an HAT medium. Furthermore, that the antibody produced by the selected cell has intended reactivity is confirmed.

Each hybridoma is screened based on the reactivity of the antibody. Namely, a hybridoma that produces an antibody that binds to human PTPRS is selected by the process as mentioned above. Preferably, the selected hybridoma is subcloned, and in the case when the production of the objective antibody is finally confirmed, it is selected as a hybridoma that produces the monoclonal antibody of the present invention.

Specifically, the objective hybridoma can be selected based on the reactivity with a human cell or the reactivity with a transforming cell that expresses human PTPRS gene. The antibody that binds to the cell can be detected by the principle of an immunoassay. For example, ELISA utilizing a cell as an antigen can be utilized for the detection of the objective antibody. Specifically, a culture supernatant of a hybridoma is contacted with a support on which human pDC, or a transforming cell utilized as an immunogen is fixed. In the case when the culture supernatant includes the objective antibody, the antibody is captured by the cell fixed on the support. Then, the solid-phase is separated from the culture supernatant, and washed as necessary, thereby the antibody captured on the solid-phase can be detected. An antibody that recognizes the antibody can be utilized for the detection of the antibody. For example, a mouse antibody can be detected by an anti-mouse immunoglobulin antibody. If an antibody that recognizes the antibody is labeled in advance, the detection thereof is easy. As the label, an enzyme, a fluorescent pigment, a light emission pigment or the like can be utilized.

On the other hand, as the support for fixing the cell, particles, or an inner wall of a microtiter plate can be utilized. The cell can be fixed by physical adsorption on the surface of particles or a container made of a plastic. For example, beads or a reaction container made of polystyrene can be utilized as the support for fixing the cell.

In the selection of a hybridoma, production of an antibody against not human PTPRS but the host cell of the transforming cell used for the immunogen is expected in some cases. For example, as shown in Examples, when a human cell is used as an immunogen and a mouse is utilized as an animal to be immunized, the human cell is recognized as a foreign substance, and production of an antibody that binds thereto is expected. The present invention aims at obtaining an antibody that recognizes human PTPRS. Therefore, it is not necessary to obtain an antibody that recognizes a human cell antigen other than human PTPRS. In order to exclude a hybridoma that produces such antibody by screening, an antibody that is not intended can be absorbed in advance before confirmation of the reactivity of the antibody.

The antibody that is not intended can be absorbed by an antigen to which an antibody whose presence is expected binds. Specifically, for example, antibodies against human cell antigens other than human PTPRS can be absorbed by cells in which the expression of human PTPRS cannot be detected. In the present invention, the host cell used as the immunogen is preferable as the antigen for absorbing the antibody that is not intended.

Where necessary, the actual effect on the activity of pDC of the monoclonal antibody whose binding activity against the antigen has been confirmed is confirmed. The effect on pDC can be confirmed by, for example, the method as mentioned below.

The monoclonal antibody of the present invention can be collected from a culture obtained by culturing a hybridoma that produces the monoclonal antibody. The hybridoma can be cultured in vitro or in vivo. The hybridoma can be cultured in vitro by using a known medium such as RPMI1640. In the culture supernatant, an immunoglobulin secreted by the hybridoma is accumulated. Therefore, the monoclonal antibody of the present invention can be obtained by collecting the culture supernatant and purifying as necessary. The purification of the immunoglobulin is easier in the case when serum is not added to the medium. However, for the purposes of more rapid proliferation of the hybridoma and acceleration of the production of the antibody, about 10% of fetal bovine serum can be added to the medium.

The hybridoma can also be cultured in vivo. Specifically, by inoculating the hybridoma in the abdominal cavity of a nude mouse, the hybridoma can be cultured in the abdominal cavity. The monoclonal antibody is accumulated in ascites fluid. Therefore, a desired monoclonal antibody can be obtained by collecting the ascites fluid and purifying as necessary. The obtained monoclonal antibody can be suitably modified or processed according to the purpose.

The monoclonal antibody of the present invention can be expressed by obtaining cDNA that codes for an antigen-binding region of the antibody from the hybridoma, and inserting this into a suitable expression vector. A technique for obtaining a cDNA that codes for a variable region of an antibody and expressing in a suitable host cell is known. Furthermore, a technique for binding a variable region including an antigen-binding region to a constant region to form a chimeric antibody is also known.

For example, as a preferable monoclonal antibody in the present invention, a monoclonal antibody produced by hybridoma 9H5-4 that was deposited as Accession No. FERM ABP-11356, hybridoma 10F7-38 that was deposited as Accession No. FERM ABP-11357, hybridoma 13G5-52 that was deposited as Accession No. FERM ABP-11358, hybridoma 13G5-57 that was deposited as Accession No. FERM ABP-11359, hybridoma 14A8-85 that was deposited as Accession No. FERM ABP-11360, hybridoma 22H8-84 that was deposited as Accession No. FERM ABP-11361, hybridoma 49F2-30 that was deposited as Accession No. FERM ABP-11362 or hybridoma 55E7-79 that was deposited as Accession No. FERM ABP-11363, or the like can be represented.

As the chimeric antibody including a variable region, or the humanized antibody to which CDR that constitutes a variable region has been transplanted, an antibody having a constant region derived from IgG or IgM is encompassed in the preferable antibody in the present invention. The present inventors have confirmed that a monoclonal antibody against PTPRS has a CDC action against the PTPRS-expressing cell. Therefore, the antibody having a constant region derived from IgG or IgM has a cytotoxic action against a PTPRS-expressing cell by the CDC action. Such antibody is useful for suppressing the cell number of the PTPRS-expressing cell such as pDC.

The chimeric antibody that recognizes human PTPRS, or the humanized antibody can be produced by gene engineering by using a polynucleotide that codes for the antibody.

About four years have already passed since the structure of human PTPRS was clarified in WO2007/041317 (JP2009-510102A); however, an antibody that can specifically recognize human PTPRS has not been obtained yet. An antibody that recognizes human PTPRS was first provided by the immunogen of the present invention. Namely, the present invention provided an antibody that recognizes human PTPRS, which can be obtained by the following processes:

(1) administering to an animal to be immunized a protein including an extracellular domain of human PTPRS;

(2) selecting an antibody-producing cell that produces an antibody that binds to human PTPRS from the antibody-producing cell of the immunized animal; and (3) culturing the antibody-producing cell selected in (2), and collecting an antibody that recognizes human PTPRS from the culture.

It was clarified that human PTPRS is specifically expressed in human pDC. The specific expression in human pDC was also confirmed in the gene expression analysis by SAGE by the present inventors. However, in the past reports, the expression level of human PTPRS was analyzed based on mRNA in all cases. Since an antibody by which detection of human PTPRS is enabled was not provided, the expression state of a protein was not analyzed in the past. The antibody that binds to an extracellular domain of human PTPRS, which was provided by the present invention, realized the analysis of a human PTPRS protein.

According to the actual confirmation by the present inventors, the monoclonal antibody that binds to an extracellular domain of human PTPRS based on the present invention specifically detected human pDC. Namely, the present invention relates to a method for the detection of a plasmacytoid dendritic cell, which includes contacting a monoclonal antibody that binds to an extracellular domain of human PTPRS or a fragment including an antigen-binding region thereof with a subject cell, and detecting the monoclonal antibody or fragment including an antigen-binding region thereof, which has bound to the cell.

By detecting human PTPRS based on the present invention, whether or not a certain cell is pDC can be confirmed. Namely, the present invention provides a method for the identification of pDC using human PTPRS as an index. Alternatively, human pDC can be separated by separating the cell in which human PTPRS has been detected according to the present invention. Namely, the present invention provides a method for the separation of pDC using human PTPRS as an index.

In the present invention, a monoclonal antibody that binds to an extracellular domain of human PTPRS, or a fragment including an antigen-binding region thereof can be labeled in advance. For example, the antibody can be detected readily by labeling with a light emission pigment or a fluorescence pigment. More specifically, a fluorescence pigment-labeled antibody is contacted with a cell aggregate that possibly includes pDC, thereby a cell to which the antibody of the present invention has bound can be detected using the fluorescence pigment as an index. Furthermore, if the cell in which the fluorescence pigment has been detected is separated, pDC can be separated. The series of processes can be readily carried out by the principle of FACS.

Alternatively, the antibody of the present invention can be bound to a solid-phase support such as magnetic particles in advance. The antibody bound to the solid-phase support recognizes human PTPRS, and pDC is captured by the solid-phase support. As a result, pDC can be detected and separate.

The antibody required for the detection of pDC based on the present invention can be supplied as an agent for detecting pDC. Namely, the present invention provides an agent for detecting pDC including a monoclonal antibody that binds to an extracellular domain of human PTPRS, or a fragment including an antigen-binding region thereof. For the agent for detecting pDC of the present invention, besides the antibody, a positive control or negative control can be combined. For example, the transforming cell that expresses an extracellular domain of human PTPRS, which was utilized as an immunogen, pDC collected from a human, or the like can be utilized as the positive control. Generally, human pDC can be obtained only little from peripheral blood. Therefore, the transforming cell is specifically preferable as the positive control in the agent of the present invention. On the other hand, any cell that does not express human PTPRS can be utilized for the negative control.

Namely, the present invention provides a kit for detecting human pDC, which includes a monoclonal antibody that binds to an extracellular domain of human PTPRS, or a fragment including an antigen-binding region thereof.

Furthermore, the present inventors have analyzed the effect of the antibody that binds to an extracellular domain of human PTPRS on pDC. As a result, they have confirmed that the antibody that binds to an extracellular domain of human PTPRS suppress the activity of pDC. Namely, the present invention relates to a method for suppressing the activity of an interferon-producing cell, which includes contacting any of the following components with pDC:

(a) a monoclonal antibody that binds to human PTPRS to suppress the activity of pDC, or a fragment including an antigen-binding region thereof, and (b) an immunoglobulin to which a complementarity determining region of the monoclonal antibody of (a) has been transplanted, or a fragment including an antigen-binding region thereof.

Alternatively, the present invention relates to a method for suppressing of the activity of pDC in a living body, which includes administering any of the following components to the living body:

(a) a monoclonal antibody that binds to human PTPRS to suppress the activity of pDC, or a fragment including an antigen-binding region thereof, (b) an immunoglobulin to which a complementarity determining region of the monoclonal antibody of (a) has been transplanted, or a fragment including an antigen-binding region thereof, and (c) a polynucleotide that codes for the component described in (a) or (b).

In the present invention, pDC refers to a cell that has an ability to produce IFN, and expresses human PTPRS on a cellular surface. Hereinafter, unless otherwise indicated, pDC encompasses not only a cell that is a precursor cell of a dendritic cell but also a cell that has an ability to produce IFN and expresses human PTPRS on a cellular surface. A method for identifying such pDC is known. For example, pDC can be distinguished from other blood cells using several cellular surface markers as indice. Specifically, the profile of the cellular surface marker of human pDC is as follows (Shortman, K. and Liu, Y J, Nature Reviews 2: 151-161, 2002). It was also reported in recent years that BDCA-2 positive cell is positioned as pDC (Dzionek, A. et al. J. Immunol. 165: 6037-6046, 2000).

[Profile of Cellular Surface Antigen of Human pDC]
CD4 positive, CD123 positive, Lineage (CD3, CD14, CD16, CD19, CD20, CD56) negative, CD11c negative Therefore, a cell having the expression profile of these known markers and also having an ability to produce IFN can also be referred to pDCs. Furthermore, even a group of cells having a profile that is different from the expression pattern of the expression profile of these markers, a cell in a living body having an ability to produce IFN, the cells are encompassed in pDCs.

Furthermore, as characteristics that are commonly observed in human pDC, the following characteristics can be shown.

[Characteristics in Form of Cell]
it resembles a plasma cell.
it is a round cell having a smooth cellular surface.
it has a relatively large nucleus. [Functional characteristics of cell]
it produces a large amount of Type I IFN within a short period during viral infection.
it differentiates into a dendritic cell after viral infection.

In the present invention, suppression of the activity of pDC refers to suppression of at least one function possessed by pDC. As the functions of pDC, production of IFN and cell survival can be shown. In other word, cell survival can be said to be a cell number. Therefore, suppression of one or both of these functions refers to suppression of the activity of pDC. It was clarified that Type I IFN produced by pDC causes various diseases. Therefore, it is useful to suppress the cell number of pDC and the production of IFN as therapeutic strategies for those diseases.

For example, a relationship between the pathological conditions of autoimmune diseases and IFNα was pointed out. Most of IFNα is produced by pDC. Therefore, if the production thereof is suppressed, the pathological conditions brought by IFNα can be alleviated. Meanwhile, in the present invention, suppression of IFN production by pDC refers to suppression of production of at least one kind of IFN among IFNs produced by pDC. Type I IFNs are preferable IFNs in the present invention. Among these, IFNα is important.

Namely, the present invention relates to an agent for suppressing the production of IFN, which includes an antibody that binds to an extracellular domain of human PTPRS as an active ingredient. Alternatively, the present invention provides a method for suppressing the production of IFN, which includes administering an antibody that binds to an extracellular domain of human PTPRS. Furthermore, the present invention relates to use of an antibody that binds to an extracellular domain of human PTPRS in the production of a pharmaceutical composition for suppressing the production of IFN.

pDC includes a cell that produces a large amount of IFN by a small number of cell. For example, a precursor cell of a dendritic cell that has been stimulated by a virus or the like produces most of IFN produced by a living body. Suppression of the cell number of pDC that produces a large amount of IFN consequently leads to suppression of the production amount of IFN. Therefore, the pathological conditions brought by IFNα can also be alleviated by suppressing the cell number of pDC.

In a preferable embodiment of the present invention, it was confirmed that an anti-human PTPRS monoclonal antibody binds to a human PTPRS-expressing cell and imparts a cytotoxic action by a CDC (Complement Dependent Cytotoxicity) action. The CDC action is one of important mechanisms of action in antibody medicaments. The anti-human PTPRS monoclonal antibody of the present invention also has a strong cytotoxic action against human PTPRS-expressing cells such as pDC by the CDC action thereof. Namely, an effect of suppression of IFN production can be expected also by a cytotoxic action against pDC besides the mechanism of suppression of IFN production in a preferable embodiment.

The antibody that recognizes an extracellular domain of human PTPRS used in the present invention can be obtained based on the method as previously mentioned. The antibody in the present invention may be of any class. Furthermore, the species of the organism from which the antibody is derived is also not limited. Furthermore, a fragment including an antigen-binding region of the antibody can be used as the antibody. For example, an antibody fragment that includes an antigen binding site that is generated by enzymatically digestion of IgG can also be used as the antibody in the present invention. Specifically, an antibody fragment such as Fab or F(ab')2 can be obtained by digestion by papain or pepsin. It is well-known that these antibody fragments can be utilized as antibody molecules having binding affinity for antigens. Alternatively, an antibody constructed by gene recombination can also be used as long as it maintains necessary antigen binding activity. Examples of the antibody constructed by gene recombination may include chimeric antibodies, CDR transplant antibodies, single chain Fv, diabodies and linear antibodies, and multi-specific antibodies formed from antibody fragments, and the like. Methods for obtaining these antibodies based on monoclonal antibodies are known.

In the present invention, the antibody can be modified as necessary. According to the present invention, an antibody that recognizes an extracellular domain of human PTPRS has an action to suppress the activity of pDC. Namely, a possibility that the antibody itself has a cytotoxic action against pDC was considered. The subclass of the antibody showing a strong effector action is known. Alternatively, by modifying the antibody with a cytotoxic substance (a cytotoxic agent), the effect of suppressing the activity of pDC can further be enhanced. Examples of the cytotoxic substance may include the following substances.

Toxins: *Pseudomonas* Endotoxin (PE), diphtheriatoxin Lysine

Radioisotope elements: Tc99m, Sr89, I131, Y90

Anticancer agents: calicheamicin, mytomycin, paclitaxel

Toxins composed of a protein can be bound to an antibody or a fragment thereof, or the like by a bifunctional agent. Alternatively, a gene that codes for toxins can be joined to a gene that codes for an antibody to give a fusion protein of the two genes. A method for binding a radioisotope element to an antibody is also known. For example, a method for labeling an antibody with a radioisotope element by utilizing a chelating agent is known. Furthermore, an anticancer agent can be bound to an antibody by utilizing a sugar chain or a bifunctional agent.

In the present invention, an antibody whose structure has been modified artificially can also be utilized as an active ingredient. For example, various modification methods for ameliorating cytotoxic action and stability of an antibody are known. Specifically, an immunoglobulin in which a sugar chain of a heavy chain has been modified is known (Shinkawa, T. et al., J. Biol. Chem 278:3466-3473. 2003). By modifying the sugar chain, the ADCC (Antibody Dependent Cell-mediated Cytotoxicity) activity of the immunoglobulin was enhanced.

When the antibody that binds to an extracellular domain of human PTPRS is contacted with pDC, the activity thereof is suppressed. Therefore, these antibodies can be utilized for an agent or method for suppressing the activity of pDC. Namely, the present invention provides an agent for suppressing the activity of pDC, which includes at least one kind of component selected from the group consisting of the following (a)-(c) as an active ingredient. Alternatively, the present invention relates to a method for suppressing the activity of pDC, which includes administering at least one kind of component selected from the group consisting of the following (a)-(c). Furthermore, the present invention relates to use of the component selected from the group consisting of the following (a)-(c) in the production of an agent for suppressing the activity of pDC.

(a) An antibody that binds to an extracellular domain of human PTPRS, or a fragment including an antigen-binding region thereof, and (b) An immunoglobulin to which a complementarity determining region of the monoclonal antibody of (a) has been transplanted, or a fragment including an antigen-binding region thereof.

In the present invention, as the monoclonal antibody that suppresses the activity of pDC, a monoclonal antibody that recognizes an extracellular domain of human PTPRS can be utilized. In the present invention, one kind or plural kinds of monoclonal antibody can be utilized. For example, plural kinds of monoclonal antibodies that recognize an extracellular domain of human PTPRS can be incorporated and utilized in the present invention.

That an antibody has an action of suppressing the IFN-producing activity of pDC can be confirmed as follows. pDC produces a large amount of IFN by the stimulation of a virus. By providing an antibody before or after the stimulation with the virus against pDC, or simultaneously with the stimulation with the virus, and using pDC to which the an antibody is not provided as a control, the abilities of producing IFN are compared. The abilities of producing IFN can be evaluated by measuring IFN-α and IFN-β included in the culture supernatant of pDC. As a result of the comparison, when the amount of IFN in the supernatant is decreased significantly by adding the antibody, it can be confirmed that the tested antibody has an action of suppressing the ability of producing IFN. A method for measuring these IFNs is known. pDC is a cell that produces most of IFNs in a living body. Therefore, by suppressing the ability of producing IFN of pDC, the state of production of IFN in a living body can be modulated.

In the present invention, the activity of pDC includes maintenance of the cell number of pDC. Therefore, suppression of the activity of pDC in the present invention includes suppression of the cell number of pDC. If that the cell number of pDC is suppressed in the presence of an antibody is confirmed, it is found that the antibody suppresses the activity of pDC. As a control for comparison, an inert immunoglobulin derived from the same animal species as that for an antibody whose activity is to be confirmed can be used as in the production of IFN. The cell number of pDC can be compared quantitatively by counting the number of the cell. The cell number can be counted by an FACS or microscope.

Furthermore, it is also considered that pDC differentiates into a cell that induces Th2 called DC2 (Dendritic Cell 2) as a result of infection with a virus or the like. If the production of IFN of pDC by stimulation with a virus can be suppressed, it is also possible that the differentiation into Th2 can be suppressed. Therefore, therapeutic effects on various allergy diseases can be expected for the monoclonal antibody of the present invention that suppresses IFN production.

In the case when the antibody that recognizes an extracellular domain of human PTPRS is administered to a host that is different from an organism species from which the antibody is derived, it is desirable to process the antibody into a shape that is hardly recognized as a foreign substance for the host. For example, by processing into the following molecules, the immunoglobulin can become difficult to be recognized as a foreign substance. The technique for processing an immunoglobulin molecule as follows is known.

A fragment including an antigen-binding region that lacks a constant region (Monoclonal Antibodies: Principles and Practice, third edition, Academic Press Limited. 1995; Antibody Engineering, A Practical Approach, IRL PRESS, 1996)

A chimeric antibody that is constituted by an antigen-binding region of a monoclonal antibody and a constant region of an immunoglobulin of a host (Experimental Manual for Gene Expression, Kodansha Ltd., 1994 (edited by Isao Ishida and Tamie Ando))

A CDR-substituted antibody obtained by substituting a complementarity determining region (CDR) in an immunoglobulin of a host with a CDR of a monoclonal antibody (Experimental Manual for Gene Expression, Kodansha Ltd., 1994 (edited by Isao Ishida and Tamie Ando)).

Alternatively, an immunoglobulin variable region gene of a human can be acquired by a phage display process (McCafferty J. et al., Nature 348: 552-554, 1990; Kretzschmar T et. al., Curr Opin Biotechnol 2002 December: 13 (6): 598-602). In the phage display process, a gene that codes for a human immunoglobulin variable region is incorporated into a phage gene. A phage library can be prepared by using various immunoglobulin genes as sources. A phage expresses the variable region as a fusion protein of a protein that constitutes the phage itself. The variable region on the surface of the phage, which is expressed by the phage, maintains the binding activity with the antigen. Therefore, by selecting a phage that binds to a cell that has expressed an antigen or antigen, or the like, a phage that has expressed a variable region having an intended binding activity can be screened from a phage library. Furthermore, a gene that codes for a variable region having an intended binding activity is retained in the phage particles selected by such way. Namely, in the phage display process, a gene that codes for a variable region having an intended binding activity can be acquired by using the binding activity of the variable region as an index.

In the agent or method for suppressing the activity of pDC according to the present invention, the antibody that recognizes an extracellular domain of human PTPRS, or an antibody fragment including at least an antigen-binding region thereof can be administered as a protein or a polynucleotide that codes for the protein. In order to administer the polynucleotide, it is desirable to utilize a vector to which a nucleotide that codes for an intended protein has been disposed under the control of a suitable promoter so that an intended protein can be expressed. An enhancer or terminator can also be disposed on the vector. A vector that can retain genes of a heavy chain and a light chain that constitute immunoglobulin and can express an immunoglobulin molecule is known. The vector that can express an immunoglobulin can be administered by introducing into a cell. In administration to a living body, a vector that can be transmitted to a cell by administering to the living body can be administered as it is. Alternatively, a vector can be introduced in a lymphocyte that has been once separated from a living body and thereafter returned to the living body (ex vivo).

In the agent or method for suppressing the activity of pDC according to the present invention, the amount of the monoclonal antibody to be administered to a living body as an immunoglobulin is generally from 0.5 mg to 100 mg, for example from 1 mg to 50 mg, preferably from 2 mg to 10 mg, per 1 Kg body weight. The intervals of administration of the antibody to a living body can be suitably modulated so that the effective concentration of the immunoglobulin in a living body during a therapeutic period can be maintained. Specifically, the antibody can be administered at intervals of from 1 to 2 weeks. The route of administration is optional. A person skilled in the art can suitably select an effective administration route for a therapy. Specifically, oral or parenteral administration can be shown. For example, the antibody can be administered systemically or topically by intravenous injection, intramuscular injection, peritoneal injection or subcutaneous injection, or the like. Examples of formulations that are suitable for the parenteral administration in the present invention may include an injection agent, a suppository, an aerosol and the like. Furthermore, when the antibody is provided to a cell, an immunoglobulin of generally 1 µg/mL, preferably 10 µg/mL or more, more preferably 50 µg/mL or more, further preferably 0.5 mg/mL or more is provided.

In the agent or method for suppressing the activity of pDC according to the present invention, the monoclonal antibody can be administered to a living body by any method. Generally, the monoclonal antibody is compounded with a pharmaceutically acceptable carrier. Where necessary, additives such as a thickening agent, a stabilizer, an antiseptic agent and a solubilizer can be incorporated into the monoclonal antibody. Examples of such carrier or additive may include lactose, citric acid, stearic acid, magnesium stearate, sucrose, starch, talc, gelatin, agar, vegetable oils, ethylene glycol and the like. The term "pharmaceutically acceptable" refers to having been accepted by the supervisory of the government of each country, or being listed in the pharmacopoeia of each country or a generally-recognized pharmacopoeia with respect to use in animals, mammals, and specifically in humans. The agent for suppressing the activity of pDC of the present invention can be provided in the form of a lyophilized powder or tablet including one dose or plural doses. The lyophilized powder or tablet can further be combined with injectable sterilized water, physiological saline or buffer for solving the composition so as to give a desired concentration prior to administration.

Furthermore, when administered in the form of a vector that expresses an immunoglobulin, each plasmid can be administered by from 0.1 to 10 mg, for example from 1 to 5 mg per 1 kg body weight, considering that a heavy chain and a light chain are co-transfected as separate plasmids. Furthermore, for introducing into a cell in vitro, a vector of from 1 to 5 µg/$10^6$ cell is used.

Hereinafter the present invention will be explained more specifically with referring to the Examples.

All of the prior art documents cited herein are incorporated herein by reference.

Hereinafter the present invention will be explained more specifically with referring to the Examples, but the present invention is not construed to be limited by the Examples.

EXAMPLES

Example 1

A. Analysis of Expression of PTPRS
A-1) Analysis Using SAGE Library

Expressions of a gene in human monocyte, pDC, and pDC treated with herpes simplex virus (HSV) were compared and analyzed by an SAGE' (Serial Analysis of Gene Expression) process. The analysis method is as follows.

A monocyte was isolated as a CD14 positive cell and pDC was separated as a BDCA-4 positive cell from human peripheral blood mononuclear cells by a cell sorter. Furthermore, pDC was cultured in the presence of HSV for 12 hours to prepare activated pDC. RNAs were obtained from the respective cells, and an SAGE library was prepared by using an I-SAGE' kit (Invitrogen). The obtained base sequence data of about 100,000 tags was analyzed by SAGE Analysis Software (Invitrogen). As a result, as a gene having a score value of monocyte/pDC/pDC+HSV of 0/7/0, i.e., a gene that shows pDC-specific expression, a known gene: PTPRS (GenBank Acc # NM 002856.3) was found. PTPRS is coded by the base sequence shown in SEQ ID NO:2. Furthermore, it is a single transmembrane domain having an immunoglobulin-like domain (Ig-like domain) and a Fibronectin Type III-like domain in the extracellular region. In addition, it has two protein tyrosine phosphatase regions (PTP domains) in the intracellular region (FIG. 1).

A-2) Analysis of Expression of PTPRS mRNA in Various Human Immune Competent Cells by Quantitative RT-PCR The expression of PTPRS in immune cells was analyzed in more detail. Each cell was isolated from human peripheral blood by a cell sorter. RNA was extracted from the isolated each cell population, and cDNA was synthesized. Using the obtained cDNA as a template, quantitative RT-PCR was conducted according to a general process to analyze the expression level of PTPRS mRNA. By normalization with the expression level of a GAPDH (glyceraldehyde-3-phosphate dehydrogenase) gene that is known to express constantly, the expression of the PTPRS gene was compared between immune cells.

The base sequences of the used primers, and the conditions for PCR are as follows.

```
Forward primer for PTPRS:
                                (SEQ ID NO: 3)
5' CAC GGC CTA TGA CCT CCA 3'

Reverse primer for PTPRS:
                                (SEQ ID NO: 4)
5' AAG TTC TTG GGC GAG ACT TG 3'

Forward primer for GAPDH:
                                (SEQ ID NO: 5)
5' CCA CCC ATG GCA AAT TCC 3'

Reverse primer for GAPDH:
                                (SEQ ID NO: 6)
5' TGG GAT TTC CAT TGA TGA CAA G 3'
```

1 cycle at 50° C. for 2 minutes,
1 cycle at 95° C. for 10 minutes, and
50 cycles [at 95° C. for 15 seconds and at 60° C. for 60 seconds].

A monocyte, pDC, pDC stimulated with HSV, a B-cell (CD19+ cell), a T-cell (CD3+ cell), an activated T-cell stimulated with PMA (Phorbol 12-myristate 13-acetate) and an NK cell (CD56+ cell) were analyzed, and it was shown that PTPRS was expressed in a pDC-specific manner. Furthermore, it was found as a characteristic that the expression of PTPRS is decreased by the pDC stimulated with HSV (FIG. 2).

A-3) Analysis of Expression of PTPRS mRNA in Human Tissue by Quantitative RT-PCR Furthermore, expression in tissues was studied by quantitative PCR using ABI PRISM 7000 (Applied Biosystem). As cDNA panels, BD™ MTC multiple tissue cDNA panel (Human I; Cat. No. 636742, Human immune; Cat. No. 636748, Human blood fractions; Cat. No. 636750; all by Becton Dickinson) were used. The base sequences of the primers used are shown below.

```
Forward primer for PTPRS:
                                (SEQ ID NO: 7)
5' ACT CAC CCA CAC CCT ACA AGA 3'

Reverse primer for PTPRS:
                                (SEQ ID NO: 8)
5' CTT GGT GGT ACG GCC ATC 3'

Forward primer for GAPDH:
                                (SEQ ID NO: 5)
5' CCA CCC ATG GCA AAT TCC 3'

Reverse primer for GAPDH:
                                (SEQ ID NO: 6)
5' TGG GAT TTC CAT TGA TGA CAA G 3'
```

Using an SYBR green PCR master mix kit (Applied Biosystem), PCR was conducted by ABI PRISM 7000 available from the same company. Sequence Detection System Software available from the same company was used for the analysis. The reaction conditions are as follows.

Step 1: 1 cycle at 50° C. for 2 minutes

Step 2: 1 cycle at 95° C. for 10 minutes

Step 3: 40 cycles at 95° C. for 15 seconds and at 60° C. for 1 minute

Figure 3:
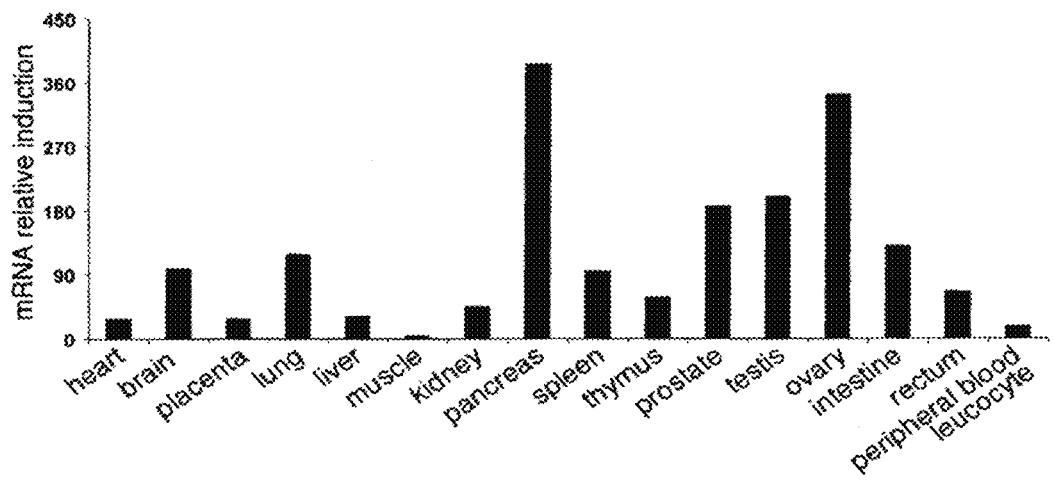
FIG. 3 is a graph showing the comparison of expression of PTPRS gene between tissues. PTPRS mRNA shows relatively high expression in the spleen and ovary, and also expresses broadly in other tissues.

By normalization with the expression level of a GAPDH (glyceraldehyde-3-phosphate dehydrogenase) gene that is known to express constantly, the expression of the PTPRS gene was compared between tissues. As a result, PTPRS mRNA was expressed widely in the tissues (FIG. 3).

B. Preparation of PTPRS Expression Vector

In order to express a PTPRS protein, preparation of an expression vector of a PTPRS gene was conducted. Only a PTPRS gene was taken out from a PTPRS cDNA Clone that had been incorporated in a pCR4-TOPO cloning vector (Open Biosystem cc # MHS1010-98052887) and incorporated into a pcDNA3.1 expression vector (PTPRS/pcDNA3.1). Using the obtained PTPRS/pcDNA3.1 plasmid as a template, the PTPRS gene was amplified with a primer including EcoRI, Not I and Kozak sequence (GCC GCC ACC) (the information on the primer is shown below). The PCR product was cloned into a pMX-IP retroviral vector at EcoRI and Not I sites (PTPRS/pMX-IP). For the PCR reaction, one unit of KOD Plus DNA polymerase (TOYOBO) was used, and the reaction conditions were 1 cycle at 94° C. for 2 minutes and 25 cycles [at 94° C., 15 seconds and at 68° C. for 4 minutes and 30 seconds].

Forward primer (SEQ ID NO: 9):
5' aaa GAA TTC gcc gcc acc ATG GCG CCC ACC TGG GGC CCT3'

Reverse primer (SEQ ID NO: 10):
5' aaa gcg gcc gcT TAG GTT GCA TAG TGG TCA AAG C3'

In the above-mentioned base sequences, the small characters represent the cleavage sites of the restriction enzyme EcoRI or the sites of Not I. The aaa at the 5' terminus is an additional base for enzymatic cleavage.

C. Preparation of Human PTPRS (hPTPRS)-Expressing Cell

Figure 4:
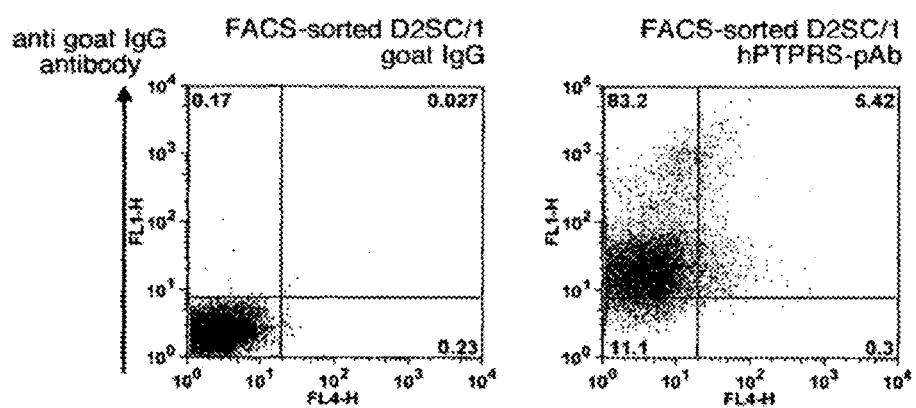
FIG. 4 shows selection of the human PTPRS (hPTPRS)-expressing cell by FACS sorting.

To make a retro virus containing PTPRS gene, HEK-293T cell that is a kidney cell strain of a human embryo was transiently transfected with PTPRS/pMX-IP and a retro virus packaging vector PCL-ECO by FuGENE kit (Roche). Two days later, the cell culture supernatant in which a virus including a hPTPRS gene was collected and infected with a D2SC/1 cell that is a dendritic cell derived from the spleen of a BALB/c mouse (this was prepared based on Paglia et al., J. Exp. Med., 178, 1893-1901 (1993)). Since the pMX-IP retroviral vector includes a puromycin resistance gene, only a cell that expresses hPTPRS becomes possible to survive by culturing the infected D2SC/1 cell with puromycin, thereby selection becomes possible. hPTPRS-expressing D2SC/1 cells were selected by FACS sorting and cultured. In order to confirm the expression of hPTPRS, 10 µg/mL of goat IgG (SantaCruz) and a commercially available hPTPRS polyclonal antibody (pAb; R&D) were added to the selected hPTPRS/D2SC/1 cells by 100 µL each, and the mixture was incubated at 4° C. for 30 minutes. The cell was washed with PBS, and then a FITC-labeled anti-goat IgG antibody (SantaCruz) diluted by 100-fold was added by 50 µL, and the mixture was incubated at 4° C. for 30 minutes. After washing with PBS, data was imported by FACSCalibur (BD) (FIG. 4).

Example 2

A. Preparation of Anti-Human PTPRS Monoclonal Antibody

A-1) Immunization

As a cell used as an immunogen, the above-mentioned hPTPRS/D2SC/I cell was used. BALB/c mice were anesthetized, and a Freund's Complete Adjuvant (CFA) emulsion was injected subcutaneously to the footpads by 50 µl per each foot. The total was 100 µl/mouse. On the next day, an emulsion was prepared by using a hPTPRS/D2SC/1 cell prepared as an immunogen and a Freund's Incomplete Adjuvant (IFA) and injected subcutaneously to the footpads (50 µl/foot, total 100 µl/mouse). Immunization was done every two days for three times in total, and the drawing lymph nodes were collected at 3 days after the last immunization.

A-2) Cell fusion

The drawing lymph node cells were collected from the both feet of an immunized mouse and mixed with a mouse myeloma cell P3-X63-Ag8.563 that had been cultured in a RPMI1640 medium (SIGMA) including 10% FBS so that the ratio of the lymph node cells and the myeloma cells became 5:4, and the cells were collected by centrifugation. PEG1500 (Roche) was added to the mixed cells for cell fusion. The fused cell (hybridoma) was washed and cultured in 10% Fetal Bovine Serum (FBS) including a cell growth supplement+HAT (Sigma)-RPMI1640 medium (including 2 mM L-Glutamine, 100 Unit/ml Penicillin, 100 µg/ml Streptomycin, 10 mM HEPES, 1 mM Sodium Pyruvate, 50 µM 2-ME).

A-3) FACS Screening of Hybridoma Using Immunized hPTPRS/D2SC/1 Cell

Figure 5:
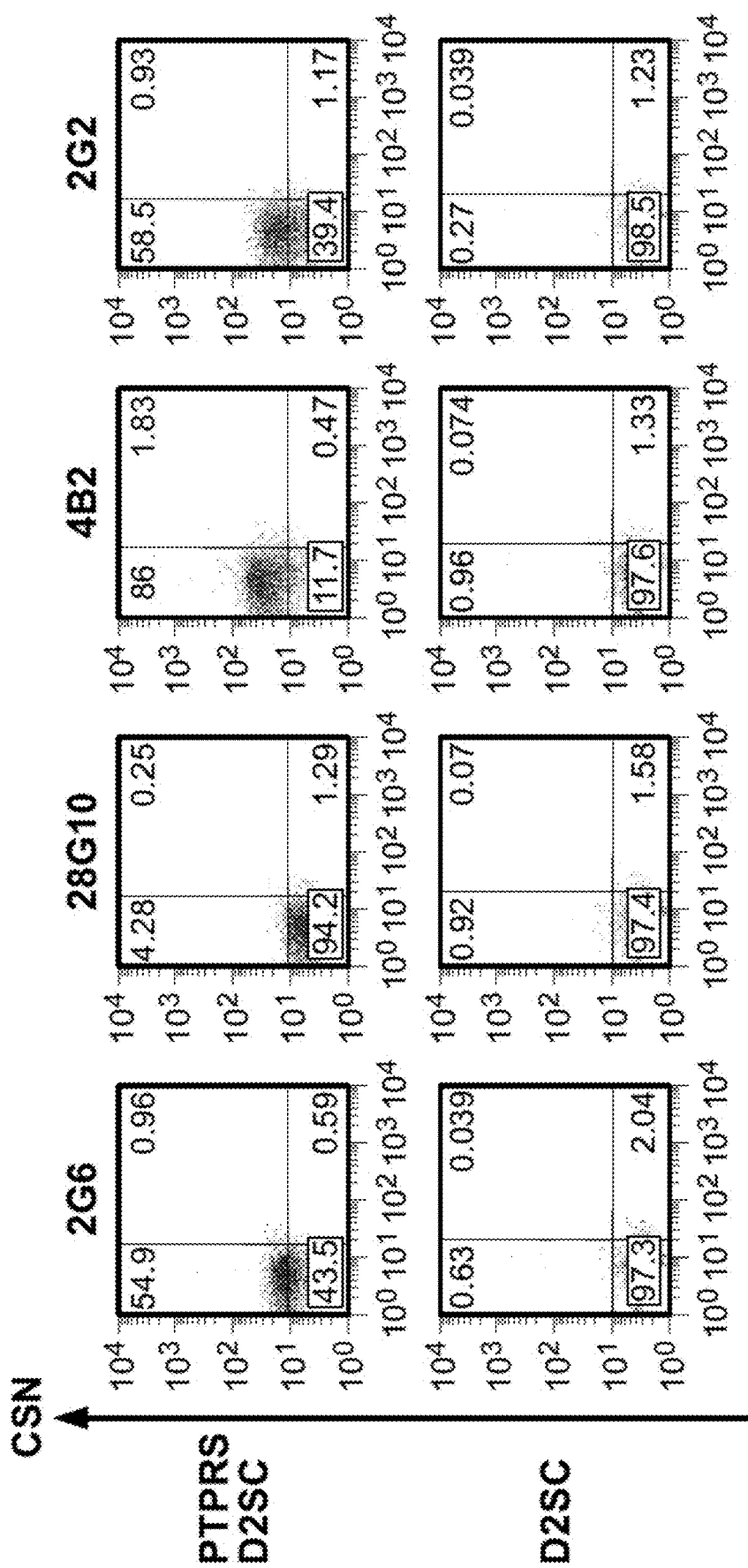
FIG. 5 shows FACS screening of hybridomas using immunized hPTPRS/D2SC/1 cell. Thirteen hybridomas that produce an anti-hPTPRS antibody were obtained.
Figure 5:
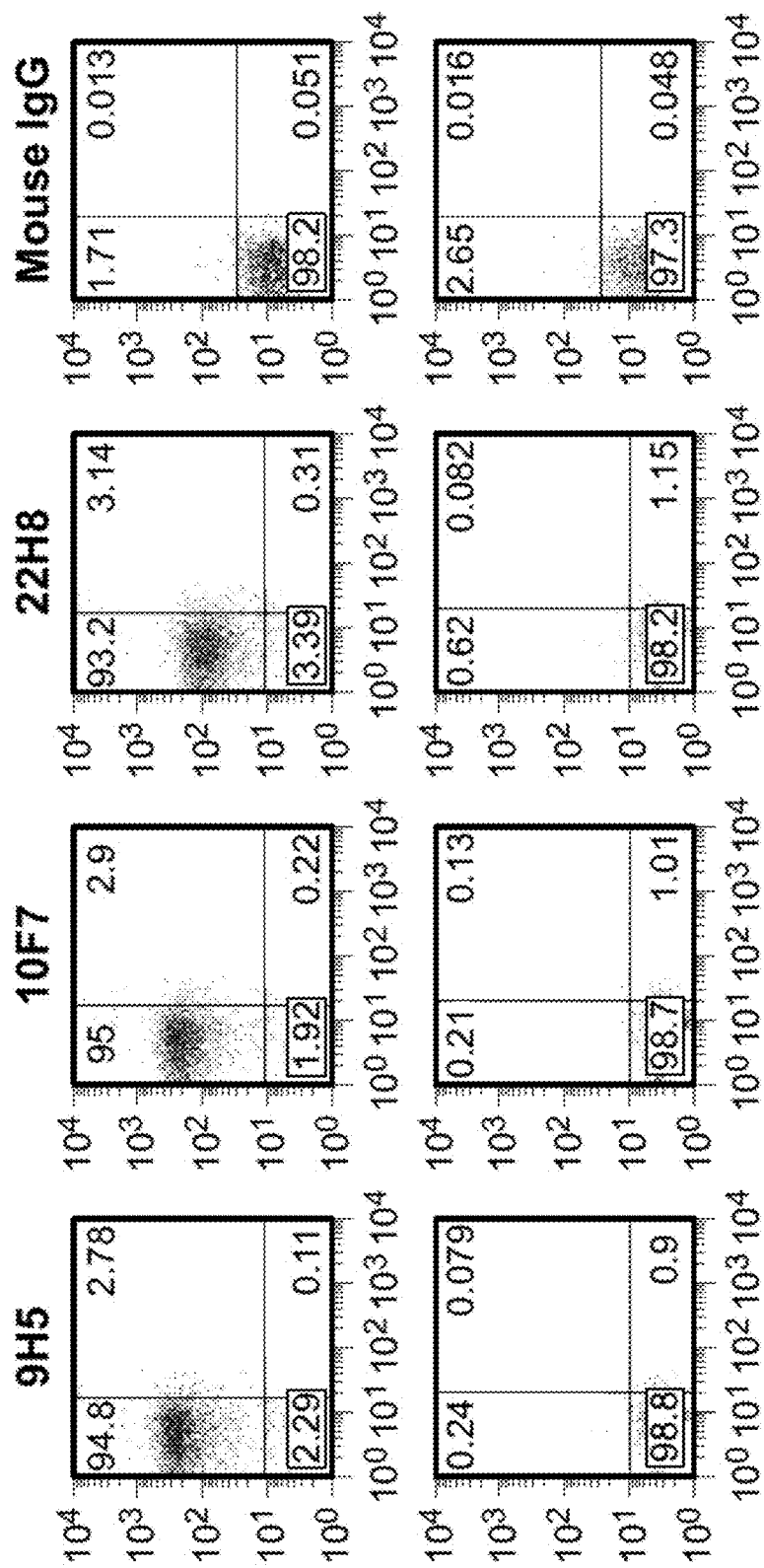
Figure 5:
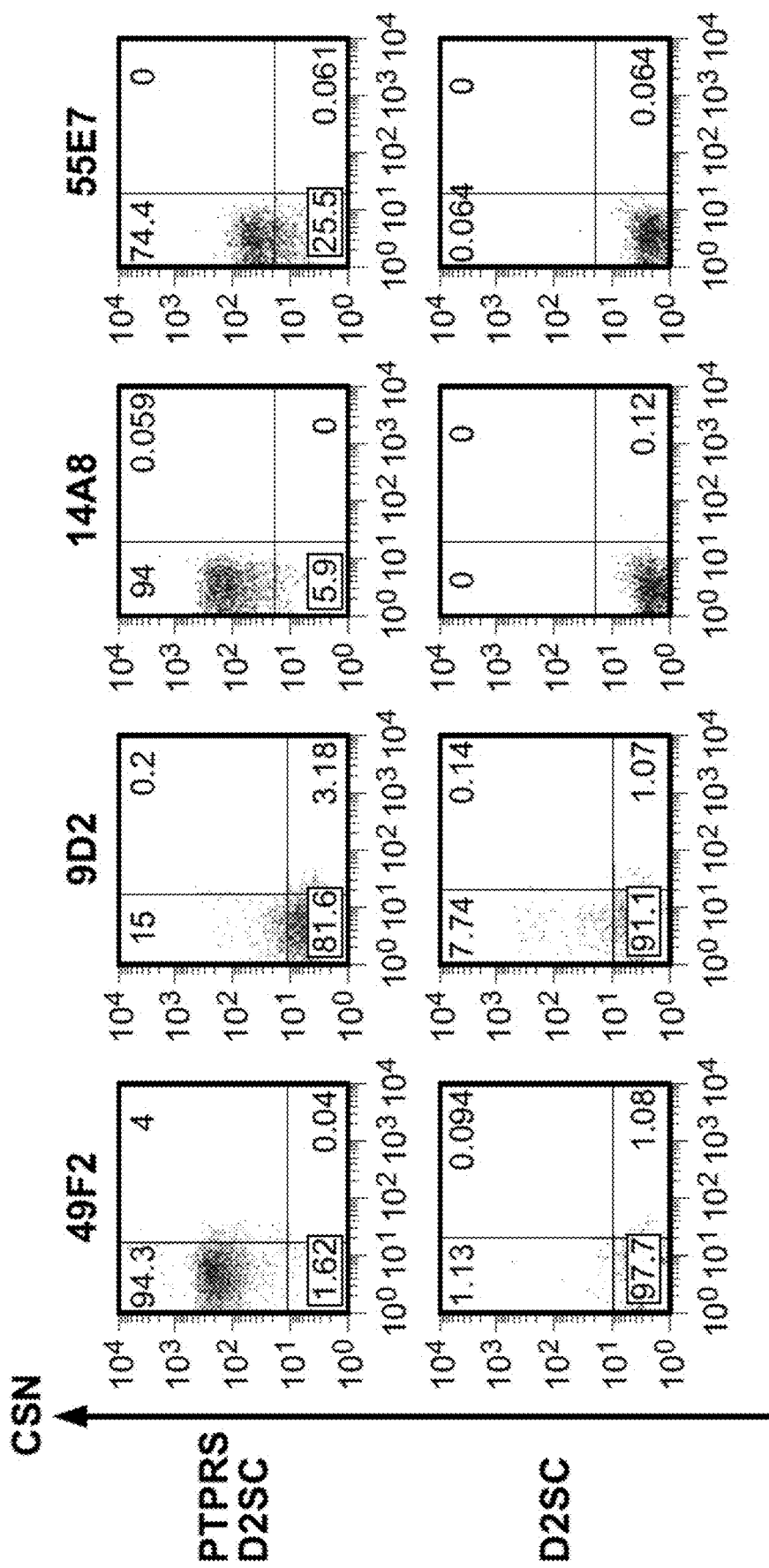
Figure 5:
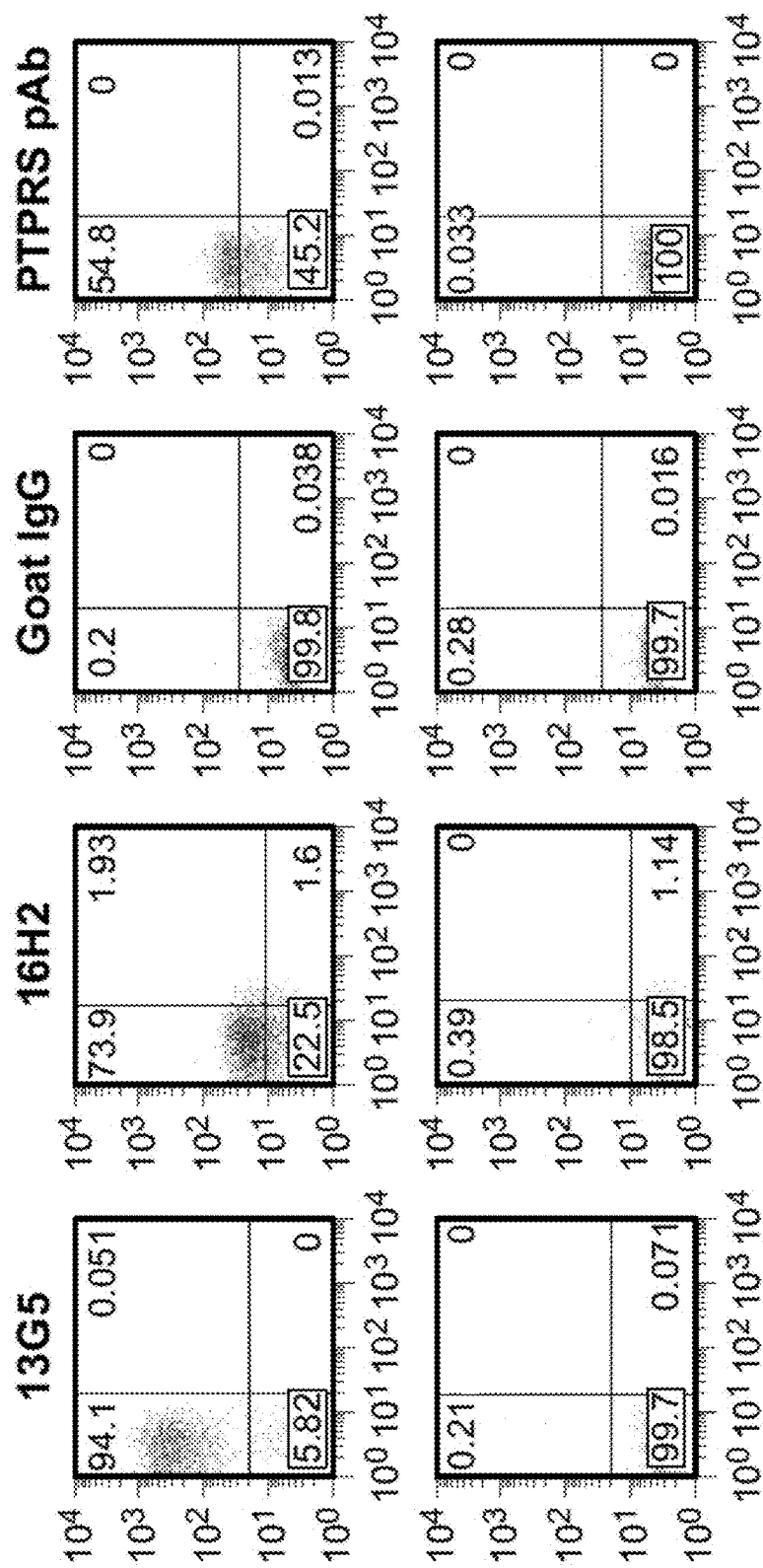

An anti-CD16/32 (2.4G2) prepared to 2.5 µg/ml was added by 504 to 3×10⁵/well of the D2SC/1 cell or hPTPRS/D2SC/1 cell to block an FC receptor. After washing with PBS, a goat IgG prepared to 10 µg/ml, a commercially available anti-hPTPRS pAb (R&D), a mouse $IgG_{2ak}$ (BioLegend) and the culture supernatant of the cultured hybridoma were added by 60 µl each, and the mixture was incubated at 4° C. for 60 minutes. After washing with PBS, a 50-fold diluted FITC-labeled anti-goat IgG antibody and a 100-fold diluted PE-labeled anti-mouse IgG antibody (BD) were added to the cells by 50 µl each, and the mixture was incubated at 4° C. for 30 minutes under light shielding. After washing with PBS, the cell was suspended in 200 µl of PBS. Data was collected by FACS Calibur (BD). The collected data was developed by dot plots of FSC and SSC to gate a living cell. The data was collected until the data of the cell in this gate reached 2,000 count. As a result, 13 hybridomas that produces an anti-hPTPRS antibody could be obtained (2G6, 28G10, 4B2, 2G2, 9H5, 10F7, 22H8, 49F2, 9D2, 14A8, 55E7, 13G5, 16H2) (FIG. 5).

A-4) FACS Screening Using CAL-1 Cell

Figure 6:
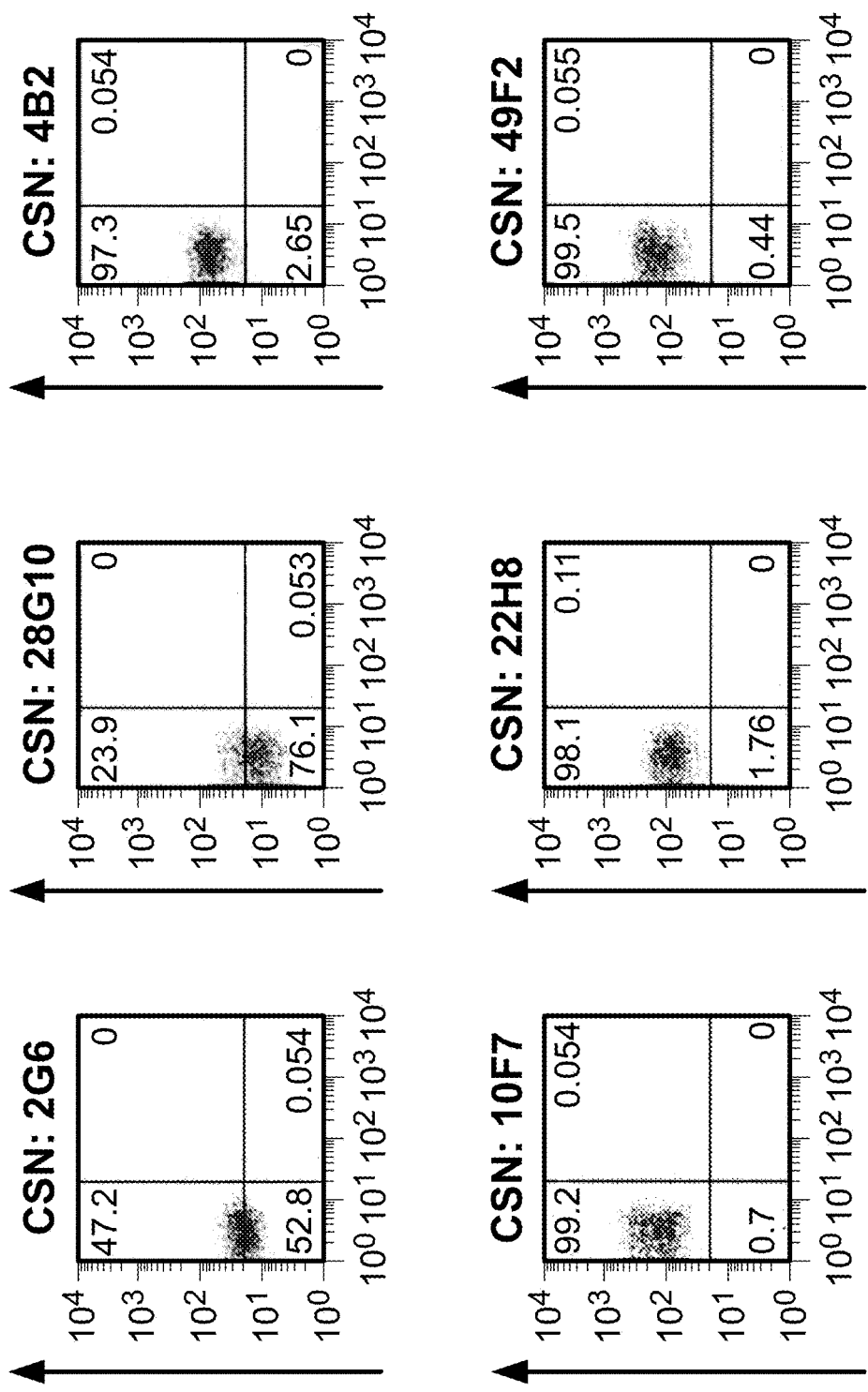
FIG. 6 shows FACS screening using CAL-1 cell.
Figure 6:
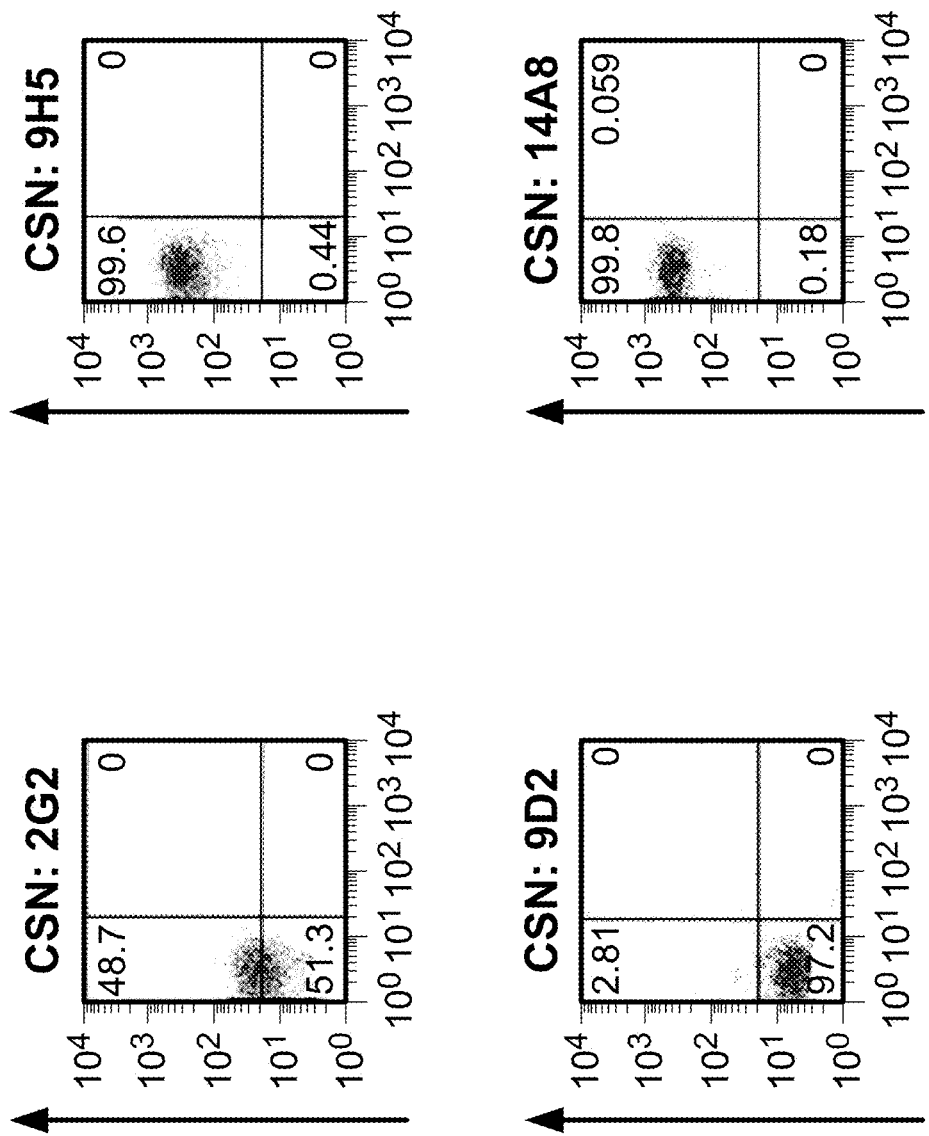
Figure 6:
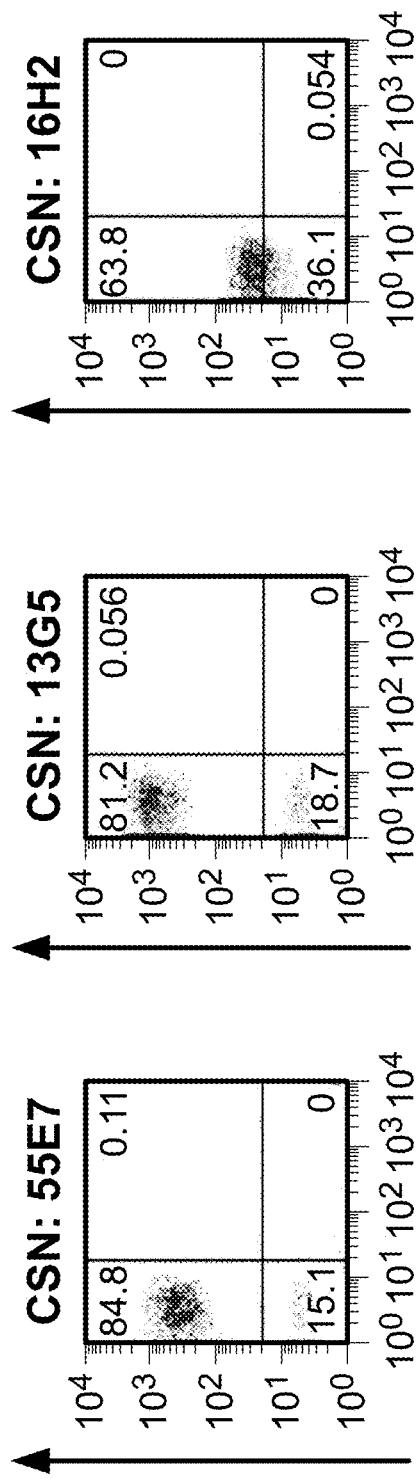
Figure 6:
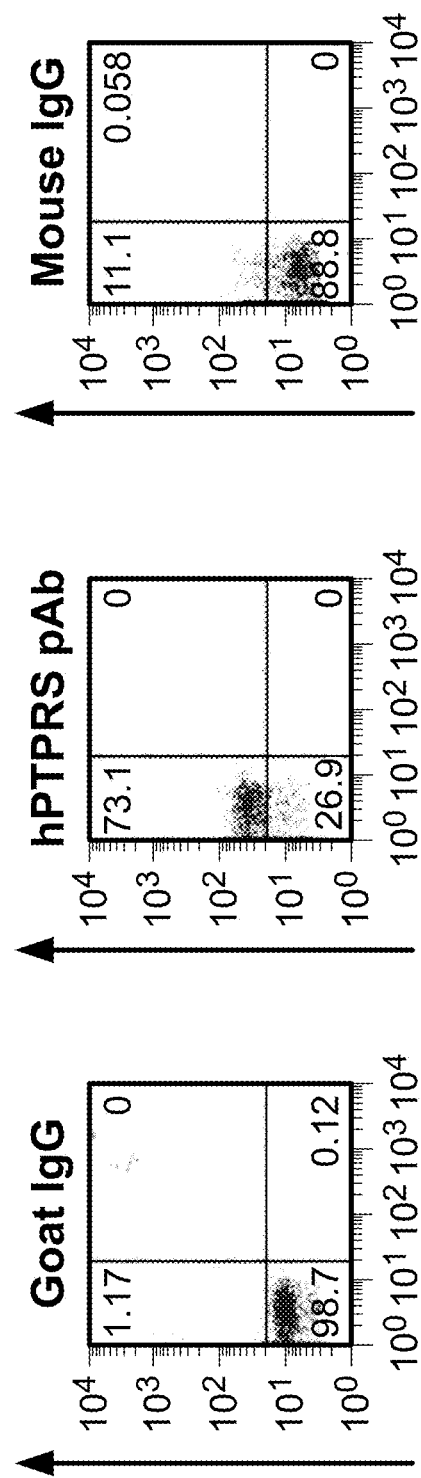

3×10⁵ of a human pDC-like cell strain CAL-1 cells were stained in 50 µl of the culture supernatant of the above-mentioned each hybridoma for 15 minutes at 4° C. The cells were washed once with FACS buffer (1% FBS+PBS) and then centrifuged to remove the supernatant. 2 µg/ml of a PE-labeled anti-mouse IgG antibody was then reacted at 4° C. for 20 minutes. The cells were washed once with an FACS buffer and centrifuged. The cell pellet was re-suspended by an FACS buffer and analyzed by Calibur. As a result, 2G6, 4B2, 2G2, 9H5, 10F7, 22H8, 49F2, 14A8, 55E7, 13G5 and 16H2 in the hybridoma culture supernatant reacted well with CAL-1. On the other hand, 28G10 and 9D2 reacted little (FIG. 6).

A-5) FACS Screening Using Human Peripheral Blood pDC

[Isolation of Human PBMC]

Figure 7:
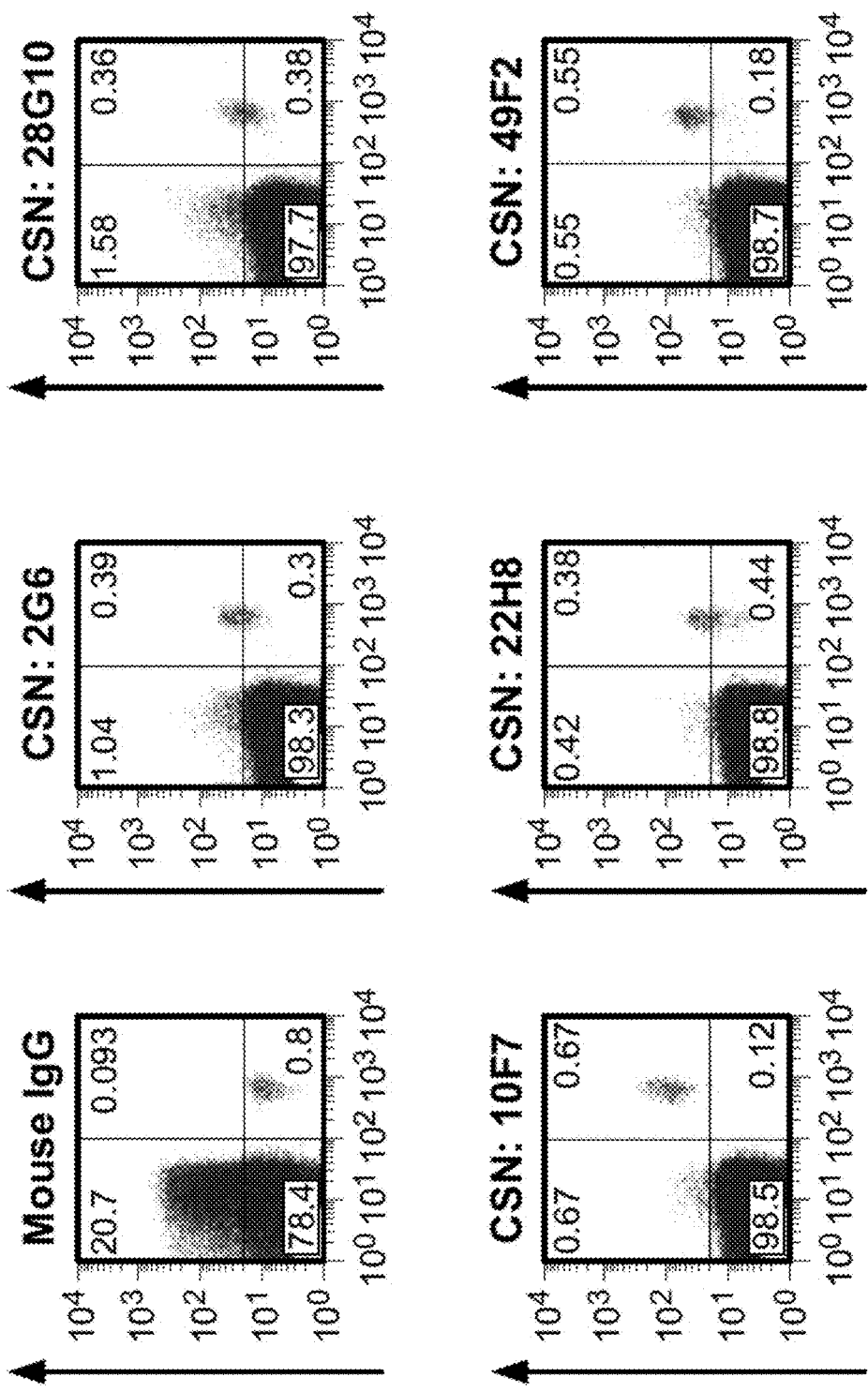
FIG. 7 shows FACS screening using human peripheral blood pDC.
Figure 7:
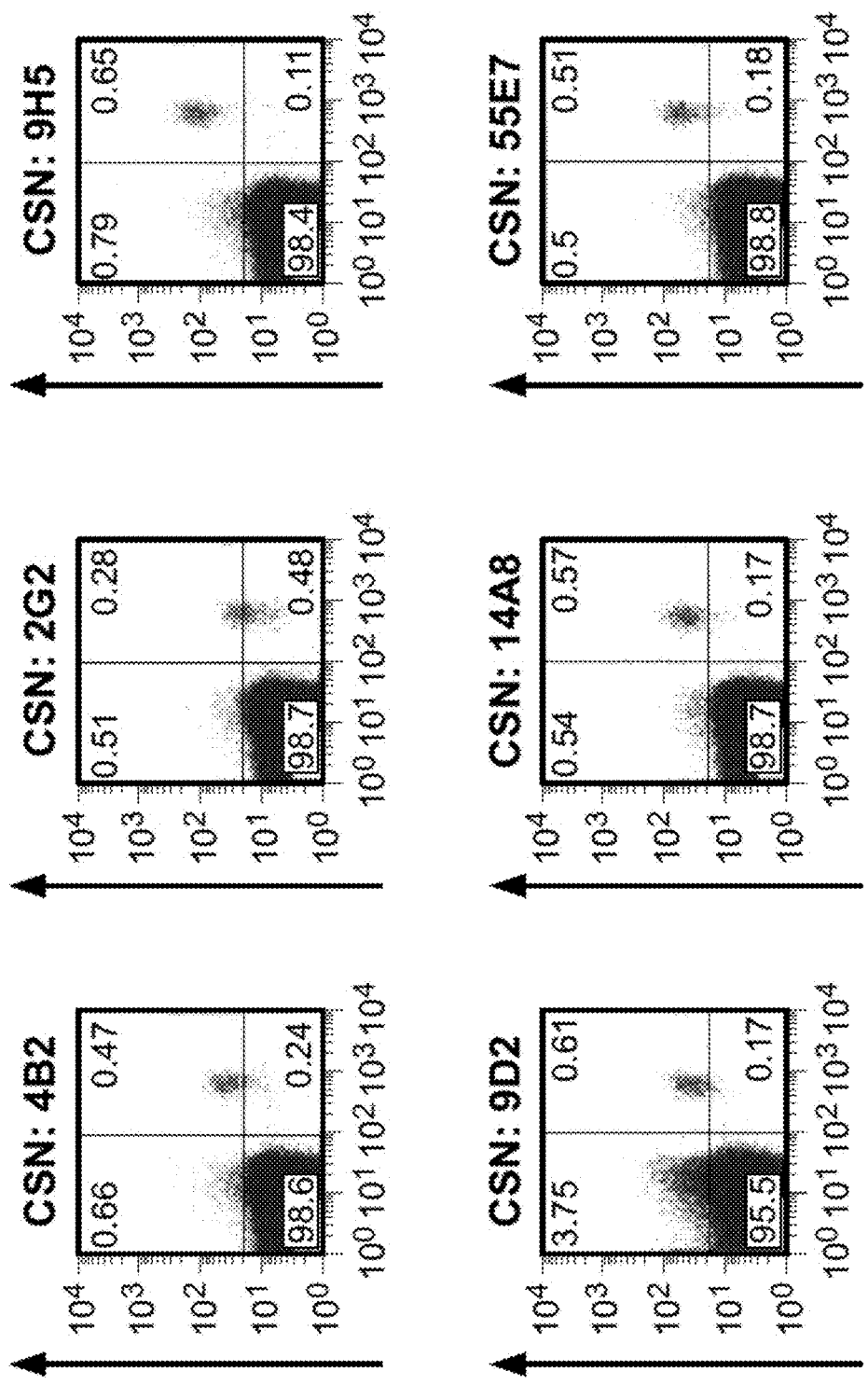
Figure 7:
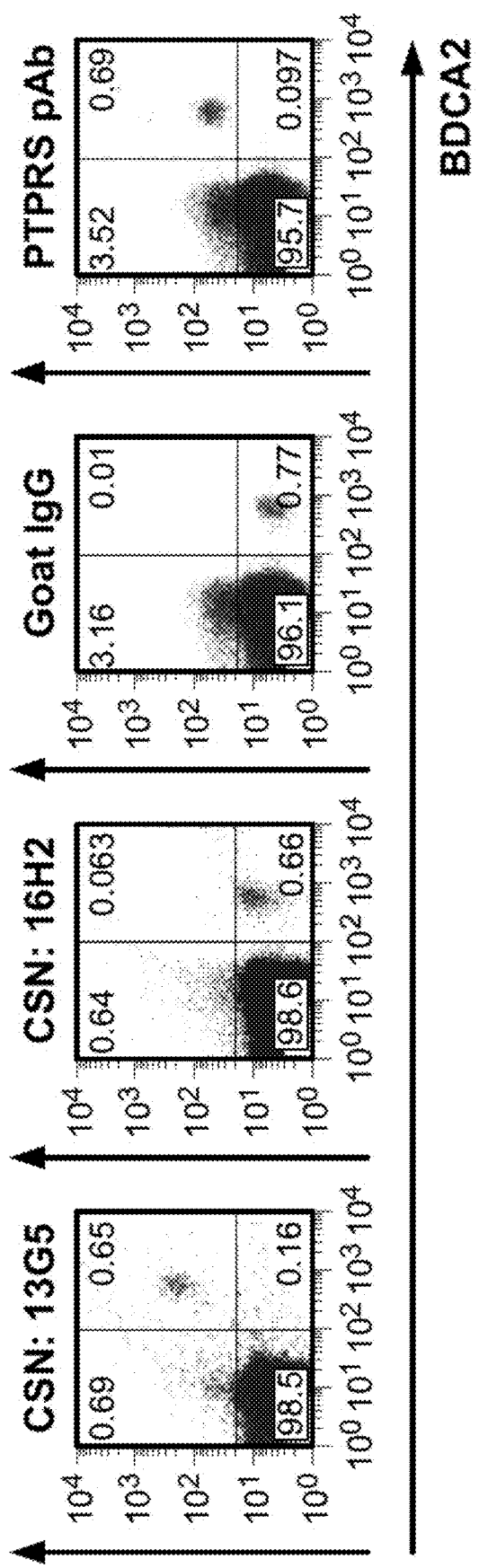

20 ml of peripheral blood was collected from a healthy human, and peripheral blood mononuclear cells (PBMCs) were isolated by specific gravity centrifugation using HIS-TOPAQUE-1077 (SIGMA). 1×10⁶ of PBMCs were stained with each sample. The cells were washed with an FACS buffer, a Fc block reagent (Miltenyi) was added by 25 µl by 5-fold dilution, and a reaction was done at 4° C. for 15 minutes. After washing with an FACS buffer, 50 µl of the cell culture supernatant of each hybridoma, 10 µg/ml of a goat IgG, an anti-hPTPRS pAb and a mouse IgG2a,κ were added, and a reaction was done at 4° C. for 20 minutes. After washing with an FACS buffer, 8 µg/ml of an FITC-labeled anti-goat IgG antibody or 2 µg/ml of a PE-labeled anti-mouse IgG antibody was added, and a reaction was done at 4° C. for 20 minutes. After washing with an FACS buffer, 50 µl of an APC-labeled anti-BDCA2 antibody by 10-fold dilution was reacted at 4° C. for 20 minutes. After washing with an FACS buffer, the cell was resuspended in 300 µl of a FACS buffer and analyzed by FACS calibur. As a result, 2G6, 28G10, 4B2, 2G2, 9H5, 10F7, 22H8, 49F2, 14A8, 55E7 and 13G5 showed a binding reaction specific to the pDC cell population. 9D2 showed binding to pDC, and also showed reactions with the cell group other than pDC (BDCA2-). 16H2 did not show a reaction for PBMCs (FIG. 7).

Test on Specificity of Anti-PTPRS Antibody

PTPRS belongs to the PTPR family, and the amino acid sequences of the several family molecules therefrom have high homology against the amino acid sequence of PTPRS (FIG. 8).

Figure 9A:
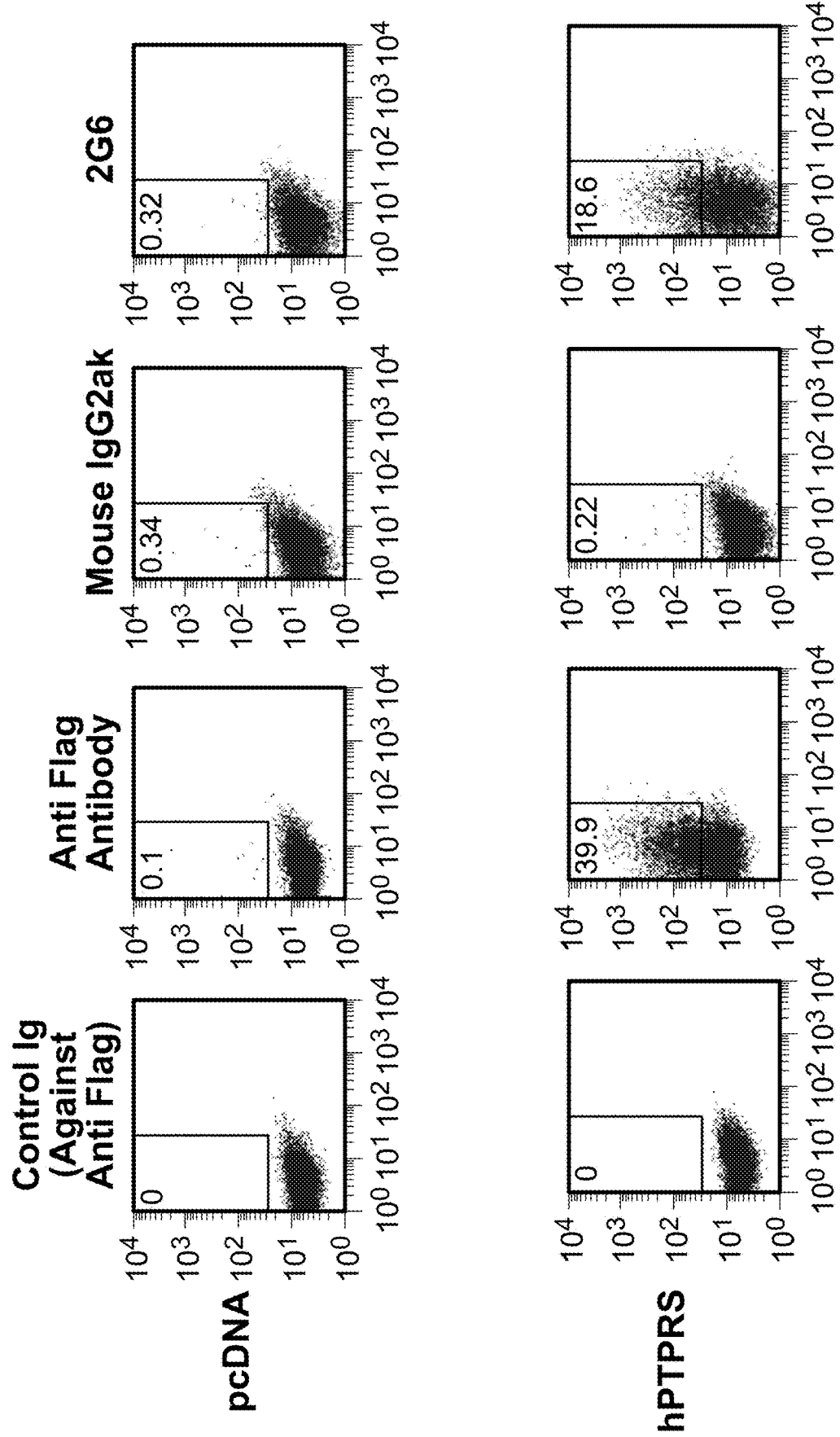
FIGS. 9A-9D are the test results showing whether or not the ten kinds of hybridoma cell culture supernatants (2G6, 4B2, 2G2, 9H5, 10F7, 22H8, 49F2, 14A8, 55E7, 13G5) that recognize PTPRS and produce an antibody that specifically binds to human pDC specifically bind to only PTPRS (hPTPRE did not express on the cellular surface). As a result thereof, 2G6 showed cross-reactivity with PTPRF (FIG. 9D), and 4B2 showed cross-reactivity with PTPRD (FIG. 9C). Other 9 kinds of antibodies showed PTPRS-specific binding (FIGS. 9A-D)
Figure 9A:
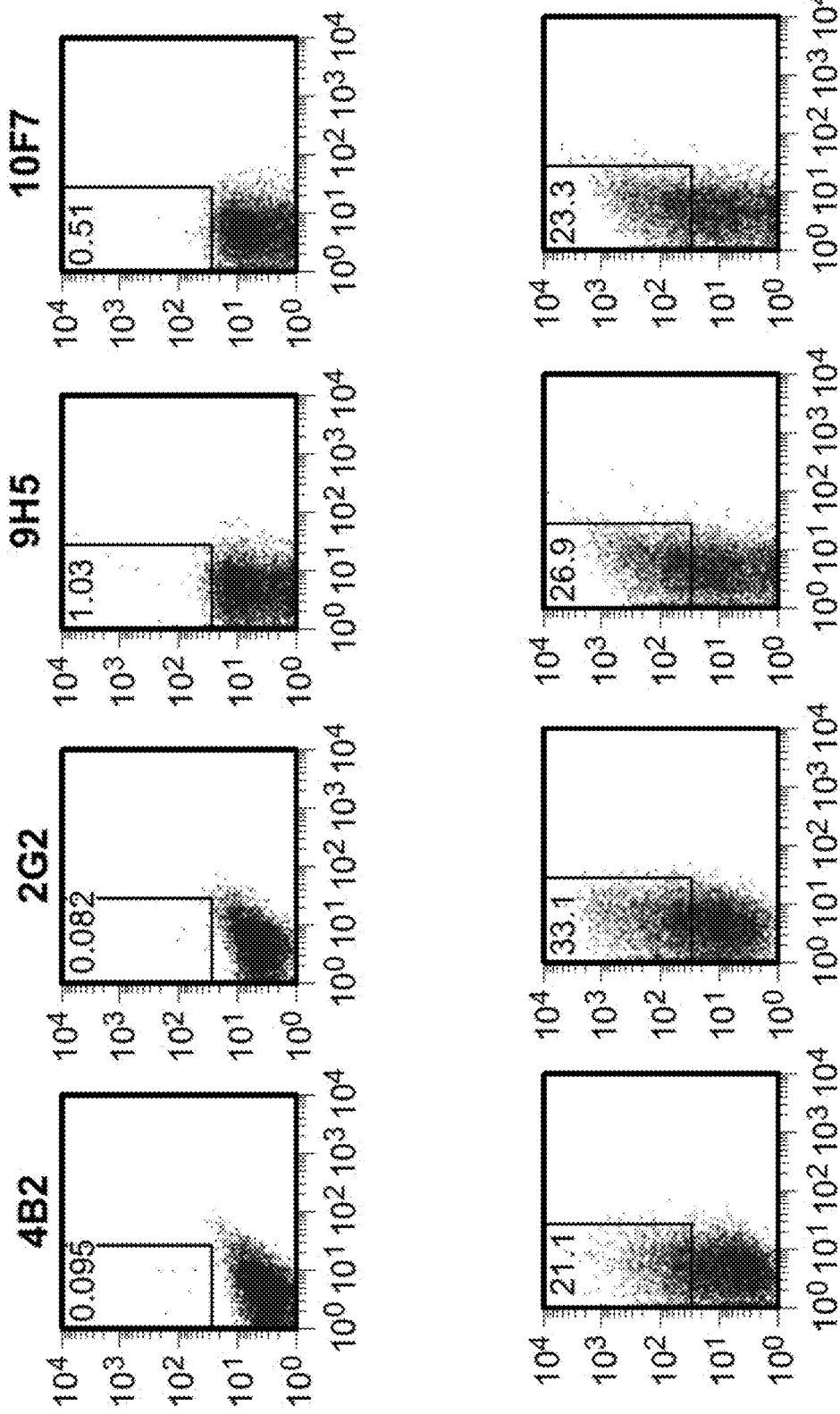
Figure 9A:
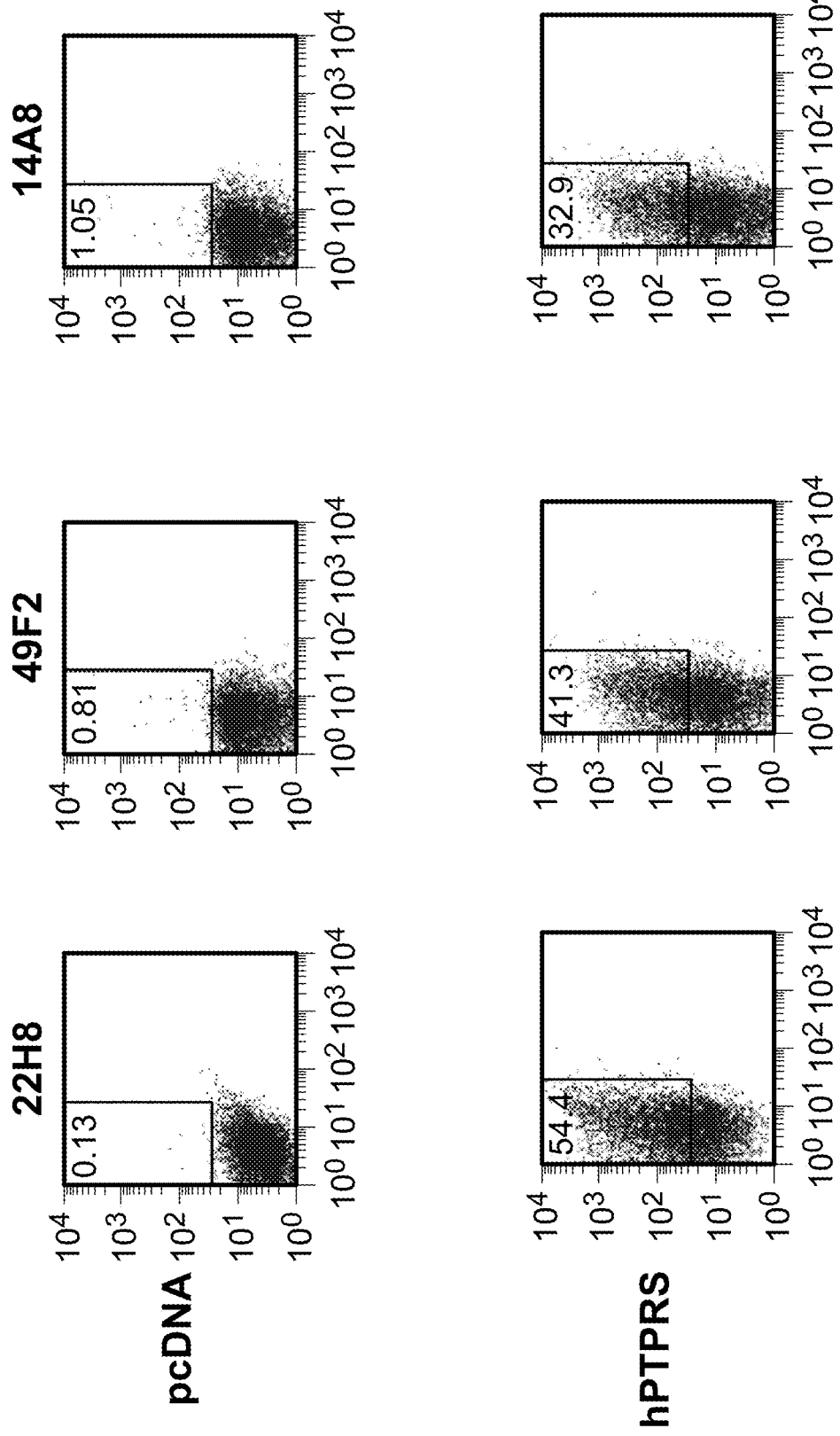
Figure 9A:
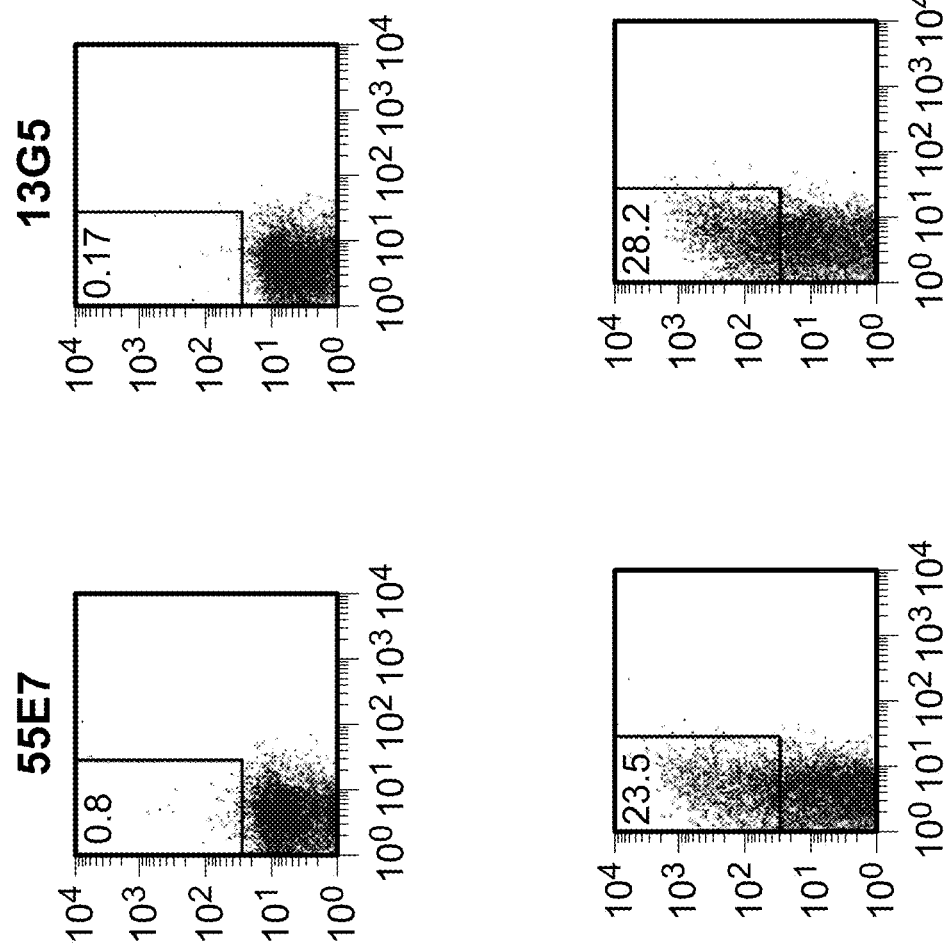
Figure 9B:
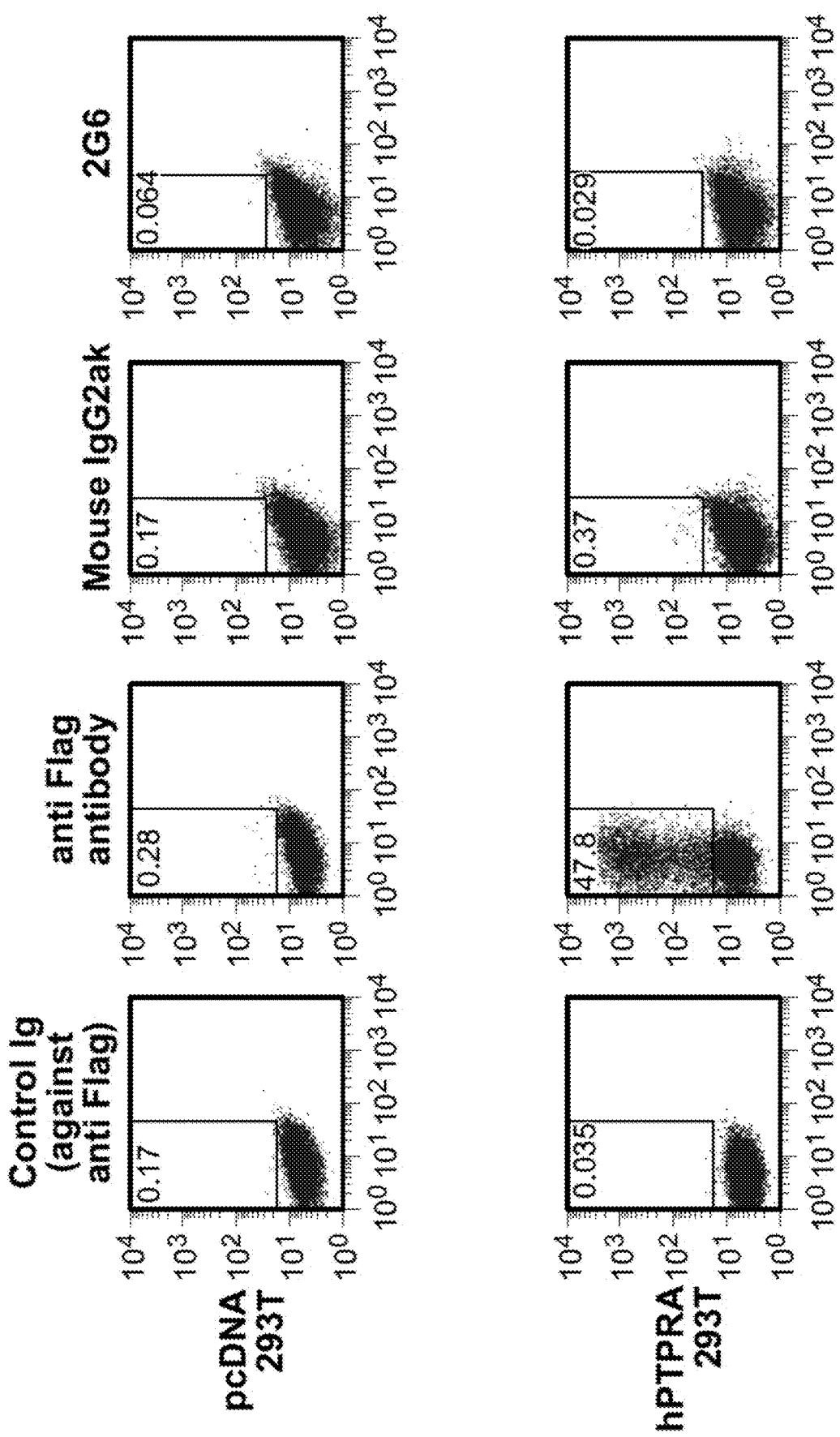
Figure 9B:
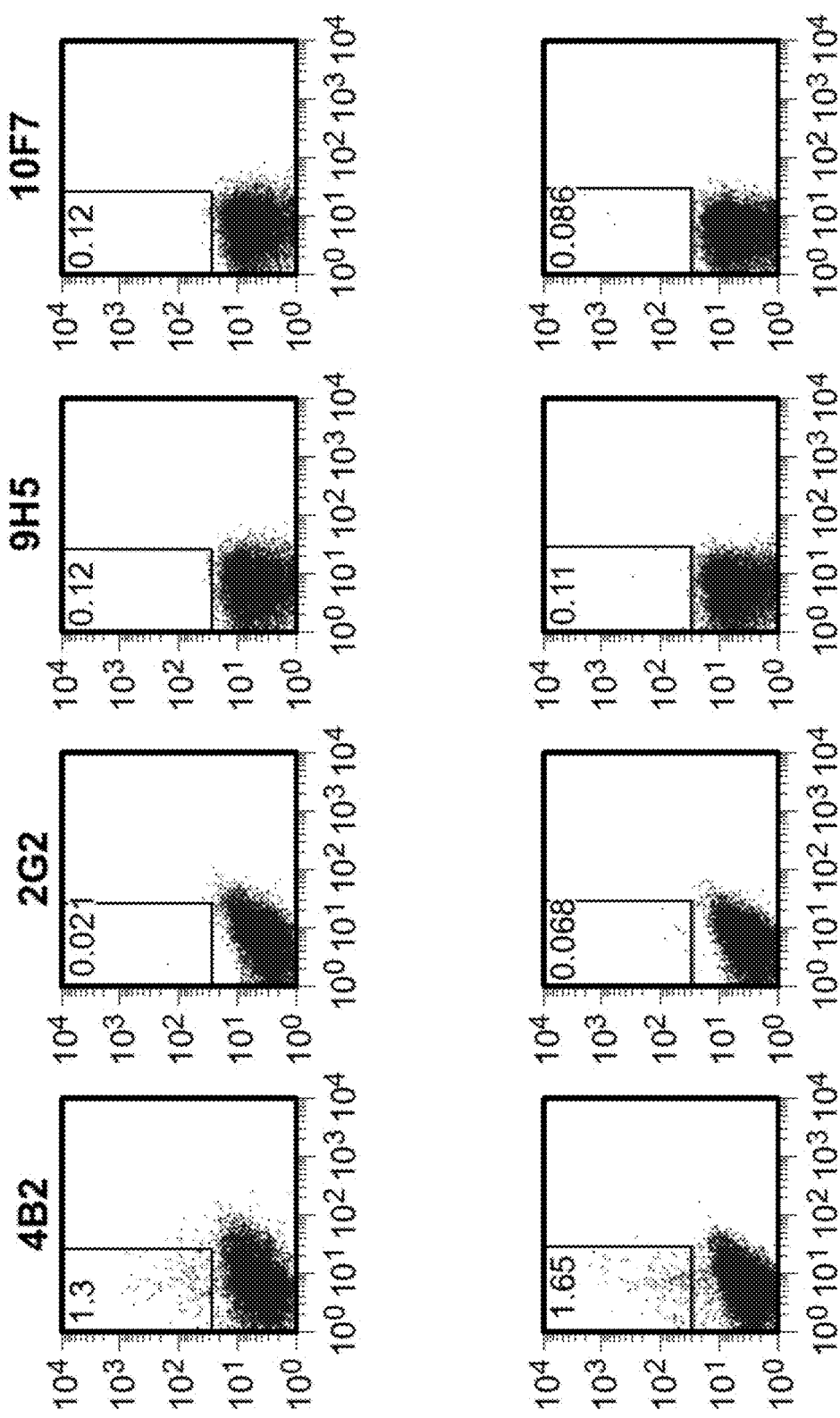
Figure 9B:
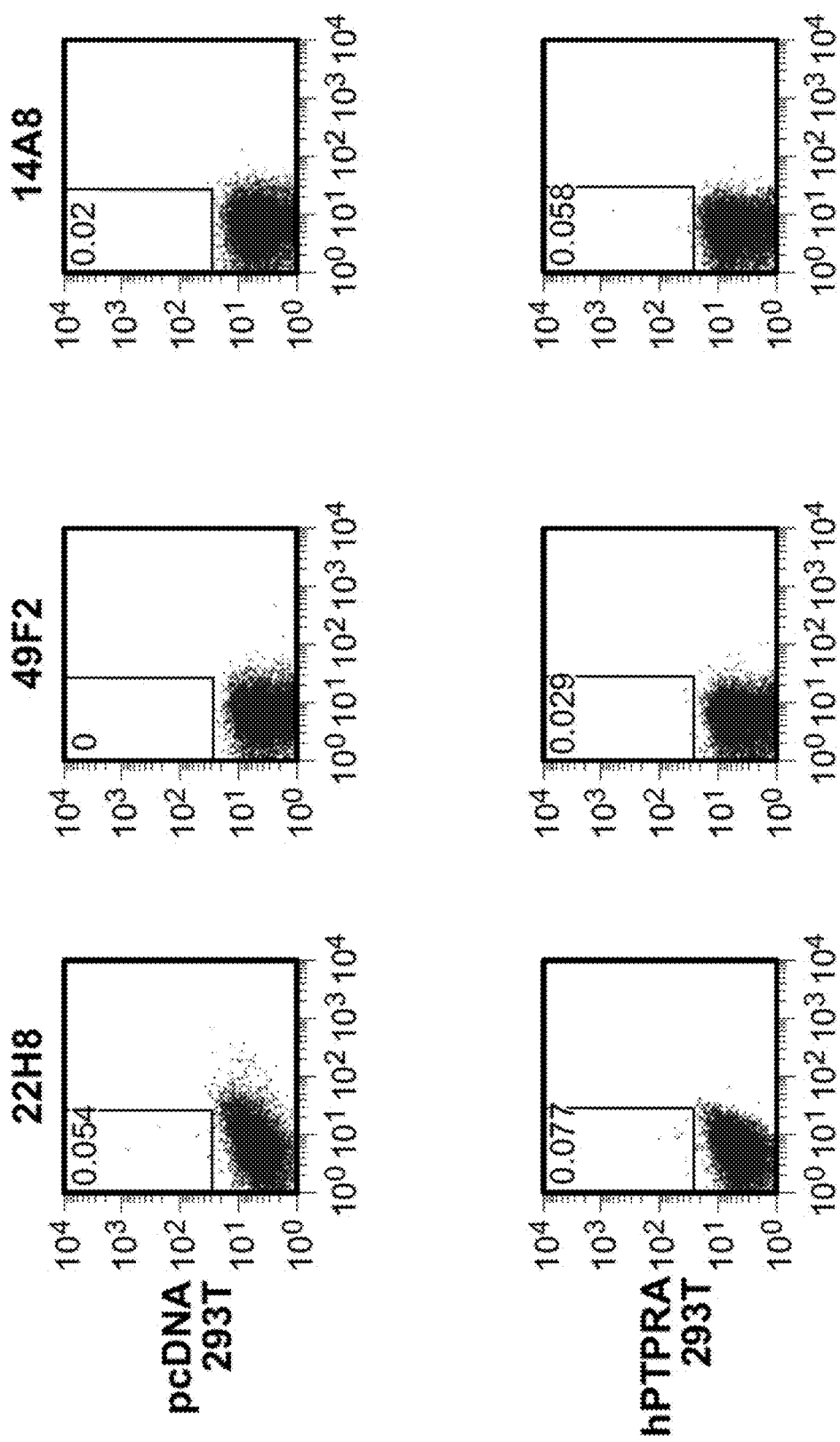
Figure 9B:
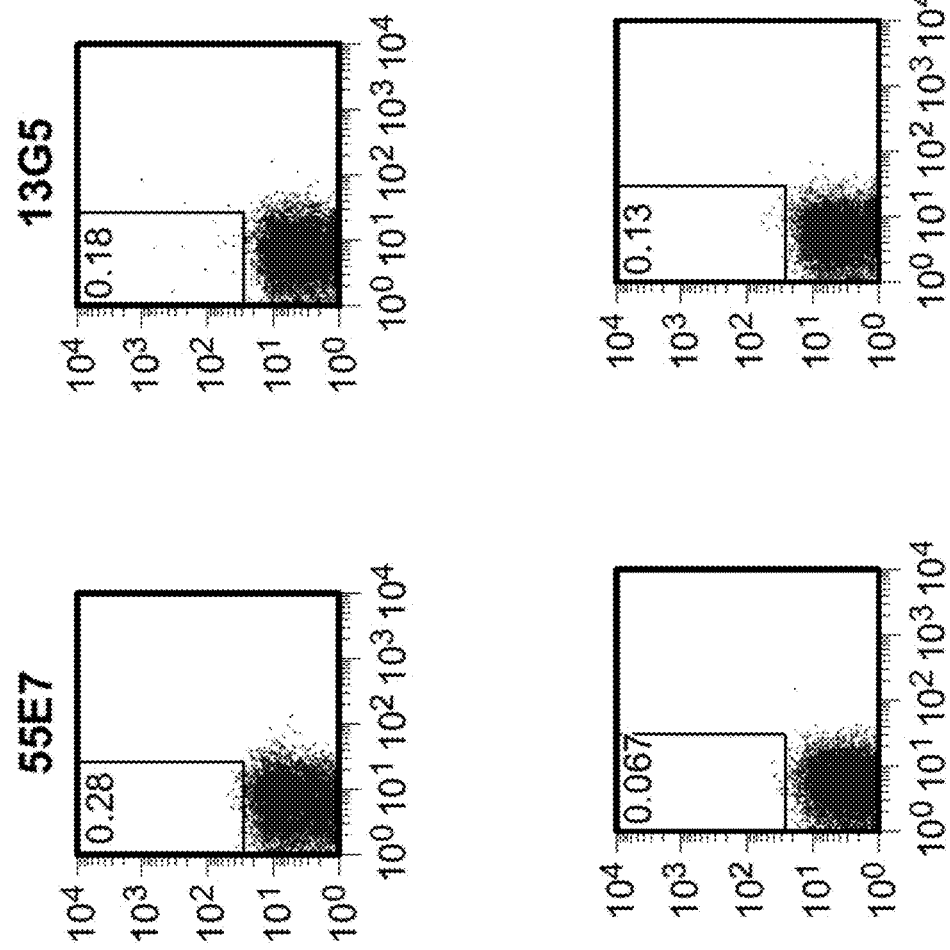
Figure 9C:
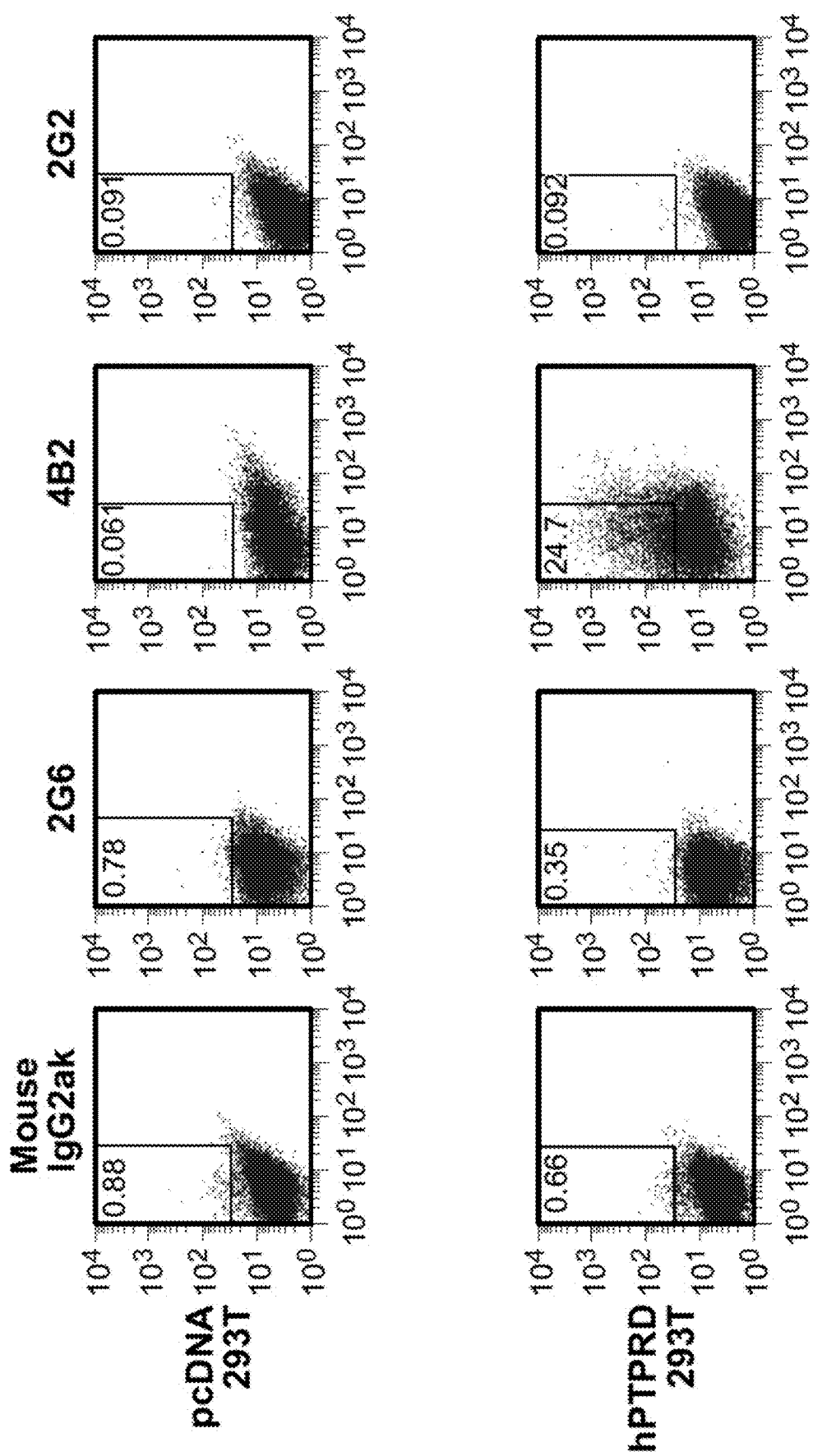
Figure 9C:
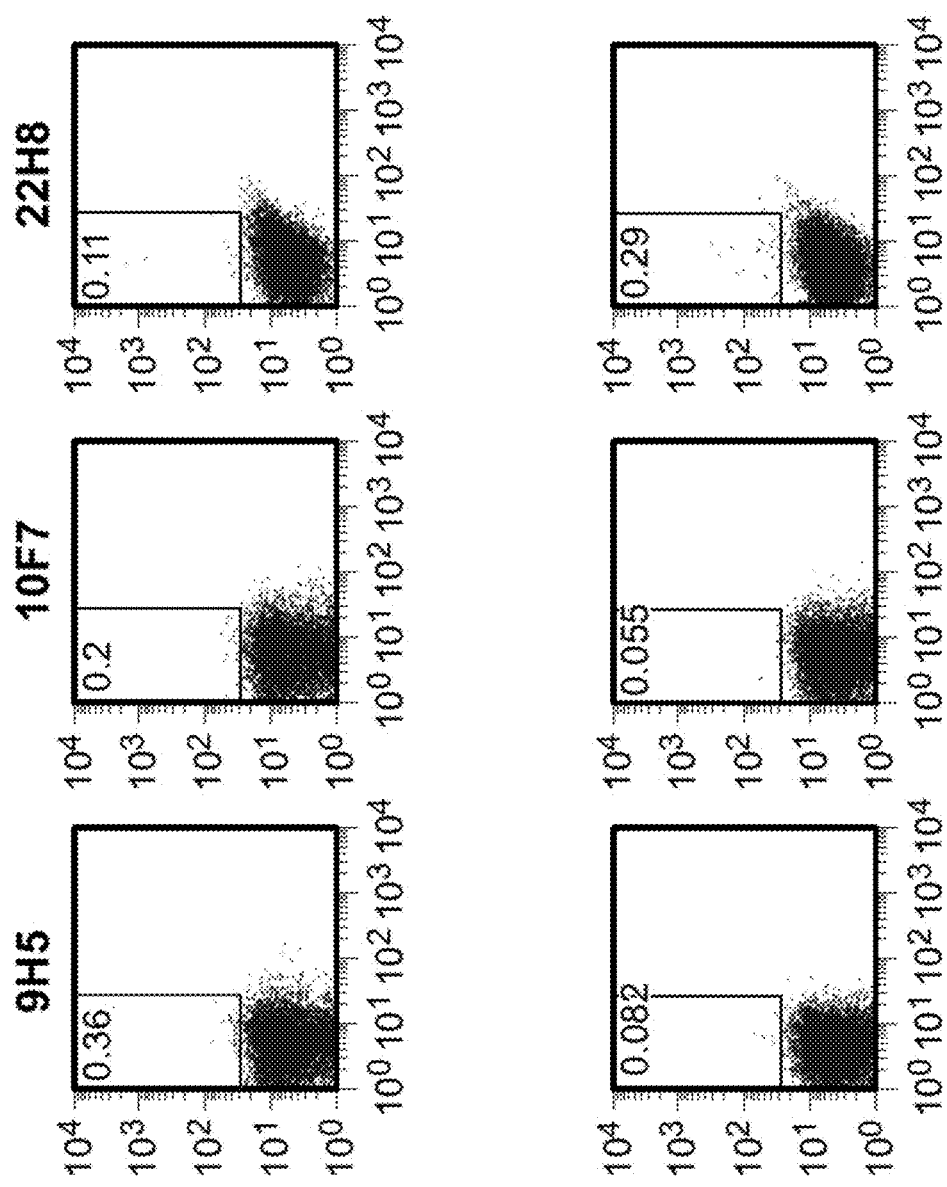
Figure 9C:
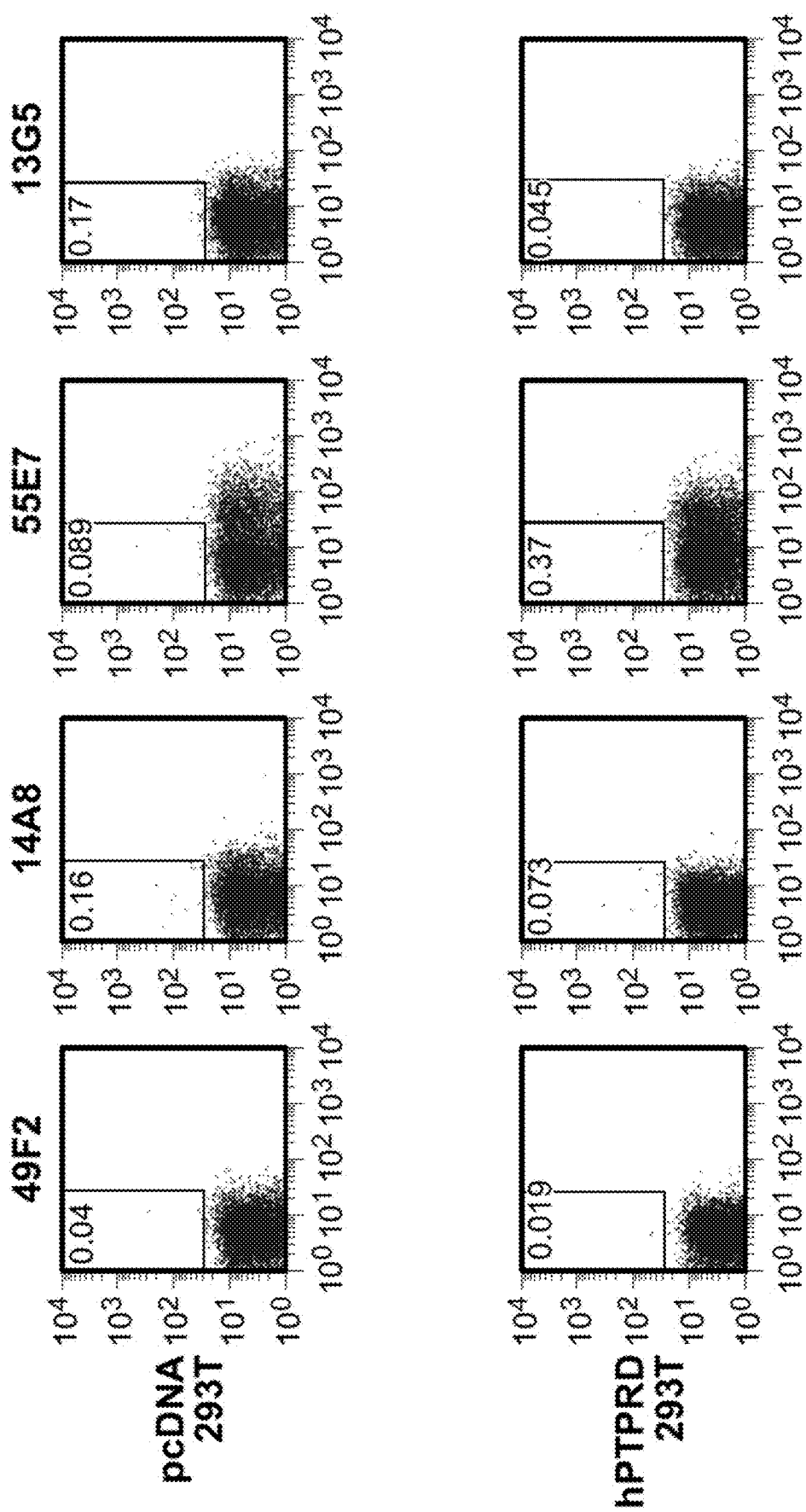
Figure 9D:
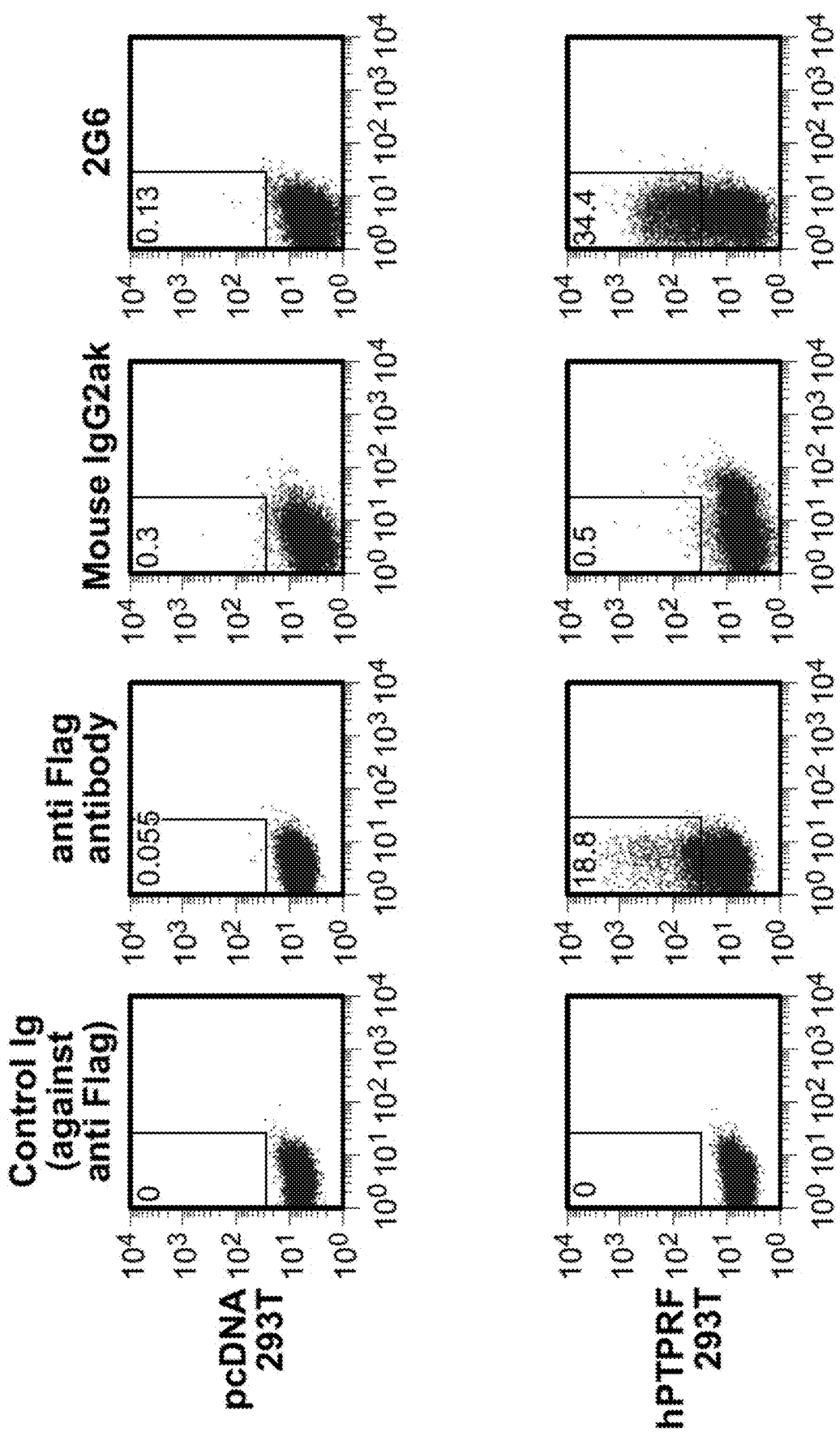
Figure 9D:
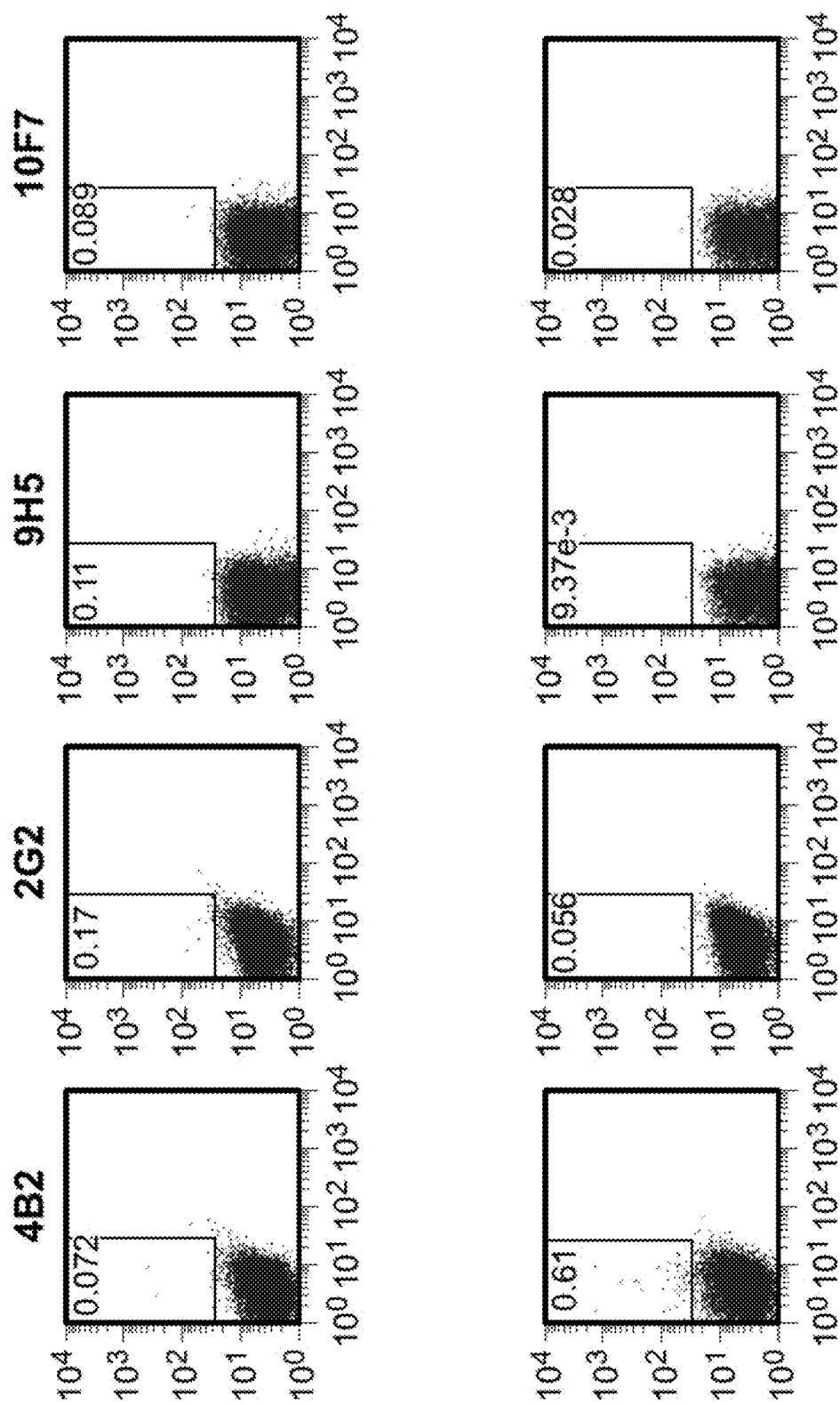
Figure 9D:
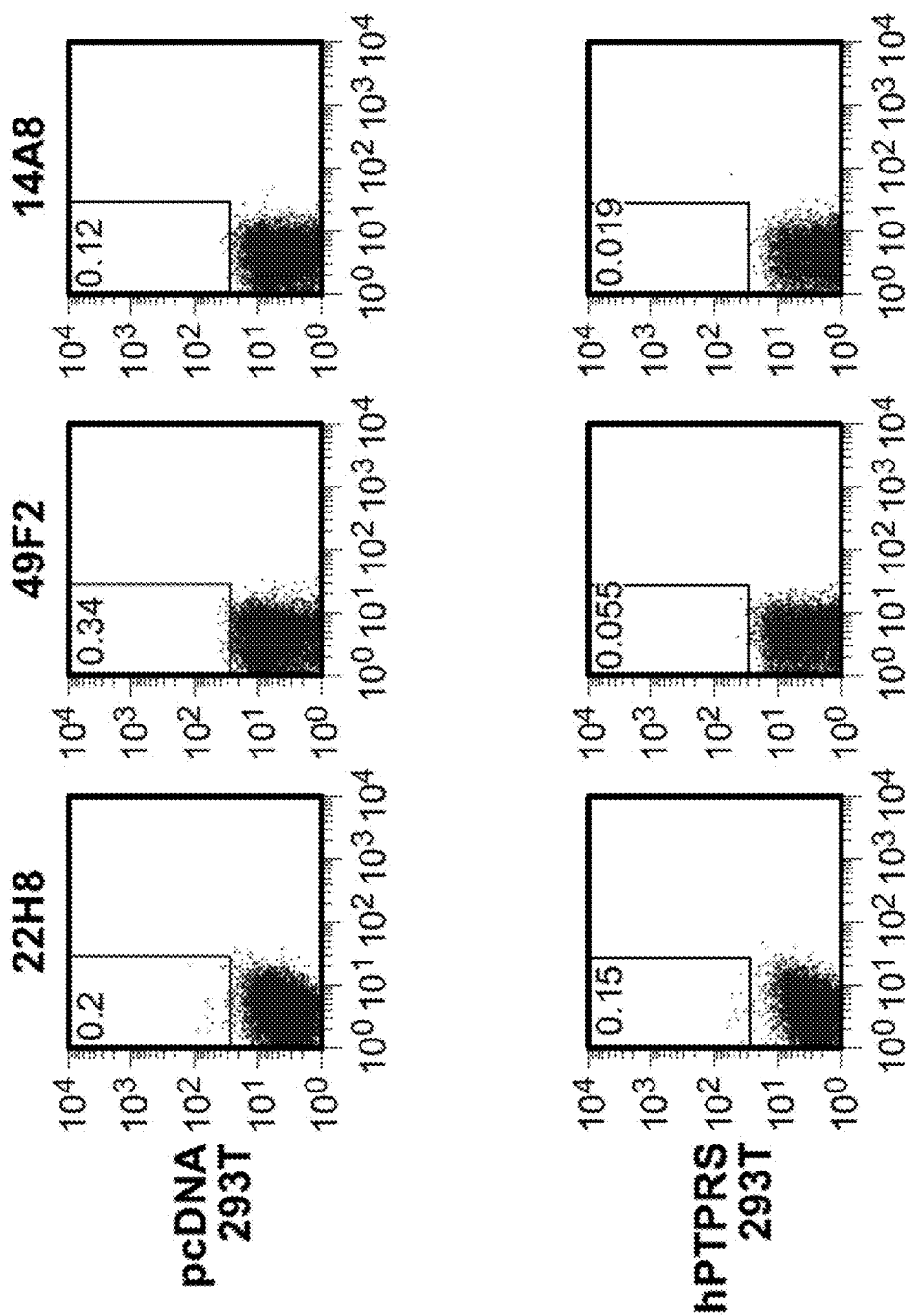
Figure 9D:
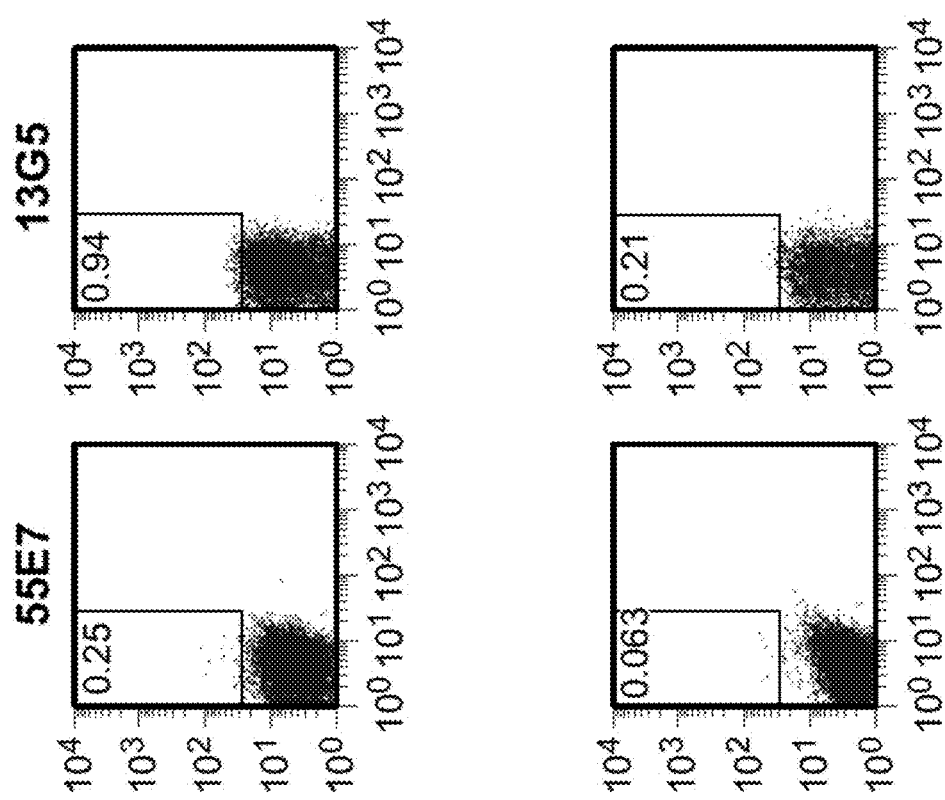

A-6) Whether or not the 10 kinds of hybridoma cell culture supernatants that generate an antibody that recognizes PTPRS and specifically binds to human pDC (2G6, 4B2, 2G2, 9H5, 10F7, 22H8, 49F2, 14A8, 55E7, 13G5) specifically binds to only PTPRS was examined. The transfected cells of PTPRA (40%), PTPRD (76%) and PTPRF (67%) that had specifically high homology with PTPRS were prepared by expressing an FLAG tag to the N terminus of the molecule, and stained. The expression of hPTPRE in the transfected cells was confirmed by Western Blot, but expression on the cellular surface could not be confirmed. Therefore, hPTPRE did not express on the cellular surface. As a result, 4B2 reacted with hPTPRD (FIG. 9C), and 2G6 showed cross-reactivity to hPTPRF (FIG. 9D). Other 8 kinds of antibodies showed PTPRS-specific binding (FIGS. 9A-D).

A-7) Cross-Reactivity of Anti-PTPRS Antibody to Monkey

Figure 10:
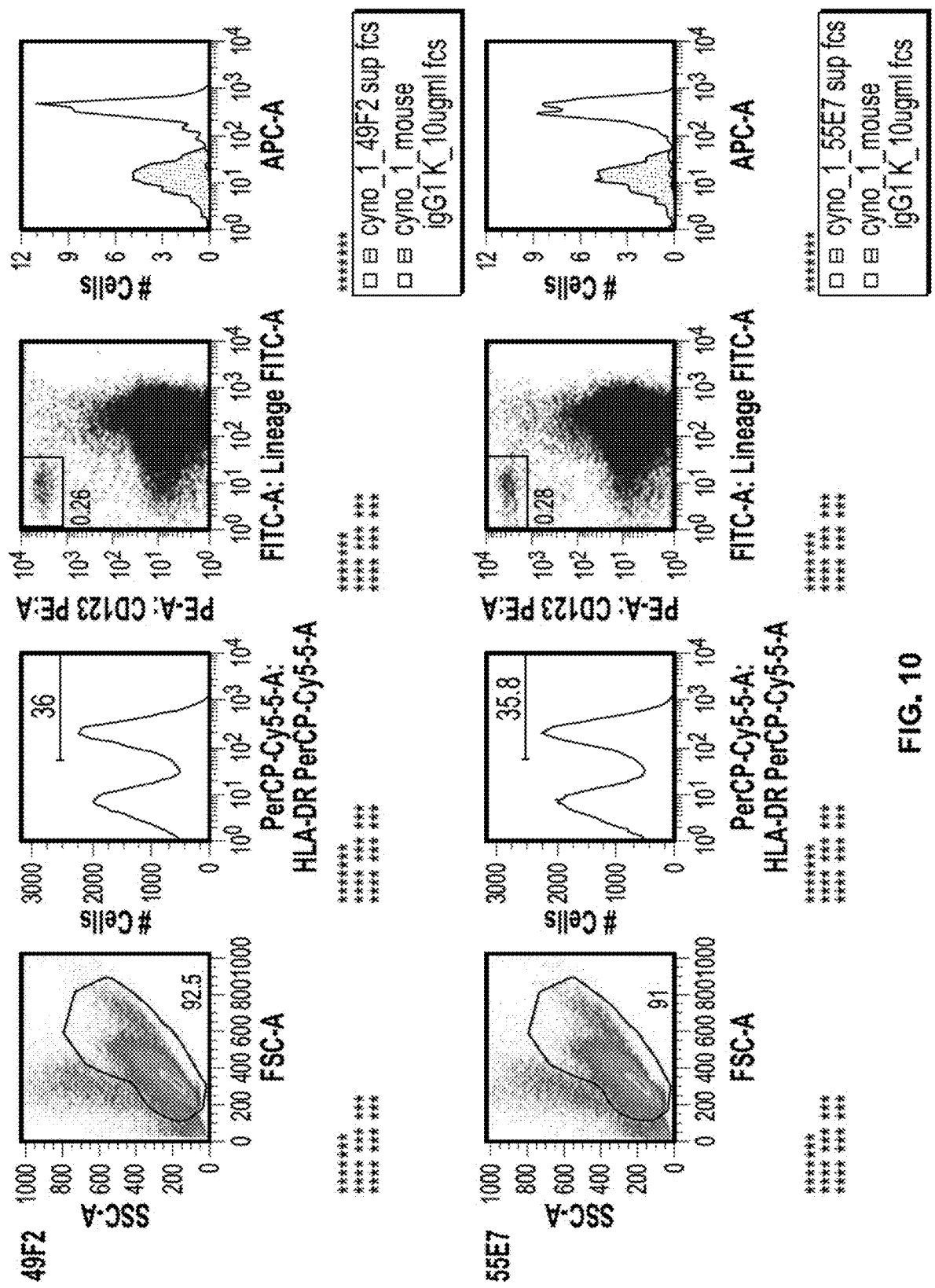
FIG. 10 is the test result of the cross-reactivity of the anti-PTPRS antibody with a monkey. All hybridoma cell culture supernatants specifically bonded to the pDC cell group (Lineage-CD123+ HLA-DR+) of a cynomolgus monkey.
Figure 10:
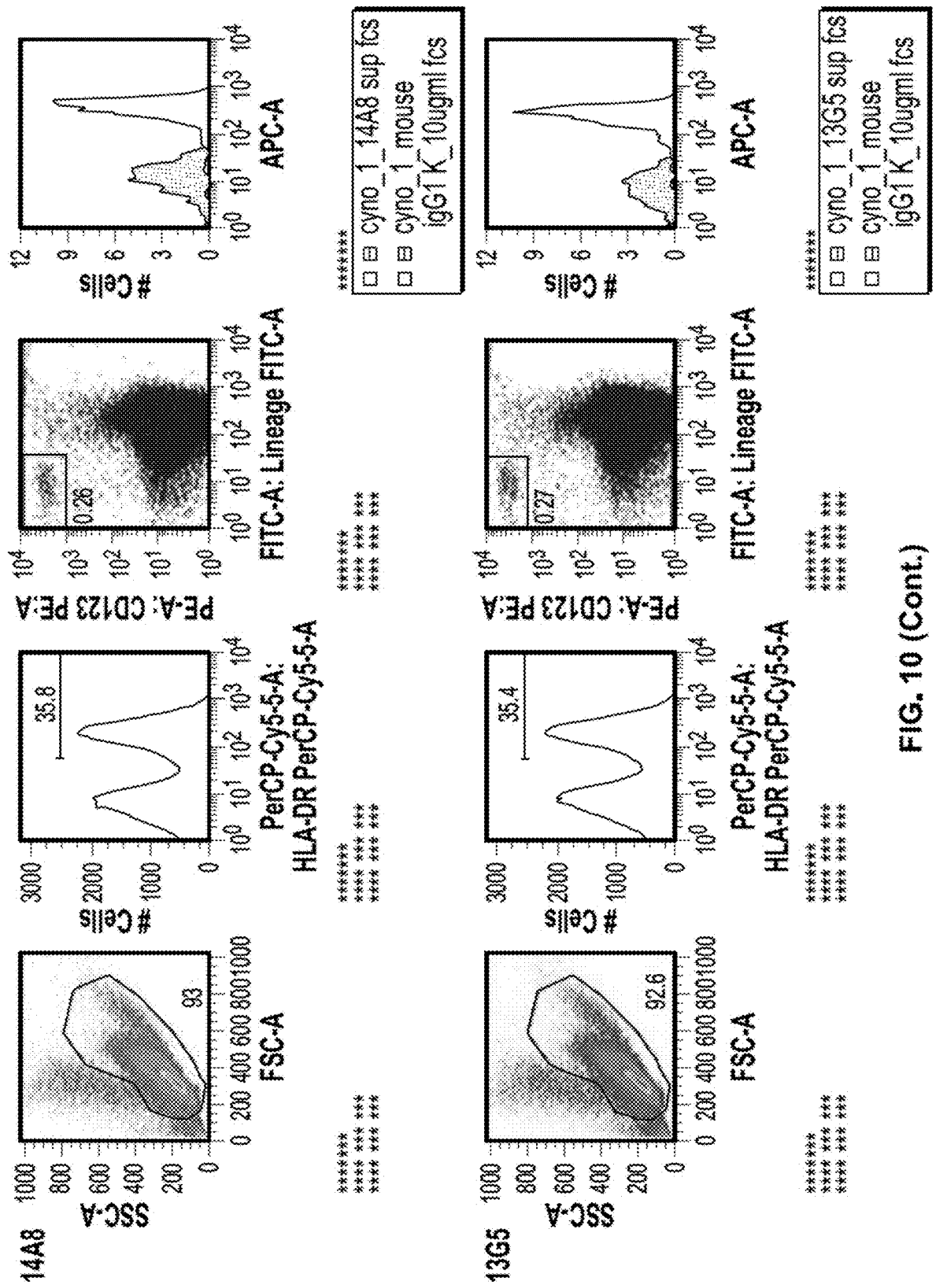
Figure 10:
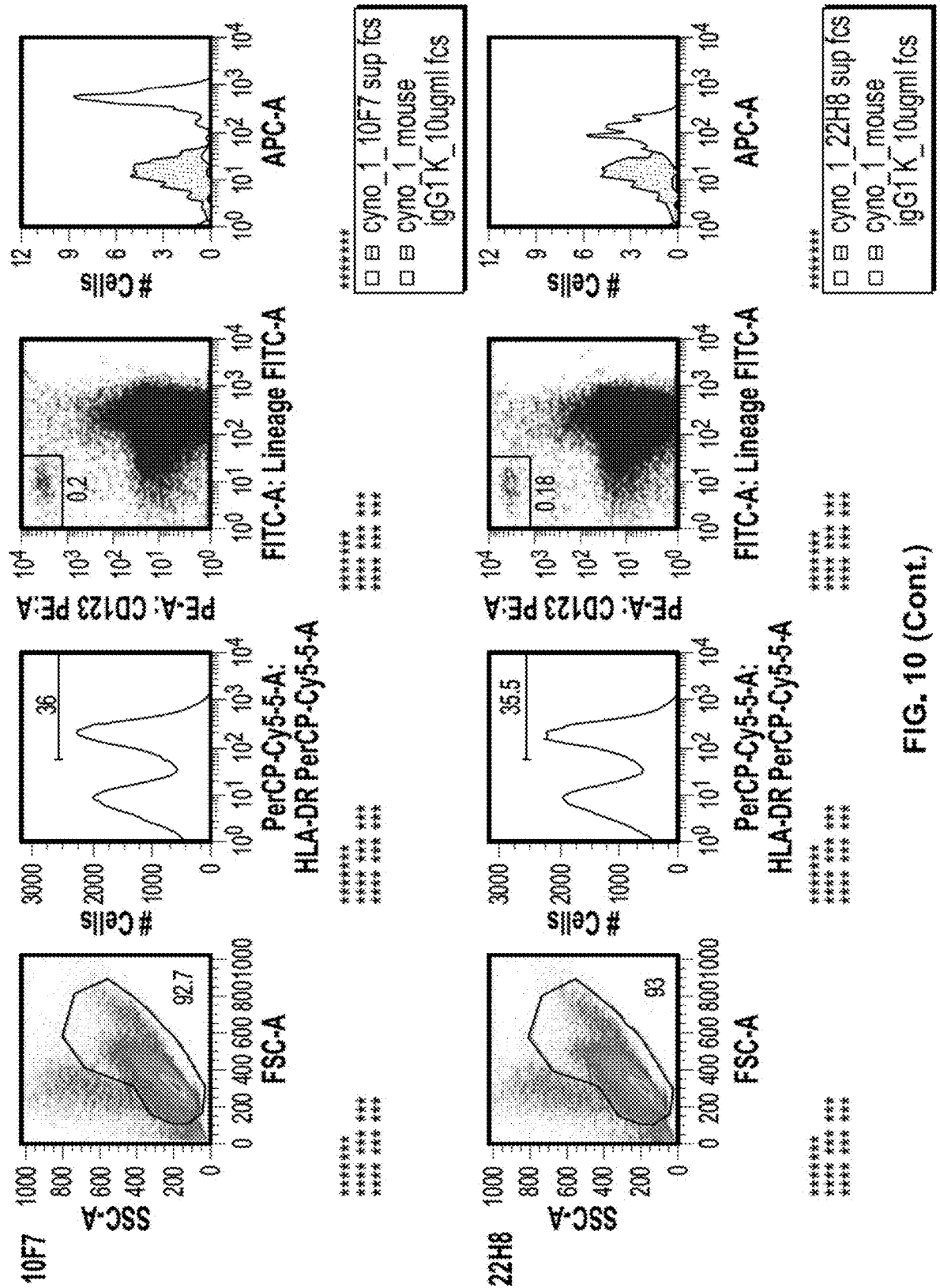
Figure 10:
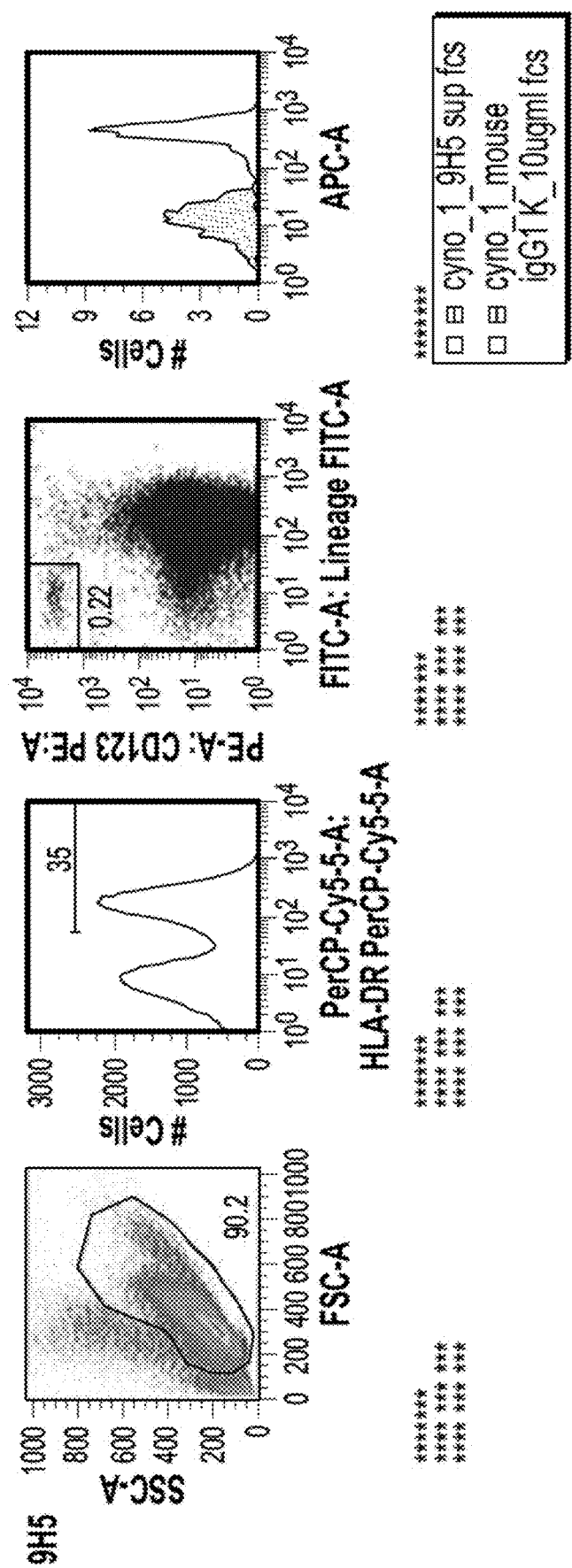

PBMCs of a cynomolgus monkey were isolated from peripheral blood (10 ml; Shin-Nippon Biomedical Laboratories, Ltd.) by specific gravity centrifugation using HIS-TOPAQUE-1077 (SIGMA). For FACS, $5 \times 10^5$ cells were used per one sample. The cells were washed with a FACS buffer, and 10 μl of 10% cynomolgus serum diluted with a FACS buffer was added thereto, and a reaction was conducted at 4° C. for 20 minutes. After washing with a FACS buffer, 100 μl of the cell culture supernatant of each hybridoma and 10 μg/ml of a mouse IgG2a,κ or mouse IgG1, κ (BioLegend) were added, and a reaction was conducted at 4° C. for 15 minutes. After washing with a FACS buffer, 1 μg/ml of an APC-labeled anti-mouse IgG antibody (BD) was added, and a reaction was conducted at 4° C. for 20 minutes. After washing with a FACS buffer, an FITC-labeled anti-Lineage1 antibody (BD), a PE-labeled anti-CD123 antibody (BD), and a PerCP7Cy5.5-labeled anti-HLA-DR antibody (BD) by 25 μl by 10-fold dilution were reacted at 4° C. for 15 minutes. After washing with a FACS buffer, the cells were resuspended in 300 μl of an FACS buffer and analyzed by FACS calibur. As the hybridoma culture supernatants used, 7 kinds: 49F2, 55E7, 14A8, 13G5, 10F7, 22H8 and 9H5 that are PTPRS-specific and bind well to a CAL-1 cell and human pDC were selected. As a result, all hybridoma cell culture supernatants specifically bound to the pDC population group (Lineage-CD123+HLA-DR+) of the cynomolgus monkey (FIG. 10).

A-8) Singlization of Hybridoma

Figure 11A:
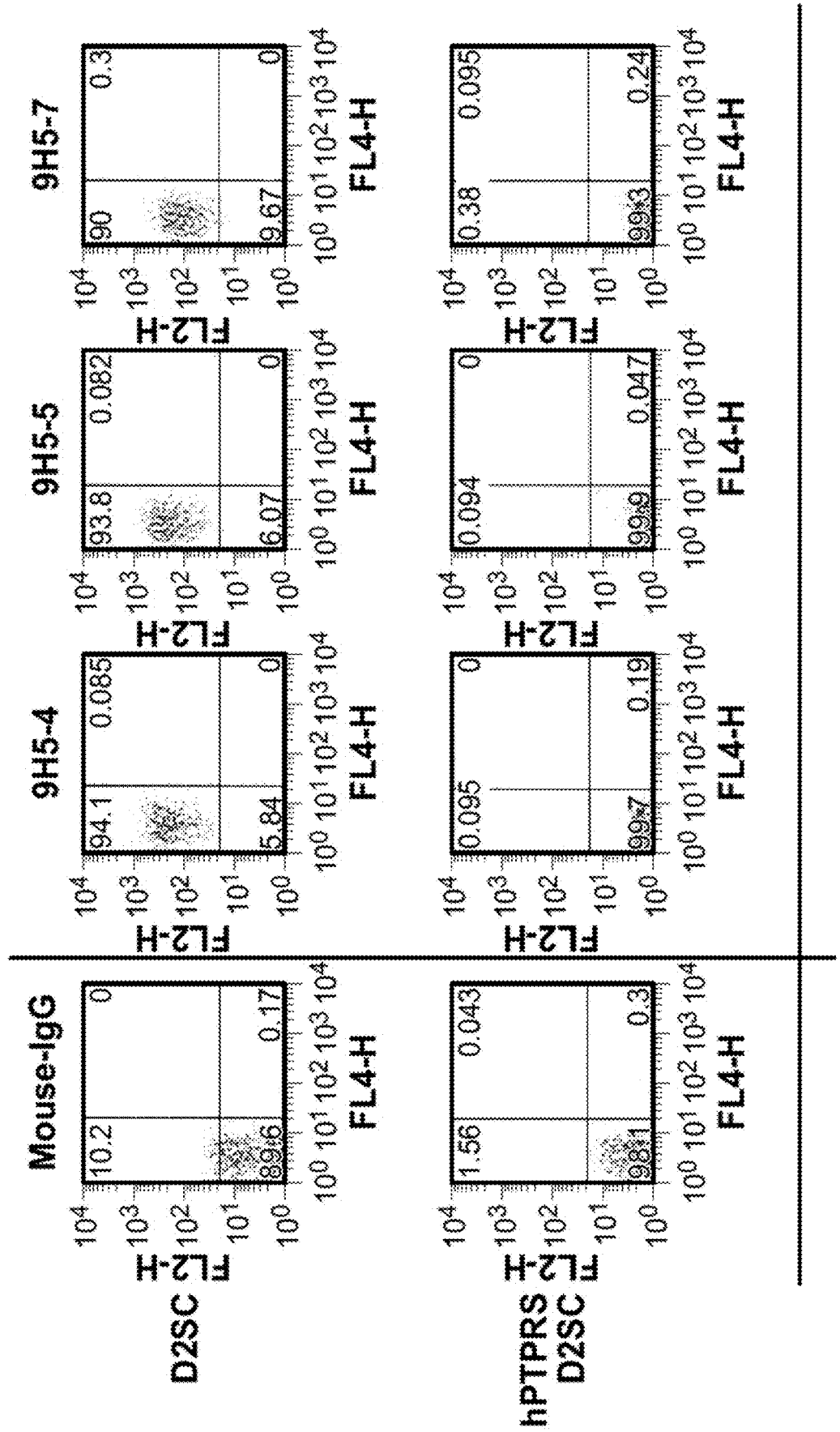
FIGS. 11A-11D show the singlization sorting of the hybridomas. Single cell sorting was conducted by using FACS Aria (BD), and D2SC/1 cell and hPTPRS/D2SC/1 cell (FIGS. 11A and B), CAL-1 cell (FIG. 11C) and human pDC (FIG. 11D) were stained by using the cell culture supernatants of the hybridomas, and single hybridomas were selected.
Figure 11A:
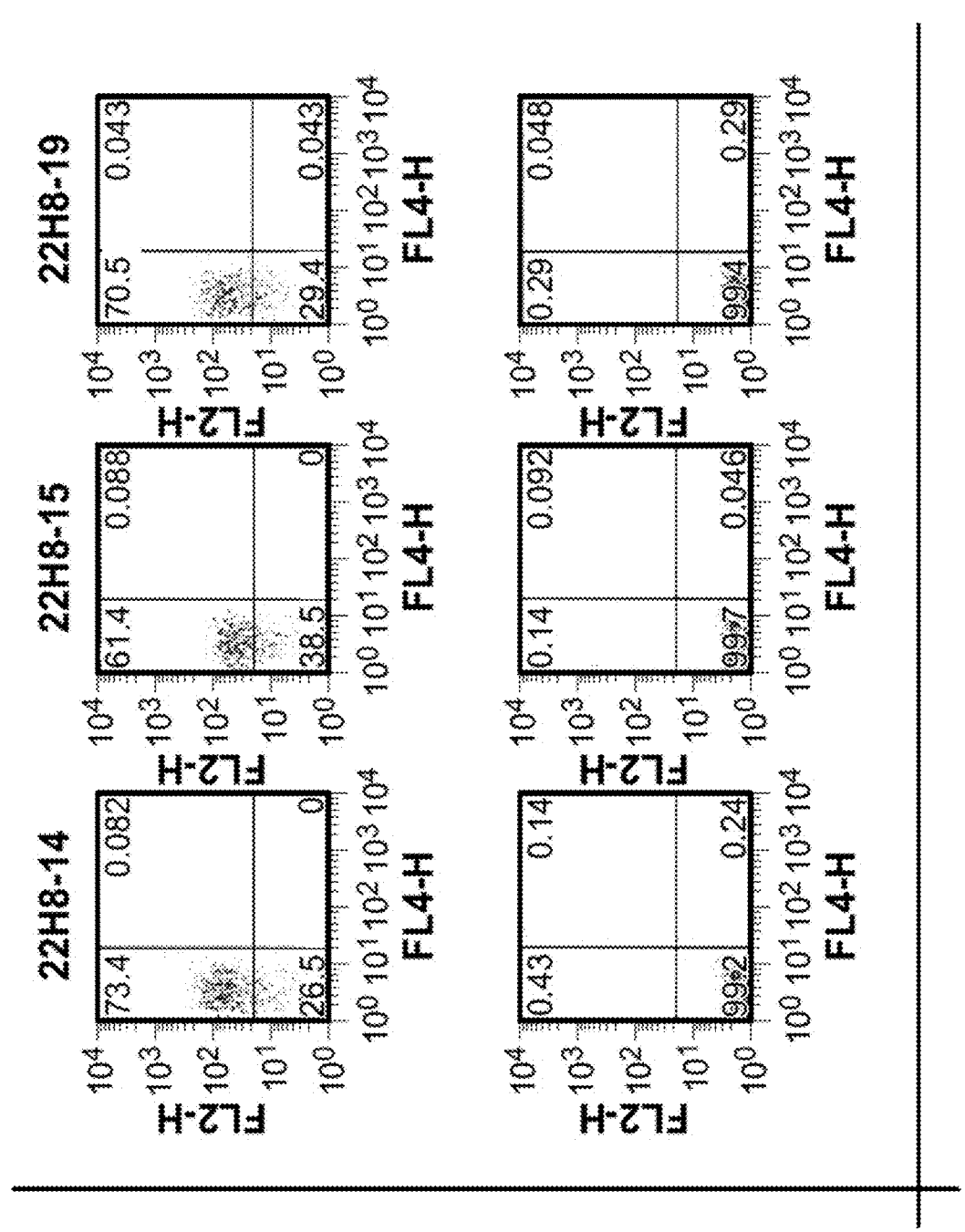
Figure 11A:
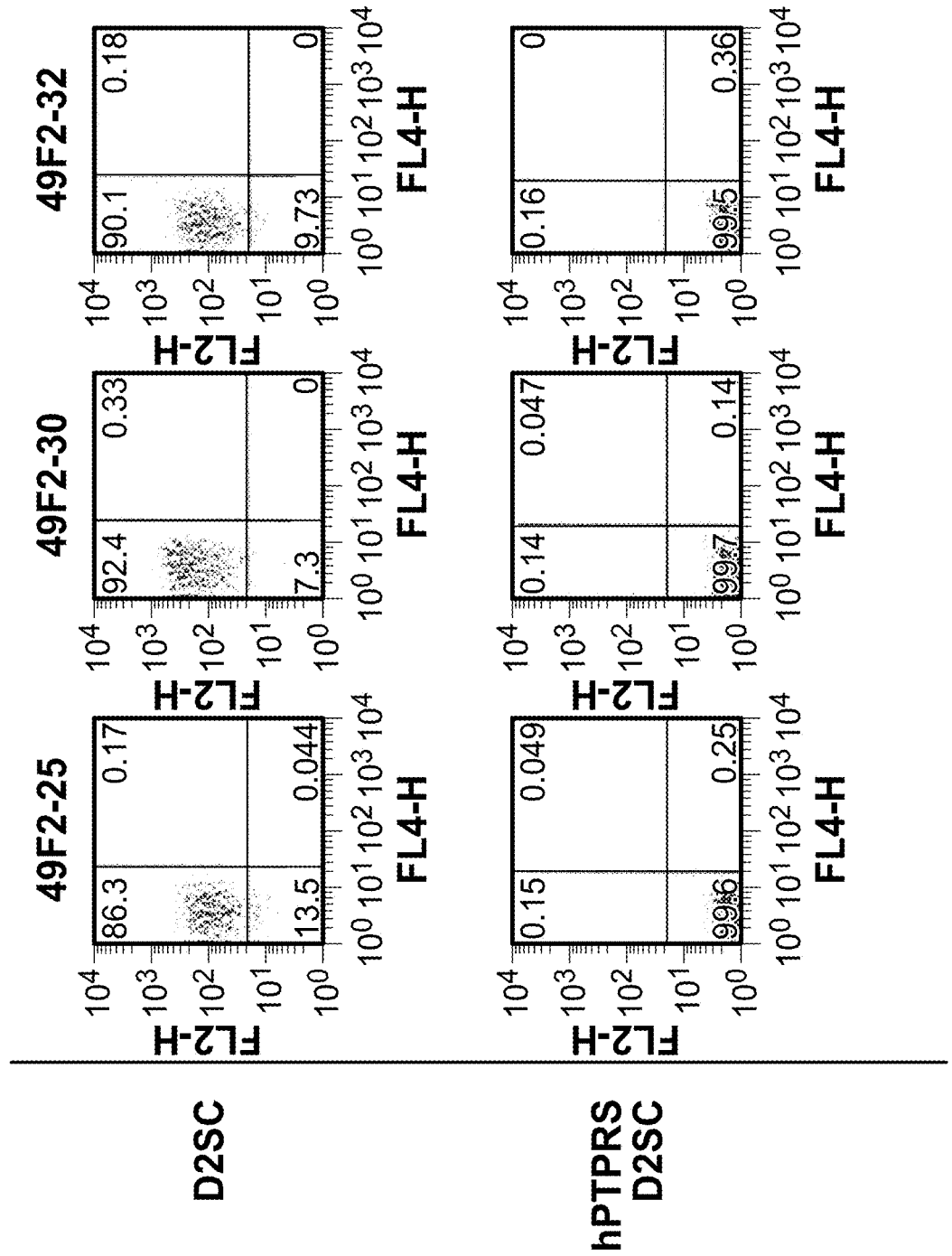
Figure 11A:
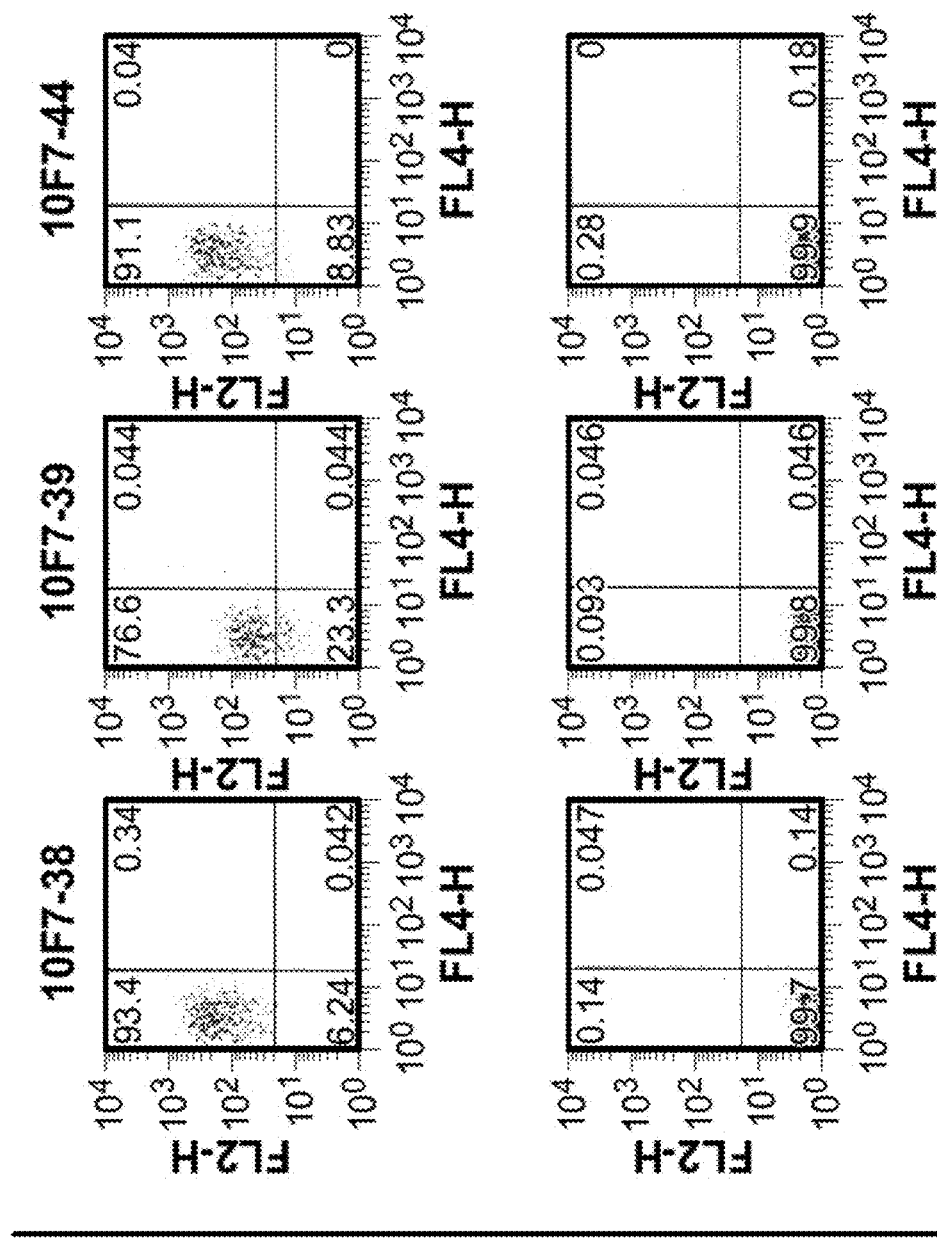
Figure 11B:
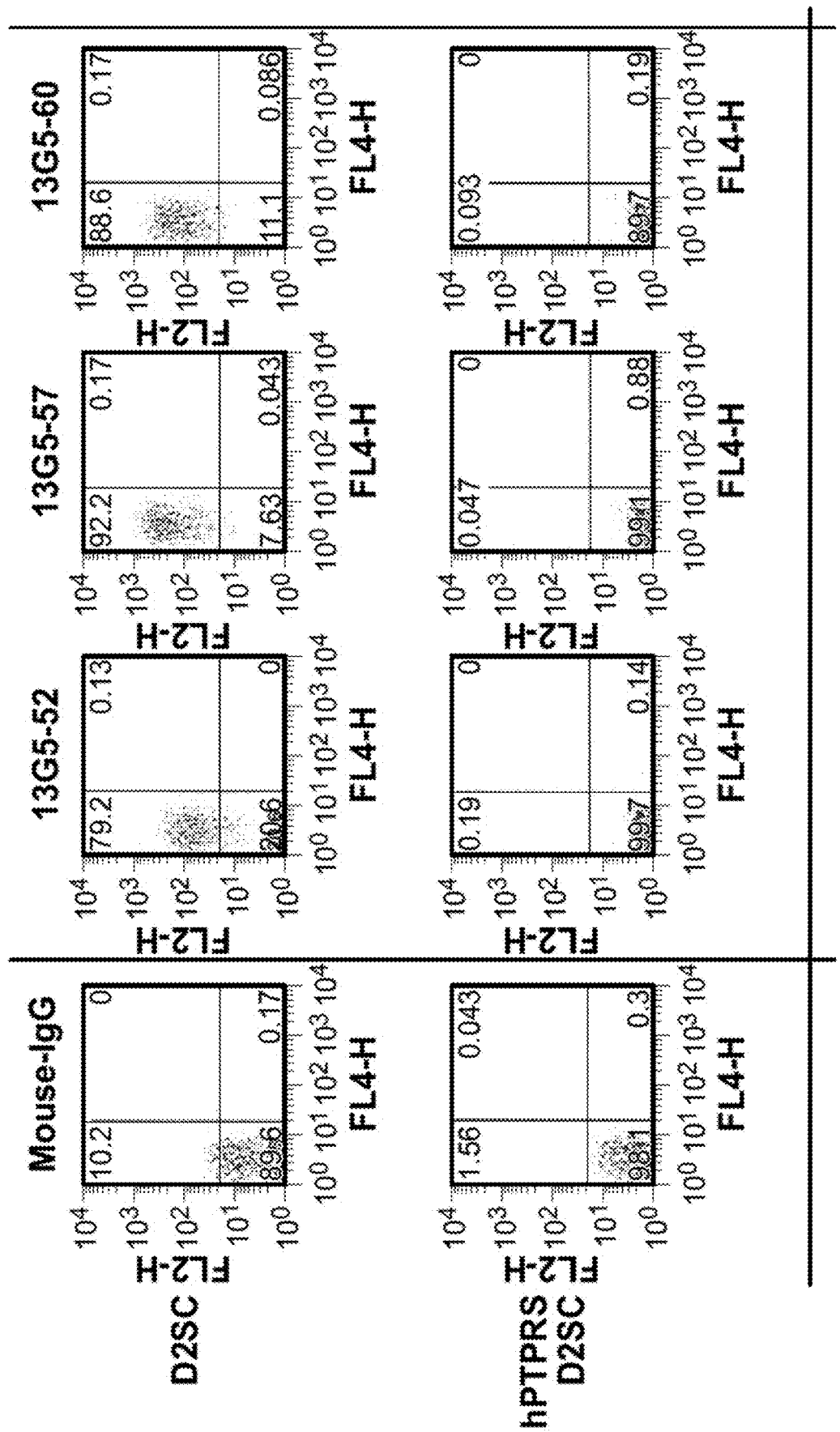
Figure 11B:
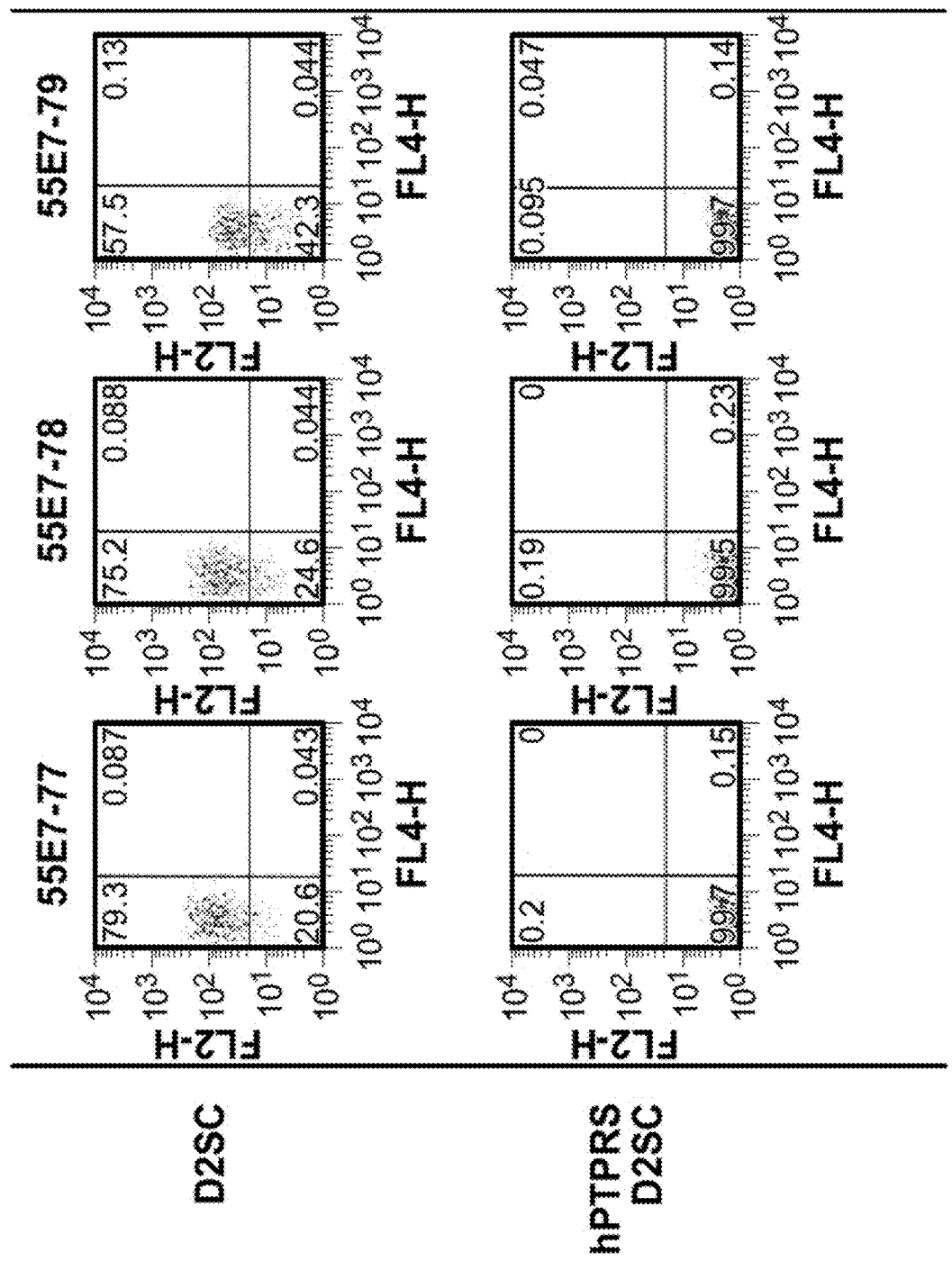
Figure 11B:
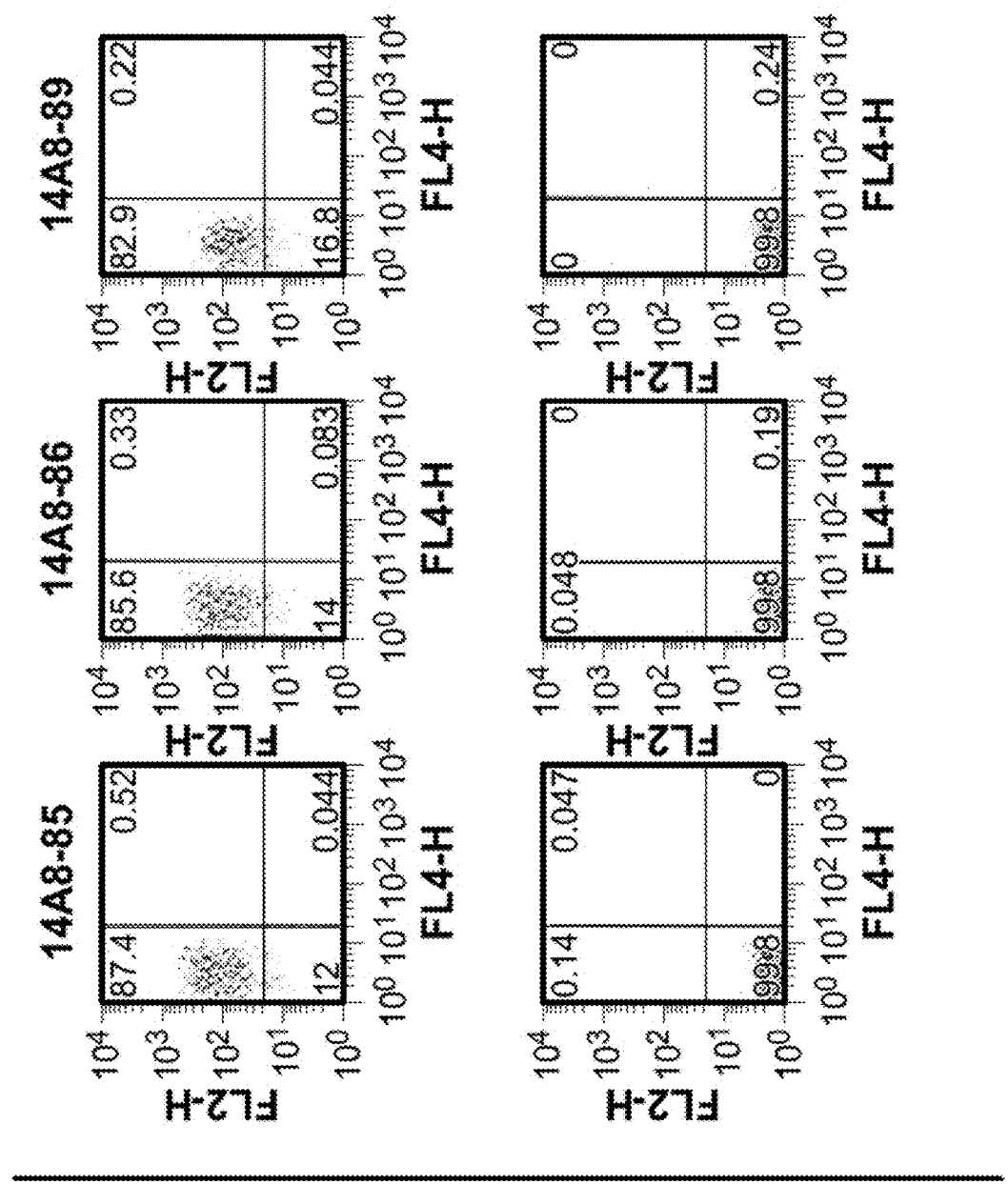
Figure 11C:
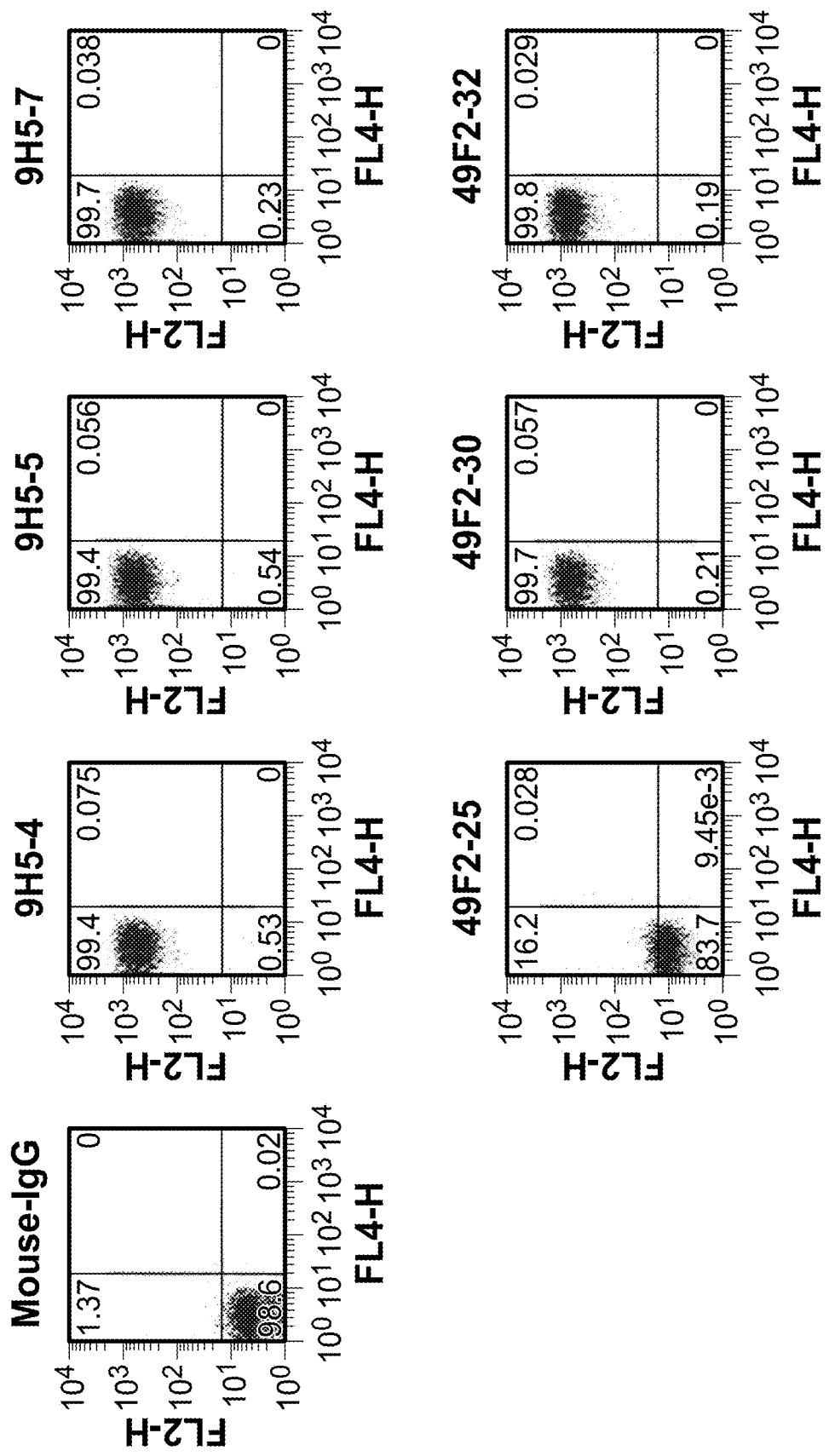
Figure 11C:
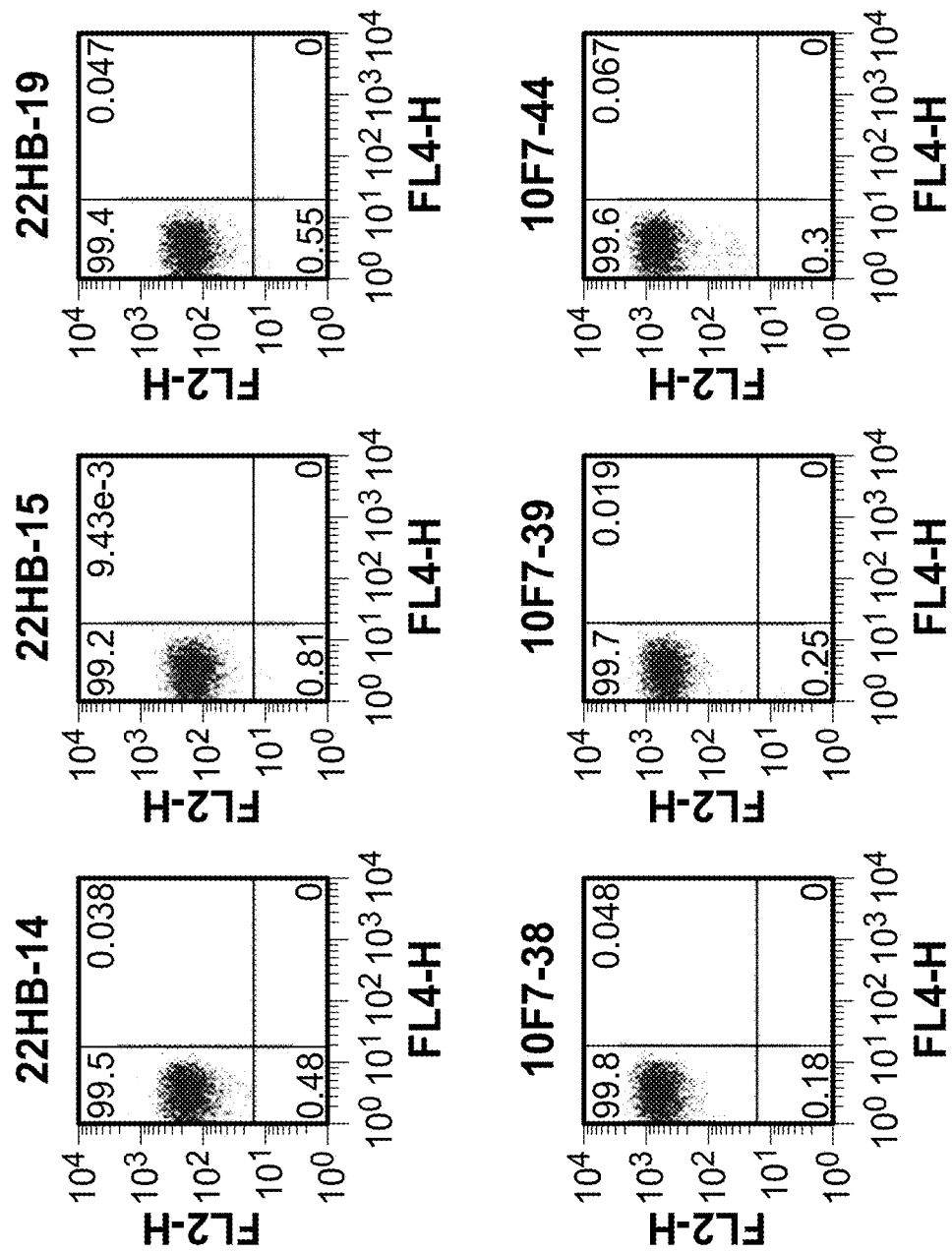
Figure 11C:
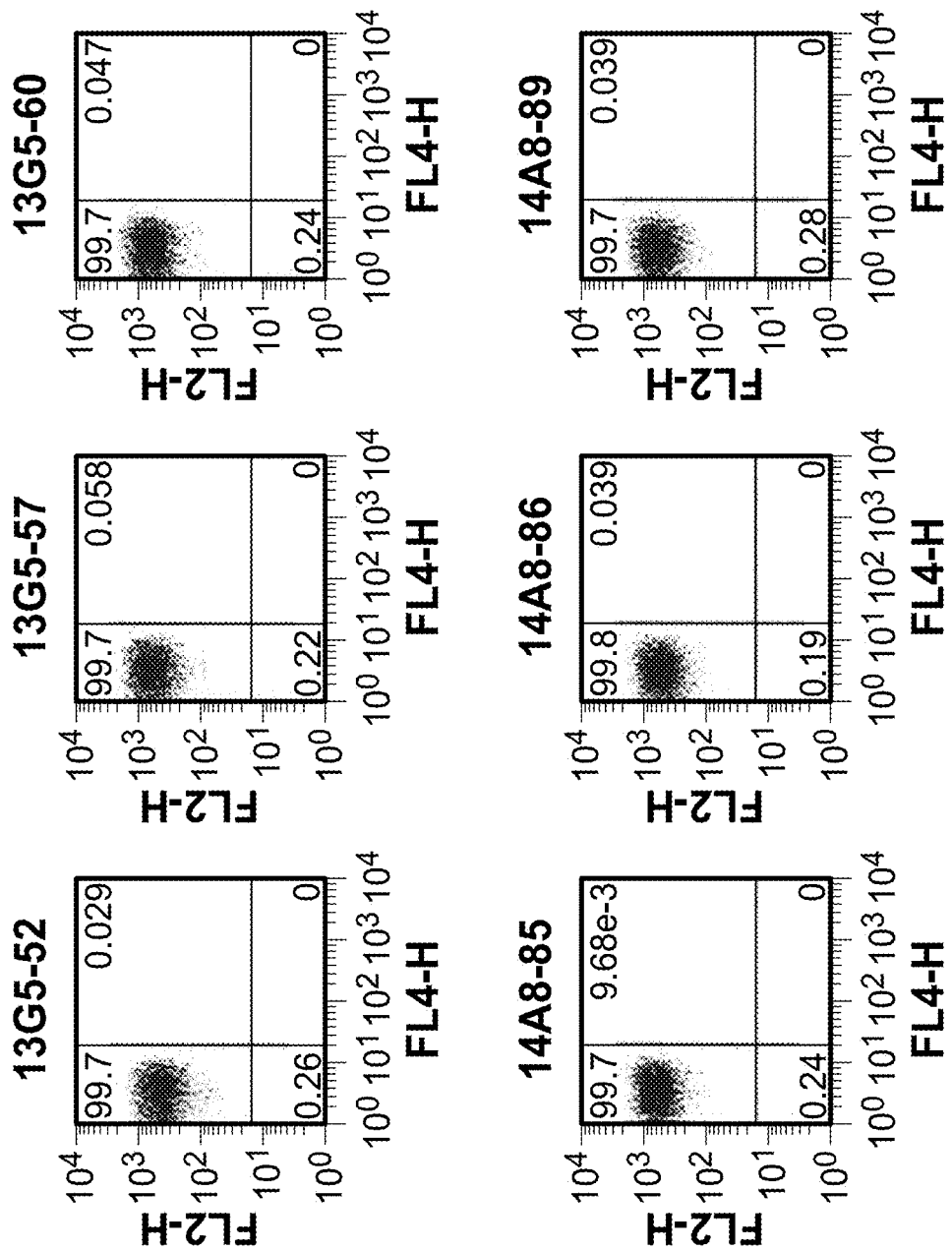
Figure 11C:
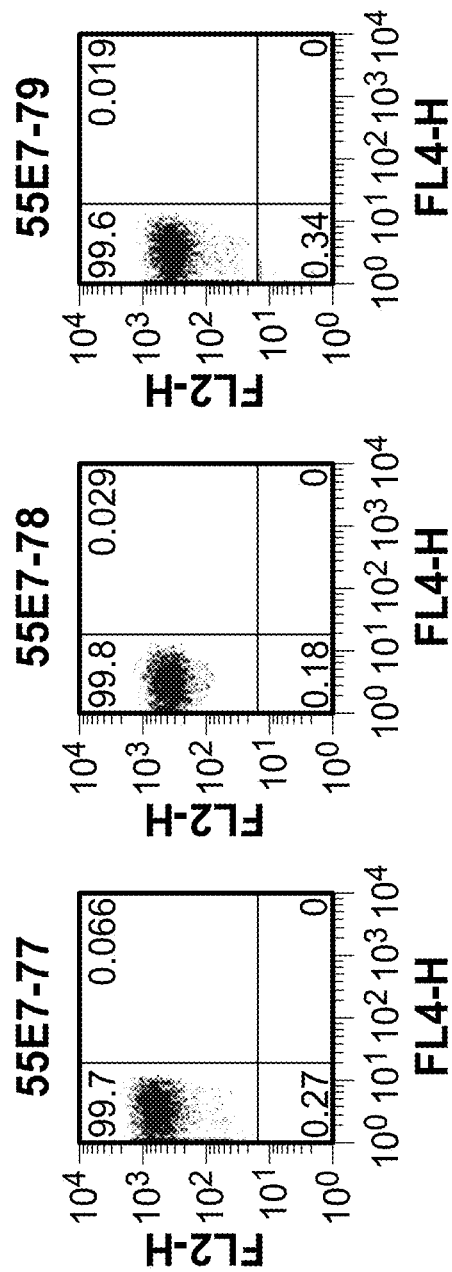
Figure 11D:
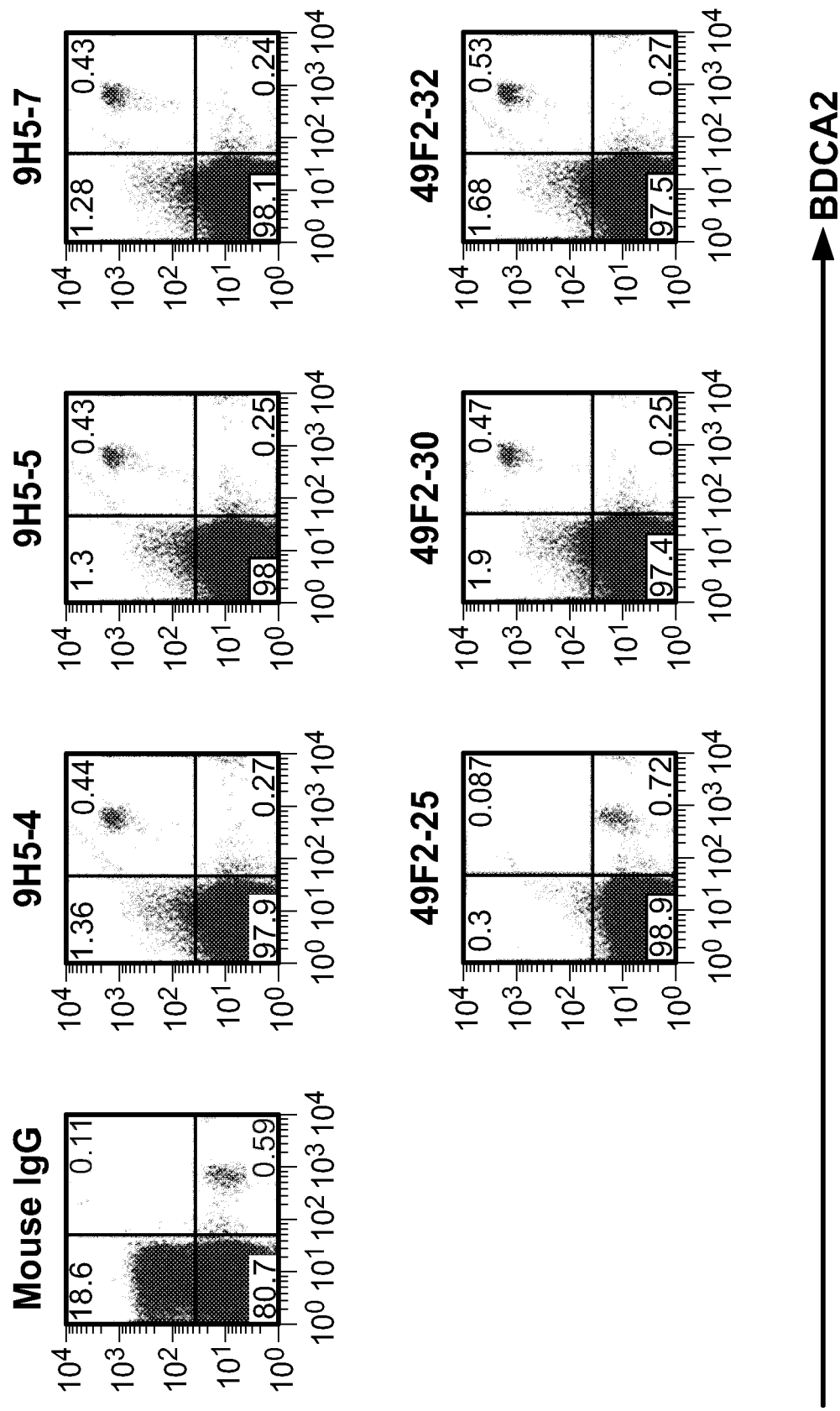
Figure 11D:
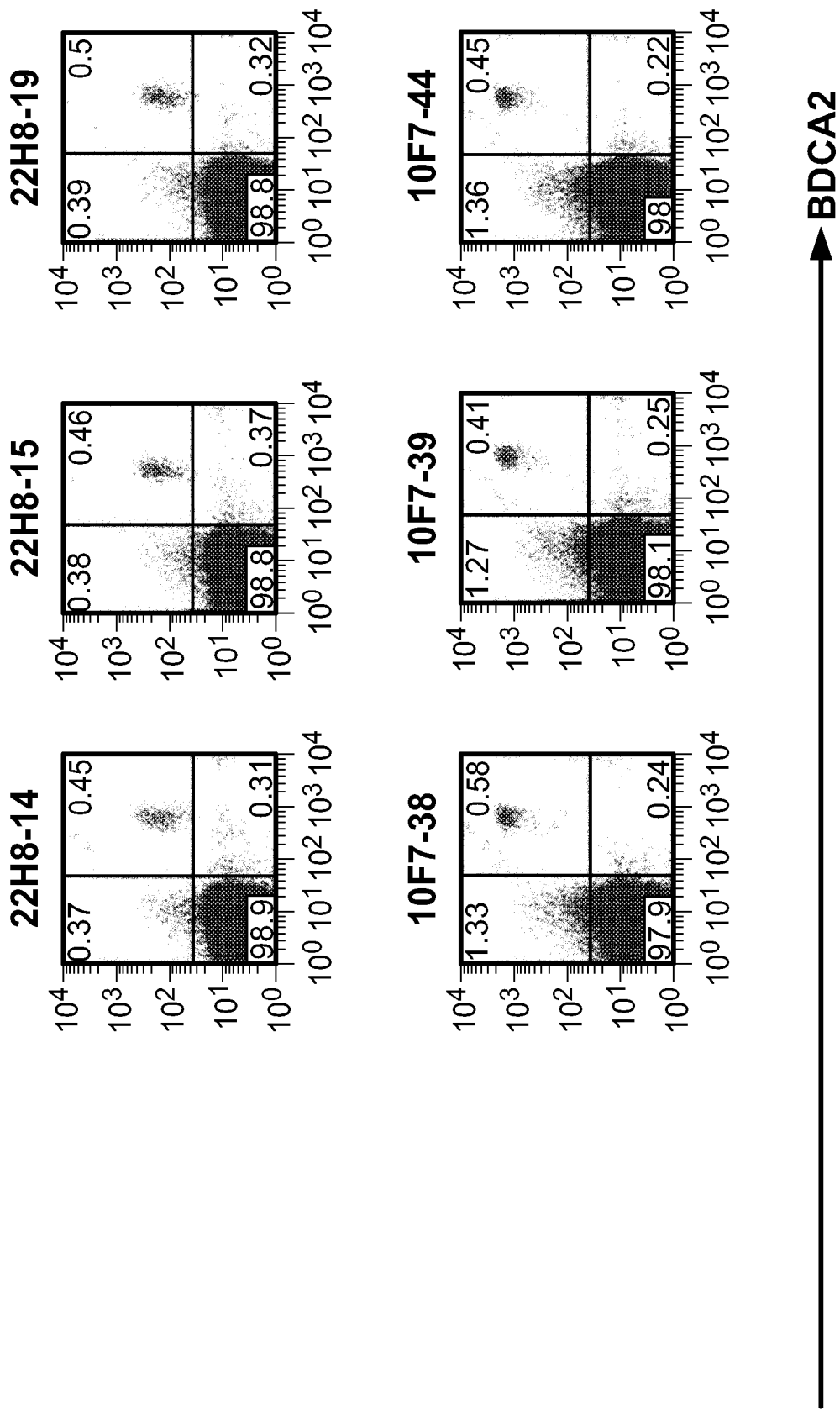
Figure 11D:
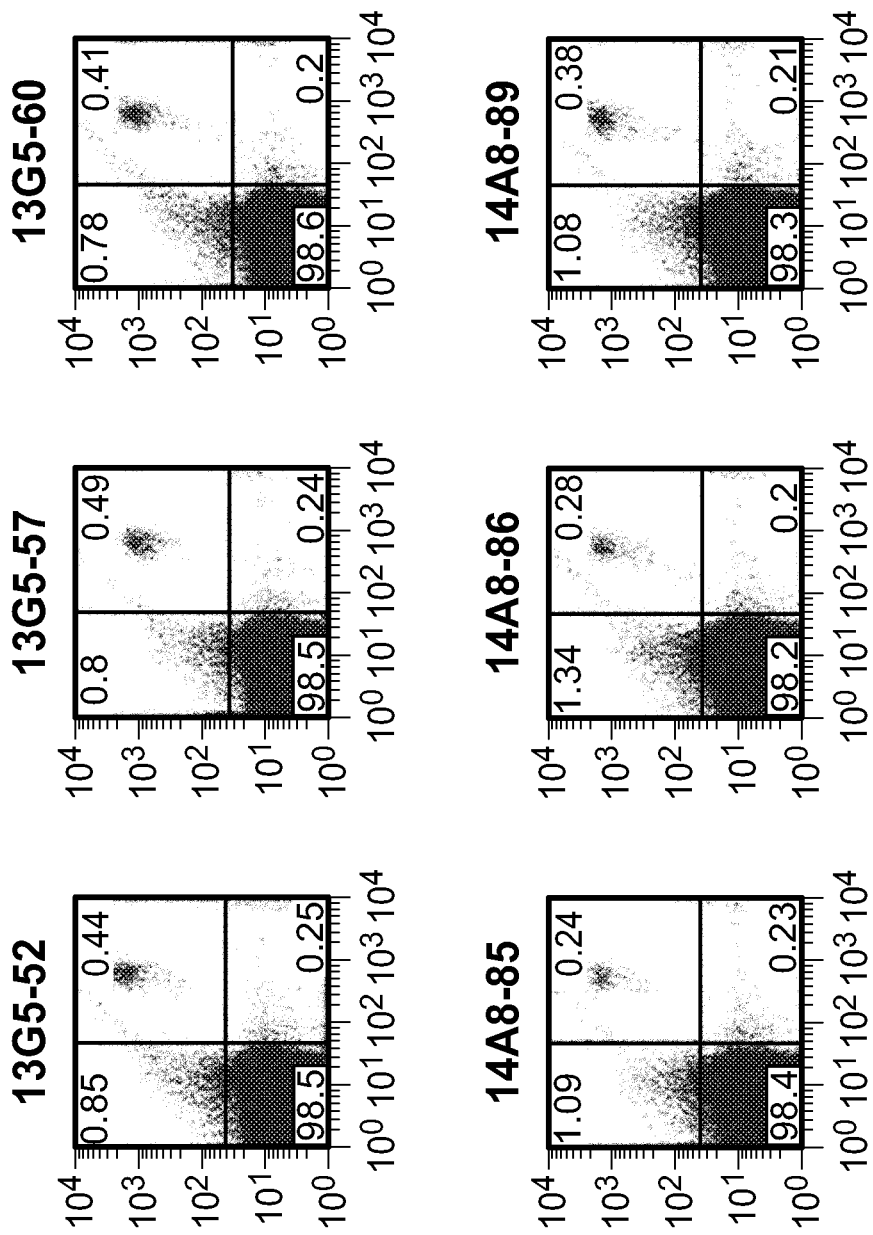
Figure 11D:
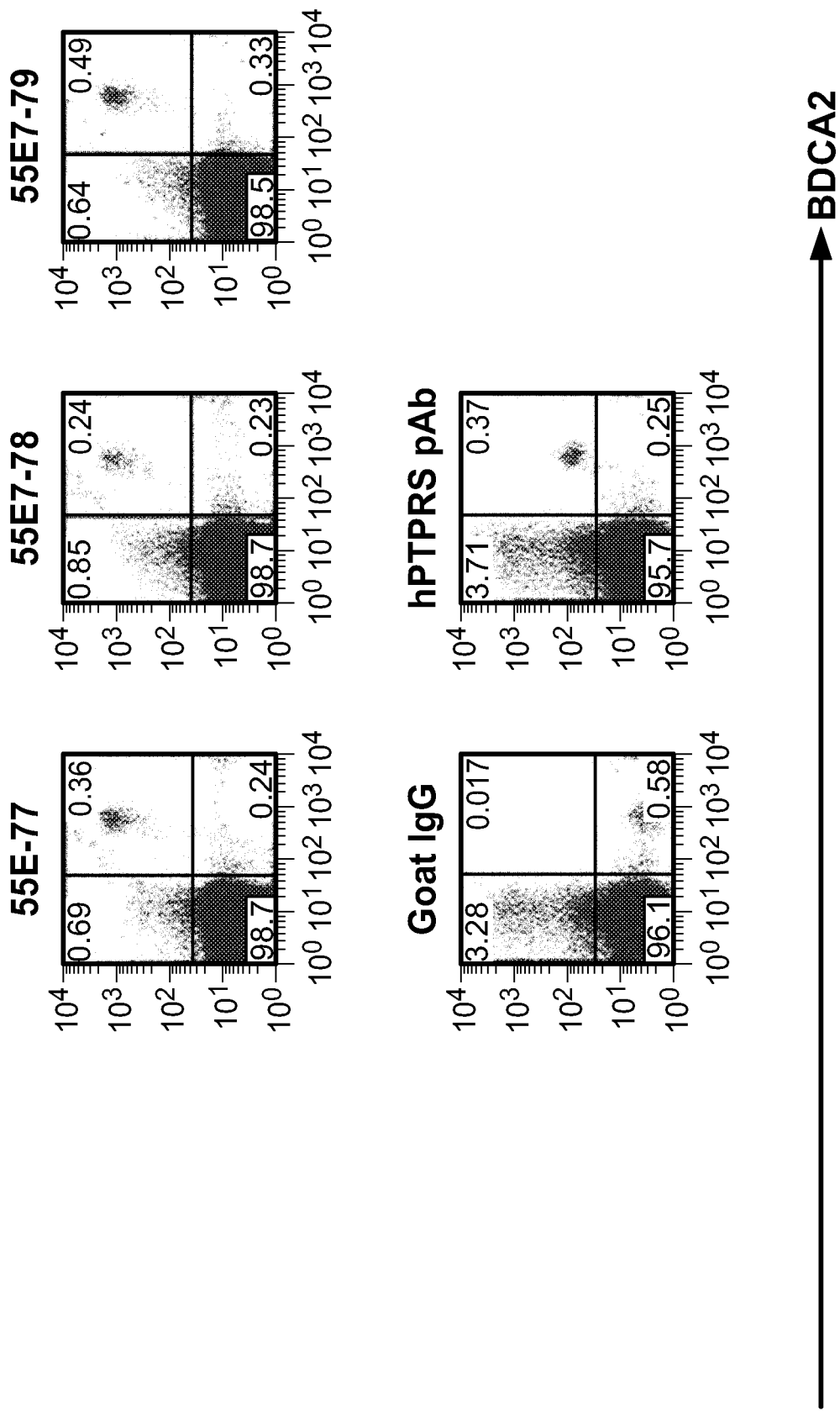

The above-mentioned 7 kinds of hybridomas (49F2, 55E7, 14A8, 13G5, 10F7, 22H8 and 9H5) were each collected and suspended in a sorting buffer (1% FBS/PBS) so as to become $1 \times 10^5$ cells/ml. Using FACS Aria (BD), single cell sorting was conducted. The data was collected, and the collected data was developed by two-dimensional dot plot of X axis: FSC and Y axis: SSC. The live cells were gated on the dot plot. Gating for removing doublets from the cell in the living cell gate was conducted, and the cell population was dispensed to a 96-well flat bottom plate so as to be 1 cell/well. The cell subjected to the single cell sorting was cultured in an HAT medium (RPMI1640+2 mM L-Glutamine, 100 Unit/ml Penicillin, 100 μg/ml Streptomycin, 10 mM HEPES, 1 mM Sodium Pyruvate, and 50 μM 2-ME)+a hybridoma growth supplement HFCS (Roche). Thereafter D2SC cell and hPTPRS/D2SC cell (FIGS. 11A and B), CAL-1 cell (FIG. 11C) and human pDC (FIG. 11D) were stained by using the cell culture supernatant of the hybridoma, and a single hybridoma was selected.

Example 3

Purification of Antibody

Figure 12:
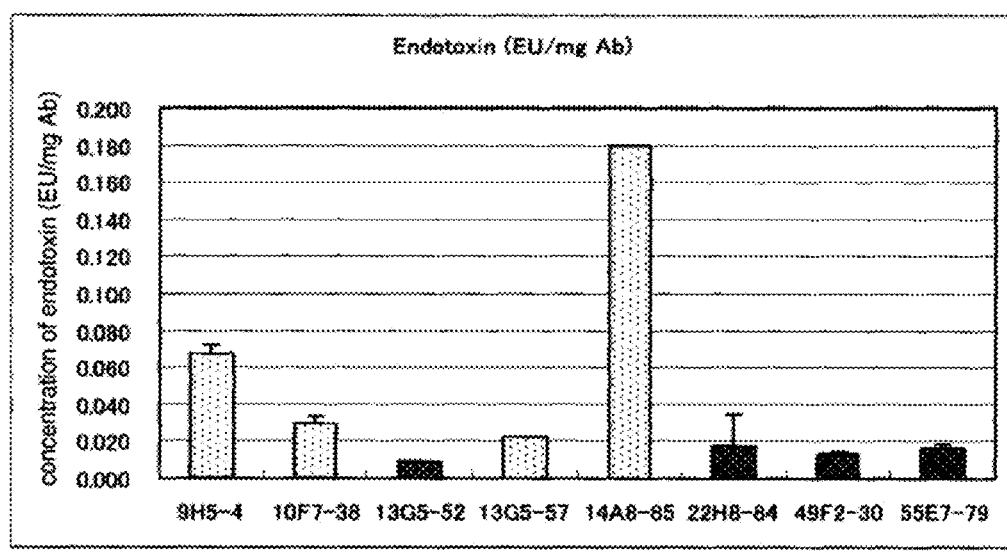
FIG. 12 shows the concentrations of the endotoxin in the purified antibodies obtained from the culture supernatants of the hybridomas. All concentrations were the standard value 0.3 Eu/mg Ab or less.

Eight kinds of purified antibodies (9H5-4, 10F7-38, 13G5-52, 13G5-57, 14A8-85, 22H8-84, 49F2-30 and 55E7-79) were obtained from the culture supernatant of the hybridomas by purification using Protein G Sepharose Fast-Flow (GE Healthcare). Using Pierce rapid ELISA mouse mAb Isotyping Kit (Thermo Fisher Scientific), isotypes were determined. As a result, 13G5-52 and 13G5-57 were mouse IgG2b, κ, 55E7-79 had both mouse IgG2b, κ and mouse IgGI, κ, and others were mouse IgG1, κ. If the purified antibody includes endotoxin, it may affect the result of a property determination test. Therefore, the concentration of endotoxin was measured. The kits used were Endospecy ES-50M set, Toxicolor DIA-MP set and Endotoxin standard product CSE-L set (all by Seikagaku Biobusiness Corporation). As a result thereof, all purified antibodies had an endotoxin concentration equal to or less than the standard value 0.3 EU/mg Ab (FIG. 12).

Study on Reactivity of Purified Antibody

Figure 13:
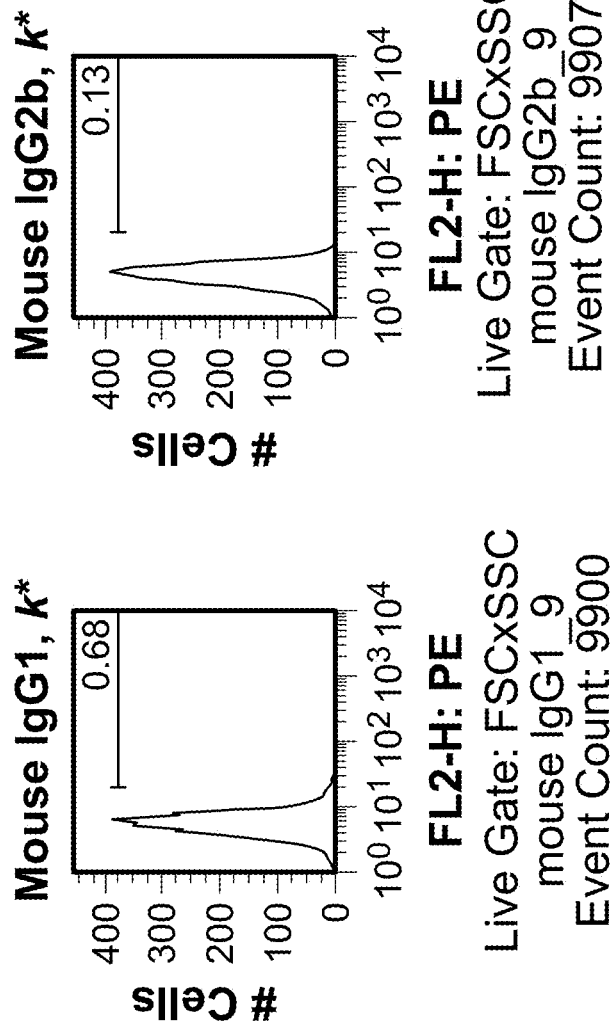
FIG. 13 is the test result of the abilities of the purified antibodies to bind human PTPRS on the cellular surface. It could be confirmed that all of the antibodies maintained their binding ability.
Figure 14:
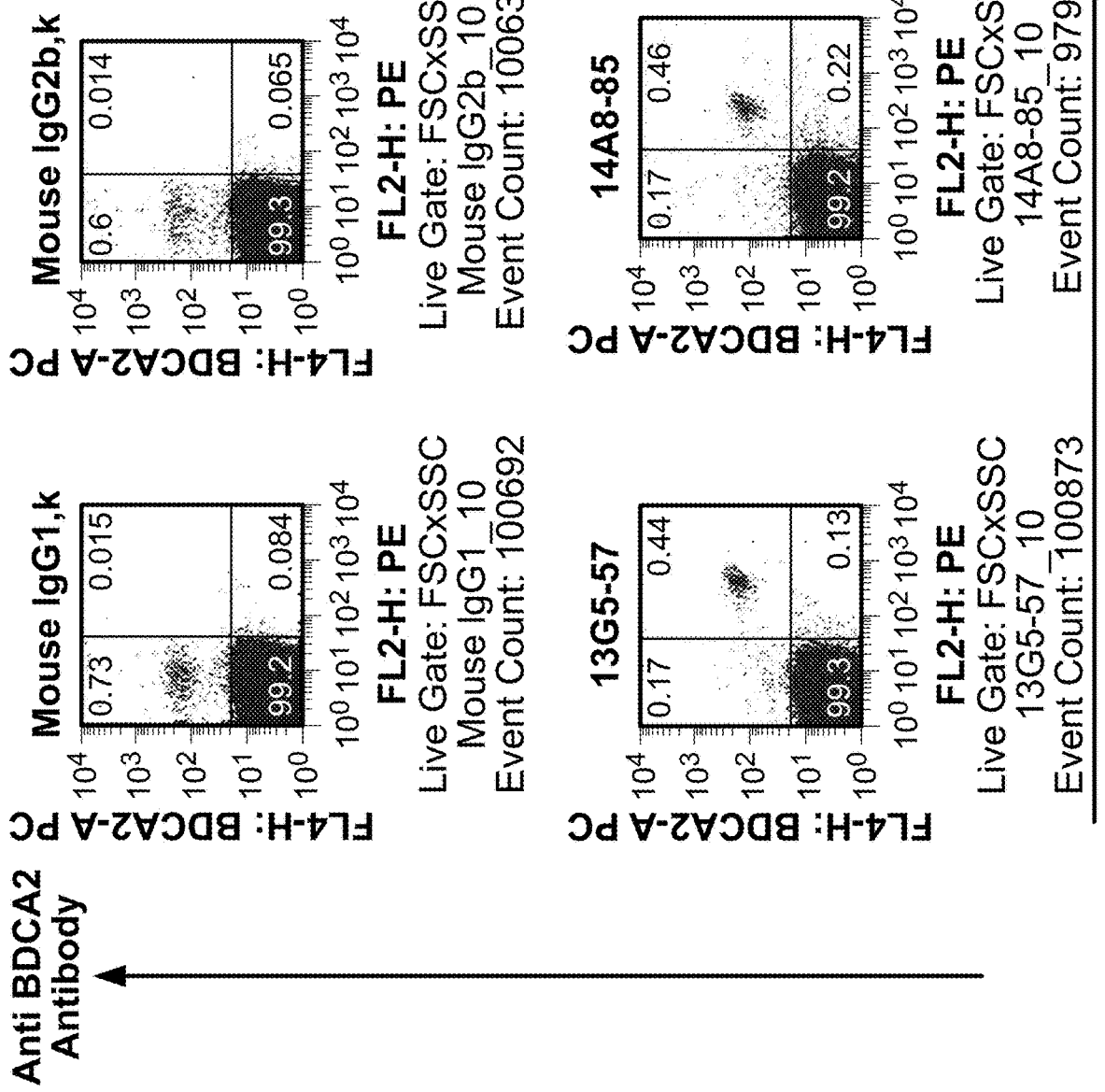
FIG. 14 shows the specific binding of the purified antibodies to the pDC cell groups (BDCA2+) of human peripheral blood.

The binding abilities of the purified antibodies were confirmed by a human pDC-like cell strain CAL-1 cell (FIG. 13). In addition, all of the antibodies maintained a binding ability against the human pDC population of human peripheral blood (BDCA2+) (FIG. 14).

The homology of the amino acid sequence of human PTPRS against mouse PTPRS (mPTPRS) is about 96%. Since they are remarkably similar to each other, whether or not the prepared anti-human PTPRS antibody also binds to mouse PTPRS was studied. A CHO cell in which the gene of mPTPRS had been forcibly expressed (Chinese hamster ovary cell; hereinafter referred to as mPTPRS/CHO) was stained by 10 μg/ml of each anti-PTPRS antibody. The cell number was $2 \times 10^5$ per one sample. After washing with a FACS buffer, a PE-labeled anti-mouse IgG antibody was diluted by 50-times and stained with 25 μl. As a result, 49F2-30, 13G5-52, 13G5-57 and 22H8-84 bound to mPTPRS/CHO (FIG. 15).

Example 4

Figure 16A:
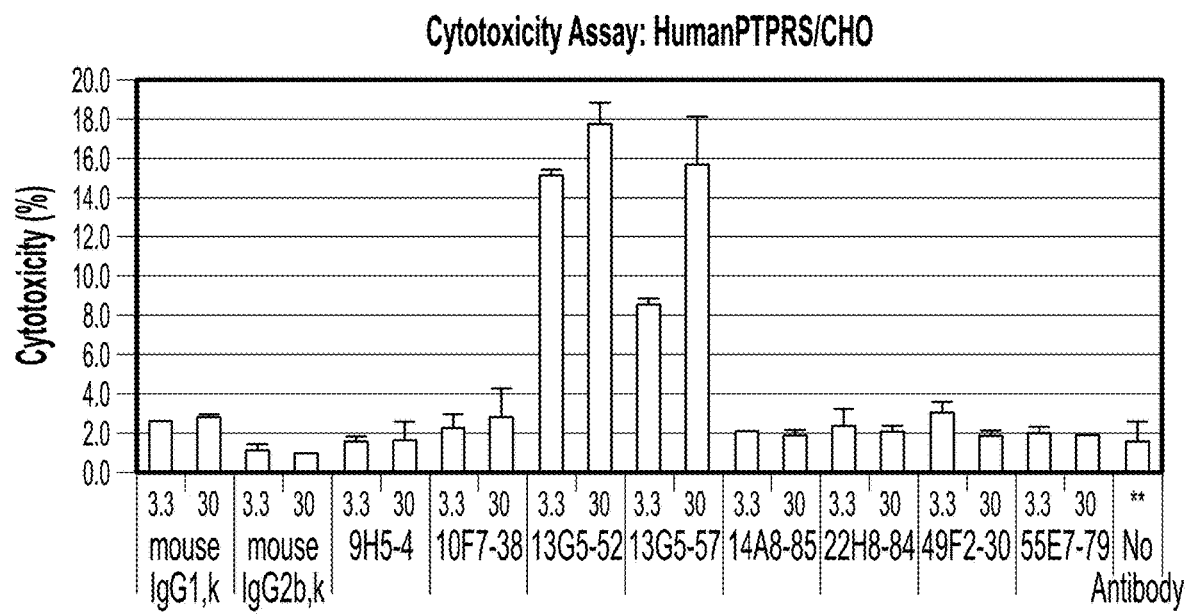
FIGS. 16A-16B show the complement-dependent cytotoxic activities of the anti-PTPRS antibodies against an hPTPRS-expressing cell. The complement-dependent cytotoxic activities of the anti-PTPRS antibodies against human PTPRS/CHO (FIG. 16A) and mouse PTPRS/CHO (FIG. 16B) were measured. As a result, 13G5-52 and 13G5-57 showed about 20% of CDC activity against the target of human PTPRS/CHO (FIG. 16A), whereas 13G5-52 and 13G5-57 showed about 100% of CDC activity against the target of mouse PTPRS/CHO (FIG. 16B)
Figure 16B:
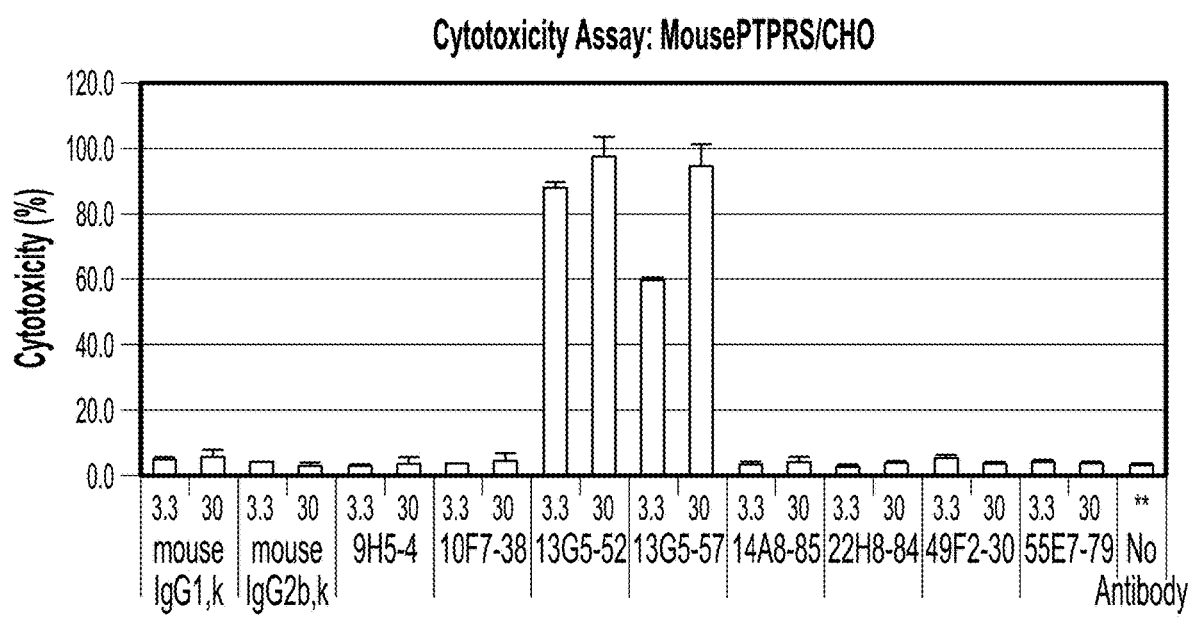

Complement-Dependent Cellular Cytotoxicity of Anti-PTPRS Antibody to hPTPRS-Expressing Cell Using baby rabbit complement, the complement-dependent cellular cytotoxicity (hereinafter referred to as CDC activity) of the anti-PTPRS antibody against a CHO cell that expresses human PTPRS (hereinafter referred to as hPTPRS/CHO) and a mouse PTPRS/CHO cell (hereinafter referred to as mPTPRS/CHO) was measured. The activity was obtained by using cell toxicity that was calculated from a measured value of lactase dehydrogenase (LDH) released from the cell as an index. Each cell was dispensed to a 96-well U bottom plate by $2 \times 10^4$ cells/50 μl/well. A 18% Complement (CEDARLANE) was prepared by a CDC medium (RPMI1640+0.1% BSA+10 mM HEPES+2 mM L-Glutamine+100 Unit/ml Penicillin+100 μg/ml Streptomycin). Two kinds: 3.3 μg/ml and 30 μg/ml were prepared for a control antibody (mouse IgG1, κ or mouse IgG2b, κ) and an anti-PTPRS antibody. An assay was conducted by using a kit of CytoTox 96 Non-Radioactive Cytotoxicity Assay (Promega). As a result, 13G5-52 and 13G5-57 showed about 20% of CDC activity against the target of hPTPRS/CHO (FIG. 16A). On the other hand, 13G5-52 and 13G5-57 showed about 100% of CDC activity against the target of mPTPRS/CHO (FIG. 16B).

Example 5

Preparation of Chimerized Antibody

As a hybridoma for the production of a mouse anti-PTPRS antibody, the following one was used.

Hybridoma 9H5-4 (Accession No.: FERM ABP-11356)
Hybridoma 10F7-38 (Accession No.: FERM ABP-11357)
Hybridoma 13G5-52 (Accession No.: FERM ABP-11358)
Hybridoma 13G5-57 (Accession No.: FERM ABP-11359)
Hybridoma 14A8-85 (Accession No.: FERM ABP-11360)
Hybridoma 22H8-84 (Accession No.: FERM ABP-11361)
Hybridoma 49F2-30 (Accession No.: FERM ABP-11362)

1. Confirmation of Isotype of Constant Region

The isotype of the constant region of each of mouse antibody produced from seven hybridomas(9H5-4,10F7-38, 13G5-52, 13G5-57, 14A8-85, 22H8-84 and 49F2-30) was confirmed.

For the confirmation, a mouse monoclonal antibody iso-typing kit (Catalog No.: MMT1; Serotec Product; Oxford, UK) or Pierce Rapid ELISA mouse mAb Isotyping Kit (Thermo Fisher Scientific), and such 9H5-4,10F7-38,13G5-52, 13G5-57, 14A8-85, 22H8-84 and 49F2-30 hybridoma culture supernatant as a sample were used.

As a result, the isotype of the antibodies produced by the 13G5-52 and 13G5-57 hybridomas was an isotype including mouse IgG2b as a heavy chain and x as a light chain. On the other hand, the isotype of the antibodies produced by the 9H5-4, 10F7-38, 14A8-85, 22H8-84 and 49F2-30 hybridomas was an isotype including mouse IgG1 as a heavy chain and x as a light chain.

2. Cloning of cDNA that Codes for Variable Region of Mouse Anti-PTPRS Antibody 2-1) Isolation of Total RNA Using a commercially available kit "RNeasy Mini Kit" (Qiagen, Catalog No.: 74106), the total RNA was isolated from seven hybridomas according to the instruction attached to the kit. About 30 μg of the total RNA was obtained by preparation from the hybridoma cell strain of $5 \times 10^6$ cell number.

2-2) Amplification and Fragmentation of cDNA that Codes for Mouse Heavy Chain Variable Region Using 5 μg from the total RNA isolated in 2-1), cDNA that codes for mouse heavy chain variable region was amplified by the 5' RACE PCR process. In the amplification, a commercially available kit "5' RACE System for Rapid Amplification of cDNA ENDs, Version 2.0 Kit" (Invitrogen, Catalog No.: 18374-058) was used. The specifics are as follows. First, a first strand cDNA was synthesized from the total RNA obtained in 2-1) by a reverse transcriptase. At that time, the antisense primer (GSP1) shown below was used.

The GSP1 primer used for amplification of cDNA is used according to the isotype of each mouse heavy chain. For example, the following antisense primers are used for the cloning of the heavy chain variable region of the 9H5-4, 10F7-38, 14A8-85, 22H8-84 and 49F2-30 hybridomas including mouse IgG1 as a heavy chain.

```
GSP1 primer: mu IgG1 VH-GSP1
Sequence:
                                       (SEQ ID NO: 39)
5'-CCA GGA GAG TGG GAG AGG CTC TTC TCA GTA TGG TGG-3' (36-mer)

GSP2 primer: mu IgG1 VH-GSP2
Sequence:
                                       (SEQ ID NO: 40)
5'-GGC TCA GGG AAA TAG CCC TTG ACC AGG CAT CC-3' (32-mer)
```

Also, for example, the following antisense primers can be used for the cloning of the heavy chain variable region of the 9H5-4, 10F7-38, 14A8-85, 22H8-84 and 49F2-30 hybridomas including mouse IgG1 as a heavy chain.

```
GSP1 primer: mu IgGHγ1-GSP1
Sequence:
                                       (SEQ ID NO: 11)
5'-TCC AGA GTT CCA GGT CAC TGT CAC-3' (24-mer)

GSP2 primer: mu IgG Hγ1-GSP2
Sequence:
                                       (SEQ ID NO: 13)
5'-AGG GGC CAG TGG ATA GAC AGA TGG-3' (32-mer)
```

And the following antisense primers are used for the cloning of the heavy chain variable region of the 13G5-52 and 13G5-57 hybridomas including mouse IgG2b as a heavy chain.

```
GSP1 primer: mu IgGHγ 2B-GSP1
Sequence:
                                       (SEQ ID NO: 41)
5'-TCC AGA GTT CCA AGT CAC AGT CAC-3' (24-mer)

GSP2 primer: mu IgG Hγ 2B-GSP2
Sequence:
                                       (SEQ ID NO: 42)
5'-AGG GGC CAG TGG ATA GAC TGA TGG-3' (24-mer)
```

Furthermore, using a terminal deoxynucleotidyl transferase (TdT) at the 3'-terminus of the first chain cDNA, a nucleotide homopolymer dC was added. Furthermore, using an anchor primer having a nucleotide polymer that is complementary to the dC (anchor sequence) (SEQ ID NO:12), and the antisense primer (GSP2), the cDNA was amplified by a PCR process. Furthermore, using the obtained PCR product as a template, and using an AUAP primer (SEQ ID NO:14) and the antisense primer (GSP2), the cDNA was amplified by a Nested PCR process. Furthermore, this PCR product was purified by a 1.5% low melting point agalose process.

```
Anchor primer for 5'RACE (SEQ ID NO: 12):
5'-GGC CAC GCG TCG ACT AGT ACG GGI IGG GII GGG IIG-3' (36-mer)

AUAP primer for 5'RACE (SEQ ID NO: 14):
5'-GGC CAC GCG TCG ACT AGT AC-3' (20-mer)
```

2-3) Amplification and Fragmentation of cDNA that Codes for Mouse Light Chain Variable Region From the total RNA isolated in 2-1), a cDNA that codes for mouse light chain variable region was amplified in a similar manner to 2-2).

Since these seven antibodies include mouse Ig κ light chain, the following antisense primers are used for the cloning of the light chain.

```
GSP1 primer: Mu IgVL5RACE-GSP1
Sequence:
                              (SEQ ID NO: 15)
5'-TTC ACT GCC ATC AAT CTT CCA CTT-3' (24-mer)

GSP2 primer: Mu IgVL5RACE-GSP2
Sequence:
                              (SEQ ID NO: 16)
5'-GAT GGA TAC AGT TGG TGC AGC-3' (21-mer)
```

The obtained PCR product was purified by a 1.5% low melting point agalose process.

2-4) Confirmation of Base Sequence of cDNA and Determination of CDR Region

The cDNA fragments of the heavy chain variable region obtained in 2-2) and the light chain variable region obtained in 2-3) were each cloned to a pCR4Blunt-TOPO vector using a commercially available kit "Zero Blunt TOPO PCR Cloning Kit" (Invitrogen, Catalog No.: 1325137), according to the instruction attached to the kit, and introduced into an E. coli competent cell to give an E. coli tranformant. A plasmid was obtained from this transformant and a plasmid DNA sample was sent to Operon Biotechnology Co. Ltd (Tokyo) for sequence analysis to confirm the cDNA base sequence in the plasmid. For the analyses of the sequences, "Sequencher DNA sequence assembly and analysis software version 4.2.2 (Gene Codes Corporation)" and "GENETYX-MAC Version 11. 1. 1" software (GENETYX CORPORATION)" were used.

The transformants that became inactive RNAs since frame shifting, nonsense mutation and the like occurred around a complementary determination region (hereinafter referred to as "CDR region") were excluded, and transformants having correct sequences were extracted. Furthermore, the Immunoglobulins Database(IgBLAST, URL:www.ncbi.nlm.nih.gov/igblast/) and homology were confirmed for the cDNA base sequence included in the plasmid to determine the sequences of the CDR region (CDRs; CDR1, CDR2,CDR3) in each variable region, Framework region and the sequence of the variable region were determined according to the analysis method using Kabat numbering system (Kabat et al., 1991, sequences of Proteins of Immunological Interest, National Institutes of Health Publication No. 91-3242, 5th ed., United States Department of Health and Human Services, Bethesda, Md.).

The nucleic acid sequence of the heavy chain variable region of the obtained anti-PTPRS mouse 9H5-4 antibody was SEQ ID NO: 43, and the amino acid sequence was SEQ ID NO: 44. The amino acid sequences of the CDR1, CDR2 and CDR3 in the heavy chain variable region of the mouse 9H5-4 antibody were SEQ ID NO: 45, SEQ ID NO: 46 and SEQ ID NO: 47, respectively.

The nucleic acid sequence of the light chain variable region of the obtained anti-PTPRS mouse 9H5-4 antibody is SEQ ID NO: 48, and the amino acid sequence is SEQ ID NO: 49. The amino acid sequences of the CDR1, CDR2 and CDR3 in the light chain variable region of the mouse 9H5-4 antibody are SEQ ID NO: 50, SEQ ID NO: 51 and SEQ ID NO: 52, respectively.

And the nucleic acid sequences of the heavy chain variable region and the light chain variable region of obtained anti-PTPRS mouse 10F7-38 antibody and 14A8-85 antibody were the same as those of 9H5-4 antibody, including the sequences of the CDR1, CDR2 and CDR3.

The nucleic acid sequence of the heavy chain variable region of the obtained anti-PTPRS mouse 13G5-57 antibody was SEQ ID NO: 53, and the amino acid sequence was SEQ ID NO: 54. The amino acid sequences of the CDR1, CDR2 and CDR3 in the heavy chain variable region of the mouse 13G5-57 antibody were SEQ ID NO: 55, SEQ ID NO: 56 and SEQ ID NO: 57, respectively.

The nucleic acid sequence of the light chain variable region of the obtained anti-PTPRS mouse 13G5-57 antibody is SEQ ID NO: 58, and the amino acid sequence is SEQ ID NO: 59. The amino acid sequences of the CDR1, CDR2 and CDR3 in the light chain variable region of the mouse 13G5-57 antibody are SEQ ID NO: 60, SEQ ID NO: 61 and SEQ ID NO: 62, respectively.

And the nucleic acid sequences of the heavy chain variable region and the light chain variable region of obtained anti-PTPRS mouse 13G5-52 antibody were the same as those of 13G5-57 antibody, including the sequences of the CDR1, CDR2 and CDR3.

The nucleic acid sequence of the heavy chain variable region of the obtained anti-PTPRS mouse 22H8-84 antibody was SEQ ID NO: 63, and the amino acid sequence was SEQ ID NO: 64. The amino acid sequences of the CDR1, CDR2 and CDR3 in the heavy chain variable region of the mouse 22H8-84 antibody were SEQ ID NO: 65, SEQ ID NO: 66 and SEQ ID NO: 67, respectively.

The nucleic acid sequence of the light chain variable region of the obtained anti-PTPRS mouse 22H8-84 antibody is SEQ ID NO: 68, and the amino acid sequence is SEQ ID NO: 69. The amino acid sequences of the CDR1, CDR2 and CDR3 in the light chain variable region of the mouse 22H8-84 antibody are SEQ ID NO: 70, SEQ ID NO: 71 and SEQ ID NO: 72, respectively.

The nucleic acid sequence of the heavy chain variable region of the obtained anti-PTPRS mouse 49F2-30 antibody was SEQ ID NO:25, and the amino acid sequence was SEQ ID NO:26. The amino acid sequences of the CDR1, CDR2 and CDR3 in the heavy chain variable region of the mouse 49F2-30 antibody are SEQ ID NO:27, SEQ ID NO:28 and SEQ ID NO:29, respectively.

The nucleic acid sequence of the light chain variable region of the obtained anti-PTPRS mouse 49F2-30 antibody is SEQ ID NO:30, and the amino acid sequence is SEQ ID NO:31. The amino acid sequences of the CDR1, CDR2 and CDR3 in the light chain variable region of the mouse 49F2-30 antibody are SEQ ID NO:32, SEQ ID NO:33 and SEQ ID NO:34, respectively.

The nucleic acid sequence (471 bp) of the heavy chain variable region of the obtained anti-PTPRS mouse 9H5-4 antibody is shown below (SEQ ID NO: 43). The capital letters show the mouse 9H5-4 VH variable region and the small letters show the mouse IgG1 heavy chain constant region.

```
ATGGAGTTGGGACTGAGCTGGGTATTTCTTGTGGCTCTTTTGAATGGTGT

CCAGTGTCAGGTGCAGCTTGTAGAGACCGGGGGAGGCTTGGTGAGGCCTG

GAAATTCTCTGAAACTCTCCTGTGTTACCTCGGGATTCACTTTCAGTAAC

TACCGGATGCACTGGCTTCGCCAGCCTCCAGGGAAGAGGCTGGAGTGGAT

TGCTGTAATTACAGTCAAATCTGATAATTATGGAGCAAATTATGCAGAGT

CTGTGAAAGGCAGATTCACTATTTCAAGAGATGATTCAAAAAGCAGTGTC

TACCTGCAGATGAACAGATTAAGAGAGGAAGACACTGCCACTTATTATTG
```

-continued

```
TAGTAGATCGGTCTACTATGGTTACGTCCTAGCCTTTGACTACTGGGGCC

AAGGCACCACTCTCACAGTCTCCTCAgccaaaacgacaccccatctgtc tatccactggcccctaagggc
```

The amino acid sequence (157 a.a) of the heavy chain variable region of the mouse 9H5-4 antibody is shown below (SEQ ID NO: 44). The capital letters show the sequence of VH variable region and the small letters show the mouse IgG1 heavy chain constant region.

The underlined part means the signal sequence and the double-underlined part means the CDR region (CDR1, CDR2, CDR3).

MELGLSWVFLVALLNGVQCQVQLVETGGGLVRPGNSLKLSCVTSGFTFSN
YRMHWLRQPPGKRLEWIAVITVKSDNYGANYAESVKGRFTISRDDSKSSV
YLQMNRLREEDTATYYCSRSVYYGYVLAFDYWGQGTTLTVSSakttppsv
yplapkg The CDR1 of the heavy chain variable region of the 9H5-4 antibody is NYRMH (SEQ ID NO: 45), the CDR2 of the heavy chain variable region of the 9H5-4 antibody is VITVKSDNYGANYAESVKG (SEQ ID NO: 46), and the CDR3 of the heavy chain variable region of the 9H5-4 antibody is SVYYGYVLAFDY (SEQ ID NO: 47).

The nucleic acid sequence (402 bp) of the light chain variable region of the obtained anti-PTPRS mouse 9H5-4 antibody is shown below (SEQ ID NO: 48). The capital letters show the mouse 9H5-4 VH variable region and the small letters show the mouse Ig κ light chain constant region.

```
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCACCATCAGTTGCAGGGCAAGTCAGGACATTAGC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTGGAC

GTTCGGTGGAGGCACCAAGCTGGAAATCAAAcgggctgatgctgcaccaa ct
```

The amino acid sequence (134 a.a) of the light chain variable region of the mouse 9H5-4 antibody is shown below (SEQ ID NO: 49). The capital letters show the sequence of mouse 9H5-4 VH variable region and the small letters show the mouse Ig κ light chain constant region. The underlined part means the signal sequence and the double-underlined part means the CDR region (CDR1, CDR2, CDR3).

MMSSAQFLGLLLLCFQGTRCDIQMTQTTSSLSASLGDRVTISCRASQDIS
NYLNWYQQKPDGTVKLLIYYTSRLHSGVPSRFSGSGSGTDYSLTISNLEQ
EDIATYFCQQGNTLPWTFGGGTKLEIKradaapt The CDR1 of the light chain variable region of the 9H5-4 antibody is RASQDISNYLN (SEQ ID NO: 50), the CDR2 of the light chain variable region of the 9H5-4 antibody is YTSRLHS (SEQ ID NO: 51), and the CDR3 of the light chain variable region of the 9H5-4 antibody is QQGNTLP (SEQ ID NO: 52).

The nucleic acid sequence (465 bp) of the heavy chain variable region of the anti-PTPRS mouse 13G5-57 antibody is shown below (SEQ ID NO: 53). The capital letters show the mouse 13G5-57 VH variable region and the small letters show the mouse IgG2b heavy chain constant region.

```
ATGAACTTGGGGCTCAGCTTGATTTTCCTTGTCCTTGTTTTAAAAGGTGT

CCAGTGTGAAGTGAAGCTGGTGGAGTCTGGGGGAGGCTTAGTGCAGCCTG

GAGGGTCCCTGAAACTCTCCTGTGCAACCTCTGGATTCACTTTCAGTGAC

TATTACATGTATTGGGTTCGCCAGACTCCAGAGAAGAGGCTGGAGTGGGT

CGCATACATTAGTAATGGTGGTGGTAGCACCTATTATCCAGACACTGTAA

AGGGCCGATTCACCATCTCCAGAGACAATGCCAAGAACACCCTGTACCTG

CAAATGAGCCGTCTGAAGTCTGAGGACACAGCCATGTATTACTGTGCAAG

ACATGTTTACTACGGGAGGAACTATGCTATGGACTACTGGGGTCAAGGAA

CCTCAGTCACCGTCTCCTCAgccaaaacaacaccccatcagtctatcca ctggcccctaagggc
```

The amino acid sequence (155 a.a) of the heavy chain variable region of the mouse 13G5-57 antibody is shown below (SEQ ID NO: 54). The capital letters show the sequence of VH variable region and the small letters show the mouse IgG2b heavy chain constant region. The underlined part means the signal sequence and the double-underlined part means the CDR region (CDR1, CDR2, CDR3).

MNLGLSLIFLVLVLKGVQCEVKLVESGGGLVQPGGSLKLSCATSGFTFSD
YYMYWVRQTPEKRLEWVAYISNGGGSTYYPDTVKGRFTISRDNAKNTLYL
QMSRLKSEDTAMYYCARHVYYGRNYAMDYWGQGTSVTVSSakttppsvyp
lapkg The CDR1 of the heavy chain variable region of the 13G5-57 antibody is DYYMY (SEQ ID NO: 55), the CDR2 of the heavy chain variable region of the 13G5-57 antibody is YISNGGGSTYYPDTVKG (SEQ ID NO: 56), and the CDR3 of the heavy chain variable region of the 13G5-57 antibody is HVYYGRNYAMDY (SEQ ID NO: 57).

The nucleic acid sequence (465 bp) of the light chain variable region of the obtained anti-PTPRS mouse 13G5-57 antibody is shown below (SEQ ID NO: 58). The capital letters show the mouse 13G5-57 VH variable region and the small letters show the mouse Ig light chain constant region.

```
ATGAACTTGGGGCTCAGCTTGATTTTCCTTGTCCTTGTTTTAAAAGGTGT

CCAGTGTGAAGTGAAGCTGGTGGAGTCTGGGGGAGGCTTAGTGCAGCCTG

GAGGGTCCCTGAAACTCTCCTGTGCAACCTCTGGATTCACTTTCAGTGAC

TATTACATGTATTGGGTTCGCCAGACTCCAGAGAAGAGGCTGGAGTGGGT

CGCATACATTAGTAATGGTGGTGGTAGCACCTATTATCCAGACACTGTAA

AGGGCCGATTCACCATCTCCAGAGACAATGCCAAGAACACCCTGTACCTG
```

-continued

CAAATGAGCCGTCTGAAGTCTGAGGACACAGCCATGTATTACTGTGCAAG

ACATGTTTACTACGGGAGGAACTATGCTATGGACTACTGGGGTCAAGGAA

CCTCAGTCACCGTCTCCTCAgccaaaacaacaccccatcagtctatcca ctggccctaagggc

The amino acid sequence (155 a.a) of the light chain variable region of the mouse 13G5-57 antibody is shown below (SEQ ID NO: 59). The capital letters show the sequence of mouse 13G5-57 VH variable region and the small letters show the mouse Ig κ light chain constant region. The underlined part means the signal sequence and the double-underlined part means the CDR region (CDR1, CDR2, CDR3).

MMSSAQFLGLLLLCFQGTRCDIQMTQTTSSLSASLGDRVTISC<u>RASQDIS</u>

<u>NYLN</u>WYQQKPDGTVKLLIY<u>YTSRLHS</u>GVPSRFSGSGSGTDYSLTISNLEQ

EDIATYFC<u>QQGNTLPY</u>TFGGGTKLEIKradaaptvsifppsseqltsgga svvcf

The CDR1 of the light chain variable region of the 13G5-57 antibody is RASQDISNYLN (SEQ ID NO: 60), the CDR2 of the light chain variable region of the 13G5-57 antibody is YTSRLHS (SEQ ID NO: 61), and the CDR3 of the light chain variable region of the 13G5-57 antibody is QQGNTLPY (SEQ ID NO: 62).

The nucleic acid sequence (458 bp) of the heavy chain variable region of the anti-PTPRS mouse 22H8-84 antibody is shown below (SEQ ID NO: 63). The capital letters show the mouse 22H8-84 VH variable region and the small letters show the mouse IgG1 heavy chain constant region.

ATGGAATGTAACTGGATACTTCCTTTTATTCTGTCAGTAACTTCAGGTGT

CTACTCACAGGTTCAGCTCCAGCAGTCTGGGGCTGAGCTGGCAAGACCTG

GGGCTTCAGTGAAGTTGTCCTGCAAGGCTTCTGGCTACACCTTTACTAGC

TACTGGATGCAGTGGGTAAAACAGAGGCCTGGACAGGGTCTGGAATGGAT

TGGGGCTATTTATCCTGGAGATGGTGATACTAGGTACACTCAGAAGTTCA

AGGGCAAGGCCACATTGACTGCAGATAAATCCTCCAGCACAGCCTACATG

CAACTCAGCAGCTTGGCATCTGAGGACTCTGCGGTCTATTACTGTGCAAG

AAGGATTTACTACGGCTATTACTATGCTATGGACTACTGGGGTCAAGGAA

CCTCAGTCACCGTCTCCTCAgccaaaacgacaccccatctgtctatcca ctggcccc

The amino acid sequence (152 a.a) of the heavy chain variable region of the mouse 22H8-84 antibody is shown below (SEQ ID NO: 64). The capital letters show the sequence of VH variable region and the small letters show the mouse IgG1 heavy chain constant region. The underlined part means the signal sequence and the double-underlined part means the CDR region (CDR1, CDR2, CDR3).

MECNWILPFILSVTSGVYSQVQLQQSGAELARPGASVKLSCKASGYTFT<u>S</u>

<u>YWMQ</u>WVKQRPGQGLEWIG<u>AIYPGDGDTRYTQKFKG</u>KATLTADKSSSTAYM

QLSSLASEDSAVYYCA<u>RRIYYGYYYAMDY</u>WGQGTSVTVSSakttppsvyp la

The CDR1 of the heavy chain variable region of the 22H8-84 antibody is SYWMQ (SEQ ID NO: 65), the CDR2 of the heavy chain variable region of the 22H8-84 antibody is AIYPGDGDTRYTQKFKG (SEQ ID NO: 66), and the CDR3 of the heavy chain variable region of the 22H8-84 antibody is RIYYGYYYAMDY (SEQ ID NO: 67).

The nucleic acid sequence (430 bp) of the light chain variable region of the obtained anti-PTPRS mouse 22H8-84 antibody is shown below (SEQ ID NO: 68). The capital letters show the mouse 22H8-84 VH variable region and the small letters show the mouse Ig light chain constant region.

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAACTCCTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGA

GGATCCTCTCACGTTCGGTGCTGGGACCAAGCTGGAGCTGAAAcgggctg atgctgcaccaactgtatccatcaagggcg The amino acid sequence (143 a.a) of the light chain variable region of the mouse 22H8-84 antibody is shown below (SEQ ID NO: 69). The capital letters show the sequence of mouse 22H8-84 VH variable region and the small letters show the mouse Ig κ light chain constant region. The underlined part means the signal sequence and the double-underlined part means the CDR region (CDR1, CDR2, CDR3).

METDTILLWVLLLWVPGSTGDIVLTQSPASLAVSLGQRATISC<u>KASQSVD</u>

<u>YDGDSYMN</u>WYQQKPGQPPKLLIY<u>AASNLES</u>GIPARFSGSGSGTDFTLNIH

PVEEEDAATYYC<u>QQSNEDPL</u>TFGAGTKLELKradaaptvsikg

The CDR1 of the light chain variable region of the 22H8-84 antibody is KASQSVDYDGDSYMN (SEQ ID NO: 70), the CDR2 of the light chain variable region of the 22H8-84 antibody is AASNLES (SEQ ID NO: 71), and the CDR3 of the light chain variable region of the 22H8-84 antibody is QQSNEDPL (SEQ ID NO: 72).

The nucleic acid sequence of the heavy chain variable region of the anti-PTPRS mouse 49F2-30 antibody (469 bp) is shown below (SEQ ID NO:25). The capital letters show the variable region of the mouse 49F2-30 VH and the small letters show the mouse IgG1 heavy chain constant region.

ATGAACTTCGGGCTCAGGTTGATTTTCCTTGCCCTCATTTTAAAAGGTGT

CCAGTGTGAGGTGCAGCTGGTGGAGTCTGGGGGAGACTTAGTGAAGCCTG

GAGGGTCCCTGAAACTCTCCTGTGCAGCCTCTGGATTCATTTTCAGTAGC

TATGGCATGTCTTGGGTTCGCCAGACTCCAGACAAGAGGCTGGAGTGGGT

-continued
CGCAACCATTAGTAGTGGTGGTAGTGACACCTATTATCCAGACAGTGTGA

AGGGGCGATTCACCATCTCCAGAGACAATGCCAACAACACCCTGTACCTG

CAAATGAGCAGTCTGAAGTCTGAGGACACAGCCATGTATTACTGTGCAAG

ACAGGTCTACTATGGTCTTTACTGGTATTTCGATGTCTGGGGCGCAGGGA

CCACGGTCACCGTCTCCTCAgccaaaacgacaccccatctgtctatcca ctggcccctaagggcgaat

The amino acid sequence of the heavy chain variable region of the mouse 49F2-30 antibody (156 a.a) is shown below (SEQ ID NO:26). The capital letters show the VH variable gene and the small letters show the mouse IgG1 heavy chain constant region. The underlined sequences show the signal sequences, and the double-underlined sequences show the CDR regions (CDR1, CDR2, CDR3).

MNFGLRLIFLALILKGVQCEVQLVESGGDLVKPGGSLKLSCAASGFIFSS

YGMSWVRQTPDKRLEWVATISSGGSDTYYPDSVKGRFTISRDNANNTLYL

QMSSLKSEDTAMYYCARQVYYGLYWYFDVWGAGTTVTVSS akttppsvy plapkge

The CDR1 of the heavy chain variable region of the 49F2-30 antibody is SYGMS (SEQ ID NO:27), the CDR2 of the heavy chain variable region of the 49F2-30 antibody is TISSGGSDTYYPDSVKG (SEQ ID NO:28), and the CDR3 of the heavy chain variable region of the 49F2-30 antibody is QVYYGLYWYFDV (SEQ ID NO:29).

The nucleic acid sequence of the light chain variable region of the obtained anti-PTPRS mouse 49F2-30 antibody (413 bp) is shown below (SEQ ID NO:30). The capital letters show the variable region of the mouse 49F2-30 VL and the small letters show the mouse Ig light chain constant region.

ATGGAGTCACAGATTCAGGTCTTTGTATTCGTGTTTCTCTGGTTGTCTGG

TGTTGACGGAGACATTGTGATGACCCAGTCTCACAAATTCATGTCCACAT

CAGTAGGAGACAGGGTCAGCATCATTTGTAAGGCCAGTCAGGATGTGAAT

ACTGCTGTAGCCTGGTATCAACAGAAACCAGGACAATCTCCTAAATTACT

GATTTACTCGGCATCCTACCGGTACACTGGAGTCCCTGATCGCTTCACTG

GCAGTGGATCTGGGACGGATTTCACTTTCACCATCAGCAGTGTGCAGGCT

GAAGACCTGGCAATTTATTACTGTCAGCAACATTATAGTACTCCGTACAC

GTTCGGAGGGGGGACCAAGCTGGAAATAAAAcgggctgatgctgcaccaa ctgtatccatcaa

The amino acid sequence of the light chain variable region of the mouse 49F2-30 antibody (137 a.a) is shown below (SEQ ID NO:31). The capital letters show the mouse 49F2-30 VL variable region and the small letters show the mouse Ig κ light chain constant region. The underlined sequences show the signal sequences, and the double-underlined sequences show the CDR regions (CDR1, CDR2, CDR3).

MESQIQVFVFVFLWLSGVDGDIVMTQSHKFMSTSVGDRVSIICKASQDVN

TAVAWYQQKPGQSPKLLIYSASYRYTGVPDRFTGSGSGTDFTFTISSVQA

EDLAIYYCQQHYSTPYTFGGGTKLEIK radaaptvsi

The CDR1 of the light chain variable region of the 49F2-30 antibody is KASQDVNTAVA (SEQ ID NO:32), the CDR2 of the light chain variable region of the 49F2-30 antibody is SASYRYT (SEQ ID NO:33), and the CDR3 of the light chain variable region of the 49F2-30 antibody is QQHYSTP (SEQ ID NO:34).

3. Preparation of Expression Vector of Chimerized Antibody 3-1) Cloning of cDNA that Codes for Human Ig Constant Region The cDNAs of a human IgG1 heavy chain constant region and a human Ig κ light chain constant region were cloned from the total RNA of human PBMC, and were each cloned to pCR4Blunt-TOPO vector and introduced in an E. coli competent cell using a commercially available kit "Zero Blunt TOPO PCR Cloning Kit" (Invitrogen, Catalog No.: 1325137) according to the instruction attached to the kit to give an E. coli transformant. The above-mentioned plasmid was obtained from this transformant and a plasmid DNA sample was sent to Operon Biotechnology Co., Ltd. (Tokyo) for sequence analysis to confirm the cDNA base sequence in the plasmid.

3-2) Preparation of Expression Vector of Chimerized 9H5-4 (10F7-38, 14A8-85) Antibody In order to prepare a cDNA that coded for a heavy chain of a chimerized PTPRS antibody, the heavy chain variable region of the mouse 9H5-4 antibody obtained in 2-2 and the pEE6.4 vector (Lonza Biologics, Slough, UK) into which the human IgG heavy chain constant region was incorporated had been fused, and the heavy chain variable region of the mouse 9H5-4 antibody was amplified by the PCR method and the PCR product which had a length of about 450 bases was obtained. At that time, the primers were those as follows. The obtained PCR product was purified by a 1.5% low melting point agalose process.

The primer for expressing heavy chain in chimeric 9H5-4 antibody 1) forward primer: chi10F7VH-IF(Hind3)
Sequence:
(SEQ ID NO: 73)
5' ttt AAG CTT gcc gcc acc ATG GAG TTG GGA CTG AGC TGG 3' (39-mer)

2) reverse primer: chi10F7VH-462R(ApaI)
Sequence:
(SEQ ID NO: 74)
5' cga tgg gcc ctt ggt gct agc TGA GGA GAC TGT GAG AGT GGT 3' (42-mer)

"A PCR product that coded for the 9H5-4 heavy chain variable region" was obtained from the mouse 9H5-4 antibody heavy chain variable region obtained in 2-2 by the PCR process. The PCR product that coded for 9H5-4 heavy chain variable region was digested with Hind III and an Apa I restriction enzyme and purified by a 1.5% agalose gel process. This was dissolved by ddH$_2$O to give a solution of a cDNA fragment that coded for the heavy chain variable region.

The V$_H$ coding region of the 9H5-4 of the obtained cDNA was amplified by PCR from a pCR4Blunt-TOPO plasmid clone including the V$_H$ coding region of the 9H5-4, by using primers chi10F7VH-IF (Hind3) and chi10F7VH-462R (ApaI) to which preferable restriction sites for cloning into a pEE6.4 vector (Lonza Biologics, Slough, UK) (Hind III and ApaI) and an ideal Kozak sequence (GCCGCCACC) had been introduced using Hind III and ApaI as cloning sites. The chi9H5-4VH-pEE6.4 vector includes a heavy chain constant region of human IgG1. The $V_H$ PCR fragment was inserted into the pEE6.4 vector by in-frame using Hind III and ApaI. The construct was investigated by a cDNA base sequence analysis and a plasmid DNA sample was sent to Operon Biotechnology Co., Ltd. (Tokyo) for sequence analysis to confirm the cDNA base sequence in the plasmid.

In order to prepare a cDNA that coded for a light chain of a chimerized 9H5-4 antibody, the PCR product was amplified by a length of about 730 bases by a technique based on overlap extension PCR from the PCR fragment in which the mouse 9H5-4 antibody light chain variable region obtained in 2-3 and the human Ig κ light chain constant region obtained in 3-2 had been fused.

The PCR product that coded for the 9H5-4 light chain variable region was digested by Hind III and an EcoRI restriction enzyme, and purified by a 1.5% agalose gel process. This was dissolved in ddH$_2$O to give a solution of a cDNA fragment that codes for the light chain variable region.

The obtained VL-coding cDNA of 9H5-4 was amplified by PCR from a pCR4Blunt-TOPO plasmid clone including the VL region of the 9H5-4 using primers chi11G9VL-IF (Hind) and chi11G9VL-726R (RI) to which preferable restriction sites (Hind III and EcoRI) for cloning into a pEE14.4 vector (Lonza Biologics) and an ideal Kozak sequence had been introduced. The Chi9H5-4VL-pEE14.4 vector includes a kappa light chain constant region. The VL PCR fragment was inserted into the pEE14.4 vector by in-frame by using Hind III and EcoRI. The construct was investigated by a cDNA base sequence analysis. The primer for expressing light chain in chimeric 9H5-4 antibody 1) Forward primer: chi11G9VL-IF(Hind)
Sequence:
(SEQ ID NO: 75)
5' acc AAG CTT gcc gcc acc ATG ATG TCC TCT GCT CAG TTC 3' (39-mer)

2) reverse primer: chi11G9VL-408R
Sequence:
(SEQ ID NO: 76)
5' agc cac agt tcg TTT GAT TTC AGC TTG GTG GCC 3' (33-mer)

3) Forward primer: chi11G9VL-385F
Sequence:
(SEQ ID NO: 77)
5' CTG GAA ATC AAA cga act gtg gct gca cca tct 3' (33-mer)

4) reverse primer: chi11G9VL-726R(RI)
Sequence:
(SEQ ID NO: 78)
5' aaa GAA TTC cta gca ctc tcc cct gtt gaa 3' (30-mer)

3-2) Preparation of Expression Vector of Chimerized 13G5-57(13G5-52) Antibody

In order to prepare a cDNA that codes for a heavy chain of a chimerized PTPRS antibody, the heavy chain variable region of the mouse 13G5-57 antibody obtained in 2-2 and the pEE6.4 vector (Lonza Biologics, Slough, UK) into which the human IgG heavy chain constant region was incorporated had been fused. In a similar method as the 9H5-4 antibody, the PCR product was obtained and purified. At that time, the primers were those as follows.

The primer for expressing heavy chain in chimeric 13G5-57 antibody 1) forward primer: chi13G5.57VH-IF(Hind3)
Sequence:
(SEQ ID NO: 79)
5' ttt AAG CTT gcc gcc acc ATG AAC TTG GGG CTC AGC TTG 3' (39-mer)

2) reverse primer: chi13G5.57VH-456R(ApaI)
Sequence:
(SEQ ID NO: 80)
5' cga tgg gcc ctt ggt gct agc TGA GGA GAC GGT GAC TGA GGT 3' (42-mer)

In order to prepare a cDNA that codes for a light chain of a chimerized 13G5-57 antibody, the PCR product was amplified by a length of about 730 bases by a technique based on overlap extension PCR from the PCR fragment in which the mouse 13G5-57 antibody light chain variable region obtained in 2-3 and the human Ig κ light chain constant region obtained in 3-2 had been fused.

The primer for expressing light chain in chimeric 13G5-57 antibody

1) Forward primer: chi11G9VL-IF(Hind)
Sequence:
(SEQ ID NO: 81)
5' acc AAG CTT gcc gcc acc ATG ATG TCC TCT GCT CAG TTC 3' (39-mer)

2) reverse primer: chi11G9VL-408R
Sequence:
(SEQ ID NO: 82)
5' agc cac agt tcg TTT GAT TTC AGC TTG GTG GCC 3' (33-mer)

3) Forward primer: chi11G9VL-385F
Sequence:
(SEQ ID NO: 83)
5' CTG GAA ATC AAA cga act gtg gct gca cca tct 3' (33-mer)

4) reverse primer: chi11G9VL-726R(RI)
Sequence:
(SEQ ID NO: 84)
5' aaa GAA TTC cta gca ctc tcc cct gtt gaa 3' (30-mer)

In a similar manner to preparation of expression vectors of chimerized 9H5-4 antibody, expression vectors for such a heavy chain and a light chain of chimerized 13G5-57 antibody were prepared.

3-2) Preparation of Expression Vector of Chimerized 22H8-84 Antibody

In order to prepare a cDNA that codes for a heavy chain of a chimerized PTPRS antibody, the heavy chain variable region of the mouse 22H8-84 antibody obtained in 2-2 and the pEE6.4 vector (Lonza Biologics, Slough, UK) into which the human IgG heavy chain constant region was incorporated had been fused. In a similar method as the 9H5-4 antibody, the PCR product was obtained and purified.

At that time, the primers were those as follows. The primer for expressing heavy chain in chimeric 22H8-84 antibody 1) forward primer: chi22H8VH-IF(Hind3)
Sequence:
(SEQ ID NO: 85)
5' ttt AAG CTT gcc gcc acc ATG GAA TGT AAC TGG ATA CTT 3' (39-mer)

2) reverse primer: chi22H8VH-456R(ApaI)
Sequence:
(SEQ ID NO: 86)
5' cga tgg gcc ctt ggt gct agc TGA GGA GAC GGT GAC TGA GGT 3' (42-mer)

In order to prepare a cDNA that codes for a light chain of a chimerized 22H8-84 antibody, the PCR product was amplified by a length of about 730 bases by a technique based on overlap extension PCR from the PCR fragment in which the mouse 22H8-84 antibody light chain variable region obtained in 2-3 and the human Ig κ light chain constant region obtained in 3-2 had been fused.

The primer for expressing light chain in chimeric 22H8-84 antibody

1) Forward primer: chi22H8VL-IF(Hind)
Sequence:
(SEQ ID NO: 87)
5' acc AAG CTT gcc gcc acc ATG GAG ACA GAC ACA ATC CTG 3' (39-mer)

2) reverse primer: chi22H8VL-420R
Sequence:
(SEQ ID NO: 88)
5' agc cac agt tcg TTT CAG CTC CAG CTT GGT CCC 3' (33-mer)

3) Forward primer: chi22H8VL-397F
Sequence:
(SEQ ID NO: 89)
5' CTG GAG CTG AAA cga act gtg gct gca cca tct 3' (33-mer)

4) reverse primer: chi49F2VL-726R(RI)
Sequence:
(SEQ ID NO: 90)
5' aaa GAA TTC cta gca ctc tcc cct gtt gaa 3' (30-mer)

In a similar manner to preparation of expression vectors of chimerized 9H5-4 antibody, expression vectors for such a heavy chain and a light chain of chimerized 22H8-84 antibody were prepared.

3-2) Preparation of cDNA that Codes for Heavy Chain of Chimerized PTPRS Antibody In order to prepare a cDNA that codes for a heavy chain of a chimerized PTPRS antibody, the two PCR fragments were altered by a procedure based on an overlap extension PCR process in a PCR fragment in which the heavy chain variable region of the mouse 49F2-30 antibody obtained in 2-2 and the human IgG heavy chain constant region obtained in 3-1 had been fused, and the PCR product was amplified by a length of 1434 bases by a method that allows partial formation of a double filament molecule as a result of a hybrid operation. At that time, the primers (SEQ ID NOS: 17 to 24) were those as shown in Table 1. The obtained PCR product was purified by a 1.5% low melting point agalose process.

TABLE 1

| Primer name | Sequence |
|---|---|
| Primer for expressing heavy chain in chimeric 49F2-30 antibody | |
| 1) chi49F2VH-IF(Hind3) | 5' acc AAG CTT gcc gcc acc ATG AAC TTC GGG CTC AGG TTG 3' (39-mer) |
| 2) chi49F2VH-447R | 5' ctt ggt gct agc TGA GGA GAC GGT GAC CGT GGT 3' (33-mer) |
| 3) chi49F2VH-424F | 5' ACC GTC TCC TCA gct agc acc aag ggc cca tcg 3' (33-mer) |
| 4) chi49F2VH-1434R(RI) | 5' ttt GAA TTC tca ttt acc cgg aga cag gga 3' (30-mer) |
| Primer for expressing light chain in chimeric 49F2-30 antibody | |
| 5) chi49F2VL-IF(Hind) | 5' acc AAG CTT gcc gcc acc ATG GAG TCA CAG ATT CAG GTC 3' (33-mer) |
| 6) chi49F2VL-408R | 5' agc cac agt tcg TTT TAT TTC CAG CTT GGT CCC 3' (33-mer) |
| 7) chi49F2VL-385F | 5' CTG GAA ATA AAA cga act gtg gct gca cca tct 3' (33-mer) |
| 8) chi49F2VL-726R(RI) | 5' aaa GAA TTC cta gca ctc tcc cct gtt gaa 3' (30-mer) |

There is a region in which cDNA overlaps the mouse 49F2-30 antibody heavy chain variable region obtained in 2-2 and the human IgG1 heavy chain constant region obtained in 3-1. Therefore, using this region, "a PCR product that codes for the 49F2-30 heavy chain variable region" was obtained by an overlap extension PCR process was obtained. The PCR product that codes for 49F2-30 heavy chain variable region was digested with Hind III and an EcoR I restriction enzyme and purified by a 1.5% agalose gel process. This was dissolved by ddH$_2$O to give a solution of a cDNA fragment that codes for the heavy chain variable region.

The V$_H$ coding region of the 49F2-30 of the obtained cDNA was amplified by PCR from a pCR4Blunt-TOPO plasmid clone including the V$_H$ coding region of the 49F2-30, by using primers chi49F2VH-IF (Hind3) and chi49F2VH-1434R (RI) to which preferable restriction sites for cloning into a pEE6.4 vector (Lonza Biologics, Slough, UK) (Hind III and EcoRI) and an ideal Kozak sequence (GCCGCCACC) had been introduced using Hind III and EcoRI as cloning sites. The chi49F2VH-pEE6.4 vector includes a heavy chain constant region of human IgG1. The V$_H$ PCR fragment was inserted into the pEE6.4 vector by in-frame using Hind III and EcoRI. The construct was investigated by a cDNA base sequence analysis.

3-3) Preparation of cDNA that Codes for Light Chain of Chimerized PTPRS Antibody In order to prepare a cDNA that codes for a light chain of a chimerized PTPRS antibody, the PCR product was amplified by a length of 726 bases by a technique based on overlap extension PCR from the PCR fragment in which the mouse 49F2-30 antibody light chain variable region obtained in 2-3 and the human Ig κ light chain constant region obtained in 3-2 had been fused.

The PCR product that codes for the 49F2-30 light chain variable region was digested by Hind III and an EcoRI restriction enzyme, and purified by a 1.5% agalose gel process. This was dissolved in ddH$_2$O to give a solution of a cDNA fragment that codes for the light chain variable region.

The obtained V$_L$-coding cDNA of 49F2-30 was amplified by PCR from a pCR4Blunt-TOPO plasmid clone including the V$_L$ region of the 49F2-30 using primers chi49F2VL-IF (Hind) and chi 49F2VL-726R (RI) to which preferable restriction sites (Hind III and EcoRI) for cloning into a pEE14.4 vector (Lonza Biologics) and an ideal Kozak sequence had been introduced. The Chi49F2VL-pEE14.4 vector includes a kappa light chain constant region. The V$_L$ PCR fragment was inserted into the pEE14.4 vector by in-frame by using Hind III and EcoRI. The construct was investigated by a cDNA base sequence analysis.

3-4) Construction of Chimerized PTPRS Antibody Double Gene Lonza Expression Vector A chimerized PTPRS antibody (double gene) Lonza expression vector in which the heavy chain expressing vector of the chimerized PTPRS antibody and the light chain expressing vector of the chimerized PTPRS antibody had been combined in one double gene vector was constructed by a standard cloning technology.

4. Transient Expression in HEK-293F Cell

The following transient expression vector DNAs (80 µg) were used.
1) chi9H5-4VH/VL DG Lonza vector DNA
2) chi13G5-57VH/VL DG Lonza vector DNA
3) chi22H8-84VH/VL DG Lonza vector DNA
4) chi49F2-30VH/VL DG Lonza vector DNA On the previous day of transfection, a 293F cell was adjusted to 80 mL at 8×10$^5$ cells/mL in a 250 mL Erlenmeyer flask (Corning #431144), and cultured by shaking under conditions of 37° C. and a CO$_2$ concentration of 8% for 7 days.

After the culturing for 7 days, a culture liquid of a 293F cell that had undergone transfection was collected in a 50 mL tube and centrifuged under conditions of 2,070 g and 4° C. for 5 minutes. The supernatant was filtered by a syringe filter (Catalog No. 431220; CORNING) having a pore size of 0.45 µm, and the culture supernatants were gathered together.

5. Purification of Anti-PTPRS Chimerized Antibody

The chimerized 9H5-4,13G5-57, 22H8-84 and 49F2-30 antibody were purified by protein A affinity chromatography. The crude antibody liquid obtained in 4. was each purified by a protein A affinity column (rProtein A Sepharose Fast Flow (Catalog No. 17-1279-01; Lot. 311272; GE Healthcare). The column conditions are as follows. Affinity purification was conducted by using a binding buffer (20 mM Sodium phosphate, 0.15 M NaCl, pH 7.4) and an elution buffer (0.1 M Glycine-HCl, pH 2.7). The pH of the eluted fraction was adjusted to around 7.2 by adding a neutralizing buffer (1 M Tris-HCl pH 9.5). In order to substitute the buffer of the purified antibody with PBS, the buffer was replaced by using Slide-A-Lyzer MINI Dialysis unit 10kMWCO.

The concentration of the purified antibody was calculated by measuring the absorbance at 280 nm and defining 1 mg/l as 1.38 OD.

The purified anti-PTPRS chimerized antibody (ch9H5-4Ab, ch13G5-57Ab, ch22H8-84Ab and ch49F2-30Ab) was analyzed by SDS-PAGE and a Flowcytometry process.

The nucleic acid sequences and amino acid sequences of the heavy chain and light chain of the prepared chimera 9H5-4 antibody are represented respectively by the following sequence numbers.

| Heavy chain | Light chain |
| --- | --- |
| SEQ ID NO: 91 (nucleic acid sequence) | SEQ ID NO: 93 (nucleic acid sequence) |
| SEQ ID NO: 92 (amino acid sequence) | SEQ ID NO: 94 (amino acid sequence) |

The nucleic acid sequence of the heavy chain of the anti-PTPRS chimera 9H5-4 antibody (1419 bp) is shown below (SEQ ID NO: 91). The capital letters show the chimera 9H5-4 VH variable region, and the small letters show the human IgG1 heavy chain constant region.

ATGGAGTTGGGACTGAGCTGGGTATTTCTTGTGGCTCTTTTGAATGGTGT

CCAGTGTCAGGTGCAGCTTGTAGAGACCGGGGGAGGCTTGGTGAGGCCTG

GAAATTCTCTGAAACTCTCCTGTGTTACCTCGGGATTCACTTTCAGTAAC

TACCGGATGCACTGGCTTCGCCAGCCTCCAGGGAAGAGGCTGGAGTGGAT

TGCTGTAATTACAGTCAAATCTGATAATTATGGAGCAAATTATGCAGAGT

CTGTGAAAGGCAGATTCACTATTTCAAGAGATGATTCAAAAAGCAGTGTC

TACCTGCAGATGAACAGATTAAGAGAGGAAGACACTGCCACTTATTATTG

TAGTAGATCGGTCTACTATGGTTACGTCCTAGCCTTTGACTACTGGGGCC

AAGGCACCACTCTCACAGTCTCCTCAgctagcaccaagggcccatcggtc

```
ttccccctggcaccctcctccaagagcacctctgggggcacagcggccct gggctgcctggtcaaggactacttccccgaaccggtgacggtgtcgtgga actcaggcgccctgaccagcggcgtgcacaccttcccggctgtcctacag tcctcaggactctactccctcagcagcgtggtgaccgtgccctccagcag cttgggcacccagacctacatctgcaacgtgaatcacaagcccagcaaca ccaaggtggacaagaaagttgagcccaaatcttgtgacaaaactcacaca tgcccaccgtgcccagcacctgaactcctgggggaccgtcagtcttcct cttcccccaaaacccaaggacaccctcatgatctcccggacccctgagg tcacatgcgtggtggtggacgtgagccacgaagaccctgaggtcaagttc aactggtacgtggacggcgtggaggtgcataatgccaagacaaagccgcg ggaggagcagtacaacagcacgtaccgtgtggtcagcgtcctcaccgtcc tgcaccaggactggctgaatggcaaggagtacaagtgcaaggtctccaac aaagcccttccagcccccatcgagaaaaccatctccaaagccaaagggca gccccgagaaccacaggtgtacaccctgcccccatcccgggatgagctga ccaagaaccaggtcagcctgacctgcctggtcaaaggcttctatcccagc gacatcgccgtggagtgggagagcaatgggcagccggagaacaactacaa gaccacgcctcccgtgctggactccgacggctccttcttcctctacagca agctcaccgtggacaagagcaggtggcagcaggggaacgtcttctcatgc tccgtgatgcatgaggctctgcacaaccactacacgcagaagagcctctc cctgtctccgggtaaatga
```

The amino acid sequence of the heavy chain of the anti-PTPRS chimera 9H5-4 antibody (472 a.a.) is shown below (SEQ ID NO: 92). The capital letters show the chimera 9H5-4 VH variable region, and the small letters show the human IgG1 heavy chain constant region.

MELGLSWVFLVALLNGVQCQVQLVETGGGLVRPGNSLKLSCVTSGFTFSN

YRMHWLRQPPGKRLEWIAVITVKSDNYGANYAESVKGRFTISRDDSKSSV

YLQMNRLREEDTATYYCSRSVYYGYVLAFDYWGQGTTLTVSSastkgpsv fplapsskstsggtaalgclvkdyfpepvtvswnsgaltsgvhtfpavlq ssglyslssvvtvpssslgtqtyicnvnhkpsntkvdkkvepkscdktht cppcpapellggpsvflfppkpkdtlmisrtpevtcvvvdvshedpevkf nwyvdgvevhnaktkpreeqynstyrvvsvltvlhqdwlngkeykckvsn kalpapiektiskakgqprepqvytlppsrdeltknqvsltclvkgfyps diavewesngqpennykttppvldsdgsfflysklvtvdksrwqqgnvfsc svmhealhnhytqkslslspgk The nucleic acid sequence of the light chain of the anti-PTPRS chimera 9H5-4 antibody (705 bp) is shown below (SEQ ID NO: 93). The capital letters show the chimera 9H5-4 VL variable region, and the small letters show the human Ig κ light chain constant region.

```
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCACCATCAGTTGCAGGGCAAGTCAGGACATTAGC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTGGAC

GTTCGGTGGAGGCACCAAGCTGGAAATCAAAcgaactgtggctgcaccat ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacg ctgagcaaagcagactacgagaaacacaaagtctacgcctgcgaagtcac ccatcagggcctgagctcgcccgtcacaaagagcttcaacaggggagagt gctag
```

The amino acid sequence of the light chain of the anti-PTPRS chimera 9H5-4 antibody (234 a.a.) is shown below (SEQ ID NO: 94). The capital letters show the chimera 9H5-4 VL variable region, and the small letters show the human Ig κ light chain constant region.

MMSSAQFLGLLLLCFQGTRCDIQMTQTTSSLSASLGDRVTISCRASQDIS

NYLNWYQQKPDGTVKLLIYYTSRLHSGVPSRFSGSGSGTDYSLTISNLEQ

EDIATYFCQQGNTLPWTFGGGTKLEIKrtvaapsvfifppsdeqlksgta svvcllnnfypreakvqwkvdnalqsgnsqesvteqdskdstyslsstlt lskadyekhkvyacevthqglsspvtksfnrgec

<13G5-57>

The nucleic acid sequences and amino acid sequences of the heavy chain and light chain of the prepared chimera 13G5-57 antibody are represented respectively by the following sequence numbers.

| Heavy chain | Light chain |
| --- | --- |
| SEQ ID NO: 95 (nucleic acid sequence) SEQ ID NO: 96 (amino acid sequence) | SEQ ID NO: 97 (nucleic acid sequence) SEQ ID NO: 98 (amino acid sequence) |

The nucleic acid sequence of the heavy chain of the anti-PTPRS chimera 13G5-57 antibody (1413 bp) is shown below (SEQ ID NO: 95). The capital letters show the chimera 13G5-57 VH variable region, and the small letters show the human IgG1 heavy chain constant region.

```
ATGAACTTGGGGCTCAGCTTGATTTTCCTTGTCCTTGTTTTAAAAGGTGT

CCAGTGTGAAGTGAAGCTGGTGGAGTCTGGGGGAGGCTTAGTGCAGCCTG

GAGGGTCCCTGAAACTCTCCTGTGCAACCTCTGGATTCACTTTCAGTGAC

TATTACATGTATTGGGTTCGCCAGACTCCAGAGAAGAGGCTGGAGTGGGT

CGCATACATTAGTAATGGTGGTGGTAGCACCTATTATCCAGACACTGTAA
```

```
AGGGCCGATTCACCATCTCCAGAGACAATGCCAAGAACACCCTGTACCTG

CAAATGAGCCGTCTGAAGTCTGAGGACACAGCCATGTATTACTGTGCAAG

ACATGTTTACTACGGGAGGAACTATGCTATGGACTACTGGGGTCAAGGAA

CCTCAGTCACCGTCTCCTCAgctagcaccaagggcccatcggtcttcccc ctggcacctcctccaagagcacctctgggggcacagcggccctgggctg cctggtcaaggactactccccgaaccggtgacggtgtcgtggaactcag gcgccctgaccagcggcgtgcacaccttcccggctgtcctacagtcctca ggactctactcccagcagcgtggtgaccgtgccctccagcagcttggg cacccagacctacatctgcaacgtgaatcacaagcccagcaacaccaagg tggacaagaaagttgagcccaaatcttgtgacaaaactcacacatgccca ccgtgcccagcacctgaactcctgggggaccgtcagtcttcctcttccc cccaaaacccaaggacacCctcatgatctcccggacccctgaggtcacat gcgtggtggtggacgtgagccacgaagaccctgaggtcaagttcaactgg tacgtggacggcgtggaggtgcataatgccaagacaaagccgcgggagga gcagtacaacagcacgtaccgtgtggtcagcgtcctcaccgtcctgcacc aggactggctgaatggcaaggagtacaagtgcaaggtctccaacaaagcc ctcccagcccccatcgagaaaaccatctccaaagccaaagggcagccccg agaaccacaggtgtacaccctgcccccatcccgggatgagctgaccaaga accaggtcagcctgacctgcctggtcaaaggcttctatcccagcgacatc gccgtggagtgggagagcaatgggcagccggagaacaactacaagaccac gcctcccgtgctggactccgacggctccttcttcctctacagcaagctca ccgtggacaagagcaggtggcagcaggggaacgtcttctcatgctccgtg atgcatgaggctctgcacaaccactacacgcagaagagcctctccctgtc tccgggtaaatga
```

The amino acid sequence of the heavy chain of the anti-PTPRS chimera 13G5-57 antibody (470 a.a.) is shown below (SEQ ID NO: 96). The capital letters show the chimera 13G5-57 VH variable region, and the small letters show the human IgG1 heavy chain constant region.

```
MNLGLSLIFLVLVLKGVQCEVKLVESGGGLVQPGGSLKLSCATSGFTFSD

YYMYWVRQTPEKRLEWVAYISNGGGSTYYPDTVKGRFTISRDNAKNTLYL

QMSRLKSEDTAMYYCARHVYYGRNYAMDYWGQGTSVTVSSastkgpsvfp lapsskstsggtaalgclvkdyfpepvtvswnsgaltsgvhtfpavlqss glyslssvvtvpssslgtqtyicnvnhkpsntkvdkkvepkscdkthtcp pcpapellggpsvflfppkpkdtlmisrtpevtcvvvdvshedpevkfnw yvdgvevhnaktkpreeqynstyrvvsvltvlhqdwlngkeykckvsnka lpapiektiskakgqprepqvytlppsrdeltknqvsltclvkgfypsdi avewesngqpennykttppvldsdgsfflysklltvdksrwqqgnvfscsv mhealhnhytqkslslspgk
```

The nucleic acid sequence of the light chain of the anti-PTPRS chimera 13G5-57 antibody (705 bp) is shown below (SEQ ID NO: 97). The capital letters show the chimera 13G5-57VL variable region, and the small letters show the human Ig κ light chain constant region.

```
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCACCATCAGTTGCAGGGCAAGTCAGGACATTAGC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTACAC

GTTCGGAGGGGGGACCAAGCTGGAAATAAAAcgaactgtggctgcaccat ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacg ctgagcaaagcagactacgagaaacacaaagtctacgcctgcgaagtcac ccatcagggcctgagctcgcccgtcacaaagagcttcaacaggggagagt gctag
```

The amino acid sequence of the light chain of the anti-PTPRS chimera 13G5-57 antibody (234 a.a.) is shown below (SEQ ID NO: 98). The capital letters show the chimera 13G5-57 VL variable region, and the small letters show the human Ig κ light chain constant region.

```
MMSSAQFLGLLLLCFQGTRCDIQMTQTTSSLSASLGDRVTISCRASQDIS

NYLNWYQQKPDGTVKLLIYYTSRLHSGVPSRFSGSGSGTDYSLTISNLEQ

EDIATYFCQQGNTLPYTFGGGTKLEIKrtvaapsvfifppsdeqlksgta svvcllnnfypreakvqwkvdnalqsgnsqesvteqdskdstyslsstlt lskadyekhkvyacevthqglsspvtksfnrgec
```

The nucleic acid sequences and amino acid sequences of the heavy chain and light chain of the prepared chimera 22H8-84 antibody are represented respectively by the following sequence numbers.

| Heavy chain | Light chain |
|---|---|
| SEQ ID NO: 99 (nucleic acid sequence) | SEQ ID NO: 101 (nucleic acid sequence) |
| SEQ ID NO: 100 (amino acid sequence) | SEQ ID NO: 102 (amino acid sequence) |

The nucleic acid sequence of the heavy chain of the anti-PTPRS chimera 22H8-84 antibody (1413 bp) is shown below (SEQ ID NO: 99). The capital letters show the chimera 22H8-84 VH variable region, and the small letters show the human IgG1 heavy chain constant region.

```
ATGGAATGTAACTGGATACTTCCTTTTATTCTGTCAGTAACTTCAGGTGT

CTACTCACAGGTTCAGCTCCAGCAGTCTGGGGCTGAGCTGGCAAGACCTG

GGGCTTCAGTGAAGTTGTCCTGCAAGGCTTCTGGCTACACCTTTACTAGC

TACTGGATGCAGTGGGTAAAACAGAGGCCTGGACAGGGTCTGGAATGGAT
```

-continued
TGGGGCTATTTATCCTGGAGATGGTGATACTAGGTACACTCAGAAGTTCA

AGGGCAAGGCCACATTGACTGCAGATAAATCCTCCAGCACAGCCTACATG

CAACTCAGCAGCTTGGCATCTGAGGACTCTGCGGTCTATTACTGTGCAAG

AAGGATTTACTACGGCTATTACTATGCTATGGACTACTGGGGTCAAGGAA

CCTCAGTCACCGTCTCCTCAgctagcaccaagggcccatcggtcttccc ctggcacctcctccaagagcacctctggggcacagcggccctgggctg cctggtcaaggactacttccccgaaccggtgacggtgtcgtggaactcag gcgccctgaccagcggcgtgcacaccttcccggctgtcctacagtcctca ggactctactccctcagcagcgtggtgaccgtgccctccagcagcttggg cacccagacctacatctgcaacgtgaatcacaagcccagcaacaccaagg tggacaagaaagttgagcccaaatcttgtgacaaaactcacacatgccca ccgtgcccagcacctgaactcctgggggaccgtcagtcttcctcttccc cccaaaacccaaggacaccctcatgatctcccggacccctgaggtcacat gcgtggtggtggacgtgagccacgaagaccctgaggtcaagttcaactgg tacgtggacggcgtggaggtgcataatgccaagacaaagccgcgggagga gcagtacaacagcacgtaccgtgtggtcagcgtcctcaccgtcctgcacc aggactggctgaatggcaaggagtacaagtgcaaggtctccaacaaagcc ctcccagcccccatcgagaaaaccatctccaaagccaaagggcagccccg agaaccacaggtgtacaccctgcccccatcccgggatgagctgaccaaga accaggtcagcctgacctgcctggtcaaaggcttctatcccagcgacatc gccgtggagtgggagagcaatgggcagccggagaacaactacaagaccac gcctcccgtgctggactccgacggctccttcttcctctacagcaagctca ccgtggacaagagcaggtggcagcaggggaacgtcttctcatgctccgtg atgcatgaggctctgcacaaccactacacgcagaagagcctctccctgtc tccgggtaaatga The amino acid sequence of the heavy chain of the anti-PTPRS chimera 22H8-84 antibody (470 a.a.) is shown below (SEQ ID NO: 100). The capital letters show the chimera 22H8-84 VH variable region, and the small letters show the human IgG1 heavy chain constant region.

MECNWILPFILSVTSGVYSQVQLQQSGAELARPGASVKLSCKASGYTFTS

YWMQWVKQRPGQGLEWIGAIYPGDGDTRYTQKFKGKATLTADKSSSTAYM

QLSSLASEDSAVYYCARRIYYGYYYAMDYWGQGTSVTVSSastkgpsvfp lapsskstsggtaalgclvkdyfpepvtvswnsgaltsgvhtfpavlqss glyslssvvtvpssslgtqtyicnvnhkpsntkvdkkvepkscdkthtcp pcpapellggpsvflfppkpkdtlmisrtpevtcvvvdvshedpevkfnw yvdgvevhnaktkpreeqynstyrvvsvltvlhqdwlngkeykckvsnka lpapiektiskakgqprepqvytlppsrdeltknqvsltclvkgfypsdi avewesngqpennykttppvldsdgsfflysklltvdksrwqqgnvfscsv mhealhnhytqkslslspgk The nucleic acid sequence of the light chain of the anti-PTPRS chimera 22H8-84 antibody (717 bp) is shown below (SEQ ID NO: 101). The capital letters show the chimera 22H8-84VL variable region, and the small letters show the human Ig κ light chain constant region.

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAACTCCTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGA

GGATCCTCTCACGTTCGGTGCTGGGACCAAGCTGGAGCTGAAAcgaactg tggctgcaccatctgtcttcatcttcccgccatctgatgagcagttgaaa tctggaactgcctctgttgtgtgcctgctgaataacttctatcccagaga ggccaaagtacagtggaaggtggataacgccctccaatcgggtaactccc aggagagtgtcacagagcaggacagcaaggacagcacctacagcctcagc agcaccctgacgctgagcaaagcagactacgagaaacacaaagtctacgc ctgcgaagtcacccatcagggcctgagctcgcccgtcacaaagagcttca acaggggagagtgctag The amino acid sequence of the light chain of the anti-PTPRS chimera 22H8-84 antibody (238 a.a.) is shown below (SEQ ID NO: 102). The capital letters show the chimera 22H8-84 VL variable region, and the small letters show the human Ig κ light chain constant region.

METDTILLWVLLLWVPGSTGDIVLTQSPASLAVSLGQRATISCKASQSVD

YDGDSYMNWYQQKPGQPPKLLIYAASNLESGIPARFSGSGSGTDFTLNIH

PVEEEDAATYYCQQSNEDPLTFGAGTKLELKrtvaapsvfifppsdeqlk sgtasvvcllnnfypreakvqwkvdnalqsgnsqesvteqdskdstysls stltlskadyekhkvyacevthqglsspvtksfnrgec The nucleic acid sequences and amino acid sequences of the heavy chain and light chain of the prepared chimera 49F2-30 antibody are represented respectively by the following sequence numbers.

| Heavy chain | Light chain |
|---|---|
| SEQ ID NO: 35 (nucleic acid sequence) | SEQ ID NO: 37 (nucleic acid sequence) |
| SEQ ID NO: 36 (amino acid sequence) | SEQ ID NO: 38 (amino acid sequence) |

The nucleic acid sequence of the heavy chain of the anti-PTPRS chimera 49F2-30 antibody (1413 bp) is shown below (SEQ ID NO:35). The capital letters show the chimera 49F2-30 VH variable region, and the small letters show the human IgG1 heavy chain constant region.

ATGAACTTCGGGCTCAGGTTGATTTTCCTTGCCCTCATTTTAAAAGGTGT

CCAGTGTGAGGTGCAGCTGGTGGAGTCTGGGGGAGACTTAGTGAAGCCTG

GAGGGTCCCTGAAACTCTCCTGTGCAGCCTCTGGATTCATTTTCAGTAGC

-continued

```
TATGGCATGTCTTGGGTTCGCCAGACTCCAGACAAGAGGCTGGAGTGGGT

CGCAACCATTAGTAGTGGTGGTAGTGACACCTATTATCCAGACAGTGTGA

AGGGGCGATTCACCATCTCCAGAGACAATGCCAACAACACCCTGTACCTG

CAAATGAGCAGTCTGAAGTCTGAGGACACAGCCATGTATTACTGTGCAAG

ACAGGTCTACTATGGTCTTTACTGGTATTTCGATGTCTGGGGCGCAGGGA

CCACGGTCACCGTCTCCTCAgctagcaccaagggcccatcggtcttcccc ctggcaccctcctccaagagcacctctgggggcacagcggccctgggctg cctggtcaaggactacttccccgaaccggtgacggtgtcgtggaactcag gcgccctgaccagcggcgtgcacaccttcccggctgtcctacagtcctca ggactctactcccctcagcagcgtggtgaccgtgccctccagcagcttggg cacccagacctacatctgcaacgtgaatcacaagcccagcaacaccaagg tggacaagaaagttgagcccaaatcttgtgacaaaactcacacatgccca ccgtgcccagcacctgaactcctgggggaccgtcagtcttcctcttccc cccaaaacccaaggacaccctcatgatctcccggacccctgaggtcacat gcgtggtggtggacgtgagccacgaagaccctgaggtcaagttcaactgg tacgtggacggcgtggaggtgcataatgccaagacaaagccgcgggagga gcagtacaacagcacgtaccgtgtggtcagcgtcctcaccgtcctgcacc aggactggctgaatggcaaggagtacaagtgcaaggtctccaacaaagcc ctcccagcccccatcgagaaaaccatctccaaagccaaagggcagccccg agaaccacaggtgtacaccctgcccccatcccgggatgagctgaccaaga accaggtcagcctgacctgcctggtcaaaggcttctatcccagcgacatc gccgtggagtgggagagcaatgggcagccggagaacaactacaagaccac gcctcccgtgctggactccgacggctccttcttcctctacagcaagctca ccgtggacaagagcaggtggcagcaggggaacgtcttctcatgctccgtg atgcatgaggctctgcacaaccactacacgcagaagagcctctccctgtc tccgggtaaatga
```

The amino acid sequence of the heavy chain of the anti-PTPRS chimera 49F2-30 antibody (470 a.a.) is shown below (SEQ ID NO:36). The capital letters show the chimera 49F2-30 VH variable region, and the small letters show the human IgG1 heavy chain constant region.

```
MNFGLRLIFLALILKGVQCEVQLVESGGDLVKPGGSLKLSCAASGFIFSS

YGMSWVRQTPDKRLEWVATISSGGSDTYYPDSVKGRFTISRDNANNTLYL

QMSSLKSEDTAMYYCARQVYYGLYWYFDVWGAGTTVTVSSastkgpsvfp lapsskstsggtaalgclvkdyfpepvtvswnsgaltsgvhtfpavlqss glyslssvvtvpssslgtqtyicnvnhkpsntkvdkkvepkscdkthtcp pcpapellggpsvflfppkpkdtlmisrtpevtcvvvdvshedpevkfnw yvdgvevhnaktkpreeqynstyrvvsvltvlhqdwlngkeykckvsnka lpapiektiskakgqprepqvytlppsrdeltknqvsltclvkgfypsdi avewesngqpennykttppvldsdgsfflyskltvdksrwqqgnvfscsv mhealhnhytqkslslspgk
```

The nucleic acid sequence of the light chain of the anti-PTPRS chimera 49F2-30 antibody (705 bp) is shown below (SEQ ID NO:37). The capital letters show the chimera 49F2-30 VL variable region, and the small letters show the human Ig κ light chain constant region.

```
ATGGAGTCACAGATTCAGGTCTTTGTATTCGTGTTTCTCTGGTTGTCTGG

TGTTGACGGAGACATTGTGATGACCCAGTCTCACAAATTCATGTCCACAT

CAGTAGGAGACAGGGTCAGCATCATTTGTAAGGCCAGTCAGGATGTGAAT

ACTGCTGTAGCCTGGTATCAACAGAAACCAGGACAATCTCCTAAATTACT

GATTTACTCGGCATCCTACCGGTACACTGGAGTCCCTGATCGCTTCACTG

GCAGTGGATCTGGGACGGATTTCACTTTCACCATCAGCAGTGTGCAGGCT

GAAGACCTGGCAATTTATTACTGTCAGCAACATTATAGTACTCCGTACAC

GTTCGGAGGGGGGACCAAGCTGGAAATAAAAcgaactgtggctgcaccat ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacg ctgagcaaagcagactacgagaaacacaaagtctacgcctgcgaagtcac ccatcagggcctgagctcgcccgtcacaaagagcttcaacaggggagagt gctag
```

The amino acid sequence of the light chain of the anti-PTPRS chimera 49F2-30 antibody (234 a.a.) is shown below (SEQ ID NO:38). The capital letters show the chimera 49F2-30 VL variable region, and the small letters show the human Ig κ light chain constant region.

```
MESQIQVFVFVFLWLSGVDGDIVMTQSHKFMSTSVGDRVSIICKASQDVN

TAVAWYQQKPGQSPKLLIYSASYRYTGVPDRFTGSGSGTDFTFTISSVQA

EDLAIYYCQQHYSTPYTFGGGTKLEIKrtvaapsvfifppsdeqlksgta svvcllnnfypreakvqwkvdnalqsgnsqesvteqdskdstyslsstlt lskadyekhkvyacevthqglsspvtksfnrgec
```

Example 6

Antibody-Dependent Cellular Cytotoxicity of Prepared Anti-Human PTPRS Chimeric Antibody (ch49F2-30, ch9H5-4, ch13G5-57 and ch22H8-84)

Figure 17A:
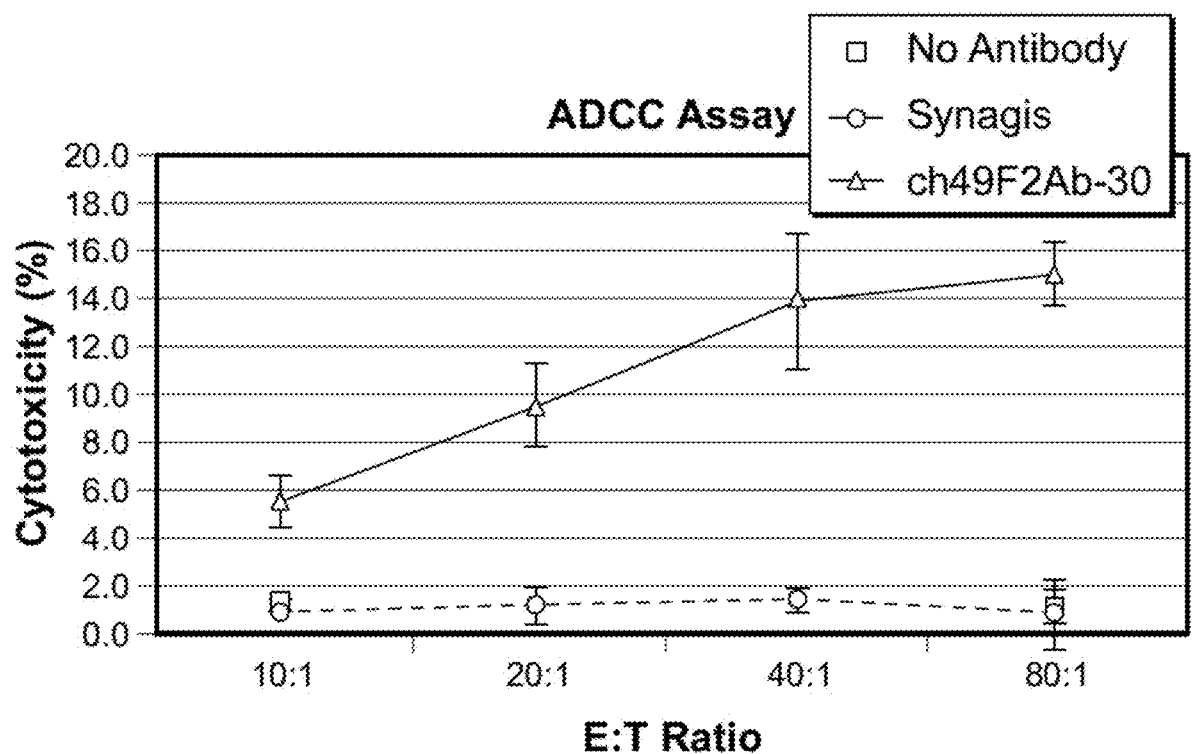
FIGS. 17A-17B show that ch49F2-30 (FIG. 17A), ch9H5-4, ch13G5-57 and ch22H8-84 (FIG. 17B) of an anti-hPTPRS chimeric antibody injure the target hPTPRS/CHO cell in an effector cell number-dependent manner.
Figure 17B:
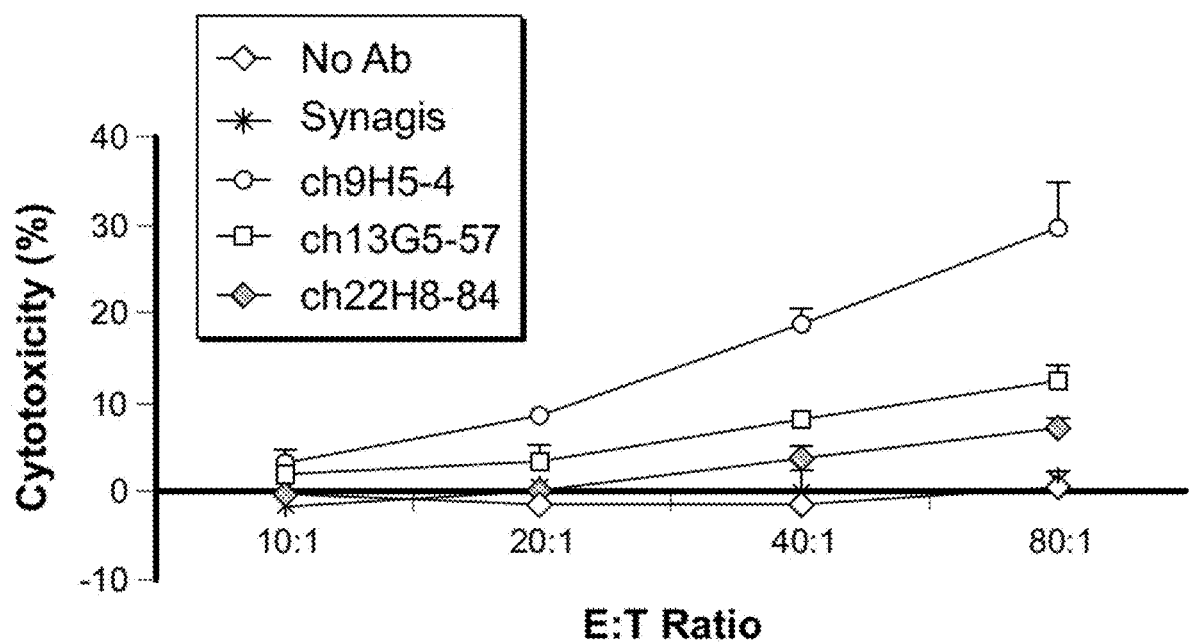

Antibody-dependent cellular cytotoxicity (ADCC activity) was measured. The activity was obtained by using the cellular cytotoxicity calculated from the measured value of lactase dehydrogenase (LDH) released from a cell as an index. Human peripheral blood mononuclear cells to be an effector cell was purified by specific gravity centrifugation using HISTOPAQUE-1077. As a cell to be a target, a forcibly-transformed cell of an hPTPRS gene using CHO (Chinese hamster ovary cell strain) was used ($2 \times 10^4$/well). The effector and target cells were mixed so that the ratio thereof became 10:1, 20:1, 40:1 and 80:1, 10 μg/ml of prepared anti-human PTPRS chimeric antibody (ch49F2-30, ch9H5-4, ch13G5-57 and ch22H8-84) or a control antibody Synagis was added, and the mixture was cultured for 4 hours at 37° C. to evaluate the cellular cytotoxicity effect of the antibody. As a result, the ch49F2-30, ch9H5-4, ch13G5-57 and ch22H8-84 of the anti-hPTPRS chimeric antibody lysed the hPTPRS/CHO cell of the target in an effector cell number-dependent manner (FIG. 17A and FIG. 17B). This result showed that the prepared anti-PTRS chimeric antibody selectively showed the cytotoxicity to the cells expressing PTPRS.

Figure 18A:
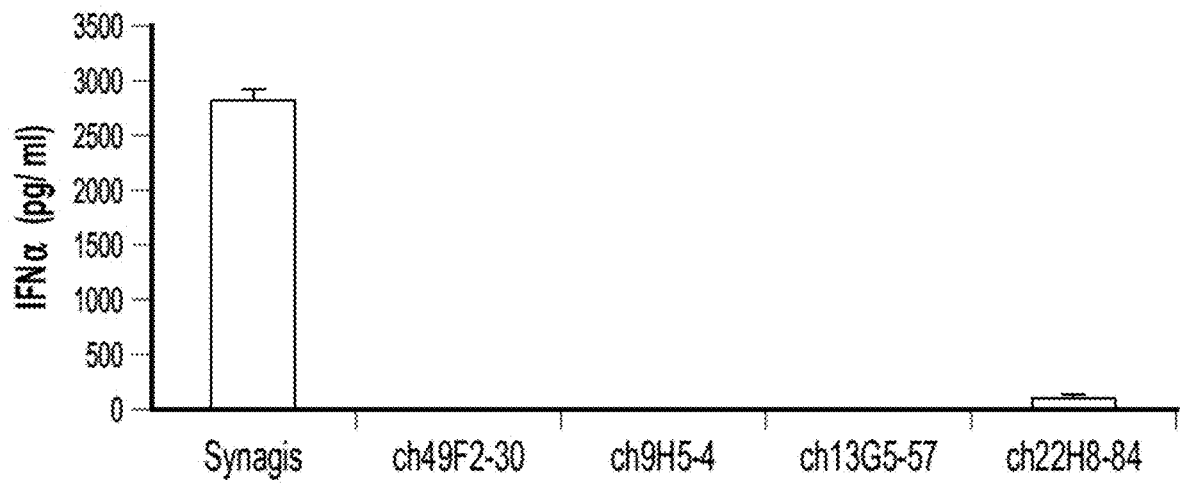
FIGS. 18A-18C show that IFNα production is completely inhibited by the treatment of the anti-PTPRS chimeric antibody with ch49F2-30,ch9H5-4,ch13G5-57 and ch22H8-84 (FIG. 18A), and it was clarified that the pDC population was decreased more than in the Synagis treatment of the control antibody (FIG. 18B and FIG. 18C).
Figure 18B:
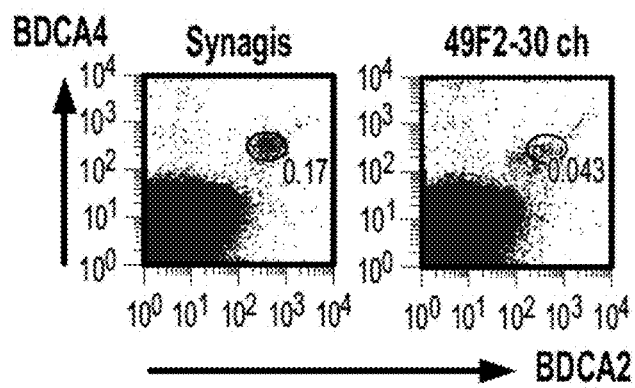
Figure 18C:
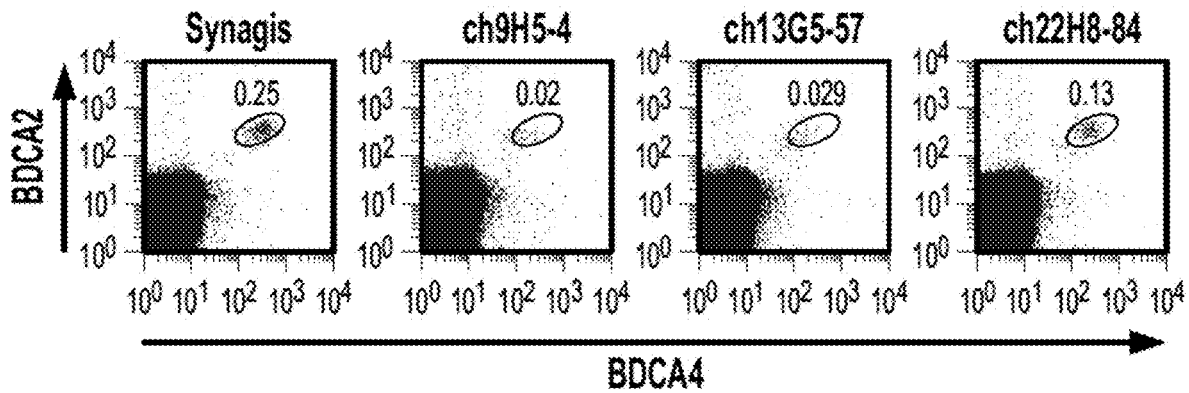

The effect of the anti-PTPRS antibody on pDC was studied. PBMCs were isolated from human peripheral blood, mixed with 10 µg/ml of an anti-human PTPRS chimeric antibody and cultured for 24 hours. Thereafter stimulation was conducted for 24 hours with CpG2216 that is a ligand of a Toll-like receptor 9 expressed in pDC to induce the production of IFNα. 24 h after CpG stimulation, the production amount of IFNα was tested. In result, the production of IFNα was completely inhibited by the treatment of prepared anti-human PTPRS chimeric antibody (ch49F2-30, ch9H5-4, ch13G5-57 and ch22H8-84) (FIG. 18A). Furthermore, when the cell was collected 6 hours after the ch49F2-30, ch9H5-4, ch13G5-57 and ch22H8-84 treatment and the pDC 1 was confirmed by double-staining with an anti-BDCA2 antibody and an anti-BDCA4 antibody, it was found that the pDC population was decreased more than the Synagis treatment of the control antibody (FIG. 18B and FIG. 18C). These results showed that the treatment of anti-PTPRS chimeric antibody depleted pDC that specifically expresses PTPRS, and consequently abolished the production of IFNα by CpG2216 stimulation.

INDUSTRIAL APPLICABILITY

The present invention provides an antibody that specifically recognizes human PTPRS, an immunogen that is useful for the production of the antibody, and a method for the production of an anti-human PTPRS antibody utilizing the immunogen.

ACCESSION NUMBERS

FERM ABP-11356
FERM ABP-11357
FERM ABP-11358
FERM ABP-11359
FERM ABP-11360
FERM ABP-11361
FERM ABP-11362
FERM ABP-11363

SEQUENCE LISTING FREE TEXT

SEQ ID NO: 3: forward primer
SEQ ID NO: 4: reverse primer
SEQ ID NO: 5: forward primer
SEQ ID NO: 6: reverse primer
SEQ ID NO: 7: forward primer
SEQ ID NO: 8: reverse primer
SEQ ID NO: 9: forward primer
SEQ ID NO: 10: reverse primer
SEQ ID NO: 11: antisense primer
SEQ ID NO: 12: anchor primer
SEQ ID NO: 12: n is deoxyinosine.
SEQ ID NO: 13: antisense primer
SEQ ID NO: 14: AUAP primer
SEQ ID NO: 15: antisense primer
SEQ ID NO: 16: antisense primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 24: primer
SEQ ID NO: 35: anti-PTPRS chimera 49F2-30 antibody heavy chain nucleic acid sequence
SEQ ID NO: 36: anti-PTPRS chimera 49F2-30 antibody heavy chain amino acid sequence
SEQ ID NO: 37: anti-PTPRS chimera 49F2-30 antibody light chain nucleic acid sequence
SEQ ID NO: 38: anti-PTPRS chimera 49F2-30 antibody light chain amino acid sequence
SEQ ID NO: 39: primer
SEQ ID NO: 40: primer
SEQ ID NO: 41: primer
SEQ ID NO: 42: primer
SEQ ID NO: 73: forward primer
SEQ ID NO: 74: reverse primer
SEQ ID NO: 75: forward primer
SEQ ID NO: 76: reverse primer
SEQ ID NO: 77: forward primer
SEQ ID NO: 78: reverse primer
SEQ ID NO: 79: forward primer
SEQ ID NO: 80: reverse primer
SEQ ID NO: 81: forward primer
SEQ ID NO: 82: reverse primer
SEQ ID NO: 83: forward primer
SEQ ID NO: 84: reverse primer
SEQ ID NO: 85: forward primer
SEQ ID NO: 86: reverse primer
SEQ ID NO: 87: forward primer
SEQ ID NO: 88: reverse primer
SEQ ID NO: 89: forward primer
SEQ ID NO: 90: reverse primer
SEQ ID NO: 91: anti-PTPRS chimera 9H5-4 antibody heavy chain nucleic acid sequence
SEQ ID NO: 92: anti-PTPRS chimera 9H5-4 antibody heavy chain amino acid sequence
SEQ ID NO: 93: anti-PTPRS chimera 9H5-4 antibody light chain nucleic acid sequence
SEQ ID NO: 94: anti-PTPRS chimera 9H5-4 antibody light chain amino acid sequence
SEQ ID NO: 95: anti-PTPRS chimera 13G5-57 antibody heavy chain nucleic acid sequence
SEQ ID NO: 96: anti-PTPRS chimera 13G5-57 antibody heavy chain amino acid sequence
SEQ ID NO: 97: anti-PTPRS chimera 13G5-57 antibody light chain nucleic acid sequence
SEQ ID NO: 98: anti-PTPRS chimera 13G5-57 antibody light chain amino acid sequence
SEQ ID NO: 99: anti-PTPRS chimera 22H8-84 antibody heavy chain nucleic acid sequence
SEQ ID NO: 100: anti-PTPRS chimera 22H8-84 antibody heavy chain amino acid sequence
SEQ ID NO: 101: anti-PTPRS chimera 22H8-84 antibody light chain nucleic acid sequence
SEQ ID NO: 102: anti-PTPRS chimera 22H8-84 antibody light chain amino acid sequence

The invention claimed is:

1. A polynucleotide encoding an antibody or antigen-binding fragment thereof that binds to human receptor-type protein tyrosine phosphatase σ (human PTPRS), wherein the antibody or antigen-binding fragment thereof comprises the heavy and light chain complementarity determining regions of the antibody produced by hybridoma 9H5-4 (deposited as Accession No. FERM BP-11356), hybridoma 10F7-38 (deposited as Accession No. FERM BP-11357), hybridoma 13G5-52 (deposited as Accession No. FERM BP-11358), hybridoma 13G5-57 (deposited as Accession No. FERM BP-11359), hybridoma 14A8-85 (deposited as Accession No. FERM BP-11360), hybridoma 22H8-84 (deposited as Accession No. FERM BP-11361), hybridoma 49F2-30 (deposited as Accession No. FERM BP-11362), or hybridoma 55E7-79 (deposited as Accession No. FERM BP-11363).

2. The polynucleotide of claim 1, wherein the antibody or antigen-binding fragment thereof is chimerized or humanized.

3. A vector encoding an antibody or antigen-binding fragment thereof that binds to human receptor-type protein tyrosine phosphatase σ (human PTPRS), wherein the antibody or antigen-binding fragment thereof comprises the heavy and light chain complementarity determining regions of the antibody produced by hybridoma 9H5-4 (deposited as Accession No. FERM BP-11356), hybridoma 10F7-38 (deposited as Accession No. FERM BP-11357), hybridoma 13G5-52 (deposited as Accession No. FERM BP-11358), hybridoma 13G5-57 (deposited as Accession No. FERM BP-11359), hybridoma 14A8-85 (deposited as Accession No. FERM BP-11360), hybridoma 22H8-84 (deposited as Accession No. FERM BP-11361), hybridoma 49F2-30 (deposited as Accession No. FERM BP-11362), or hybridoma 55E7-79 (deposited as Accession No. FERM BP-11363).

4. The vector of claim 3, wherein the antibody or antigen-binding fragment thereof is chimerized or humanized.

5. A cell comprising the vector of claim 3.

6. A cell comprising the vector of claim 4.

7. A method for the production of an antibody or antigen-binding fragment thereof, comprising:
culturing in a cell culture a cell producing an antibody or antigen-binding fragment thereof that binds to human receptor-type protein tyrosine phosphatase σ (human PTPRS), wherein the antibody or antigen-binding fragment thereof comprises the heavy and light chain complementarity determining regions of the antibody produced by hybridoma 9H5-4 (deposited as Accession No. FERM BP-11356), hybridoma 10F7-38 (deposited as Accession No. FERM BP-11357), hybridoma 13G5-52 (deposited as Accession No. FERM BP-11358), hybridoma 13G5-57 (deposited as Accession No. FERM BP-11359), hybridoma 14A8-85 (deposited as Accession No. FERM BP-11360), hybridoma 22H8-84 (deposited as Accession No. FERM BP-11361), hybridoma 49F2-30 (deposited as Accession No. FERM BP-11362), or hybridoma 55E7-79 (deposited as Accession No. FERM BP-11363); and
collecting the antibody or antigen-binding fragment thereof from the cell culture.

8. The method of claim 7, wherein the antibody or antigen-binding fragment thereof is chimerized or humanized.

* * * * *